US007078185B2

(12) United States Patent
Farnet et al.

(10) Patent No.: US 7,078,185 B2
(45) Date of Patent: Jul. 18, 2006

(54) GENE ENCODING A NONRIBOSOMAL PEPTIDE SYNTHETASE FOR THE PRODUCTION OF RAMOPLANIN

(75) Inventors: Chris M. Farnet, Outremont (CA); Emmanuel Zazopoulos, Outremont (CA); Alfredo Staffa, St-Léonard (CA)

(73) Assignee: Ecopia BioSciences Inc., Saint-Laurent (CA)

( * ) Notice: Subject to any disclaimer, the term of this patent is extended or adjusted under 35 U.S.C. 154(b) by 207 days.

(21) Appl. No.: 09/976,059

(22) Filed: Oct. 15, 2001

(65) Prior Publication Data

US 2002/0164747 A1 Nov. 7, 2002

Related U.S. Application Data

(60) Provisional application No. 60/283,296, filed on Apr. 12, 2001, provisional application No. 60/239,924, filed on Oct. 13, 2000.

(51) Int. Cl.
*C12P 21/06* (2006.01)
(52) U.S. Cl. ............... 435/69.1; 435/320.1; 435/252.3; 435/254.11; 435/419; 435/325; 536/23.1; 536/23.2
(58) Field of Classification Search ............... 536/23.1, 536/23.2; 435/320.1, 252.3, 254.11, 419, 435/325, 69.1
See application file for complete search history.

(56) References Cited

U.S. PATENT DOCUMENTS

| 4,303,646 A | 12/1981 | Cavalleri et al. |
| 4,427,656 A | 1/1984 | Cavalleri et al. |
| 2003/0054353 A1* | 3/2003 | Farnet et al. ................... 435/6 |

FOREIGN PATENT DOCUMENTS

| EP | 0 427 142 A | 5/1991 |
| EP | 259780 | 3/1993 |
| WO | WO 01 53533 A | 7/2001 |
| WO | WO 200231155 A2 * | 4/2002 |
| WO | WO 2003089641 A2 * | 10/2003 |

OTHER PUBLICATIONS

GenBank Accession No. AX417445. Sequence 1 from patent WO0231155. Jun. 18, 2002.*
Mootz et al. Design and application of multimodular peptide synthetases. Curr Opin Biotechnol. (Aug., 1999) 10(4): 341-348.*
Hubbart BK et al., Chem. & Biol., (2000) vol. 7, pp. 931-942 "Biosynthesis of L-P-hydroxyphenylglycine, a non-proteinogenic amino acid contituent of peptide antibiotics".
Choroba OW et al., J. Am. Chem. Soc., (2000) vol. 122, pp. 5389-5390 "Biosynthesis of the vancomycin group of antibiotics: involvement of an unusual dioxygenase in the pathway to (S)-4-hydroxyphenylglycine".
Dockel S., Marahiel M.A., Metabolic Engineering, (2001) vol. 3, pp. 64-77 "Biosynthesis of natural products on modular peptide synthetases".
Ecopia BioSciences, Inc., conference—Oct. 17, 2000 "From Genes to Molecules".
Marahiel M.A. et al., Chem. Rev., (1997) vol. 97, pp. 2651-2673 "Modular peptide synthetases involved in nonribosomal peptide synthesis".
Ciabatti et al. (1989) *J. Antibiot (Tokyo)*, vol. 42, No. 2, pp. 254-267 "Ramoplanin (A-16686), a new glycolipodepsipeptide antibiotic".
Gastaldo et al (1992), *J. Ind. Microbiol*, vol. 11, No. 1, pp. 13-18 "Isolation, structure determination and biological activity of A-16686 factors A 1, A 2 and A 3 glycolipodepsipeptide antibiotics".
Konz & Marahiel (1999) *Chem. Biol.*, vol. 6, pp. R-39-R48 "How do peptide synthetases generate structural diversity?".
Quadri et al. (1998) *Chem. Biol.*, vol. 5, pp. 631-645 "Identification of a Mycobacterium tuberculosis gene cluster encoding the biosynthetic enymes for assembly of the virulence-conferring siderophore mycobactin".
Challis et al. (2000) *Chem. Biol.*, vol. 7, pp. 211-224 "Predictive, structured-based model of amino acid recognition by nonribosomal peptide synthetase adenylation domains".
Nicas et al., *Biotechnology of Antibiotics*, Marcel Dekker Inc. 1997, pp. 363-392 "Vancomycin and Other Glycopeptides".
Altschul et al., 1997, *Nucleic Acids Res.*, vol. 25, pp. 3389-3402 "Gapped BLAST and PSI-BLAST: a new generation of protein database search programs".
Stachelhaus et al., 1999, *Chem. Biol.*, vol. 6, pp. 493-505 "The specificity-conferring code of adenylation domains in nonribosomal peptide synthetases".
Stachelhaus et al., 1995, *Science*, vol. 269, pp. 69-72 "Rational Design of Peptide Antibiotics by targeted Replacement of Bacterial and Fungal Domains".
Schneider et al., 1998, *Mol. Gen. Genet.*, vol. 257, pp. 308-318 "Targeted alteration of the substrate specificity of peptide synthetases by rational module swapping".
de Ferra et al., 1997, *J. Biol. Chem.*, vol. 272, pp. 25304-25309 "Engineering of Peptide Synthetases".

(Continued)

*Primary Examiner*—Kathleen Kerr
*Assistant Examiner*—Lindsay Odell
(74) *Attorney, Agent, or Firm*—Ywe J. Looper

(57) ABSTRACT

The present invention relates to an isolated genetic sequence encoding a nonribosomal peptide synthetase (NRPS) protein which directs the biosynthesis of the antibiotic ramoplanin in microorganisms such as *Actinoplanes* sp. The isolated gene sequence serves as a substrate for bioengineering of antibiotic structures.

25 Claims, 16 Drawing Sheets

OTHER PUBLICATIONS

Guenzi et al., 1998, *J. Biol. Chem.*, vol. 273, pp. 14403-14410 "Coordinate Transcription and Physical Linkage of Domains in Surfactin Synthetase Are Not Essential for Proper Assemble and Activity of the Multienzyme Complex".

Weber et al., 1994, *Curr. Genet.*, vol. 26, pp. 120-125 "The peptide synthetase catalysing cyclosporine production in Tolypocladium niveum is encoded by a giant 45.8-kilobaseopen reading frame".

Scott-Craig et al., 1992, *J. Biol. Chem.*, vol. 267, pp. 26044-26049 "The Cyclic Peptide Synthetase Catalyzing HC-toxin Production in the Filamentous Fungus *Cochliobolus carbonum* Is Encoded by a 15.7-Kilobase Open Reading Frame".

Pfeifer et al., 1995, *Biochem.*, vol. 34, pp. 7450-7459 "Characterization of Tyrocine Synthetase 1 (TY1): Requirement of Posttranslational Modification for Peptide Biosynthesis".

Stein et al., 1995, *Biochem.* vol. 34, pp. 4633-4642 "Gramicidin S Synthetase 1 (Phenylalanine Racemase), a Prototype of Amino Acide Racemases Containing the Cofactor 4-Phosphopantetheine".

Chung et al., 1986, *J. Antibiotics*, vol. 1986, pp. 642-651 "Biosynthethic studies of aridicin antibiotics".

Hosoda et al., 1977, *Agric. Biol. Chem.*, vol. 41, pp. 2007-2012 "Incorporation of 34C-Amino Acids into Nocardicin A by Growing Cells".

van Wageningen et al., 1997, Chem. Biol. vol. 5, pp. 155-162 "Sequencing and analysis of genes involved in the biosynthesis of a vancomycin group antibiotic".

Casey & Davidson, Nucl. Acid Res. (1977) vol. 4, pp. 1539-1552 "Rates of formation and thermal stabilities of RNA:DNA and DNA. DNA duplexes at high concentrations of formamide".

Towbin et al., Proc. Natl. Acad. Sci. USA,(1979) 76:4350 "Electrophoretic transfer of proteins from polyacrylamide gels to nitrocellulose sheets:Procedure and some applications".

Laemmli, Nature (1970) 227:680 "Cleavege of Structural Proteins during the Assembly of the Head of Bacteriophage T4".

Kunkel et al., Proc. Natl. Acad. Sci. USA (1985) 82:488 "Rapid and efficient site-specific mutagenesis without phenotypic selection".

Nielsen et al., Science (1991) 254:1497 "Sequence-Selective Recognition of DNA by Strand Displacement with a Thymine-Substituted Polyamide".

Southern, J. Mol. Biol. (1975) 98:503-517 "Detection of Specific Sequences Among DNA Fragments Separated by Gel Electrophoresis".

Dunn et al., Cell (1977) vol. 12, pp. 23-36 "A Novel Method to Map Transcripts: Evidence for Homology between an Adenovirus mRNA and Discrete Multiple Regions of the Viral Genome".

Hoffmann et al., Nucleic Acids Research (1999) vol. 27, No. 1, pp. 215-219 "The Prosite database, its status in 1999".

Hammond et al., 1982, J. Chem. Soc. (Chem. Comm.), vol. 1982, pp. 344-346.

Sosio M. et al., Mol. Gen. Genet. (2000) vol. 264, pp. 213-221 "Multiple peptide synthetase gene clusters in Actinomycetes".

McCafferty D. G. et al., Biopolymers (2002) vol. 66(4), pp. 261-284 "Chemistry and biology of the Ramoplanin Family of Peptide Antibiotics".

Micklefield J., Chemistry & Biology (2004) vol. 11, pp. 887-895 "Daptomycin Structure and Mechanism of Action Revealed".

* cited by examiner

```
Orf12        ------------------------ERRRLLDEWN-ATAAPSSDTVLARFEEQAARTPEAPAVVC
Orf13|M1     ------------------------ERSRLLVEWNDTARPVVESSVPALFAKRVAATPDATAVVG
Orf13|M2     ---------------------------NATAVPAQPALVPELFTAQAARTPTWPALVT
Orf13|M3     ----------------------DRLLTAWNEAREPAPP-VTLPDLFDRQARRTPEAVALTA
Orf13|M4     ------------------------EIERVVHSWNDTARPVVESSVPALFAEQVAAAPDATAVVG
Orf13|M5     ------------------------ERSRLLVEWNDTARPVVESSVPALFAEQVAAAPDAVAVVG
Orf13|M7     ---------------------------------TVPELVAAQVARRPGAVALRS
Orf14|M1     ----------------------------NDTAAPAPAGLVPDLFAAQAARTPDAVAVAG
Orf14|M2     ----------------------------NDTARRVRQASVPELFAERVAAAPGAPAVAA
Orf14|M3     ------------------EESRLMLAAGEEPAPALPEITVAALVAEQCARTPGAVAVTG
Orf14|M4     ----------------------------NETRRAVTRASVPELFAKQVAATPDAIAVAG
Orf14|M5     ------------------ERRLVLTGWNDTTAAVPAVAVPELIERRAAAEPEAGAVWC
Orf14|M6     ------------------ERREVLRTPNATARDVAAATLPAIVGEWARTTPGATAVTA
Orf14|M7     ------------------EREAVLSGGNGGTAPVPVTTVPALFAEQARRTPGAVAALS
Orf14|M8     ------------------ERSRLLVEWNDTARPVVESSVPALFAERVAAAPDAVAVVG
Orf17        ----------------------RTLTGLFAEQVAARPTAVAVSD
GrsA_Adomain MLNSSKSILIHAQNKNGTHEEEQYLFAVNNTKAEYPRDKTIHQLFEEQVSKRPNNVAIVC
                                           :   .     *  *

A1                                                    A2
Orf12        GDVTVTYAELEAGANRLARVLRARGAGPESVVALCLPRGPEVVTGILAAWKAGAAYLPVD
Orf13|M1     EGVSWSYRELDRRSDVLARRLVAAGVGVESPVVVALERSPEVLSAFLAVAKAGGVFVPVD
Orf13|M2     AGAIMSYAELEERSNRLARWLAGRGVGADDRVALMMRRGPELMVAILAVLKAGAAYLPVD
Orf13|M3     DGVSLTYRELSERANRIARLLTSRGIGPESLVGVVLPRSADLVVALLGVLQAGAAYVPVD
Orf13|M4     EGVSWSYRELDARSDALARSLVAAGVGVESPVVVALERSPEVLSAFLAVAKAGGVFVPVD
Orf13|M5     EGVSWTYRELDARSDALARSLVAAGVGVESPVVVALERSPEVLSAFLAVAKAGGVFVPVD
Orf13|M7     EDGEITYAELDARAGRLAAVLRRRGIGPESRVAVLLPRGVEQVVAFLAVVRAGGTYLPID
Orf14|M1     PDRELTYAELDERSGRLARWLIRRGVAADTRVALVLERSAELPVAILAVLKAGGAYLPID
Orf14|M2     GDLRWTYADLDARSDALARSLVAAGVTAESPVVVALERSADVLTAFLAVAKAGGVFVPVD
Orf14|M3     PDASLTYAELDERAARIARWLRRHGAGPGAAVCVLMERSAELVAVLLGVMRAGAAYVPVD
Orf14|M4     EGVSWSYRELDVRSDALARSLVAAGVGIESPVVVALDRSPEVPTAFLAVAKAGGVFVPVD
Orf14|M5     GDTHLRYGELNARANRLARLLVERGAGPESIVAVCLERSADLVVTLLAVLKTGAAYLPID
Orf14|M6     ENDRLTYAELDARANRLARSLIARGVGPGAVVGMLLPRSPGLVVAMLAIVKAGGAYLPLD
Orf14|M7     EGMSLTYADLAARVNRLARHLVSLGAGPETVVGIAMSRGLDMLVAVLAVGQAGAAYLPVD
Orf14|M8     EGVSWSYRELDRRSDVLARSLVAAGVGLESPVVVALERSADVLTAFLAVAKAGGVFVPVD
Orf17        DRGRHTYRELDEWSGRLARGLRKAGVRDGDAVGVCLDRSAELVAVLLAVLKAGAAYVPLD
GrsA_Adomain ENEQLTYHELNVKANQLARIFIEKGIGKDTLVGIMMEKSIDLFIGILAVLKAGGAYPID
                  *  :*.        :*  :    *    :  : :.     .*.  ::*..::*:*

Orf12        TELPAERVAYLLGDSAAAVRLG--TAETLAALPDGP---------------AADVDVHA
Orf13|M1     LSWPQARVDAVVADCAARVAVA--DRPMSGLTVVSAGL------------GGDSAVVSA
Orf13|M2     PDLPRDRVDYLLADAAPAFVLA--ERATAPWVPVA--------------GGIPVLVVDA
Orf13|M3     ADYPAERIGYILGDAGAVCVLT--VDATAGAVPPG--------------VPKLVLDH
Orf13|M4     LSWPQARIDAVVADCAARVAVA--DRPMSGLTVVPA-----------------
Orf13|M5     LSWPQARVDAVVADCGARIAVA--DRPMSGLTVVSAGL------------GGDSAVVSG
Orf13|M7     PAYPRDRVDYLVRDAEPACLLT--VAGHRAAAPAAP-------------AVVELDD
Orf14|M1     PAQPPRRIADIVADAAPALVLA--QASTADVVADASPALVLAPASDGVPTGAVPVHLLDS
Orf14|M2     LSWPRARVDAVIADCAAWIAVA--DRPMGLTVVPAN---------------
Orf14|M3     PAYPAERIRFVVTDARAACVVS--ESASAGLVPDG--------------VPCLAIDD
Orf14|M4     LSWPQARVDAVIADCAARVAVA--DRPMTGLTVVPA----------------
Orf14|M5     PGYPAGRIAYMLADARPALLVTSPAVASGDSLPDGG-------------AQRIVLGD
Orf14|M6     PGYPAPRLARMVEDAAPALLLA--TAGTADAVPAGP-------------QRLLLDD
Orf14|M7     PSYPDERKEFMLTDAGAAYVLT--LASDADRVPPGTP------------AAAVVLDE
Orf14|M8     LSWPQTRIDAVIAD-S--------RPVLVLDSVDLP----------------
Orf17        AAYPADRIAYTVGDAGLAVVVT--TSADFPDV-DG--------------VRLLAPES
GrsA_Adomain IEYPKERIQYILDDSQARMLLT--QKHLVHLIHNIQFN-----------GQVEIFEE
                *    *        . *
```

Figure 3A

```
                                                           A3
Orf12         PEIARE-----SP----SPLRLEPLPDQLAYVIYTSGSTGLSKGVGVSHGGLANYVGWAS
Orf13|M1      DLTADRAVVLPSRPVP---------GAAVYRMYTSGSTGRPKGVVTTHQNLVDLAT---
Orf13|M2      PAVAAEVAAHSGEAVTDRDRRAALRGGHLAYVIYTSGSTGRPKGVLITHDGLANLTL-DH
Orf13|M3      PETVTALAACDTAPLGEAERAGELLPEHPAYVIYTSGSTGTPKGVLIPHRNVVELFAATR
Orf13|M4      DQVGDSAVVLPAGPVP---------GAAVYRMYTSGSTGRPKGVVTTHQNLVDLAT---
Orf13|M5      DLTADRAVVLPACPVP---------GAAVYRMYTSGSTGRPKGVVTTHQNLVDLAT---
Orf13|M7      PATAAEIADAEPEPP------VAVRPTHSAYLIYTSGSTGRPKGVVVTHRGVAALVATQA
Orf14|M1      PAVRDEVAQCPAGAVTDADRRGVLLGGHAAYVIYTSGSTGRPKGVVVSHDAFANLVL-DQ
Orf14|M2      -RAGDPAVALPPRPLP---------GAAAYRMYTSGSTGRPKGVVTTHQNVVDLVT---
Orf14|M3      P----AAAAEPAEPGDDPGDAAGPRPDDPAYIIYTSGSTGTPKGVVVSHRNVVALLTATR
Orf14|M4      DAAGDPAAELPPRPLP---------GAEVYRMYTSGSTGRPKGVVTTHQNLVDLAT---
Orf14|M5      PDTAAALDGLAGTDLLVSERRGVTHPAHPAYVIYTSGSTGRPKGVVVPHGALTNFVAAMS
Orf14|M6      PGTAAELARLDGDPIRDEERTHPLRPGHPAYLMFTSGSTGRPKGVLVPHAGIDRMVR-RS
Orf14|M7      PVTAARIAGLDPADLTDADRVAPLLPAHRAYVIYTSGSTGRPKGVAVEHRTVVNLLSWAA
Orf14|M8      ----AAEADLPRVPA----------GAGVYRMYTSGSTGRPKGVVTTHQNLVDLAT---
Orf17         ------LAEAGDDPGIPLATPAG--PERPAYVIYTSGSTGRPKGVVVPHANVSALLDATR
GrsA_Adomain  DTIKIREGTNLHVPSK---------STDLAYVIYTSGTTGNPKGTMLEHKGISNLKVFFE
                                         .* ::***:** .**.   *    .

A4
Orf12         VLYGGLSAP---LHSSLAFDLTVISVFVPLVCGGSVVVSAAGGGRGLASLLAAGDG--FS
Orf13|M1      -DTCWGPTPRVLFHAPHAFDASSYEIWVPLLNGGTVVVAPQRSID-ATVLKDLIRAHDLT
Orf13|M2      GRFGLGPGARVAQFASPGFDMFVDEWSMALLAGAALTFVPPERRL-GADLAAFLAEYGVT
Orf13|M3      GSFHFGEGDVWSWFHSVAFDFSVWELWGALLHGGRVVMVPFAVSRSPRDFWELLVRERVT
Orf13|M4      -DTCWGPTPRVLFHAPHAFDASSYEIWVPLLNGGTVVVAPQRSID-ATVLRDLIRGHELT
Orf13|M5      -DTCWGPTPRVLFHAPHAFDASSYEIWVPLLNGGTVVVAPRRSID-ATVLRDLIGAHELT
Orf13|M7      ERLAVTGESRVLQFASVGFDASIWEMVMALCAGATLVVAPADDLLPGPALAATLSGHAVT
Orf14|M1      RRLGIGPGSRVAQFASPGFDMFVDEWSMALLAGAALVIVPPERRL-GADLAAFLTERGVT
Orf14|M2      -DRCWGPTPRVLFHAPHAFDASSEELWVPLLTGGTVVVAPGESID-TGVLRQLIRAHELT
Orf14|M3      PLFGFAGDEVWSWFHSVAFDFSVWELWGALTHGGRVVVVPYAVSRSPRDFWELVVREGVT
Orf14|M4      -DTCWGPTPRVLFHAPHAFDASSYEIWVPLLNGGTVVVAPGRSID-AAVLGELIRAHELT
Orf14|M5      DRLALGAGDRLLAVTTVAFDIHVLELYVPLVGGAGVVVAEDAVVRDPAAVAALLDRHAVT
Orf14|M6      TCLQLAPDDVLPHLSSVSFDAATEEIWGALLNGATLAVAPAETLS-VAELRAFLADRGAT
Orf14|M7      GRFGGADFARTLAATSLNFDVSVFEIFGPLVSGGSIEIVTDLLALADPASPAWEA----S
Orf14|M8      -DTCWGSTPRVLFHAPHAFDASSYEIWVPLLNGGTVVVAPRSID-ATVLRDLVRGHELT
Orf17         EEYGLGPGDVWTFFHSAAFDFSVWEIWGCLLTGGHLVVVPYWVSRSPEQFHDLLAERGVT
GrsA_Adomain  NSLNVTEKDRIGQFASISFDASVWEMFMALLTGASLYIILKDTINDFVKFEQYINQKEIT
                               **  .       *  *:. .

A5
Orf12         LVKVVPGHLRLLAELVPAGEMAAVG----SLVAGGEVLAGGDVREWLSRVPGS--VVVNE
Orf13|M1      HVHVTA---GLLRVL---DPSCFAG--LTEVLTGGDAVSAEAVRRVKDANPGL--RVRQL
Orf13|M2      HATLPP---AVVGTIPDGVLPPSF-----VLDVCGDVLPGDLARR--WLRDGR--VLFNS
Orf13|M3      VLSQTP---SAFYQLAAAA-DDTPD-ALRVVVFGGEALDPGRLAGWRERRPDG--PRLVN
Orf13|M4      HVHVTA---GLLRVL---DPSCFAG--LTEVLTGGDAVSAEAVRRVREANPGL--RVRQL
Orf13|M5      HVHVTA---GLLRVL---DPSCFAG--LTEVLTGGDAVSAEAVRRVKDANPGL--RVRQL
Orf13|M7      HATLPP---AVLAASAPGDLAPLA------VLVSAGEALGPDLVR---QFAPGR--ALVN
Orf14|M1      HATLPP---AVVATLPEESLPRSF-----VLDIGGDALPDDLARR--WLRDGR--WLGNS
Orf14|M2      HVHVTA---GLLRVLAE-DPSCFAG--LTEVLTGDVPAEAVRRVLDANPGV--RVRQL
Orf14|M3      VLSQTP---SAFAQLMAAAGDDDRD-ALRFVVFGGEALDPGRLAGWLARRPDK--PRLVN
Orf14|M4      HVHVTA---GLLRVL---DPSCFAG--LTEVLTGGDAVSAEAVRRVMEANPGL--RVRQL
Orf14|M5      IVQATP---ALWQALLAGHADAVRD---VRLLVGGEALPPALAG--RMAAAGR--GVTNL
Orf14|M6      KLFLTT---GLLHEVIDADVTALAG--LKAVYTGGDVLSPAHCRSLLDRVPGL--ELYNA
Orf14|M7      LVSGVP---SAFSRVLDRGDIAART---RSVVLAGEALTADVVNATRAALPGV--RVANL
Orf14|M8      HVHVTA---GLLRVL---DPSCFAG--LTEVLTGGDAVSAEAVRRVKEANPGL--RVRQL
Orf17         VLNQTP---SSFTQLVAADRGAERDLAVRLVIFGGEPLDARTVLPWLDRRPEARCRLVNM
GrsA_Adomain  VITLPP---TYVVHLDPERILSIQT-----LITAGSATSPSLVNKWKEKVT-----YINA
                                                 :  .*.
```

Figure 3A cont'd

```
                      A5                                                      A6
Orf12         YGPTETVGCSVFSVAAGDVVGD--VVPVGRPVANTRLFVLDEGLRPVPAGVAGELYVAG
Orf13|M1      YGPTEVTLCATQHLLD-DG-------VPIGRPLDNTRVYVLDDLLQPVPVGVTGELYVAG
Orf13|M2      YGPTETTVNAATWR-AEAGDWGS--VAPIGTPVPNLRAYVLDGWLRPVPVGAIGELYVSG
Orf13|M3      YGITETTVHVTHQDLAPAD-TTG--S-PIGRGIPGLSVYVLDEALRPVPPGVAGEVYVAG
Orf13|M4      YGPTEVTLCATQHLLV-DG-------VPIGRPLDNTRVYVLDDLLQPVPVGVTGELYVAG
Orf13|M5      YGPTEVTLCATQHLLD-DG-------VPIGRPLDNTRVYVLDDLLRPVPTGVVGELYVAG
Orf13|M7      YGPTETTVCATASAPLGPEDPPH-----IGAPVADSRVYVLDDALTPVPPGVTGELYVSG
Orf14|M1      YGPTETTVNAATWR-CEPGTWEG--ATPIGRPVANLRAYVLDGRLRPVPVGVEGELYVSG
Orf14|M2      YGPTEVTLCATQHVVREPSPV-----LPIGRPLDNTRVYVLDGLLQPVPVGVTGELYIAG
Orf14|M3      YGITETTVHTTYQHIAPG--TTG--S-VIGRGLPGFGLYVLDEALRPVPAGVEGEVYARG
Orf14|M4      YGPTEVTLCATQQVLDGTG-------VPIGRPLDNTRVYVLDDLLQPVPVGVTGELYVAG
Orf14|M5      YGPTEVTVWATVADLGA-SPAG---PVPIGTPLRNTRAFVLDDALRPVPPGVEGELYLAG
Orf14|M6      YGPTENTIITTLHR-VRPEDLDAGTGVPIGVPISDTRVYVLDDALRPVPVGVAGELYTSG
Orf14|M7      YGPTEATVYSTAWHTDR-DVTGG--AAPIGRPVTNTRAYVLDDRLTPVPPGVVGELYLAG
Orf14|M8      YGPTEVTLCATQHLLD-DG-------VPIGRPLDNTRVYVLDDLLRPVPTGVVGELYVAG
Orf17         FGITETTVHVTAVDVTRAAALAG--SRSVGRPLPGWAVRVLDEQRREVPPGVEGEIYVGG
GrsA_Adomain  YGPTETTICATTWVATKETIGHS---VPIGAPIQNTQIYIVDENLQLKSVGEAGELCIGG
              :*  **  .    :                :*     : .      ::*    . *  **:   *

A6                     A7                    A8
Orf12         SQVARGYVGRSGLTASRFVACPFG-VGERMYRTGDVVRLAG-GDLVFVGRVDEQVKIRGY
Orf13|M1      AGVARGYAGMPGLTAERFVADPFNT-GGRLYRTGDLVRWTDDGVLHFAGRADDQVKIRGY
Orf13|M2      AGLARGYLNRAGLTAERFVACPFEP-GERMYRTGDVVRWTAEGRLVFAGRSDDQVKIRGF
Orf13|M3      RQLARAYLGRAALTGTRFVACPFLPAGERMYRTGDRARWSR-GRLQFAGRTDDQVQIRGF
Orf13|M4      AGLARGYAGMPGLTAERFVADPFSV-GGRLYRTGDLVRWTDDGVLHFAGRADDQVKIRGY
Orf13|M5      SGLARGYAGMPGLTAERFVADPFNT-GGRLYRTGDLVRWADDGVLHFAGRADDQVKIRGY
Orf13|M7      ASLARGYAGRAALTAERFVACPFAP-GERMYRTGDRARWDAAGRLTFAGRADDQVKIRGF
Orf14|M1      AGLARGYLNRAGLTAGSFVACPFEP-GERMYRTGDIVRWDARGRLVYAGRADDQAKIRGF
Orf14|M2      AGVARGYADMPGTTAERFVADPFTA-GGRLYRTGDLVRWTGEGELVFAGRADDQVKIRGY
Orf14|M3      PQVARGYIGRPGLTAERFVASPFAP-GERMYRTGDVARWTADGRLVFAGRSDDQIKIRGF
Orf14|M4      AGLARGYAGMPGLTAERFVADPFSS-GGRLYRTGDLVRWTDDGVLVFAGRADDQVKIRGY
Orf14|M5      DQLARGYHGRAGLTAERFVADPFG-RGERMYRTGDRVRWTRGGSLEFLGRVDDQVKIRGF
Orf14|M6      IGLAHGYAGRPAPTAERFVACPFAP-GERMYRTGDLVRWTADGRLLFAGRADNQVKIRGF
Orf14|M7      AQLARGYLGRPGLTGERFVACPFGPGGERMYRTGDRVRWNADGDLVFAGRADDQVKIRGF
Orf14|M8      SGLARGYAGMPGLTAERFVADPFSV-GGRLYRTGDLVRWTDDGVLHFAGRADDQVKIRGY
Orf17         AGVAIGYINRPELTAERFVTG---PDGRRWYRSGDRGRLLPDGTLEHLGRLDDQVKLRGF
GrsA_Adomain  EGLARGYWKRPELTSQKFVDNPFVP-GEKLYKTGDQARWLSDGNIEYLGRIDNQVKIRGH
              :*  .*   .  *.  **          *  : *::**   *      *  :  .  ** *:* ::**.

A8                      A9
Orf12         RVEPDEVRLVVAGHPRVAGAAVVARPDAVGE---RQLVAYVVAAGEPAG---LAESVRAH
Orf13|M1      RVEPGEVEAVLAQHPDVSQVAVVVREDTPGD---KRLVAYVVGG----------DIEAY
Orf13|M2      RIEPGEVEAVLAAGPGVSQAAVIVREDVPGD---KRLVAYVVGG----D----VEALRSY
Orf13|M3      RIEPGEVQAVVAAHPEIAAAAVVVREDVPGD---PRLTAYVVPAGPRTAPAAVAETVRRF
Orf13|M4      RVEPGEVEAVLAQHPDVSQVAVVVREDTPGD---KRLVAYVVGG-----------DVEAY
Orf13|M5      RVEPGEVEAVLAQHPDVSQVAVVVREDTPGD---KRLVAYVVGG-----------DVEAY
Orf13|M7      RVEPGEVAAVLGEHPAVARAAVVARTDGPQG---ARLVAYLVAADP--AGPDLAAAVRAY
Orf14|M1      RVEPGEVEAVLAAGPGVNQVAVIVREDVPGD---KRLVAYVVGG----D----VETLRSY
Orf14|M2      RVEPGEVEAVLAALPGVSQAAVIVREDVPGD---KRLVAYLVAPE------TVEAARAH
Orf14|M3      RIEPGEVEAVLAAGPGVSQAAVIVREDVPGD---KRLVAYVVGG--------DAETLRSH
Orf14|M4      RVEPGEVEAVLAAHPDVAQVAVVVREDTPGD---KRLVAYVVGG-----------DVEAY
Orf14|M5      RIELGEVEAALAAFGPVARAAAAVREDVPGD---RRLVGYVVPAAGEPE--PDPAAVRAH
Orf14|M6      RVEPGELETVLSGHPAVARAAVLAREDTPGA---KRLVAYVVPARPDEDGDALAESVRAY
Orf14|M7      RIEPGEVQAVVARQAGVARAVVLARSDSPGD---ARLVAYVVPADRDADRRALAATVRSD
Orf14|M8      RVEPGEVEAVLAQHPDVSQVAVVVREDAPGD---KRLVAYVVGG-----------DVEAY
Orf17         RIELDEIRGVLTECAGVAAAAVVIRRSTPDDPATARLDAYVVAEAG------ATPPVAEH
GrsA_Adomain  RVELEEVESILLKHMYISETAVSVHKDHQEQ---PYLCAYFVSEKHIP-----LEQLRQF
              *:*  *:    :        :     ... : .       * .*.*
```

Figure 3A cont'd (2)

```
                                                    A10
Orf12          VAERLPEYMVPAAVVTLDEIPLTVNGKVDRAALPEP---------------
Orf13|M1       GQERLPGYMVPSAFVHLDALPLTSNQKVDRAALPAPSMESG-----------
Orf13|M2       AQQRLPGYMVPSAFVELDRLPLTVNGKLDRRALPVPDLARG-----------
Orf13|M3       AADRLPAYMLPSAVVVLDALPLTDHGKLDRRALPAPQHT-------------
Orf13|M4       AQERLPGYLVPSAFVHLDALPLTSNQKVDRAALPAPSVESGV----------
Orf13|M5       AQERLPGYMVPSAFVQLDALPLTSNQKVDRAALPAPSMESG-----------
Orf13|M7       AAATLPAHLLPAAFVPLDRLPLTINGKLDRAALPEPETGAG-----------
Orf14|M1       AQQRLPGYLVPSAIVALAELPLTHSAKVDRRALPVPD---------------
Orf14|M2       AEQRLPSYLVPSAFVQLDALPLTGNQKVDRAALPAP----------------
Orf14|M3       AQQRLPGYLVPSAFVELDRLPLTVNGKLDRRALPVPD---------------
Orf14|M4       AQERLPGYLVPSAFVHLDALPLTSNQKVDRAALPAPSVESG-----------
Orf14|M5       VAAQLPAYMVPSAVVVLPDLPLTANGKLDRKALPAPDYGAASAGRAPADE--
Orf14|M6       AARQVPDYLMPAATVVLPDLPLTSSGKVDRAALPAPDVPGG-----------
Orf14|M7       TARELPAYLVPAAVVVLDELPVTANGKLDRRALPAPGL--------------
Orf14|M8       AQERLPGYMVPSAFVHLEALPLTANQKVDRAALPAPE---------------
Orf17          AARMLPAYMCPATFTFLDALPMTPNGKVDKAALPEP----------------
GrsA_Adomain   SSEELPTYMIPSYFIQLDKMPLTSNGKIDRKQLPEPDLTFGMRVDYEAPRNE
                :*  ::  *:        *   :*:*   *:*:   ** *
```

Figure 3A cont'd (3)

| | 235 | 236 | 239 | 278 | 299 | 301 | 322 | 330 | |
|---|---|---|---|---|---|---|---|---|---|
| Orf13\|M1\|HPG | D | A | Y | H | L | G | L | L | |
| Orf13\|M4\|HPG | D | A | Y | H | L | G | L | L | |
| Orf13\|M5\|HPG | D | A | Y | H | L | G | L | L | |
| Orf14\|M2\|HPG | D | A | F | H | L | G | L | L | HPG |
| Orf14\|M4\|HPG | D | A | Y | H | L | G | L | L | |
| Orf14\|M8\|HPG | D | A | Y | H | L | G | L | L | |
| emb\|CAB38518.1\|Cda1\|M6\|HPG | D | V | Y | H | L | G | L | L | |
| emb\|CAA11795.1\|CepB\|M2\|HPG | D | A | V | H | L | G | L | L | |
| emb\|CAA11795.1\|CepB\|M1\|HPG | D | I | F | H | L | G | L | L | |
| | | | | | | | | | |
| Orf13\|M3\|Thr | D | F | W | S | V | G | M | V | |
| Orf14\|M3\|Thr | D | F | W | S | V | G | M | V | |
| Orf17\|M1\|Thr | D | F | W | N | I | G | M | V | Thr |
| gb\|AAC38442.1\|AcmB\|M1\|Thr | D | F | W | N | V | G | M | V | |
| emb\|CAB38518.1\|Cda1\|M2\|Thr | D | F | W | N | V | G | M | V | |
| emb\|CAA09819.1\|FenD\|M2\|Thr | D | F | W | N | I | G | M | V | |
| | | | | | | | | | |
| Orf13\|M2\|Orn | D | M | D | T | D | G | S | V | |
| Orf14\|M1\|Orn | D | M | D | T | D | G | S | V | |
| gb\|AAC06347.1\|BacB\|M1\|Lys | D | A | E | S | I | G | S | V | Orn |
| gb\|AAC82550.1\|FxbC\|M1\|5hOrn | D | M | E | N | L | G | L | I | |
| gb\|AAC82550.1\|FxbC\|M3\|5hOrn | D | M | E | N | L | G | L | I | |
| | | | | | | | | | |
| Orf12\|M1\|Asn | D | L | T | K | V | G | E | V | |
| emb\|CAB38517.1\|Cda2\|M3\|Asn | D | L | T | K | V | G | E | V | Asn |
| gb\|AAC06348.1\|BacC\|M5\|Asn | D | L | T | K | I | G | E | V | |
| gb\|AAC45930.1\|TycC\|M1\|Asn | D | L | T | K | I | G | E | V | |
| | | | | | | | | | |
| Orf13\|M7\|Phe | D | A | W | T | V | A | A | V | |
| emb\|CAA33603.1\|GrsA\|M1\|Phe | D | A | W | T | I | A | A | I | Phe |
| gb\|AAC45929.1\|TycB\|M3\|Phe | D | A | W | T | I | A | G | V | |
| gb\|AAC06348.1\|BacC\|M2\|Phe | D | A | F | T | V | A | A | V | |
| | | | | | | | | | |
| Orf14\|M5\|Gly | D | I | L | Q | L | G | L | V | |
| emb\|CAB38517.1\|Cda2\|M2\|Gly | D | I | L | Q | L | G | L | I | Gly |
| emb\|CAB15186.1\|DhbF\|M1\|Gly | D | I | L | Q | L | G | L | I | |
| gb\|AAF17280.1\|NosC\|M2\|Gly | D | I | L | Q | L | G | L | I | |
| | | | | | | | | | |
| Orf14\|M6\|Leu | D | A | F | F | Y | G | A | T | |
| emb\|CAA82227.1\|CssA\|M2\|Leu | D | A | W | L | Y | G | A | V | Leu |
| emb\|CAA82227.1\|CssA\|M3\|Leu | D | A | W | L | Y | G | A | V | |
| gb\|AAC06346.1\|BacA\|M3\|Leu | D | A | W | F | L | G | N | V | |
| | | | | | | | | | |
| Orf14\|M7\|(Ala) | D | V | F | S | V | A | I | V | |
| gb\|AAC06348.1\|BacC\|M2\|Phe | D | A | F | T | V | A | A | V | (Ala) |
| gb\|AAC83656.1\|PchE\|M1\|Cys | D | L | F | N | L | S | L | I | |
| emb\|CAA82227.1\|CssA\|M11\|Ala | D | V | F | I | Y | A | A | I | |

Figure 3B

```
Orf26                        ------------------------------MVIDAATQPTVPDAFRAQ
gb|AAB52538.1|acyl_CoA_L|Mb   ------------------------------MAMSVRSLPAALRAC
emb|CAB05426.1|fadD29|Mt      MKTNSSFHAAGEVATQPAWGTGEQAAQPLNGSTSRFAMSESSLADLLQKA
gb|AAG02359.1|blmVI|M1|Sv     ------------------------------MSRPAGIVDIARRH
gb|AAC44128.1|safB|M1|Mx      --------------------MACRPDSLHASAVTSRRRMRHTLVELLQER
gb|AAF08795.1|MycA|M1|Bs      ------------------------------MYTSQFQTLVDVIRNR
                                                                  :    :

Orf26                        AIARPGEPALVVLPG--DPDAEPVTLTYAELDRRAAARAAWLAARFPAGE
gb|AAB52538.1|acyl_CoA_L|Mb   ACLQPHDPAFTFMDYEQDWDGVAITLTWSQLYRRTLNVARELSRCGSTGD
emb|CAB05426.1|fadD29|Mt      ASQYPNRAAYKFIDYDTDPAGFTETVTWWQVHRRAMIVAEELWIYASSGD
gb|AAG02359.1|blmVI|M1|Sv     AERTPARPAYAFLP---DGETESVRFSFADIDRRARAVAAVLQDRGLAGE
gb|AAC44128.1|safB|M1|Mx      ALSEPRHEAFTFLG---EAGVPAVRVDYSSMDVLARAIAARLQADGRVGE
gb|AAF08795.1|MycA|M1|Bs      SNIS--DRGIRFIE----SDKIETFVSYRQLFDEAQGFLGYLQHIGIQPK
                               :    .  . .:          . : .:     :      *     .

AL1
Orf26                        R-ILIALPTGAE FVELYLACLYAGLVAVPA PPPGGS--SGASERTVGIAA
gb|AAB52538.1|acyl_CoA_L|Mb   R-VVISAPQGLE YVVAFLGALQAGRIAVPL SVPQGG---VTDERSDSVLS
emb|CAB05426.1|fadD29|Mt      R-VAILAPQGLE YIIAFMGVLQAGLIAVPL PVPQFG---IHDERISSALR
gb|AAG02359.1|blmVI|M1|Sv     R-VLVAYPSGPE YVQAFLGCLYAGVVAVPC DEPR-S---GPSAERLAGIRA
gb|AAC44128.1|safB|M1|Mx      R-ALLLYAPGPE YVAAFFGCLYAGVVAVPV YPPDTARLERSLLRLRTVAR
gb|AAF08795.1|MycA|M1|Bs      QEIVFQIQENKS FVVAFWACLLGGMIPVPV SIGEDNDHKLKVWRIWNILN
                               :  .    . .::  :  . * .*  :.**                *

Orf26                        DCSPALAVVN----ADDAAPLTA------VLRERGLSGLPVGALPPLAAE
gb|AAB52538.1|acyl_CoA_L|Mb   DSSPVAILTTS---SAVDDVVQ---HVARRPGESPPSIIEVDLLDLDAPN
emb|CAB05426.1|fadD29|Mt      DSAPSIILTTS---SVIDEVTTYAPHACAAQGQSAPIVVAVDALDLSSSR
gb|AAG02359.1|blmVI|M1|Sv     DARPALALTA----GAPEAGLA------------GLATLDVAGVPDSAAG
gb|AAC44128.1|safB|M1|Mx      DSRASVVLTTSFLQGLAGAMFEL------APELGELSWVATDGIALEEAG
gb|AAF08795.1|MycA|M1|Bs      NPFLLASETVLDKMKKFAADHD-------LQDFHHQLIEKSDIIQDRIYD
                              :             .                                :

AL2
Orf26                        AIRPPRGPRPDSL AVLQYSSGSTGSPKGVML SHRAVLAN LRAFDRSSGHN
gb|AAB52538.1|acyl_CoA_L|Mb   GYTFKEDE-YPST AYLQYTSGSTRTPAGVVMSHQNVRVN PEQLMSGYFAD
emb|CAB05426.1|fadD29|Mt      ALDPTRFE-RPST AYLQYTSGSTRAPAGVVLSHKNVITN CVQLMSDYIGD
gb|AAG02359.1|blmVI|M1|Sv     AWTDPVAG-PDAL AFLQYTSGSTRRPRGVMVGHGNLLAN ERCIAAACGHD
gb|AAC44128.1|safB|M1|Mx      AWKPPGLS-GDSV AFLQYTSGSTADPKGVVLTHRNLMHN LSVIHERFQLN
gb|AAF08795.1|MycA|M1|Bs      HPASQYEPEADEL AFIQFSSGSTGDPKGVMLTHHNLIHN TCAIRNALAID
                                            * :*:***  *  ** :: *     :          :

AL3
Orf26                        SDDVF------ GSWLPLHHDMGLF AMLTAGLLNGAGVVLMSPTAFVRRPA
gb|AAB52538.1|acyl_CoA_L|Mb   TDGIPPPNSAL VSWLPFYHDMGLV TGICAPILGGYPAVLTSPVSFLQRPA
emb|CAB05426.1|fadD29|Mt      SEKVP---STP VSWLPFYHDMGLM GIILPMINQDTAVLMSPMAFLQRPA
gb|AAG02359.1|blmVI|M1|Sv     RDSTF------ VGWAPFFHDMGLV ANLLQPLYLGSLSVLMPPMAFLQRPA
gb|AAC44128.1|safB|M1|Mx      RGSRG------ VIWLPPYHDMGLI GGVLTPIFGGLPVDLMSPLSFLQEPL
gb|AAF08795.1|MycA|M1|Bs      LKDTL------ LSWMPLTHDMGLI ACHLVPALAGINQNLMPTELFIRRPI
                                         *  * *****.           *  ..  *::.*
```

Figure 3C

```
                                            AL4
Orf26                       DWLRMMDRYRVTI SAAPNFAYDL CVRAVRDEQIAGLDLSRIRTLYNGSEP
gb|AAB52538.1|acyl_CoA_L|Mb RWMHLMASDFHAF SAAPNFAFEL AARRTTDDDMAGRDLGNILTILSGSER
emb|CAB05426.1|fadD29|Mt    RWMQLLAKHRAQI SSAPNFGFEL AVRRTSDDDMAGLDLGHVRTIVTGAER
gb|AAG02359.1|blmVI|M1|Sv   RWLRAVSRYRAHT SGGPNFAYDL CVDRVGEDERAGLDLSGWKVAYNGAEP
gb|AAC44128.1|safB|M1|Mx    RWLKTLSERRGTC SGGPNFAYEL CVRKISDEQKAGLDLSSWELAFCGAEP
gb|AAF08795.1|MycA|M1|Bs    LWMKKAHEHKASI LSSPNFGYNY FLKFLKDNKSYDWDLSHIRVIANGAEP
                             *::           ..***.::   ::.  .**.      *:*

AL5
Orf26                       VNPATVRAFTERFAPFGLHTHAVN PCYGMAEFTA YVSTKVFEAPAVFLPA
gb|AAB52538.1|acyl_CoA_L|Mb VQAATIKRFADRFARFNLQERVIR PSYGLAEATV YVATSKPGQPPETVDF
emb|CAB05426.1|fadD29|Mt    VNVATLRRFTERFAPFNLSETAIR PSYGLAEATV YVATAGPGRAPKSVCF
gb|AAG02359.1|blmVI|M1|Sv   VRADTLRRFTDRFAPHGFTPGAHF PTYGLAEATI LVATGPKGVPPRTLTA
gb|AAC44128.1|safB|M1|Mx    IRPDTLEAFSKAFEPCGFRREAFY PCYGLAEGTL IVTGVSKGRAARVEHF
gb|AAF08795.1|MycA|M1|Bs    ILPELCDEFLTRCAAFNMKRSAIL NVYGLAEASV GATFSNIGERFVPVYL
                             :    *        .:  .      **:**    .:

Orf26                       DPRALEDAASPALRPADP-AAAREIP---GVGRV-PDFEVLIVDPDGLRP
gb|AAB52538.1|acyl_CoA_L|Mb DTESLSAGH---AKPCAGGG-ATSLIS----YMLPRSPIVRIVDSDTCIE
emb|CAB05426.1|fadD29|Mt    DYQQLSVGQ---AKRAENGSEGANLVS----YGAPRASTVRIVDPETRME
gb|AAG02359.1|blmVI|M1|Sv   DRAALRAGR---LRPAGPGEAGLELV---GNGTAGLDTTLRIVDPATARE
gb|AAC44128.1|safB|M1|Mx    QREALEAHR--AVAASSPGEAARDTVRHVSCGTVVPDEQILVVDPETRTA
gb|AAF08795.1|MycA|M1|Bs    HRDHLNLGE----RAVEVSKEDQNCASFVEVGKPIDYCQIRICN-EANEG
                             . *           .                     : : :

AL6
Orf26                       LPEGRVGEIWLRGPGAGAGYWGRTELNPGIFDARPAGDG---QDGG WVRT
gb|AAB52538.1|acyl_CoA_L|Mb CPDGTVGEIWVHGDNVGNGYWQKPDESERTFGGKIVTPSPGTPEG WLRT
emb|CAB05426.1|fadD29|Mt    NPAGTVGEIWVQGDNVGLGYWRNPQQTEATFRARLVTPSPGTSEG WLRT
gb|AAG02359.1|blmVI|M1|Sv   CPPGEVGEVWVRGPGVARGYFGRPRESAPLLAARLPGG-----EG YLRT
gb|AAC44128.1|safB|M1|Mx    LPPGHIGEIWVRGPSVAQGYWLRPEETARTFQARLAGG----TEAF WLRT
gb|AAF08795.1|MycA|M1|Bs    LEDGFIGHIQIKGENVTQGYYNNPESTNRALTP----------DG WVKT
                                * :*.:  ::*  ..  **:  ..    :              :::*

AL6             AL7
Orf26                       GDLG ALTGGELFLT GRLKELLIVHGRNLAPHDLE REARAAHDAVDHQIGA
gb|AAB52538.1|acyl_CoA_L|Mb GDSG FVTDGKMFII GRIKDLLIVYGRNHSPDDIE ETIQEITRGR----CA
emb|CAB05426.1|fadD29|Mt    GDLG VIFEGELFIT GRIKELLVVDGANHYPEDIE ATIQEITGGR----VV
gb|AAG02359.1|blmVI|M1|Sv   GDLG ALHDGELFLT GRHKDLIVIRGQNHHPHDLE RTAEQAHPALRPTCAA
gb|AAC44128.1|safB|M1|Mx    GDLG FLHDGELFVS GRRKDLLVIRGRNYYPQDLE LTVERSHPALRPGCAA
gb|AAF08795.1|MycA|M1|Bs    GDLG FIRKGNLVVT GREKDIIFVNGKNVYPHDI  RVAIELEDIDLG-RVA
                            ** *   :  *::.:  ** *:::.:  *  *.*:*

Orf26                       AFGVPAP--DERIVLVQEVHPRTPLDELPR-----VASAVSRRLTVSFGV
gb|AAB52538.1|acyl_CoA_L|Mb AISVPGDRRTEKLVAIIELKKRGDSDQDAMARLGAIKREVTSALSSSHGL
emb|CAB05426.1|fadD29|Mt    AIAVPDDR-TEKLVTIIELMKRGRTDEEEKNRLRTVKREVASAISRSHRL
gb|AAG02359.1|blmVI|M1|Sv   AFAVPGDG-AERLVLVCELTSYRAVDPAA------VAEAVRAALAARHGV
gb|AAC44128.1|safB|M1|Mx    VFSVSVGA-SEEVVVVQEVDRRYPGGDWPD-----VIAAIRRDISEQHAL
gb|AAF08795.1|MycA|M1|Bs    ACGVYDQETRSREIVLFAVYKKSADRFAP------LVKDIKKHLYQRGGW
                             . *     ..  :: :                    :  :

Figure 3C cont'd
```

```
                                                     AL8
Orf26                       PVRNVLLVRRGTVRRTTSGKIRRTAVRERFLAGGITALHAELEPALRPVQ
gb|AAB52538.1|acyl_CoA_L|Mb  SVADLVLVAPGSIPITTSGKVRRGACVEQYRQDQFARLDA----------
emb|CAB05426.1|fadD29|Mt     RVADVVMVAPGSIPVTTSGKVRRSASVERYLHHEFSRLDAMA--------
gb|AAG02359.1|blmVI|M1|Sv    APHTLVVLRRGGIPKTTSGKVRRGHCRTAYLDGTLPVHTAVRLP------
gb|AAC44128.1|safB|M1|Mx     RVHAVVLIKSGSLLKTSSGKVQRGATREAYLEGQLDTVSADAAQEPVGE-
gb|AAF08795.1|MycA|M1|Bs     SIKEILPIR--KLPKTTSGKVKRYELAEQYESGKFALESTKIKEFLEG--
                             :: :      :  :.***::*        :     :       :

Orf26                       AGAGR
gb|AAB52538.1|acyl_CoA_L|Mb  -----
emb|CAB05426.1|fadD29|Mt     -----
gb|AAG02359.1|blmVI|M1|Sv    -----
gb|AAC44128.1|safB|M1|Mx     -----
gb|AAF08795.1|MycA|M1|Bs     -----
```

Figure 3C cont'd (2)

```
pfam00753    LVEDDDGAALIDTGFTAPAAKALLRLLKDG-- GKKIDAIILTHAHADHIGGVPELLER
1SML         LVQTPDGAVLLDGGMPQMASHLLDNMKARGVTPRDLRLILLSHAHADHAGPVAELKRR
ORF 10       VMQTEQAAVVTDP-FISTDNRHGDRYTLDDL- PDHIDLVLITHGHQDHIVLETLLQLR
             :::  :.*.: *      :        :  .   .:  ::::*.***    . * *
```

Figure 5A

```
pfam00067    DPE--RFLDEN- GKFKKSYAFLPEGAGPRNCLGERLARMELFLFLATLLQRFELE
ORF 10       DPVLYRYIRDHVGQVD----- MAFL-G-MECDGAPLNWLYKGLLTKPVNKKMSAS
             **    *:: :: *:..      :.* * :** *  :  *:  .: :::. .
```

Figure 5B

SEQUENCE LISTING

```
<160> NUMBER OF SEQ ID NOS: 34

<210> SEQ ID NO 1
<211> LENGTH: 88421
<212> TYPE: DNA
<213> ORGANISM: Actinoplanes sp.
<220> FEATURE:
<221> NAME/KEY: misc_feature
<222> LOCATION: (2077)..(3078)
<223> OTHER INFORMATION: ORF 1; positive strandedness
<221> NAME/KEY: misc_feature
<222> LOCATION: (3118)..(4032)
<223> OTHER INFORMATION: ORF 2; positive strandedness
<221> NAME/KEY: misc_feature
<222> LOCATION: (4038)..(5048)
<223> OTHER INFORMATION: ORF 3; positive strandedness
<221> NAME/KEY: misc_feature
<222> LOCATION: (4038)..(5048)
<223> OTHER INFORMATION: ORF 3; positive strandedness
<221> NAME/KEY: misc_feature
<222> LOCATION: (6665)..(5814)
<223> OTHER INFORMATION: ORF 4; negative strandedness
<221> NAME/KEY: misc_feature
<222> LOCATION: (7703)..(6693)
<223> OTHER INFORMATION: ORF 5; negative strandedness
<221> NAME/KEY: misc_feature
<222> LOCATION: (9464)..(8130)
<223> OTHER INFORMATION: ORF 6; negative strandedness
<221> NAME/KEY: misc_feature
<222> LOCATION: (9691)..(10761)
<223> OTHER INFORMATION: ORF 7; positive strandedness
<221> NAME/KEY: misc_feature
<222> LOCATION: (12751)..(10829)
<223> OTHER INFORMATION: ORF 8; negative strandedness
<221> NAME/KEY: misc_feature
<222> LOCATION: (13617)..(12802)
<223> OTHER INFORMATION: ORF 9; negative strandedness
<221> NAME/KEY: misc_feature
<222> LOCATION: (15203)..(13614)
<223> OTHER INFORMATION: ORF 10; negative strandedness
<221> NAME/KEY: misc_feature
<222> LOCATION: (15591)..(15863)
<223> OTHER INFORMATION: ORF 11; positive strandedness
<221> NAME/KEY: misc_feature
<222> LOCATION: (15880)..(19035)
<223> OTHER INFORMATION: ORF 12; positive strandedness
<221> NAME/KEY: misc_feature
<222> LOCATION: (19032)..(39713)
<223> OTHER INFORMATION: ORF 13; positive strandedness
<221> NAME/KEY: misc_feature
<222> LOCATION: (39713)..(65800)
<223> OTHER INFORMATION: ORF 14; positive strandedness
<221> NAME/KEY: misc_feature
<222> LOCATION: (65826)..(66530)
<223> OTHER INFORMATION: ORF 15; positive strandedness
<221> NAME/KEY: misc_feature
<222> LOCATION: (66546)..(67370)
<223> OTHER INFORMATION: ORF 16; positive strandedness
<221> NAME/KEY: misc_feature
<222> LOCATION: (67384)..(70059)
<223> OTHER INFORMATION: ORF 17; positive strandedness
<221> NAME/KEY: misc_feature
<222> LOCATION: (70099)..(70662)
<223> OTHER INFORMATION: ORF 18; positive strandedness
<221> NAME/KEY: misc_feature
<222> LOCATION: (70659)..(71906)
<223> OTHER INFORMATION: ORF 19; positive strandedness
```

```
<221> NAME/KEY: misc_feature
<222> LOCATION: (73439)..(71964)
<223> OTHER INFORMATION: ORF 20; negative strandedness
<221> NAME/KEY: misc_feature
<222> LOCATION: (74216)..(73563)
<223> OTHER INFORMATION: ORF 21; negative strandedness
<221> NAME/KEY: misc_feature
<222> LOCATION: (75424)..(74213)
<223> OTHER INFORMATION: ORF 22; negative strandedness
<221> NAME/KEY: misc_feature
<222> LOCATION: (75535)..(76464)
<223> OTHER INFORMATION: ORF 23; positive strandedness
<221> NAME/KEY: misc_feature
<222> LOCATION: (78110)..(76449)
<223> OTHER INFORMATION: ORF 24; negative strandedness
<221> NAME/KEY: misc_feature
<222> LOCATION: (79864)..(78107)
<223> OTHER INFORMATION: ORF 25; negative strandedness
<221> NAME/KEY: misc_feature
<222> LOCATION: (81624)..(79861)
<223> OTHER INFORMATION: ORF 26; negative strandedness
<221> NAME/KEY: misc_feature
<222> LOCATION: (81909)..(81682)
<223> OTHER INFORMATION: ORF 27; negative strandedness
<221> NAME/KEY: misc_feature
<222> LOCATION: (82346)..(82062)
<223> OTHER INFORMATION: ORF 28; negative strandedness
<221> NAME/KEY: misc_feature
<222> LOCATION: (82587)..(84446)
<223> OTHER INFORMATION: ORF 29; positive strandedness
<221> NAME/KEY: misc_feature
<222> LOCATION: (84481)..(85548)
<223> OTHER INFORMATION: ORF 30; positive strandedness
<221> NAME/KEY: misc_feature
<222> LOCATION: (85556)..(86845)
<223> OTHER INFORMATION: ORF 31; positive strandedness
<221> NAME/KEY: misc_feature
<222> LOCATION: (87372)..(86803)
<223> OTHER INFORMATION: ORF 32; positive strandedness
<221> NAME/KEY: misc_feature
<222> LOCATION: (87494)..(88420)
<223> OTHER INFORMATION: ORF 33; positive strandedness; N-terminus only

<400> SEQUENCE: 1
ggcgaactgc ttgtcctcgc tcggcggcag gctgttccac ctgtccttct cggccatcgg      60
cacgatcacc tcgttgaaga gggggttgcc gagccgggag acctgcacct gcgggccgac     120
ggtcacatcg ccggaggagg agccgtcgcg gacctgaacc tgacggcgac tggccgaggt     180
ccacaccccg atgaccgcgc ccgcgtcacg tccgcgcacc cgcttcttgc cgtcacggcg     240
caccatgtgt acgggatct gcagcgcgat gctgtgcacg ttggtcttgt cggtggcgtt     300
gaccgccttg ccgcgtagt tgaacaggtt ctgcccgacc aggtgcttgt cctggaacgg     360
gcgcagcgtg ccgaggtcga agatggcgcc cagatcgacg aagaaggcgt cggcgcgctg     420
gccggcgaag accttctcgc cggtcttcag cttgtgcacg cgtcggcgg cgaggccgtc      480 gtagtcggcg atcgacacct tgccgacgtt gcacggcggg cagggcagct tgctcgccag     540
caccgtgctc ttgccgtgct tgtcgacctt cgtcaccgag tagaactggc ggcgattcca     600
gttctcgctg tcgagcgact cgatcgggcc ggtgttgtag aggaacgtct tgttgttgcg     660
cagctcggtg cggaaccgga actggtaggt gatctcggcg cgggcgtcac cgtccgagtc     720
gatgtggatc tcgtagacga cgtcgtcgcc gaactcgaag aagttcgggc cgctcgccgg     780
cagctgcaac ggcacgtagt tggcgatcag ggtgaccgtg tcgggctcgt cggggctgac     840
gaaggcgtac aggtcggagc tgtcggccac cgggtccttg ctgatctcgg gtgcttcgcg     900
gtgtgaagac atgtcatgcc ctcccggcgg ccttgatcag gctcgcgacg agcttcttgt     960
cggtgatcgt cttgagctgc tcgcccgaga agacgtcgat cgtgcccttc ttggcgtccc    1020
```

```
ggatggagac gacgatcggg gagccgtcac cggtgggctc gttctcgccg gcgaggctca   1080
gcccggcgac cgaggcggcc gatacgccga cgccggtcgc ggcgagggcg aggacccggc   1140
gacgggaaag ccacgacgt gctgccgggg cgcgatagcg agtgcgactc atgctcgacc    1200
tttcgtcttt cttacggtcg gtggtgcgag gactggaacg ggcgttgcgt gtcgacgccc   1260
gtcagtacgt gatccaccgg cctgcggttc aaagacgaat tggagcgctc ccaacgggac   1320
gactcgagcc gcgccgggc gggcacggca ccggccgtgc ccgccccgcg tgcgcggtca    1380
ccgccagttg gcgtgatccg cggcggcggc gcggtcgcgc tcgtcggcgg cccggcggcc   1440
cttgtcgacc tcgcgcatcg accagccgat cgcgacggcg ccaggtagg cgagggtgcc    1500 gagcaccgcc acggcccgga agccgccggt cacccagcag gccaggaaca cggccaggcc   1560
accggcgcca tgcccgccg cccacgagga cggcagccgg cggatcgccg agccgaccag    1620
cacggccagg cccagcgacg cgatcgggct cggctcctgc ggcaggtcgg cgaagtggga   1680
gacgagcacg gcgatcaggc cgaggcccac gcccgccgcc gcggtcatcg ccgggttgat   1740
ccggcgggcc agggccaggc cggtcatcag cacggcgacg atcgtgtcga agaccgcgta   1800
accggcgccc cagctgtcgg agagcatgta gacggtgaac gcgatgccgg ccagcgcgat   1860
cagcccgaac accacgtcga aggcgacacc ggcccgcggg gccggccttg ctgaagtagt   1920
catgccgccc acgctaggaa atcggcccgt ccggcgaacc ggtcgaaagt acggtcggcg   1980
ccgcggcgaa ccctgctttg gaccgatgct cgcgacgggg tgcttccccg agggtgatgg   2040
catgcgtttc taccacgagg tgcgccgatg atctggatga gctggcgcca gttccgctgg   2100
caggccctgg ccggtgccgt cgccctggtg ccgttggtgg cctacttgat cgtcacgagc   2160
ctggacatcc ggcgcgccca cgaccgctat caggcgcagt gcgcgtccat cggcaactgc   2220
gccgaggcga tgctccagtt ccagaacgac ttccgcaccc gcctgctgct gctcgccatc   2280
ctgctggccg cgatccccgg catcctcggg gtgttctggg gcgcgccgct ggtggcccgc   2340
gagctcgaga ccggcacgca ccgcctggtc tggaaccaga gcgtcacccg cgccggtgg    2400 ctggcggtca aggtgctgtt cgtcggtgtc gccgcgatgg ccgtggccac gctcgtcagc   2460
acgctgctga cctgggcgag cagcccggtc gacgcggtgt cgcaggaccg gttcggcgcg   2520
ctggtgttcg acgcccgcaa catcgtgccg gtcgcgtacg ccgccttcgc cctcgtcctc   2580
ggcacggtga tcggcctgct cgtgcgccgc accatcccgg ccatggcgct caccatgctc   2640
gtcttcgccg tcgtgcagtt caccgtgccg gcgctggccc ggccgcacct gatggcgccg   2700
gagacccaga cccggcagat gacgttgcag gagttcggcg aggtgcgcgg cttcggcgac   2760
gagcccacgg tcaacgggct gagcatccgg ggcgcgtggg tgaccagcac cagcccgctg   2820
ctcaccgccg acgggacccg gctcgacaag gccacgtacc gcaaatgcgt gaccgacccc   2880
ccggccgtct cgggcggagc tcccggcgtc ggcggcaccg tcgcctgcct ggccgacctc   2940
gatctgcacg tcgaggtggc ctaccagccc aacgaccggt actggacctt ccagtggatc   3000
gagtcggccc tctacctggc gctcggtgga ctgctcctcg ccgtgggcct gtggcgcatc   3060
cgccgccacg tcatctgatc gtcccccccgt ccgcacggat tcgaaggata gaaagacatg   3120
ccacacgagg attcctcgcc cgttctgcag gcggagggct tgaccaaacg ctacggtcgg   3180
cgcaccgccc tgcaggactg caacctgacc attccgcgcg gcgggtgat cggcctggtc    3240 ggcccgaacg gcgccggcaa gtcgacgctg ctccagctgg cctgcgggct gatcacgccg   3300
tcggagggct cgctgcgcgt gctcggcgag acgccggccg cgaacgccgg ccacctcgcc   3360
aaggtcggct tcgtcgcaca ggacaccccg gtctacagca acttcacggt cggcgaccac   3420
```

```
ctgaagatgg gtgccaagct caacccgacg tgggaccagg cgctcgccga gcgccgcgtc   3480
gcgcaggtcg ggctcaacca cggccagaag gcgggccggc tctccggcgg tcagcgcgcc   3540
cagctcgccc tgacgcttgc cgccgccaag cgcccggaac tgctgatgtt cgacgagccg   3600
gccgccgcgc tcgacccgct ggcccgcgac ggcttcctgc agaacctgct cgagttcgtc   3660
accgagctcg acgccagcgc gatcctgtcg tcgcacctgc tcggcgacgt cgagcgcgtc   3720
tgcaactacc tgatcgtgct ctgcgcctcc cgggtgcagg tcgccggcga cgttcccgac   3780
ctgctcaaca cgcactaccg catcgtcgcg ccccgcggcg agctggacca tccgccggcc   3840
ggcctcgagg tcatccgggc gcagcacgcc gaccggtaca ccaccgccgt cgtgcgcggc   3900
gacggcagcc ggccgagcac ctggacgatc gagcccatcc agctcgagga gctcgtgctg   3960
gcgtacatga cgcgggcgat gggcgtcacc ggcgagccgc tgatggccgc gtccggggag   4020
gtcgtccgtt gatctggatg agctggcggc agttccgcgg tcaggccgtc gtcggggtcg   4080
tcgtgctggc cctgctcgcc gcatacctgg tctacctcgg cgtcgacatc cgcggcgcct   4140
acgacgacta tcgggcgcag tgccccgcgg gcggcgactg cgccgggccc ctgggccagt   4200
tcagcctcga ctacgagaac acgttgctct atctggccgg cgtgctggcg ctggtgcccg   4260
gcctgctcgg catgttctgg ggcgcgcccc tgatcacccg ggagctggag aacggcaccc   4320
agcgcctggt gtggaaccag agcgtgaccc gccgccgatg gctgctgatc aagctactcg   4380
tcgtgggctt ggcctgcatg gtggtggccg gggtgccgag cctgctgctg acctgggccg   4440
ccgcgccggt cgacaatgtg gccgacaacc ggttcagcac ggtgatgttc ggagcccggt   4500
tcctgccgcc gatcgcctac gccgccttcg cgttcgtgct cggcacgctc atcggcctgc   4560
tggtccgccg gacggtgccg gcgatggcgc tcacgctcgt ggcgttcgtg atcttccagt   4620
tcctggtgcc gaacctggtg cgcccccacc tcatgccggc caagcacctg gtcaagccga   4680
tgacggtgag cgccatcaac gaggccaagt cgctgggcag catcaccggc gcgccggtgc   4740
tgaacggcct gtcgatctcg cagggctgga tcaccgacgt cagcgcgctc aagaccgccg   4800
acggccggtc gctggacgcg aagacgttcg acaactgcta catgaacgcg cccaagaccg   4860
gtgcgaccga gggcccgtac ggtgacgtcg cggtctgcct ggccaagctg gacctgcacg   4920
tcgacatcgc ctaccagccg tggaaccggt actgggcctt ccagttcctc gaatcggggt   4980
tctatgtgct gctcagcggc ctgctgatcg gcgccgcggt gtggcgcgtc cagcggcggc   5040
ccagctgaga tgagcgcgca cagcaccgtg accgagccgg gcgcactcgt ccgtggcacc   5100
cgggaagccg ggggcggcgg cgagcgtcgt gccgcggtgg ccgccctggt catcggcggg   5160
gcggcggtgc ggtaccgcac ggtgctggtg gcgctgggaa gcccgccgac cgacagcgac   5220
gaagcagttc tcgggctggt ctccctgcac atcgcgcagg gacgcgacgc accggtccat   5280
ctgtacggcc aggactacat gggcatgctc gaggcccacc tggccgcacc gctggtccgg   5340
gcgttcggcg ccggggtggt gccggtccgt gcgccgctgc tcgtcctgtt cgcgctgttc   5400
ctggtcgtca tgtaccagct cacccggaga ctgtggtcgc cgggcgtcgc ggtggcgacg   5460
gtgctggtgc tcggtctcgg cgccgaccgc gtgctgagcg ccgagttgac ggccggcggc   5520
gggtacccgg agatcgccgt tctcggcgcg ctcctgttcc tcctcgcggt gcggatcggc   5580
cgcggggagg tccgccgccc ggtgctgccc ctggccgaat tcgggcttgc gctgggcctc   5640
ggcgtgtcga tggtggccaa cctctgcccg ggcgaccgct gcggcactac gagtttctgg   5700
tggccgccga tctgtctcgc gctgctcgcg gtgacggccg ggccggcggt gcgtgcgctg   5760
```

```
cggcgcgccg ttccggagcc ggcggcgatc cggtcgcgcc cgccgacgcg cggtcagggg    5820
ctggcggcga tgcggtcgcg cccgtcgacg ccgcgctgga gcatgccggt gagcgcggcg    5880
agcgcctccg cgcggcccgg atgggcctcc agctcgcgca gcgccgagat ggtcgccgcc    5940
agctcggcgg acaggtcgtc gagcacgtcg gcgaccgcgc cggcgttggc ggccaggatc    6000
tccgtccaca gtgccgcgcg accgcccgcg atccgcgtgg tgtcccgcac gccctggccg    6060
gccaggccca gctgggccgg ggtgccgtcc agcatccgcg cggccagcag gccggccacc    6120
aggtgcggca cgtgcgagac gagggccacc gcccggtcgt gctcctcggc gctcatcagc    6180
accggcgtgg cgccgcaggc cgaaaccacg gccagggccc cgtcgacggc ggcggtgctg    6240
cttcgccggc cggggagag cacccagggc cgcccctcga cagcgagcc ccgggccgcg      6300 tgcggtccgg agcgttcgct gccggcgagg ggatgcccgc cgacgtggga ggaggcgtcg    6360
cagccgagca cctcgatctg ccgggagggc agcactttca cgctcgccgc atcggtgtgc    6420
acccgggccg ttccccgccg ctggaggtcg gccagcacgg gagcgacggc cgccggcggc    6480
accgcgatca cggcgacgtc cacccgggtg cgcggctcgc ccgcgatgcc cgcgccgagc    6540
gccgccgcgg cgcgcgcggc ggcgggatcg cgtccagca ggtgaacggt gatgtcacgt     6600
tgggtgagag cgaggccgac cgaggtcccg atcagcccgg tgccgacgac gaccgcgctg    6660
cgcacaaggc ctcccatcgc cgcattcgct gttcaggccg cgttcttctc gagtgtttcg    6720
gcgaattcca accactcttg tgaacaacgc cgggccacgt tcgccaggac gtacgtgcaa    6780
tgcgacggaa ccgcgtcgag catgtctttc cactcatcat cttgaaccgt gcgggcaaga    6840
acccatcgca aaagattgcg gccggattcg gtaaatcgca gcgacgggtc gttcttcaag    6900
ccttgaagta ttgaccgcac ggtcggctcg agcagccgaa tcgtgttttc cttgtcgaag    6960
gaaatgtcgt cgcggtgacc gcccgtgcgg cgggggccgg gcagcgggtc ctcgccgcgc    7020
tgcaggcgat tgcgcacgtc acgcgcggtc gagggcgata cgccggcgtt cttggcgatc    7080
tcccgcaggg aggcgtcggg ctgttgctga atgtagctga cggccttcag tcggccctcg    7140
gaattgtcca gcgggcgcac ccggccgtcc cggccgacgc gggtgcgcga gccctgcccg    7200
atgtcgccgg agagctcgag gcgccggcgt atgttgccca cggtgcgggc gctgagtccg    7260
ctggaggccg ctattgtgcg gtctgaccag gacggatgcg actcgatgat ccgttccgcg    7320
gcgcgcgtgc ggtccgctgt ggacagtggc aggccgtgcc cgatgttcgc cttgacgccg    7380
aggacgaatg cctcctgctc gctgccctcg aacatcgcgg ccttgatcag ctcgtcgccg    7440
cgcagccggg ccgcgcccag ccggtgcgcg ccgtcgatga cccgcatgct tgcgcggtgc    7500
acgatgatcg gcggcagttc ggcgtcgagg ctggccagca tctgggtgtg ccgcggatcc    7560
tcgccggcca gccggggtga atcgagcatt tccagtgaat ccacaggtag ccactcgacg    7620
cgcatcattg acgagtgtt catctgtgtt tcgtcgtgcc gatccggctc gtggcgcgct     7680
gacgcgatgt gcaatgactc cataccaacc cccgaatggc tggactccga tgaccgctgg    7740
acacgatgca ccgcaggtct caacgagatg ctttgacgac cgtcggccgg ctcggccgtc    7800
gtggccgagt gcgcttgtgc agcgggcttt caatgtccga cactaatcga ggcggcgctg    7860
gctcgccaag ctcgtaagag gttctctgac gcatttttaa gctgtcttca cggtgaagtt    7920
tatcgatccc acgtgggtc ggtgggcgtc gagcgggatc tgatcgccac gatgcgtcat     7980
cgtgtccgtg ccgttcgtac tggtcaaccg ggagatctcg ggggtgccac ggtggacgtg    8040
ccggccgggt ccgggccgcc ccggccgagg gcgccgggga cgggttcggc cctatttctg    8100
caagttgcag actgtgcgat tcgggtgggt cacggccgga gtgccgcgat ctcggtcgtg    8160
```

```
atgaagcccg ccagccgctt gacaccctcg tcgatctcct ccggggtgag gtagctgatc    8220
gacaggcgga tgccctgttc gccgccgccg gccgggtaga agtacgacat cggcgtccag    8280
atcaccccgt ggtcctcggc gcttcgggac agggcggcgt tgtcggcggt gaagggcacg    8340
ttcacggcga ggaagaagcc gccgctcggg cggttccagc gcacgcccgt gcgtgcgcgg    8400
aaggacgccg gaaggtgctc ctcgagccgg tcgaggtgc gccgcatcgc cgcgccgtag    8460
tgcgccgagc tctccgcact cgcctcggcc gcggtgccgc cggccgcgag cagcatcccg    8520
gccacgacgc cctggctcag cggcgaggtg ttcaccgtga ccatgctctt caccttcgcc    8580
agctcgtcgg cgagcaggcc ggcgccgccc gcggcgtccg acaccggctg gtcggcgatc    8640
gcgaagccca cgcgcgcgcc cggaaagagc gtcttggaga cgatccgag gtggacgacg    8700 tgccggcccg ggtcgagggc cttgagggag ggaagctgct gccccgggct gacgagccgg    8760
tacgggctgt cctcgatcac cagcaggccg agctcgccgg cgaggtcgag cagggcgtgg    8820
cgggcctcca gcggcatcgt ggcgcccgac gggttggtgt ggtcgggcac gacatagaag    8880
gcgcggggac gccggccccg gctcagctcc gcgtggaccg cgcgggccag gtcctcggga    8940
tggaagccgt cctcgcgctc ggcgacgggc accgggtcga tgtcgagcag ccgcgcggcg    9000
ccggtgatgc cgacgtagca cgggctcgcc acgaacagcg cgtcgcgctc gtcccggatc    9060
agcgcgcgca gcgccagcag catcgcctcc tgcgcgccga ccgtcacgac gatggactcc    9120
ggagccacgt cgatgccctc gtcgcgccgc agccactgcg cgatcacctc gcggatgcgg    9180
ccggccgccg ggccgtactg gaagacgcg tccctgatct ccgcgggcga gcggccctgg    9240
ccggcgaggt gctcgagata gccgcggatg ccgcggaaga tctgctcgac gtcgaagaac    9300
ccgtcgaacg ggcggccggg cgcgaacgag acggctcgcg gatagcgggc ggtcacctcg    9360
ttgaggaagt tcatggtgtc cagcagcggg tcggacaggc tctggtgcag gtcctcgcgc    9420
cgcaggacgc ggccggtgcc cggagcctcg cgcaggatgc tcatcatggt ctcctcggtc    9480
gtcgcgaagc cctgactgtg gcaccgcatt ccgcaccgat caatcgaagc cacggcggtg    9540
accgcacacc tgtgcaactg ccgcgaacgc acggttggac accgtcggtg agctgcgttg    9600
gtggacggtt cggccgacgt ccatagtggt ccgggggctc gctcggccgc ctcgccggcg    9660
cctccaggcc gccagcgaaa ggacgccgcc gtgaccgcca ccgccctcct gccctgacc     9720 ctcgcggact acgaacagct ggcccaagcg cgaatggagc cccggtgtg ggacttcatc     9780 gccggcggcg cggggagga gctgacgctg ccgcgaaca ccgccgcctt cgcaccgccg      9840
cggctgcggc cacgggtgct gaccggcgcg ggcgcgccgg acacgggcac gacgatcctc    9900
ggacggcggt gggcggcgcc gatcggcgtc gccccgctcg gctatcacac gctcgtcgac    9960
ccggcgggcg aggtcgccac cgccgcggcg gccggcgcgg ccgggctgcc gctcgtggtg    10020
agcacgttct ccgggcggac cgtggaggac atcgccgcgg ccaccaccgc gccgcgctgg    10080
ttgcaggtct attgcttccg cgaccgggcg gtcaccgccg cgctcgtcac gagggccgtc    10140
cgcgccggct tcgaggcgct ggtgctcacc gtcgacgcgc gcggctgggg ccgccgcctg    10200
cgggacatcc gcaacgactt ccgcctgccg cccggcgtgg cgccggcaaa cctcaccggc    10260
gacggcttcg cgtcgcccag cgggcacgcg ctcggcgcgt tcgacgccgc gatgactgg    10320 accgtcgttg cctggctgcg ggagctcagc gggctgccg tgctgctcaa gggcgtgctg    10380
accgccgacg gtgccggcg ggcgctcgac gcgggtgcgg acgggatcgt cgtctccaac    10440
cacggcggcc ggcagctcga cggcgtgccg gcgacgctcg acgtgctgcc cgaggtggtg    10500
```

```
gcggccgtgg ccgggcgctg cccggtcctg ctcgacggcg gcgtgcggcg cggccgcgac    10560
gtcctgctgt cgctggccct cggcgccgac gcggtcctgg taggccgccc ggtgctgtac    10620
ggcctcgcgg tcggcggcac ggccggcgtg cggcacgtgc tcgacatcct cgcggggag    10680
ctgaccgacg acatggccct ggcgggcgtg gcctcgcccg cggacgccgg cgcggacctg    10740
gcgggcccgg tcgcgccgta gaggcggtcc atacgactgc ggcggccggg aatacccggc    10800
cgccgcaacg tcgtcctcca gggacatctc aggacggcac ggccggctgg cgctcctcgg    10860
tgcgctggcc ggcgaactgg gtccggtaca gctcggcgta caggccaccg tgcgcgatca    10920
gctcgtcgtg ggtgccgcgc tcgacgacgc ggccgtcgtc gatgacgagg atctggtcgg    10980
cgtccaggat cgtggcgagc cggtgggcga tgacgagcga cgtacgcccg gcgagcgccg    11040
tgtccagggc ccgctggatc gccgcctccg attcggagtc cagatgggcg gtggcctcgt    11100
cgagcaccac caccgggggc gatttgagca gcaggcgggc cagggcgagg cgctgcttct    11160
cgccgcccga gagccggtag ccgcgatcgc cgaccaccgt gtccagcccg tcgggcagcg    11220
aggacaccat ctcccagatg cgggccgcct cgcaggccgc gacgaggtcg cgctcgccgg    11280
cgtcgggacg gccgtagagc aggttggccc ggatggtgtc gtggaacagg tgcgcgtcct    11340
gcgtgaccac gccgatggac tcgctcagcg agcgcagggt gaggtcgcgg acgtcgtggc    11400
cggcgatccg gaccgtgccc gagtggtgt cgtagaggcg cggcaccagg tgggtgatcg    11460
tggtcttgcc ggcgcccgac gggccgacca gggcggtgag cttgccggcc ggggcgagaa    11520
agctgatccc gttgagcacc ggccgctccg cggtgccgtc ggaggaccgc tgggccacgg    11580
tctccaacga ggccagcgag acctcgtccg cgcccggata gcggaacacg acgttgtcga    11640
actcgatgtc cggcgccgcc gagcggcccg gctcggcggc cggcagggcg cgggcgcccg    11700
ggcgctcctt gacgagcggg tcgaggtcga gcacctcgaa gacccggtcg aagctcacca    11760
gcgcggtgac gacgtccacc tggatgttgg tgagctggtt caccgggccg tacagctgcg    11820
ccagcagggc gaccatggcg acaagggtgc cgatgccgag cgtgccgtcg atgaccaggg    11880
cgccgccgaa gccgtagacc atggccgtgg tcaccgtggt cagcagcgtg gcgatgatga    11940
acagcagccg tgcgtgcacg cccatcgaga tggcgatgtc acgcacccgc gcggcccgcc    12000
cggcgaaggc ggtctcctcg ctctccggcc ggccgtagag cttgaccagc atggcgccgg    12060
agacgttgaa ccgctcgttc atcatcgagc ccagctccgc gtcgacctgc atgccgccgc    12120
gggccagccg ctccagccgg cccgcgatga gcttgccggg caggaagaac agcgggatga    12180
gcaccagcgc caccagcgcg atcgcccagg agaggtagaa catcgcgccg atgaccagca    12240
cgacggtcag gaccgtggag accgtctgcg tgatcatcga ggtcatggcc tgctcggcgc    12300
cgaccacgtc ggtgttgagc cggctcacca gcgaccccgt ctgcgcccgg gtgaagaacg    12360
ccagcggctg gcgcatgacg tgggcgaaca ccttggtgcg caggtcgtag atgagaccct    12420
gcccgacgcg cccggaggcc agcgtctgca cgtggatcgc cgccacgttg accagggcga    12480
ggccggccac caccagcgac agcccgacca ccacgtccag gcggccggcc acgatgccgc    12540
ggtcgatgat ctgcttgagc agcagcgggt tggcgaccgt gagcgcggcg tcgaccacgg    12600
tcatcagcag ggcgacggcc agggaccagc ggtgtttctt cgcgtacggg aggatgcgcc    12660
gcaccgtgcc gggcctgacc ttctgcatcg gtatgaggcc gtcgacgcgc agcccgatga    12720
cgcccagatc cgggccgtcg atggttgcca cggaaccttc tctctcgcgg tagcgggtgc    12780
gccggtcgtg ccggcgcgtc cctagtggga gtcgaggaac tcgaggatcg cggcgttcac    12840
cgcgtccggc cgttccagat agccgaggtg cccgcagcgg gatatctcga ccaggtcgca    12900
```

```
gtcggggatc gcctcggcca cctcggcggc caggtgcggc ggcgtgatga ggtcgtcggc    12960
gaacgagatc acccggcagg gcgcggtgac cgagcgcagg gcggcgcgcc ggtcaccggt    13020
cagctcggcc caggcctgcc cgccggccga cgcccgtg ccggagagct cgaagatgtc     13080
gagccactcg cgcacggcca cgtcgtcgtt gagcgtcgcc ggggagaaca tcttgaagac    13140
cgcggtcgcg gcctcgtacg cggcgggcag cgtgaccccg ctctccagca ggtcgatgtc    13200
ggcctggttc tgcgccgcgc gggccgcgtc gggccgggcc agggtcgcga tcaggaccgc    13260
gcagcgcacc agctccggat ggtcgacggc cagctcctgg gcgatcatcg cgcccagcga    13320
ggtgccgacg atccggcagg gcgcgagatc gagggcctcg atgagaccgc gggtgtcggc    13380
ggtcatgtcg gcgagggagt acttgccggc gggcacgtcc gagggcggga tgccacggct    13440
gtcgaagacg acggtggaat atcccgcctc gtgcaacgcg ggcgtctggt gcaccgtcca    13500
ggtctggccg gccgagcccg atcccatgat catgagaacg ggctcgccgg ctccggagcg    13560
gcgatacgcc aggcggaccc cgttggtggt gacgaaaccg gagcccgcgg cgctcaccag    13620
cgccactcgc gcttgttgaa caggtgctcg gcggtgaagc cccggtccgc gcaccacgcg    13680
aggaactcgt cgatctgctt gagctggtag gtgtcctcgt tgtaggtcgt cgccatgacg    13740
tggccctgcc aggactcctc gcccatggcg tagatgtatc cggcggtggc gccgagctcg    13800
gtcatgatcg cgccggcctg ctccgcgttc gatccggaca ccgccgtga ggcgctcatc     13860 ttcttgttga ccggcttggt cagcagtccc ttgtagagcc agttgagcgg cgcgccgtcg    13920
cactccatgc cgaggaacgc catgtcgacc tggccgacgt ggtcgcggat gtagcggtag    13980
agcaccgggt cgatgcccga cgagtcggcc ccgatgaaga tggtgcgccc ggccatccgc    14040
acgaagtacg tcgacttccc gcggatgtcc agatcggcgt gctcgcccag gaacggcgtg    14100
gcggtgaccg tgccgcccgg gaacggcacc tcgtcgaact cctcgacctc gacgacggtg    14160
aaaccgatcc ggcgcaggta cagcgcgatc gacgggtccg ggaggttgcc gcggctggtg    14220
cgcggcacga caacggtgcc gatccggccg cgcagctgca gcagggtctc gagcacgatg    14280
tggtcctggt gcccgtgcgt gatgagcacc aggtcgatgt ggtcgggcag gtcgtcgagc    14340
gtgtaccggt cgccgtggcg gttgtcggtg ctgatgaacg ggtcggtgac caccgccgcc    14400
tgctcggtct gcatcaccac gcaggcgtga ccgtagtagc ggacccggcc gccggactcg    14460
atgtgccggt cgggcgacag gctcggctcg tcggtgagca gggcatccag cgcggccgcg    14520
ccggcgtcgt cgagctccag cgcctcgcgc aggcggttga gcgaggtggg ccgcacgcgg    14580
gcgtcgaaga gctcggtcag cccgggatgc cgcaggggca gcggaaggtc gagcacgcca    14640
gcccggggaa gccgcggtgt gctgaggatg aacgggcgct ccaccccgtc gtcgagcgag    14700
agctgcaccg actgccgccg ctcgtcgtag gccgggctgc ggtagagcag cggctcgagg    14760
aagtgcagcg agggctggtt gctggtgtcg tacgcgatct ccaccagccc gttgagcgcg    14820
gccggcagcc gggggtagag cggcgtcagg tcgtagccga ccgcgttctc gcggatcagg    14880
tcctcggcct cggccaccgc ggcggcgaag ccgagcatgt cggcccgctc gttcttgatc    14940
gtcttgagca gctcggcgac ctcgtcgctg cgggattcct cgacggcgac gaagtagccg    15000
ccgcgcatct tcgggttcgt gctcgccgcc acgtgcaccg gcggcgactg caggtacgac    15060
tcgagcagag gcacctgcag gaacgccagg ttcatggagg ccggcaccgg tgccaccgtg    15120
tgcagccacg cgtagaaacg gtcgacgagc ggttcggcga tgacgttgga gcgcaggtat    15180
ctcggctgat cggcgttgcc catgtgaacc tctccatcct gatggcgggt gcgcccggag    15240
```

```
cgggcacgat cgggcgggag ggaatgcggc ctcggtacgg ccggcgcggc aaacggcgcg    15300
tccgtccctc cggcgtgggc gcggtccact atggcatcgg cccaggagcc ggtacagcgt    15360
gcacgtgcgc ggcccgatcg cgtcgaacgc cctgtacaac cggcggtgcg acgcagtcga    15420
acagcggtga acgaccgagg cggcggcggc ccgttgatcg gccgcccgag cgcccgcata    15480
gtgaatcgcc ggaggggcct tggagagccg gcccgccgtt cccggccatc gccgggcgcc    15540
cgccctcaca aaccgatcgc ccggcgccgc cgggtcgcac ggaggtgccc atgtccgaga    15600
ccgacctgtc cgccgcccgg cacacgcccg agcagatccg ctcctggctg atcgaccgga    15660
tcgcctacta cgtgatgctg ccgacccagg agatcgagcc ggacgtgtcc ctggccgagt    15720
acggcctgga ctcggtgtac gcgttcgcgc tctgcggcga gatcgaggac acgctcggca    15780
tcccgatcga gccgaccctg ctgtgggacg tcgacaccgt cgccaccctc accgccacc     15840 tcgccgaccg cgtcaaccga taagccggag gtgaccgtcg tgcccacccc tgacctgcgc    15900
ccgctcacgc ccgcccagct cgccgtctgg cacgcgcagc agctcgcccc gcacagcccc    15960
gtctatcagg tcggcgagtt cgtcgagatc gacggcgagt gcgaccccga tctcctggtg    16020
gcggcgttgc gtcaggtcat gggcgaggcc gagagcgccc ggctgcggtt ccgcgtgatc    16080
gacggtacgc cgtggcagta cgtcgccgag gacggcgacg acccgatcca ggtcgtggac    16140
ctcggcgcgg ccgcggaccc gcgcgccgcg gcgctgggcc gcatggcggc cgacctcgac    16200
cggcccggcg acctgcgcga cggcccgctc gtcgagcacc acgtctacct gctcggcgag    16260
ggccgggtca tctggtacca ccgcgcgcac cacatcgtct cgacggcgg cagcctcggc     16320 attgtcgcct cccgggtggc cggcgtctat tccgcgctcg cggccggtgg tgacgtccgg    16380
ccgggtgcgc tgccgccgct gtcggtgttg ctgtcggccg ccgacgccta cgagcgctcc    16440
ggcgaccgcg accgggaccg cgagcactgg cgctccgcgc tggcgggcct gcccgccgag    16500
ctgctcgcgg gcgcgggccg gccgcggccg ctgcccggac cgccggtgcg ccacgagcac    16560
gacctctccg cggcggaggc gggccggctg cgcgcggggg cgcggcggct gcggaccagc    16620
gtggcgcagg ccggcatcgc ggccgcggcc ctctaccagc accggctcac cggcgcccgg    16680
gacgtgctgg tggcggtgcc cgtcgccggc cgcaccaccc gccggagtt cgacgtgccc     16740 ggcatgacgt cgaacgtggt gccggtgcgc ctcgcggtca cgcccgccac gaccgtcggc    16800
gagctgctgc gcgacgtcgc ccgtggtgtc cgcgacggc tgcggcacca gcggtacccg     16860
tacccgaaca tcgtggacga cctcggcctg gccgaccgtg ccgcgctgcg cccggtgacc    16920
gtcaacgccc tggcgctggg acggccgctg cgcttcggct cggcggtggg tgtgcgctcc    16980
ggcctgtcgg cgggcccggt ggacgacgtc accatcggcc tctacgaaaa ggtcagcggc    17040
ggcggcatgc agacgatcgc cgagctgaac cccgggcgca cggaccgccc ggacgcggcg    17100
gaggtctccc gctggttccg tacgctgctg cgcgggctgg ccgagagcga cgccggcgac    17160
ccggtggccc gcatcgacat cgtcgacgag cccgagcgcc gccggctgct ggacgagtgg    17220
aacgccaccg cggcgccgtc gagcgacacc gtcctcgcgc gtttcgagga gcaggcggcg    17280
cgtacgcccg aggcgcccgc cgtcgtctgc ggcgacgtga cggtcaccta cgccgagctg    17340
gaggccggcg ccaaccggct cgcccgcgtc cttcgcgcgc gcggcgccgg accggagtcg    17400
gtcgtggccc tctgcctgcc ccgcggcccc gaggtcgtga ccggcatcct cgccgcctgg    17460
aaggcgggcg ccgcctacct gccggtcgac accgaactgc cggccgagcg cgtcgcctat    17520
ctgctcggcg acagccgccg ccgtcgcc ctcggcaccg ccgagacgct cgccgccctc      17580
ccggacggcc ccgccgccga cgtcgacgtc cacgcaccgg agatcgcccg ggaatcgccc    17640
```

-continued

```
tcgcccctgc ggctcgagcc cttgccggat cagttggcgt atgtgattta tacgtcgggt    17700
tcgacggggt tgagcaaggg tgtcggtgtt tcgcatggtg ggttggcgaa ttatgtgggt    17760
tgggcgtcgg ttttgtatgg gggtttgtcg gcgccgttgc attcttcgtt ggcttttgat    17820
ttgacggtga cgagtgtttt tgtgccgttg gtgtgtggtg gttcggtggt ggtgtcggcg    17880
gccggtggtg gtcggggttt ggcgtcgttg ttggcggctg gtgatggttt ttcgttggtg    17940
aaggtggtgc cgggtcattt gcgtttgctg gcggagttgg tgccggcggg tgagatggcg    18000
gcggtgggtt cgttggtggc cggtggtgag gttttggccg gtggtgatgt gcgtgagtgg    18060
ttgtcgcggg tgccgggttc ggtggtggtg aatgagtacg ggccgacgga gaccgtggtg    18120
ggttgttcgg ttttctcggt ggccgcgggt gatgtggttg gtgatgtggt gccggttggc    18180
cggccggtgg cgaatacgcg tttgtttgtt ttggatgagg gtttgcggcc ggttccggct    18240
ggggtggcgg gtgagttgta tgtggctggt tcgcaggtgg cgcggggtta tgtgggtcgt    18300
tctggtttga cggcttcgcg ttttgtggcg tgtccgttcg gtgtgggtga gcggatgtat    18360
cgcacgggtg atgtggtgcg gttggccggt ggtgatctgg tgtttgtggg ccgggtcgat    18420
gagcaggtga agattcgtgg ttatcgggtg gagccggatg aggtgcggtt ggtggtggcg    18480
gggcatccgc gggtagcggg tgcggcggtg gtggctcggc cggatgcggt gggtgagcgg    18540
cagttggtgg cctatgtggt cgctgccggt gagccggccg ggttggcgga gtcggtacgc    18600
gcccacgtcg ccgagcgcct gcccgaatac atggtcccgg ccgccgtcgt gaccctcgac    18660
gagatcccgc tgaccgtgaa cggcaaggtc gaccgcgccg ccctgcccga gcccggcccc    18720
gtcgccaccg gcaacgccga ccgcgagccc acgaccgagc gcgaatcgct gctctgcggc    18780
gccttcgccg acgtgctcgg catcgagcgg gtcggcgtcg acgacgactt cttcagcctc    18840
ggcggccatt ccctgctcgc caccagcctg gtgagccggg tacgcctcgt gctcggtgag    18900
gaactgccca tcgaggagct cttcgccacg cccacccccg ccgagctggc ggcctggctg    18960
caacgcaacg cggaccggcc gcaaccggcc cggccggcgc tgcgcccgat gcacgaaagg    19020
gaaacgaccg catgacccgg atgtcgtacg cccagcgccg tctctggttc cagctgcggg    19080
tcgagggccc cgacgccacg tacaacagtc ccgccgtcct gcgcctcacc ggcgagctcg    19140
acaccgccgc cctggagcac gcgctgcgcg acgtcctcga acggcacgag gtcctgcgca    19200
cggtctatcc cgacgtcggc ggcgagccgc ggcagcgcgt ggttcgcccg gacgacatgg    19260
tgtgggagct gccacgacc cgggtgtccg gtgccggcgc gggcgacgac cggctcgtca    19320
cgctcgacga gctgccctgg gaccgcccgg tgctcgacct gccgtcgccc gcaccggccg    19380
gccgggaacc ggacggcgag atcaccgtcg acgagctgcc cggcgcgatc gcccgggtgg    19440
cggcccaccc cttcgacctc tccatcgaga tcccggtgcg ggcgcggctg ttcgccctgg    19500
gcccgcggca ccacgtcctc gtcgtcgtgc tccaccacat cgccaccgac ggcagctccg    19560
gcgggccgtt cgcccgcgac ctcgccgccg cctaccgcgc ccgccgcacc ggaacggcgc    19620
cccagtgggc acccttccg gtgcagtacg ccgactacgc ggcctggcag caggaactgc    19680
tcggcgccga ggacgacccc gacagcgtca tctcgcggca gctcgcccac tggcaggagc    19740
ggctggccgg catgccggtc gagctggatc tgccggccga ccgtccgcgg cccgccgaac    19800
ccgggcacgg cgggcacacc aaggcgctga gcctgccccc ggccgtgcac cgaggactgg    19860
ccacgctggc ccggcggcgc cgcgccacgc ttcaaatggt cgtgcagacc ggcgtcgcga    19920
tcctgctgtc caagctcggc gccggccgcg acgtcccgct cggcatcccg gtcgccgggc    19980
```

```
gcaccgacgc cgcgctcgac gacctgatcg gtttcttcgt caacaccttg gtcgtacgcg    20040
ccgacctgtc cggcgacccc acggtggccg acgcgctggg ccgggtgcgc ggaggcgcgg    20100
tggccgccct ggccgaccag gacgtgccct tcgacaaact cgtcgagcgg ctggcgccgg    20160
cccgcgtgct cgggcggcac ccgctgttcc aggtcatggt cgcgccgctc gacgacggga    20220
cgccgatcga cctggacggg gtgcgaggcg agccgctcac catcggccgc tccggtgcca    20280
agttcgacgt cgaggtgatg accggagagg tacgcgcggc ggacgcgcg ccggccggca     20340
tccgcggaat cctgacgctc tcggccgacc tgttcgacga ggcgacggcc ggccggatgg    20400
ccgccgggct ggtgcgggtg ctgaccgcga tggccgaggc cccggagcgg cggctctccg    20460
gcatcgaggt gctgtcgccg ggggagcggt cgcggctgct ggtggagtgg aacgacacgg    20520
ctcgtccggt ggtggagtcg tcggtgccgg cgttgttcgc gaagcgggtg gcggccacgc    20580
cggacgcgac ggcggtggtg ggcgaggtg tgtcgtggtc ctatcgcgaa ctcgatcgtc      20640
gctcggatgt gctggcgcgg cgtctggtgg cggcgggtgt gggtgtggag tcgccggtgg    20700
tggtggcgtt ggagcggtcg ccggaggtgc tgtccgcgtt tttggcggtg gcgaaggccg    20760
gtggtgtgtt tgttccggtg gatttgtcgt ggccgcaggc gcgtgtcgat gcggtggttg    20820
ctgactgtgc cgcgcgggtg gcggtggctg accggccgat gagcgggctg acggtcgtgt    20880
ccgccggcct gggcggggat tcggccgtcg tgtccgccga cctgaccgcg gatcgggccg    20940
ttgtgttgcc gtctcgcccg gtgccgggtg cggcggtcta ccggatgtac acctccggct    21000
cgacgggccg cccaagggt gtggtgacca cccaccagaa cctggtggat ctggcgaccg      21060
acacgtgttg gggtccgacc ccgcgggtgc tgttccacgc cccgcacgcc ttcgacgcgt    21120
cgtcgtacga aatctgggtg cctctgttga atggcggcac ggtcgtggtc gccccgcagc    21180
gcagcatcga cgccaccgtc ctgaaggatc tgatccgcgc gcatgatttg acgcacgtgc    21240
acgtcaccgc gggcctgctg cgggtgctgg acccgtcgtg cttcgcgggc ctgaccgagg    21300
tgctcacggg tggcgatgcg gtgtcggcgg aggcggtgcg ccgggtcaaa gacgcgaacc    21360
cgggtctgcg ggtgcggcag ctgtacggcc cgaccgaggt gacgctgtgc gcgacgcagc    21420
atctgctgga tgacggggtg ccgatcgggc ggccgttgga caacacccgc gtgtatgtcc    21480
tggacgactt gctgcagccg gtgccggtcg gtgtgaccgg cgagctgtat gtggccggtg    21540
ccggcgtggc gcgtggctat gcgggcatgc ccgggttgac ggccgagcga tttgtcgccg    21600
acccgttcaa caccgcggt cgcctctacc gcacggtga tctggtgcgg tggaccgatg        21660
acggtgtgct gcatttcgcc ggccgagccg atgatcaggt gaagatccgc ggctatcggg    21720
tggagccggg cgaggttgaa gcggttctgg ctcaacatcc cgatgtcagc caggtcgcgg    21780
tggtcgtccg ggaggacacc ccaggcgaca agcgtcttgt cgcgtatgtc gtcggcggtg    21840
acatcgaggc gtatggccag gagcgccttc ccggttacat ggtcccgtcg gcattcgtac    21900
atctggatgc gttgccgctg accagcaacc agaaggtgga tcgggccgca ctgcccgcgc    21960
cgtccatgga gtccggcgcc ggtcgagctc ccgcggatgc ccgcgaggag ttggtgtgtg    22020
ccgcgttcgc cgaggtgctc ggcctggatc gggtcggtgt cgacgacgac ttcttcgctc    22080
tcggcggtca ctcgctgctt gccgtctccc ttgtggagga tttgcggcag cgtggcctgc    22140
acgtctccgt tcgcgcgctc ttcgccacgc cgaccccgc ggcgctggcc gtctcgaccg      22200
tggcggcccc gatcgaggtg ccgcccaacc tcatccccca gggcggcgcc cgggaactga    22260
cccccgacat gctgccctg gtcgacctga cggcgaggga gctggccacc atcgtggccg      22320
cggtgcccgg cggcgctgcc aacatcgccg acatctaccc cctagccccg ctgcaagagg    22380
```

```
gcatcttctt ccaccacctc atgaccgagg gcgacaccgc cgacgtctac gcgctgccgt   22440
acctgctgcg cgttggcacg cgtgagcagc tcgacgcctt cctcgggget ttgcagcagg   22500
tggtggaccg ccacgacgtc taccgcacgg ccatcgcctg gcagaacctg cgcgagcccg   22560
tccaggtcgt gcaccgccac gccaccctgc ccgtcaccga agtcaccccc gaccaactgc   22620
acgccgccgc caccggcggc cggctcccgc tcgaccacgc cccctgctc agcgtccaca    22680
tcgcacccga acccgacggc ggctggctcg ccctactgcg catgcaccac ctcgtgcagg   22740
accacaccgc cctcgacatc gtcctcgacg agatccgcac catcctcgcc ggcgcaaccg   22800
accacctccc cccgcccgta ccgttccgca atttcgtggc gcgctcgcgg cgtggtgccg   22860
ccgaggccgc gcaccgcgac tacttcaccg gcctgctcgg cgacgtcacc gagaccaccg   22920
ccccgtacgg cctcaccgac gtgcacggtg agcactccgg cgtgcgccgg ggccggctcg   22980
ccgtgtccgc cgggctcgcc ggccgggtgc gggagaccgc tcgcgaccgg ggcgtcagcc   23040
ccgccaccct cttccacctg gcctgggcgc gcgtgctcgc cgccgtctcg ggccgcgacg   23100
acgtcgtctt cggcaccgtg ctgctgggcc ggatggatgc cggcccgggc gccgaccggg   23160
tgccgggcct tttcatgaac accctgccgg ttcgcgtacg cctcggcggc cgcaccgtcg   23220
acgaggcgct gcacgggatg cgcgcccagc tcgccgacct gctcacccac gagcacgccc   23280
cgctggtgct cgcgcagcag tcggccggcc tgcccggcgg cagcccctg ttcacctcgc    23340
tgttcaacta ccggcacaac gcgaccgaca tcgagcgctc cggaacgggc atcgacggcg   23400
tcgaggcgct gcccaccggc gacccgtcga actatccgct cgacgtctcg gtcaaccaga   23460
gcccgctcgg cttcgagctc gtcgtcgagg ccaccgagcc ggccgacccg gaccagctct   23520
gccggctcct gcacgcctgc ctcgacgacc tgatcgccgc cctcgacgag cagcccggcc   23580
gcgcgctcgg caccctcgac gtcgtcgccg gacgggagcg cgacctcctc ctggacggct   23640
ggaacgccac ggcggtcccg gcccagccgg ccctggtgcc ggagctcttc acggcgcagg   23700
cggcgcggac acccacctgg ccggcgctgg tgacggccgg cgcggagatg tcctacgccg   23760
agctcgagga gcggtccaac cggctggcgc gctggctggc cgggcgcggg gtgggcgccg   23820
acgaccgggt ggccctgatg atgcgccgcg gcccggagct gatggtggcg atcctggccg   23880
tgctcaaggc gggcgcggcg tatctgcccg tggatccgga cctgccccgc gaccgggtgg   23940
actacctgct cgcggacgcg gccccggcgt tcgtgctggc cgagcgggcc accgcgccgt   24000
gggtgccggt ggccggtggg attccggtgc tggtcgtgga cgcgccggcc gtcgccgccg   24060
aggtggcggc ccactcgggc gaggccgtca ccgaccggga ccggcgcgcc gccctgcgcg   24120
gcggccacct cgcctacgtc atctacacct cgggatccac cgggcggccc aagggcgtgc   24180
tgatcacgca cgacggcctc gccaatctca cgctcgacca cggccggttc ggcctcggtc   24240
cgggtgcccg ggtggcgcag ttcgcctcgc ccggcttcga catgttcgtc gacgagtggt   24300
cgatggcgct gctggccggc gccgcgctga ccttcgtgcc gccggagcgg cgactgggcg   24360
ccgacctggc cgcgttcctc gccgagtacg gcgtgacgca cgcgacgctg ccgcccgcgg   24420
tcgtgggcac gatcccggac ggtgtgctgc cgccgtcgtt cgtgctcgac gtcggcggcg   24480
acgtgctgcc gggcgacctc gcgcgccggt ggctgcgcga cggccgggtg ctgttcaact   24540
cgtacggccc gacggagacc acggtcaacg cggcgacgtg gcgggccgag gccggtgact   24600
ggggaagcgt ggcgccgatc ggcacgcccg tgccgaatct gcgggcgtac gtgctcgacg   24660
gctggctgcg cccggtgccg gtgggcgccg acggcgagct gtacgtctcg ggcgccggac   24720
```

```
tcgcccgcgg ctatctgaac cgggccggcc tgaccgcgga gcggttcgtg gcgtgcccgt  24780
tcgagccggg ggagcggatg taccgcaccg gcgacgtggt gcggtggacc gccgaggggc  24840
gcctggtgtt cgccggtcgc tcggacgacc aggtcaagat ccgcggattc cggatcgagc  24900
ccggcgaggt ggaggccgtg ctggccgccg gaccgggtgt gagccaggcc gcggtgatcg  24960
tgcgtgagga cgtgccgggt gacaagcgct tggtggcgta cgtcgtgggc ggtgacgtcg  25020
aagctctccg gtcgtacgcg cagcagcggt tgccgggtta catggtgccg tcggctttcg  25080
tggagctgga ccggttgccc ttgacggtga acggcaagct cgaccgccgg gccctgccgg  25140
tgcccgacct cgcccgcggc acgggatccg gccggcccgc cggcacgccg cgcgagcagc  25200
tgttgtgcgc gggcttcgcg gccgtcctgg gcgtggacga cgtcggcgcc gacgacgact  25260
tcttcgcgct cggcggtcat cgctgttgg tggtttctct ggtggagtgg ctgcgccgtc  25320
gtggggtctc ggtgccggtg cgggcgttgt tcaccacgcc gaccccggcc gggctggccg  25380
aggcggtcgg tgatggtgcc gtggtggtgc cgccgaacct gattccggaa ggtgcggccg  25440
agctgacccc ggagatggtg ccgctggccg atctgacgtc cgaggagctg gcgatcgtcg  25500
tcgcatcggt gccgggcggt gcggccaatg tggccgatgt gtatccgttg gcgccgttgc  25560
aggagggcat cttcttcccc gtagccacag gcccccagtg ctacgccacg gtgggagtt  25620
cactcccgga cgatggcggt tctgcccctt gcagcaggtt tcgccgtcga tgtgtatcga  25680
cgagtgtggt gtggcagggg ctgcgtgagc cggtgcaggt ggtgtggcgg cacgcgcggc  25740
tgcccgtcga ggaggtcgtg ctgcacgagg gggccgaccc ggtcgagcag atgatggcgc  25800
tcgccggcgg ttggatggac ctcacccggg cgccgctcat cgacgtccac atcgccgccg  25860
gccccggcgg cgaccgctgg ctggccgtgc tgcgcatcca ccacctcgtg caggaccaca  25920
ccgccctgga gacgctgctc gacgagctgc agtccttcct ggagggccgc ggtggcgagc  25980
ttgccgagcc ggtgccgttc cgcgagttcg tggcgcaggc gcggctcggt gtgccgcgcg  26040
aggagcacga gcggtatttc gcggagttgc tcggcgacat caccgagacc accgcgccgt  26100
acgacctgac cgacgtgcac ggcgacggca ccggatacga ccacggcgcg ctgccgctgg  26160
acgccaccgt cgcggcccgc gtccgggagg cggcccgaac cctcggcgtc agcccggcga  26220
cgctcttcca cctcgcgtgg gcgcgggtgc tcggcacgct ggccgggcgc gacgacgtcg  26280
tcttcggcac cgtcctgttc ggacggatga actcgggtgc cggcgccgac cgggtctccg  26340
gcctgttcat caacacgctg ccggtgcggg tgcggctcgg cgcgccacc ggcgacgccc  26400
tcggcgacct ccgcgaccag ctcgccgagc tgctcgtgca cgagcacgcc tccctcgcct  26460
ccgcgcagaa ggcgagcggc ctgcccggcg ggagccccct gttcacgtcg atcttcaact  26520
accggcacaa ccaggtgagc gccgaacggg agaccgccgc gctgcccggc atccgcgtcc  26580
tcgcggcccg cgactccacg aactatccgc tcaccgtcgc ggtggacgac gacgggcacg  26640
gcttcacgct cgtggtcgag gtcgcgtcca cagtcgacgc cgcgggcgtc tgcgaactgc  26700
tgcacaccgc cgtggacaac ctcatcgcgg ccctcaccga ccggccgggc gggccgctgg  26760
ccgaggtcga catcctcgaa cgcggtctgc gggaccgcct gctgaccgcc tggaacgagg  26820
cccgggagcc cgcaccgccg gtgaccctgc cgacctgtt cgaccggcag gcccgccgca  26880
cgcccgagcc ggtcgcgctc accgcggacg gcgtctcgct gacctaccgc gagctgtcgg  26940
agcgcgccaa ccggatcgcc cggctgctca cctcccgggg gatcggcccg gagtcgctcg  27000
tcggtgtcgt cctgccccgc tcggccgacc tggtcgttgc gctgctcggc gttctccagg  27060
ccggcgcggc ctacgtgccg gtcgacgccg actaccggc cgagcggatc gggtacatcc  27120
```

-continued

```
tcggcgacgc gggcgcggtt tgcgtgctca cagtggacgc gaccgcgggc gccgttcctc    27180
ccggcgtacc gaaactggtg ctggaccacc cggaaaccgt gaccgcgctg cggcgtgtg     27240
acacggcacc gctcggcgag gccgagcggg ccggcgaact gctgccggag cacccccgcct   27300
acgtcatcta cacctccggc tccaccggca cgcccaaggg cgtgctcatc ccgcaccgca    27360
acgtggtcga gctcttcgcc gccacccgcg gctcgttcca cttcggcgag ggtgacgtgt    27420
ggtcgtggtt ccactcggtc gccttcgact tctcggtctg ggagctgtgg ggcgcgctgc    27480
tgcacggcgg ccgcgtggtc atggtgccgt tcgccgtctc ccgctcaccg cgggatttct    27540
gggaactgct cgtgcgcgag cgggtcaccg tgctcagcca gacgccgtcc gccttctacc    27600
agctcgccgc ggccgccgac gacacgccgg acgcgctgcg cgtggtggtc ttcggcggcg    27660
aggccctcga cccgggacgg ctcgccggat ggcgggaacg gcgcccggac ggaccgcgcc    27720
tggtcaacat gtacggcatc accgagacga cggtccacgt cacccaccag gacctcgcac    27780
cggccgacac caccggcagc cccatcggac gcggcatacc gggcctgtcc gtctacgtcc    27840
tcgacgaggc gctgcggccg gtgccgcccg gggtcgccgg cgaggtgtac gtggccggtc    27900
gccagctggc ccgggcctac ctcggccgcg ccgcgctgac cggcacccgc ttcgtcgcct    27960
gccccttcct cccggccggg aacggatgt accgcaccgg cgaccgtgcc cgctggagcc     28020
gcggccggtt gcagttcgcc gggcgcaccg acgaccaggt gcagatccgc ggcttccgca    28080
tcgaaccggg cgaggtgcag gccgtcgtcg ccgcccaccc tgagatcgcc gcggcggccg    28140
tcgtcgtgcg cgaggacgtg cccggcgacc cgcgcctgac cgcctacgtg gtgccggccg    28200
gcccgcgcac cgcgccggcg gccgtcgcgg aaaccgtgcg gcgcttcgcc gccgaccggc    28260
tgccggccta catgcttccc tccgcggtcg tcgtgctgga cgccctgccg ctgaccgacc    28320
acggcaagct cgaccggcgc gcccttcccg caccgcagca cacgggcgcc gcgagcggcc    28380
gggcgccggc caccgtggcc gaggaggtgc tgtgcgccgc cttcgccgag gtgctgggcg    28440
tcgagcgggt cggtgtcgac gacgacttct tcgccctcgg cggccactcg ctgctcatcg    28500
tctcgctcgt cgagcgcgtc cgccgcgccg gcctggcgat cccggtccgc gccctgttcc    28560
gcagcgccac cccggccggg ctggccgcgc tcgcccggcc gtaccgggtc gacatcccgc    28620
ccaacctcgt cccggacggc gcccgcgaga tcaccccgga catgctgacc ctggccgcgc    28680
tcaccgaggc cgagatcgcc acggtgctcg cgaccgtgcc cggcggggcg gtgaacgtgg    28740
ccgacatcta tccgctggcc ccgctccagg agggcatctt cttccaccac ctcatggcgg    28800
acgccggccg ggccgacgcc tacgcgatgc cgtacgtgct gcacctggac acggcggagc    28860
ggctggacgt cctcctcggc gccctccagc gggtgatcga ccgtaacgac atctaccgca    28920
ccggcgtggt ctcggccggc ctgcgcgaac cggtgcaggt ggtgtggcgg tcggccgtcc    28980
tgccccgtcga ggaggtggcg ctggacgcg gccacgaccc ggtcgagcag ttgctcgccg    29040
ccgccggcga ggagttcgac ctgacccggg cgccgctgat ccgggcgcac gtggcggcgc    29100
atccggacgg cggccggctg ctcctgctgc gcatccacca cctcgtgcag gaccacacga    29160
cgttcgacgt ggtgctgggc gagctgcggg ccttcctcga gggccgcggc ggcgagcttg    29220
ccgagcggt gccgttccgc gagttcgtgg cgcaggcgcg gctcggtgtg ccgcgcgagg    29280
agcacgagcg gtatttcgcg gagttgctcg gcgacgtcac cgagaccacc gcgccgtacg    29340
gcctgaccga cgtgcacggc gacgctcccg ggccgtcca gtctcgctg ccggtcgccg     29400
aggccctcgc cgtccgcgtc cgcgaggtgg cccggacact cggcgtcagc ccggccaccg    29460
```

```
tcttccacct ggcctgggcg cgcgtgctga gcgtcatcgc gggccgcgac gacgtggtgt   29520
tcggaaccat cctcttcgga cggatgaact cgggcgcccg cgccgaacgc gtgcccggcc   29580
tgttcatcaa cacgctgccg gtgcgggtgc gactgaacgg cacgagcgtg ggggaggcgc   29640
tgaccgccct gcgcgaccag atggccgagc tgatggcgca cgagcacgcg ccgctcgcgc   29700
tggcgcagcg ggccggcggc gtgcccgcgg gcagtccgct gttcacgtcg ctgttcaact   29760
atcggcacaa cgtcgcgggc ggcggcgacg gcggagcgct cgagggcgtc acgccggtgc   29820
tgcaccgcga caccacgaac tatcccgtgg tggtctcggt cgacgacgac ggcacgagct   29880
tcgacctggt ggtggaggcg gtcgcgcccg cggaggcggg tcgcgtcggg cggctcatgc   29940
acgaatgcct ggccgagctg gtgggcgccc tggccggtgc gccggagacg cccctgtccc   30000
gcgtgcgggt gatcgacgag gccgagatcg aacgggtcgt tcacagctgg aacgacacgg   30060
ctcgcccggt agtggagtcg tcggtgccgg cgttgttcgc cgagcaggtg gcggctgcgc   30120
cggatgcgac ggcggtggtg ggcgagggtg tgtcgtggtc ttatcgcgag cttgatgcgc   30180
gatcggatgc gctggcccgg agcctggtgg cggccggtgt gggtgtggag tcgccggtgg   30240
tggtggcgtt ggagcggtct cccgaggtgc tgtccgcgtt cctggcggtg gcgaaggccg   30300
ggggcgtgtt tgttccggtg gacctttcgt ggccgcaggc gcgtatcgat gcggtggttg   30360
ctgactgtgc cgcgcgggtt gcggtggctg accggccgat gagcgggctg acggtcgtgc   30420
cggccgacca ggtcggggat cggctgtcg tcctgccggc cggtccggtg ccgggtgcgg   30480
cggtctaccg gatgtacacc tccggctcca cgggccggcc caagggtgtg gtgaccaccc   30540
accagaacct cgtggatttg gcgaccgaca cgtgttgggg tccgaccccg cgggtgttgt   30600
tccatgcccc gcacgcgttt gatgcgtcgt cgtatgagat ctgggtgccg ttgttgaatg   30660
gcggcacggt cgtggtcgct ccgcagcgca gcatcgacgc gacggtcttg agggacctga   30720
tccgcgggca tgagttgacg cacgtgcatg tgaccgccgg tctgttgcgg gtgctggacc   30780
cgtcgtgttt tgcggggctg accgaggttt tgaccggcgg ggatgcggtg tcggcggagg   30840
cggtgcgccg ggtccgggaa gcgaacccgg gtctgcgggt gcggcagctt tatggcccga   30900
ccgaggtgac cttgtgcgcg acgcagcatc tgctggtcga cggggtgccg atcgggcggc   30960
cgttggacaa caccccgcgtg tatgtcctgg atgacttgct gcagccggtc ccggtcggtg   31020
tgactggcga gctgtatgtg gccggggccg gcttggcgcg tggctatgcg ggcatgcccg   31080
ggttgacggc cgagcggttc gtcgccgacc cgttctcggt tggtggtcgc ctctaccgca   31140
cgggtgatct ggtccgctgg actgacgacg gggtgctgca tttcgccggg cgggccgatg   31200
atcaggtgaa gattcgtggc tatcgggtgg agccgggcga ggttgaagcg gtcctggctc   31260
aacaccccga cgtcagccag gtggcagtgg tcgtccgcga ggacacgcca ggggataagc   31320
ggctggtcgc ctatgtcgtc ggcggtgacg tcgaggcgta tgcgcaggag cgccttccgg   31380
gctacctggt cccgtcggca ttcgtacatc tggatgcgct gccgctgacc agcaaccaga   31440
aggtcgaccg ggccgcactg cccgcgccgt ccgtggagtc cggcgtcggg cgggcgcccg   31500
ccgacgcgcg tgaagagctg atgtgtgccg cgttcgctga ggtgctcgac ctggatcggg   31560
tcggtgtcga cgacgacttc ttcgctttgg gtgggcattc gctgttggtg gtgcggttgg   31620
tgggccgtat tcggcaggtg ttcggggtgg aggtgtcggc tcggctggtc ttcgatgcgc   31680
ggactccggg cggtgtggtg gcccgcttgt ccgagggcgg cacggcccgg gaggccgtac   31740
gggcgcgggt gcgtccggcg cgggtgccgt tgtcgttcgc gcaacgccgg ttgtggttcc   31800
tgtcccagct ggagggtccg agcgcgacct acaacatccc ggtggcgctg cggctggacg   31860
```

-continued

```
gtcctctgga tcgcgatgct ctaacggcgg cgttgcacga tgtggtggcc cggcacgagg    31920
tgttgcgtac cgtcttcacc gtcgccgacg gcgagccgtg gcaacagatc ctcgacgatc    31980
cgcaggtctc cgttccggtc gtcgaggtca cgcccgaccg gctgcccgag gcggtggccc    32040
tcgccgcggg gcaccggttc gacctcggcc gggaactgcc gctgcgggcg gtcctgctgg    32100
cgaccggcga cgacgtgcac gtgctggtgc tcgtggtgca tcacattgcc gccgacggct    32160
ggtcgatgcg gccgctcgcc cgggacttgg cggccgccta cgcggccagg atcgacgcga    32220
cggcgccggc cctcggcgcg ctgccggtgc agtacgccga ctacgccctc tggcagcgcg    32280
acgtgctcgg ttccgagcac gacccggaca gcgtcatctc ccaacaggtt gcctattggc    32340
ggcggcagct ggccggcgta ccggaggaat tggatctgcc ggtggaccgg gcgcgccccgg   32400
ccgaggcatc gcatcgcggc cacaccgtgg agttcgccgt gccccggcc gtgcaccacc     32460
aactcgccga actcgcccgc cgcaacggcg tcacgtcctt catgaccgtg caaaccgccc    32520
tcgccgtcct cctgtccaaa ctcggcgccg gcaccgacat ccccatcggc gtcgccgtcg    32580
ccggacgcac cgaccccacc ctcgacaacc tcatcggctt cttcgtcaac accctcgtcc    32640
tacgcaccga cctgaccggc aaccccacca tcaccgacct gctgcaccgc acccgcgaca    32700
ccaccctgca cgccttcacc caccaagacg tccccttcga aaactcgtc gaagacctcg     32760
cacccacccg ctccctcgcc cgccacccc tcttccaggt catgatgacc ctgcagagcg     32820
cgtcggcgga cgaagagccg ctggcgctcg ccgggctgcg ggtcaccgac ctcccggccg    32880
gggagacacc cgccaaggtg gacctcgacc tgacgctgca cgaggtggcg ggccgagacg    32940
gcatgcacgc cacgctcctc ggcgcggccg acctcttcga gcaggagacg gtgcgcgccc    33000
tcgccgaccg gttgctgcga acctggaag ccatggcggc ggccccggac gaccgcctcg     33060
accggatcga ggtgctgtcg ccggggagc ggtcgcggct gctggtggag tggaacgaca    33120
cggctcgtcc ggtggtggag tcgtcggtgc cggcgttgtt cgccgagcag gtggcggctg    33180
cgccggacgc ggtcgcggtg gtgggcgagg gtgtgtcgtg gacctatcgc gagcttgatg    33240
cgcggtcgga tgcgttggcg cggagcctgg tggcggcggg tgtgggtgtg gagtcgccgg    33300
tggtggtggc gttggagcgg tctccggagg tgctgtccgc gttttggcg gtggcgaagg     33360
ccggggggcgt gtttgttccg gtggatttgt cgtggccgca ggcgcgtgtc gatgcggtgg    33420
ttgcggactg cggcgcgcgg attgcggtgg ctgaccggcc gatgagcggg ctgacggtcg    33480
tgtccgccgg cctgggcggg gattcggccg tcgtgtccgg cgacctgacc gcggatcggg    33540
ccgttgtgtt gccggccggt ccggtgccgg gtgcggcggt ctaccgcatg tacacctcgg    33600
gttccacggg tcgcccaag ggtgtggtga ccacccacca gaacctcgtg gatttggcga     33660
ccgacacgtg ttggggtccg acccgcgggg tgcttttcca cgccccgcac gccttcgacg    33720
cgtcgtcgta tgagatttgg gtgccgttgt tgaatggcgg cacggtcgtg gtggctccgc    33780
ggcgcagcat cgacgcgacg gtcttgaggg acctgatcgg cgcgcatgag ttgacgcacg    33840
tgcatgtgac cgcgggcttg ttgcgggtgc tggaccccgtc gtgcttcgcg ggcctgaccg    33900
aggtgctcac gggcggggat gcggtgtcgg ccgaggcgg gcgccgcgtc aaagacgcga    33960
atccgggtct gcgggtgcgg cagctgtacg gcccgaccga ggtgaccttg tgcgccacgc    34020
agcatctgct ggatgacggg gtgccgatcg gcggccgtt ggacaacacc cgcgtctacg     34080
ttctcgacga cctcctgcgg ccggtcccga caggtgtggt gggggagctg tatgtggccg    34140
ggtcgggtct ggcgcgggc tatgcggggca tgcccgggtt gacggccgag cgattcgtcg     34200
```

-continued

```
ccgacccatt caacaccggc ggtcgcctct accgcacggg tgatctggtg cggtgggccg      34260
acgatggtgt gctgcatttc gctgggcggg ccgatgatca ggtgaagatt cgtggctatc      34320
gggtggagcc gggcgaggtt gaagcggtcc tggctcaaca ccccgacgtc agccaggtag      34380
cagtggtcgt ccgcgaggac accccaggcg acaagcgcct ggtcgcctac gtcgtcggcg      34440
gggatgtcga ggcgtatgcg caggagcgcc ttccgggcta catggttccg tcggctttcg      34500
tgcagttgga tgcgctgccg ctgaccagca accagaaggt cgaccgggcc gctctcccgg      34560
cgccatccat ggagtctggc gccggccggg caccgccga cgcgcgtgaa gagctgatgt      34620
gtgccgcgtt cgccgaggtg ctcgacctgg atcgggtcgg tgtcgacgac gacttcttcg      34680
ccctcggcgg gcattcgctg ctcgccgtct ccctcgtgga gaatctgcgc cgccacggcg      34740
ttcacatctc cgttcgggcc ctcttcgcca ccccacgcc ggccgcgctg ccgcctcgg      34800
cgggaaccgc cgtcccggac gtgccgccca acctcatccc ccagggcggc gcccaggaac      34860
tgaccccga catgctgccc ctggtcgacc tgaccggcga ggaactggcc accatcgtgg      34920
ccgcggtgcc cggcggcgct cccaacatcg ccgacatcta cccctagcc ccgctgcaag      34980
agggcatctt cttccaccac ctcatgaccg agggcgatgc caccgacgtc tacctcctgc      35040
cgcggattct cggcttcggc ggccgtcccg agctggacgc cttcctcggg gccctgcagc      35100
aggtggtgga ccgccacgac gtctatcgca cggccatcgc ctggcagaac ctgcgcgagc      35160
ccgtccaggt cgtgcaccgc cacgccaccc tgcccgtcac cgaagtcacc cccgaccagc      35220
tgcacgccgc cgccaccggc ggccggctcc cgctcgacca cgcaccctg ctcagcgtcc      35280
acatcgcacc cgaacccgac ggcggctggc tcgccctgct ccgcatgcac cacctcgtgc      35340
aggaccacac cgccctcgac atcgtcctcg acgagatccg caccatcctc gccggcgcaa      35400
ccgaccacct cccccgccc gtaccgttcc gcgacttcgt ggcgcaggcc cgcctcggcg      35460
tctcccgcgc ggagcaggag cgctacttcg ccggcctgct cggcgacgtc accgagacca      35520
ccgcccgta cggcctggcc gacgtgacga acgacggcac cgcatcggtg cgggccgagg      35580
tcgagctcga cgcggcctg gcggccggc tgcgcgacct cgcccgcgac cggggcgtca      35640
gcccggcgac ggtcttccat ctggcctggg cgcgcgtgct ggcggcggtg gccgaccggg      35700
aggacgtcgt cttcggcacc gtcctgttcg gacggatggc ctccggcgcc cggcgggtgc      35760
ccggcctctt catgaacacc ctgccggttc gcgtacgcct gtccggaacc gccgccgagg      35820
ctctgggaca ggtgcgcgac cggctcgccc agctgatggc gcacgagcac gcgccgctcg      35880
cgctggccca gcaggcgagc ggcctgcccg ccgggagccc gctgttcacg tcgttgttca      35940
actaccgcta tgcccggccg ccggccgcca cgccggacga tccgctggcg ggggtgcgca      36000
cgctgttcgc gtgggaacgc aacaactacc cggtcaccgt gtcgatcgac gacgacggca      36060
ccggattcgc ggtcacggtc gacgtcgtgg cgccggccga cgccgacgag gtcgtccgcc      36120
tgctccgcac gaccctgacc cgcctggccg ccgcccctcga acgcactccc gagatgccgc      36180
tggccgacgt gcggcccggc cgcgtgtccc ggcccgccgc cggccgcgcg gtgctcgtgc      36240
cggtcccggc cggcgagcgg gcgaccggcg cgggccgggc tccggccacg cgtacgagg      36300
agctgatctg ccaggcgtac gcccaggtgc tggaggttga ccgggtggcg gccgacgacg      36360
acttcttcgc cctgggcggc aactcgctgc tcgccacgcg gctggtcagc cggatccgct      36420
cggcgctggg cgtggaggtc accatccgcg cgctcttcga gacgctcacc ccgcaacggc      36480
tggccgcccg gctgacccgc gcctcggcac ccgggcgggt cgcacccgcg ccgaggacac      36540
ggccggagcg gattccgctg tccttcgcgc aacggcgcct gtggttcctg ggcgagctgg      36600
```

```
agggcagcag cgccacctac agcaacacga ccgcgctgcg gctctccggc gagctcgacc   36660
cggccgcgct caccgcggcg ctgcacgacg tgatcggccg gcacgaggtg ctgcgcacgg   36720
tgatcccggc cgaggacggc cggccgtacc agctggttct cccgcccgag gaggcacggc   36780
cggcggtgga gatcgtcgag gtcgctcccg gcgagcttgg cgcggccgtc gacgaggtgg   36840
ccggttacgc gttcgacctc gccgccgaga taccggtccg cgcccggctg atccggctgg   36900
gcgcgaccga ccacgtcctc gtcctggtga tccaccacat cgccaccgac ggatggtcga   36960
tggcgccgct cgcccgcgac ctcgccgccg cctacgaggc ccggctggcc ggccgggcac   37020
cgcgctggga gccgctgccg ctgcagtacg ccgactacgc gctctggcag gaggagttgc   37080
tgggcgcggc cggtgacccg gagagcctgc gcgagcgcca gctcgcctac tggcgcgaca   37140
ccctggccgg gatgccgccg gagatcccgc ttccggccga ccgttcccgc ccgccggtgg   37200
cctcgcaccg cggcggcgag gtgccgatcg ccatacccgc cgacctgcac cgccgcctgg   37260
ccgagctggc cgtcgccgag cgggccaccc tcttcatggt tctgcaggcc ggcttcgcgg   37320
cgctgctgag ccggctgggt gccggcaccg acgtcccgat cggcaccgcc ctcgccggcc   37380
gcaccgacga cgccctcgac gagctggtcg gcttcttcgt caacatgctt gtgctgcgca   37440
ccgacgtgtc cggcgacccc gggttcggca cgctgctgcg ccgggtgcgc gagaccggcc   37500
tcgccgcgta cgcccatcag gacgttccct tcgaccaggt cgtcgaggag ctggtgaccg   37560
agcgttccct ggcccggcat ccgctgttcc aggtggcgct gaccgtgcag aacgcgccgg   37620
gcgcgcggcc gcggctggcc ggcctcgaag tcggcaccga ccgatcgag cacggcatcg   37680 cccgctacga cctcacgctc accgtgaccg agcggcgcga cgagcacggc gcgccggacg   37740
gcctggaggg gcatctcgag ttcagccgcg acctgttcga cgcgccgacc gtcgcgaccc   37800
tcggcgaccg gctgatccgg ctcctcaccg ccgcggtggc cgacccggag ctgccgctga   37860 gccgatcga tctgatggcc cccgcggagc gccgcaacgt gctcgagggc tggagcaccg   37920
cccggcgcga cgtgccggcg gccaccgtgc cggagctggt ggccgcgcag gtggcccggc   37980
gcccgggtgc ggtcgcgctg cggtcggagg acggcgagat cacgtacgcc gagctggacg   38040
cgcgcgccgg gcggctggcc gcggtgctgc gccgccgcgg gatcgggccg gagtcgcggg   38100
tggccgtgct gttgccgcgc ggcgtcgagc aggtggtcgc cttcctcgcc gtggtgcggg   38160
ccggcggcac ctatctgccg atcgatcccg cgtacccgcg cgaccgcgtc gactacctcg   38220
tccgggacgg ggagccggcg tgcctgctga ccgtcgccgg gcatcgcgcg gcggcgccgg   38280
cggcaccggc ggtggtcgag ctggacgacc cggcgaccgc ggccgagatc gccgatgccg   38340
aaccggagcc gccggtcgcg gtgcggccca cccactccgc ctacctgatc tacacctcgg   38400
gctcgaccgg gcggcccaag ggcgtcgtgg tcacccaccg gggtgtggcc gcgctcgtgg   38460
ccacccaggc cgagcggctc gcggtgaccg gcgagagccg cgtcctgcag ttcgccagcg   38520
tgggcttcga cgcctcgatc tgggagatgg tgatggccct gtgcgccggc gccaccctgg   38580
tcgtcgcccc ggccgacgac ctgctgcccg gccggccct ggccgccacg ctgtccgggc   38640
acgcggtgac ccacgcgacc ctgccgccgg ccgtgctcgc cgcgtccgcg cccggcgatc   38700
tcgccgcgct cgccgtgctg gtctcggccg gtgaggcgct cgggccggac ctcgtccggc   38760
agttcgcgcc cggccgcgcg ctggtgaacg cgtacgggcc gaccgagacc acggtgtgcg   38820
ccacggcgtc cgccccgctc ggcccggagg atccccgca catcggcgcc ccggtcgccg   38880
attcccgggt ctacgtgctc gacgacgcgc tcaccccggt gccgcccggg gtcaccggcg   38940
```

```
agctgtacgt ctcggggcg tcgctggccc gcggatatgc cggtcgcgcg gccctcaccg   39000
cggaacgctt cgtggcctgc ccgttcgcgc cgggtgagcg gatgtaccgg accggggacc   39060
gggcccgctg ggacgcggcc ggccggctca cgttcgccgg gcgcgccgac gaccaggtca   39120
agatccgcgg gttccgggtg gaaccgggtg aggtggccgg ggtgctcggc gaacacccgg   39180
cggtcgcccg ggcggcggtc gtggcgcgca cggacgggcc gcaggcgcg cggctggtgg   39240
cgtacctcgt cgccgccgac ccggccgggc ccgacctggc cgctgcggtg cgcgcgtacg   39300
ccgccgcgac cctgcccgcg cacctgcttc cggccgcgtt cgtgccgctc gaccgcctgc   39360
ccctgaccac gaacggcaag ctggaccggg ccgcgctgcc cgaaccggag accggcgccg   39420
ggcgcgagcc gtccggcccc gtcgaacggc tgctctgcga ggcgttcgcc gacgtgctcg   39480
gcctcgaccg ggtcggcgcc gacgccact tcttcgacct gggcggccat cgctgctcg   39540
ccacccggct gctcagccgg ctccgctcgg ccgcgggcat cgacgtcccg gtccgggtgc   39600
ttttcgagaa ccccactccc gccgggctcg ccgcctgggt ggagaccac gccggatccc   39660
gccggaagtc ccggccggcg ctgcggccga tgcgtcacca gaaggagtcc tgatgatccc   39720
cctgtcgttc gcgcagcgcc gcctgtggtt cctcggccgg ctcgaggggc cctccgccac   39780
ctacaacatc ccgctcgtgc tgggcctgac cggcaccgtc gacgccgccg ccctcgaaac   39840
cgccctgcgc gacgtgctgg agcggcacga ggtgctgcgt accgtctatc cggacgccgg   39900
cggcgagccg caccagcgga tcctgccgct cggcgagacc ggcttcggcc tgcgggtcgc   39960
cgaggtgacg gacggcgagc tggacgcggc cgtcgcggac gccaccgggc acgccttcga   40020
cctcgcgacc gagatcccgg tccgggcctc gctgctcacc gtcgagccgg gccggcacgt   40080
cctggcgctg gtgctgcacc acatcgcggc cgacggctgg tcgatggggc cgctgctgcg   40140
cgacctgtcc accgcgtaca cggcccggct ggccggcggg gaaccggcct ggtcgccgct   40200
gccggtccag tacgcggact acgcgctgtg gcagcaggag gtgctcggcg ccggtgacga   40260
cccggagagc ctcctgcgcg agcaggtcgg ctattggcgg tcggcgctcg ccggagcccc   40320
cgaggagctg cgcctgccgg ccgaccaccg gcgcccgccc gtgtcgtcgt cccgggcgca   40380
catggccgag ttcgccgtgc cggccgccgc ccacggcgac ctgaccgccc tcacccgcga   40440
gctcggcgcc acgctcttca tggccgtgca cgcggcgacc gccatggtgc tttccgggct   40500
gggcgcgggc gacgacctgc cgatcggcac ggtggtggcc ggccgcaccg acgccggcct   40560
cgacgacctc gtcggctgct tcgtcaacaa cctggtgatc cgggccgacc tgaccggcga   40620
cccgaccttc gcggacctgc tgcggcaggt ccgcgagcgg gccctcgacg cgtacggcca   40680
ccaggacgtg ccgttcgaga agctcgtcga ggagctcgcg ccgtcgcggt cgctgagccg   40740
ccacccgctg ttccaggtgg ccgtcgccgt ggagaccgac gacctgatcg gcggtcgcgg   40800
cggcggtccc gccctgcggc tgcccggcct cggcatcgag gtgctgcccg gcgagccctc   40860
cgctcgcgac ctcgacctcg acctggtggt gcgcgagacg ttcgacgccg agggacgccc   40920
cgccggtctc accggggcac tgatcggcgc ggccggcctg ttcgacgccg tcggtggga   40980
gcggctggcc gcgctgctgg cccgcgcgct cgaggcgctg gccgccgacc cgcgcacgcg   41040
cgccggcgac ctcgacctgc tctccccggc ggaccgccgg ctgatcctgc gcggctggaa   41100
cgacaccgcg gctccggcgc cggccggact ggtgccggac ctgttcgccg cccaggccgc   41160
gcgcaccccg gacgcggtcg cggtcgccgg gcccgaccgg gagctgacct atgccgagct   41220
ggacgagcgc tccggccgcc tcgcgcgctg gctgatccgg cgcggggtcg ccgccgacac   41280
ccgggtcgcg ctggtgctgg agcgctccgc ggagctgccg gtggcgatcc tcgccgtgct   41340
```

```
caaggccggc ggcgcgtatc tgccgatcga tccggcgcag ccgccgcgcc gcatcgccga    41400
catcgtggcc gacgccgccc cggcgctcgt gctggcccag gcgtccaccg ccgacgtcgt    41460
ggccgacgcg tctccggcgc tcgtgctggc cccggcgtcc gacggtgtgc ccaccggcgc    41520
cgtgcccgtg cacctgctcg actcgcccgc cgtgcgtgac gaggtcgcgc agtgcccggc    41580
cggggccgtg accgacgccg accggcgggg cgtcctgctc ggcggtcacg cggcctacgt    41640
catctacacc tcgggatcga ccggacgccc caagggtgtc gtcgtttcgc acgacgcgtt    41700
cgcgaacctc gtcctggacc agcgccggct cggcatcggg ccgggcagcc gggtggcgca    41760
gttcgcctcg ccgggcttcg acatgttcgt cgacgagtgg tcgatggcgc tgctcgccgg    41820
cgccgccctc gtgatcgtgc cgccggagcc ccggctcggc gcggacctcg ccgcgttcct    41880
caccgagcgc ggggtcaccc acgccacgct gccgccggcg gtggtggcga cgctgccgga    41940
ggagtcgctg ccacgctcgt tcgtgctgga catcggcggc gacgcgctgc cggacgacct    42000
ggcccgccgg tggctgcgcg acggccggtg gctgggcaac tcgtacggcc cgacggagac    42060
cacggtcaac gcggcgacgt ggcgctgcga gcccggcacc tgggagggcg cgaccccgat    42120
cggccggccg gtcgccaacc tgcgggcgta cgtgctcgac ggccgcctgc ggccggtgcc    42180
ggtgggcgtg gagggcgagc tgtacgtctc gggcgccggc ctcgcccgcg gctatctgaa    42240
ccgggccggc ctgaccgccg gcagcttcgt ggcctgcccg ttcgagccgg gggagcggat    42300
gtaccgcacc ggcgacatcg tgcgctggga cgcgcggggc cgcctcgtct acgccggccg    42360
cgccgacgac caggcgaaga tccgcggttt ccgggtcgag ccgggcgagg tggaggccgt    42420
gctggccgcc ggtccggggcg tgaaccaggt cgcggtgatc gtgcgtgagg acgtgccggg    42480
tgacaagcgc ttggtggcgt acgtcgtggg cggcgacgtg gagaccctcc ggtcgtacgc    42540
gcagcagcgg ttgcccggat acctcgtgcc gtccgcgatc gtcgcgctgg ccgagctgcc    42600
gctgacaccg agcgccaagg tggaccggcg ggctctgccg gtgccggact acggccggga    42660
cgccggtggt gggcgggcgc cggccaacgc tcgcgaggaa gtgttgtgcc gggcgttcgc    42720
cgaggtgctc ggcgtcgagc gggtgggtgt ggaggacgat ttcttcgcgc tgggtggtca    42780
ttcgctgctg gtggtctcgc tggtggagcg gctgcgccgg cagggatct cggtgccggt     42840 gcgggcgttg ttcaccacgc cgaccccggc cgggctggcc gaggcggtcg gtgatggtgc    42900
cgtggtggtg ccgccgaacc tgattcccga gggtgcggcg gagctgaccc cggagatgct    42960
gccgctggcc gatctgaccg ccgacgaact tgctgttgtc gtggattcgg tgcctggtgg    43020
tgcggcgaac atcgcggatg tgtatccgtt ggcgccgttg caggagggca ttttcttcca    43080
tcacatgatg gccgaccggg attcggcgga cgtgtatgtg acgccgacgg tggtggagtt    43140
cgactcccgg gaccggttgg acggcttcct ggccgccttg cagcaggtcg tcgaccgtac    43200
ggatgtgtat cggacgagtg tggtgtggca ggggctgcgc gagccggtgc aggtggtgtg    43260
gcggcacgcg cgcctgcccg tcgacgaggt ggtgctgcgg gacgacctcg accggtcga    43320 gcagctgaac gcgctcggca cggcctggat ggacctgtcc gaggcgccgc tggtgcaggc    43380
cgtcgtcgcc gcccgccccg gcgatccgca gcgctggctc gccgtgctgc gcatccacca    43440
cctcgtgcag gaccacaccg ccctcgacat cctcctcgag gagctggcgg cgtacctggc    43500
cggccgcggc ggcgacctgc ccgagccggt gccgttccgc gagttcgtcg cgcacacccg    43560
cctcggcgtg ccccgcgagg agcacgagcg ctacttcgcc gggttgctcg gcgacgtcac    43620
cgagaccacc gcgccgtacg ggctcctcga cgtgcacagc ggcggtctcg cctcggcgca    43680
```

```
ggcccacctg cggctggacg gcccgctcgg ccggcgcgtg gccgccttcg cccgggaaca    43740
cggcgtcagc ccggcgacgc tcttccacct cgcgtgggcg cgggtgctcg gcacgctggc    43800
cgggcgtgac gacgtcgtct tcggcacggt cctgttcggg cggatgaact cgggcgccgg    43860
cgccgaccgc gttcccggcc tgttcatcaa cacgctgccg gtgcgggtgc ggctcggcgc    43920
gcccgtcggc gacgccctcg acggcctgcg tgaccagctc atcgagctca tcgcccacga    43980
gcacgcgccg ctggccgtgg cccagcaggc cgcgaacctc ttcggccggc cgctcttcac    44040
ctccatcttc aactatcggt acgcccgggg ggccgagccg gccggcgccg cgctcgacgg    44100
catccgcctg ctctccgccc gcgacctcac caactatccg ctggcggtgg ccgtcgcgcg    44160
ggagggcgac acgttctcgc tcaccgtcga cgcggtggcg ccggccgacc ccgtgcaggt    44220
cggcgagctg ctcgtcaccg cgctgcgcaa cctgacccgg accgccgaga cgcgcccgg    44280
aacgccgctg gccgcggtcg gcgtgctggg cgaggacgag ctgagccggg tcgtctccgg    44340
ctggaacgac accgcccgcc gggtccggca ggcgtcggtg cccgagctct cgcggagcg    44400
ggtggcggcc gcgcccggcg cgccggccgt cgccgccggg gacctgcgct ggacgtacgc    44460
ggacctcgac gcccgttccg acgcgctcgc gcggagcctg gtggcggccg gggtgaccgc    44520
ggagtcgccg gtcgtcgtcg ccctcgagcg ctccgcggac gtgctgaccg cgttcctcgc    44580
cgtcgcgaag gccggcggtg tcttcgtccc ggtggacctc tcctggcccc gggcccgcgt    44640
cgacgcggtg atcgccgact cgccgcctg gatcgcggtg gccgaccggc cgatgaccgg    44700
cctgaccgtc gtgcccgcca accgggccgg cgatcccgcg gtcgcgctgc cgccccgccc    44760
cctgccgggc gcggcggcct accggatgta cacctccggc tccacgggcc ggcccaaggg    44820
cgtggtgacg acccatcaga acgtcgtcga cctggtcacc gaccggtgct ggggcccgac    44880
gccgcgggtc ctgttccacg ccccgcacgc cttcgacgcc tcctcgttcg agctctgggt    44940
gccgctgctg accggcggca cggtcgtggt cgcaccgggg gagagcatcg acaccggtgt    45000
gctgcggcag ctgatccggg cccacgagct gacccacgtg cacgtcaccg cgggcctgtt    45060
gcgcgtgctg gccgaggacc cgtcgtgctt cgccgggctc accgaggtgc tcaccggcgg    45120
cgacgtggtc ccggccgagg cggtgcgccg cgtgctggac gccaatcccg gcgtgcgggt    45180
gcggcagctg tacggcccga ccgaggtgac gctctgcgcc acccagcacg tggtgcgcga    45240
gcccagcccg gtgctgccca tcgggcggcc gctcgacaac cccgcgtct acgtgctcga    45300
cgggcttctc cagccggtcc cggtcggtgt caccggcgag ctgtacatcg ccggcgccgg    45360
cgtggcccgg ggctacgccg acatgccggg caccaccgcc gagcggttcg tcgccgaccc    45420
gttcaccgcc ggcggccgcc tctaccgcac cggtgacctg gtccgctgga ccggcgaggg    45480
cgagctggtg ttcgccggcc gggccgacga ccaggtgaag atccgcggct accgcgtcga    45540
gccgggcgag gtggaggcgg tcctcgccgc gttgccgggc gtcagccagg cggcggtcat    45600
cgtccgcgag gacgtacccg cgacaagcg gctggtggcc tacctggtcg cggcgccgga    45660
gacggtcgag gccgcccgcg cccacgccga gcagcggctt ccgtcctatc tcgtcccgtc    45720
cgcgttcgtg cagctggacg cgctgccgct gaccggcaac cagaaggtcg accgggcggc    45780
gctgccggca ccgctgggt tcgaagccgg tgccggccgg gcgccggcgg acgcccgcga    45840
ggagctggtc ggcgccgcct tcgccgaggt gctcgacctc ggccgggtgg gcccgacga    45900
cgacttcttc gcgctcggcg ggcactcgct gctcgccctc gcgctggtgg agcgcctgcg    45960
ccggcagggc ctgggcgtct cggtgcgtgc cgtcttcgac gcacgcaccc ccgcggcgct    46020
gacccgccgc ggcgacggcg gtgccgacga ccggccggcg ctgcgggccg gtgcgcggcc    46080
```

```
cgcgcggctg ccgctttcct acgcgcagcg ccggctgtgg ttcctggccc agctggaagg      46140
accgagcgcc acctacaaca tcccggtcgc gctgcgcctg gagggcgacc tcgaccggga      46200
tgccctgacc gccgccctgc gcgacgtggt ggcccggcac gaggtgctgc gcacggtgtt      46260
cacggtcgcc gacggcgagc cgtggcaaca catcctcgac cccgcgcggg ccgagcccgc      46320
gttgccggtc gtggacgtgc cggccggccg ggtcgaggag gcggtcgccg aagcggccgc      46380
gtacgccttc gacctggccc gggagatccc gctgcgtgcc gtgctgctcg ccccggcga      46440
cggcacccac gtgctcgtgc tggtgctgca ccacatcgcg gccgacggct ggtcgatgcg      46500
gccgctggcc cgcgacctgg cgaccgccta cgccgcgcgg cggcggggc aggcgcccga      46560
gtcggagacc ctgcccgtcc agtacgccga ctacgccctc tggcagcgtg acctgctggg      46620
ctccgacagc gacccggcga gcctgatctc ccggcagatc gcccactggc gcgagcggct      46680
cgacggcgtg ccggaggagc tggacctgcc cgccgaccgg ccgcggcccg ccgcggcctc      46740
gcaccgcggc cacctgcaca gcgcggagat cccggccgac gtgcaccgga gcctgcgccg      46800
ggtcgccgcc gaccacggcg cgaccgtctt catgaccctg caggccgccg tggcggtcct      46860
gctgtcgcgg ctcggcgcgg gcaccgacgt cccgatcggc accgtcgtcg ccggccgcgc      46920
cgaccgggcg ctggagaacc tggtcggctt cttcgtcaac acgctcgtgc tgcgcaccga      46980
cctgaccggc gacccgcggc tgaccgacgt gctcggccag gtgcgcgagc tgaccctgcg      47040
ggcgctggcc caccaggacg tcccgttcga gaagctggtc gaggagctca ccccggcccg      47100
ctcgctcgcc cggcaccccc tgttccaggt catggtcacc ctggacggcg gcgggccgga      47160
cggcgccgag ctgccgggcc tggcgatgtc ggtcgtgccg accggcgccg ttccggccaa      47220
gttcgacctc gacctcacgt tcaccgagac cttcgacgcc gcggggagc cggccggcct      47280
gcgcgtcgac ctcatcgcgg cggccgacct cttcgacgcg ggcacggccg cccggctcgc      47340
cggctacctg agccgcgttc tcggcgtgct cgcggccgat ccgcggcgcc gcctggccga      47400
ggtcgacccg ctggaggcgg aggagagccg gctcatgctc gccgccggtg aggagcccgc      47460
gccgccctg cccgagatca ccgtcgcggg gctcgtcgcc gagcagtgcg cccgcacgcc      47520
gggtgcggtc gcggtgaccg gaccggacgc gagcctgacc tacgccgagc tcgacgagcg      47580
ggcggccccg atcgcccgct ggctgcgccg ccacggtgcc gggcccggcg cggccgtgtg      47640
cgtcctgatg aacggtcgg cggagctggt cgccgtgctg ctcggcgtga tgcgcgcggg      47700
tgcggcgtac gtgccggtcg accccgccta tccggccgag cggatccggt tcgtcgtcac      47760
cgacgcccgg gccgcctgcg tggtgagcga gtcggcctcg gccggcctcg tcccggacgg      47820
ggtgccgtgc ctggcgatcg acgacccggc cgccgccgcg gaaccggccg agcccggcga      47880
cgacccgggc gacgcggccg ggccgcggcc ggacgatccg gcgtacatca tctacacctc      47940
cggatcgacc ggcacccccca agggcgtcgt ggtctcgcac cgcaacgtcg tggcgctgct      48000
gaccgccacc cggccgctgt tcggcttcgc cggcgacgag gtgtggtcgt ggttccactc      48060
ggtcgcgttc gacttctcgg tgtgggagct gtggggcgcg ctcacccacg gcggccgggt      48120
cgtcgtcgtg ccctacgcgg tgtcccgctc gccgcgcgac ttctgggagc tcgtcgtccg      48180
cgagggcgtc accgtgctga gccagacacc gtcggccttc gcgcagctca tggccgcggc      48240
gggggacgac gaccgggacg cgctgcggtt cgtcgtcttc ggcggcgagg ccctcgaccc      48300
gggccggctg gccggctggc tggcccgccc cccggacaag ccgcgcctgg tcaacatgta      48360
cggcatcacc gagacgaccg tgcacaccac gtaccagcac atcgcgcccg gcacgacggg      48420
```

```
cagcgtcatc ggccgcggac tgcccggctt cggcctctac gtgctggacg aggcgctgcg   48480
cccggtgccg gccggcgtgc ccggcgaggt gtacgcccgc ggcccgcagg tggcccgcgc   48540
ctacatcggc cgccccggcc tgaccgcgga gcggttcgtc gcctcgccct tcgcgcccgg   48600
cgagcggatg taccgcaccg cgacgtggcc cgctggacc gccgacggcc gcctggtgtt   48660
cgccggtcgc tcggacgacc agatcaagat ccgcggtttc cggatcgagc ccggcgaggt   48720
ggaggccgtg ctggccgccg gtccgggcgt gagccaggcc gcggtgatcg tgcgtgagga   48780
cgtgccgggt gacaagcgct tggtggcgta cgtcgtgggc ggcgacgcgg agaccctccg   48840
gtcgcatgcc cagcagcggt tgccgggtta tctggtgccg tcggcgttcg tggagctgga   48900
ccggttgccg ttgacggtca acggcaagct cgatcgccgg gctctgccgg tgccggacta   48960
cggccgggac gccggtggtg ggcggcgcc ggccaacgct cgcgaggagg tgttgtgccg   49020
ggcgttcgcc gaggtgctcg gcgtcgagcg ggtgggtgtg gaggacgatt tcttcgcgct   49080
gggtggtcat tcgctgctgg tggtctcgct ggtggagcgg ctgcgccggc aggggatctc   49140
ggtgccggtg cgggcgttgt tcaccacgcc gaccccggcc gggctggccg aggcggtcgg   49200
tgatggtgcc gtggtggtgc cgccgaacct gattcccgag gacgcggcgg agctgacccc   49260
ggagatgctg ccgctggccg atctgaccgc cgacgaactt gctgttgtcg tggcgtcggt   49320
gcccggtggt gcggcgaaca tcgcggatgt gtatccgttg gcgccgttgc aggagggcat   49380
tttcttccat cacatgatgg ccgaccggga ttcggcggac gtgtatgtga cgccgacggt   49440
ggtcgagttc gactcccggg accggttgga cggcttcctg gccgccttgc agcaggtcgt   49500
cgaccgcacc gatgtctacc gcaccagcgt ggtgtggcag gggctgcgcg agccggtgca   49560
ggtggtgtgg cggcacgcgc gcctgccgat cgacgaggtc gagctgcacg agggcaccga   49620
tccggccgag cagctgatcg cgctcgccac cgagcgggtg gacctcgacc gcgcgccgct   49680
gatccgcacg acgaccgcgg ccgtgccggg atcggccgg tggctcgcgc ttctgcgcat   49740
ccaccacctc gtgcaggacc acaccaccct ggacgtgctg ctcggcgagc tgcgggcctt   49800
cctcgagggc cgcggcgacg agcttcccga gccggtgccg ttccgcgagt tcgtggcgca   49860
ggcgcggctc ggtgtgccgc gcgaggagca cgagcggtac ttcgcggagt tgctcggcga   49920
cgtcaccgag accaccgcgc cgtacggcct gaccgaggtg cacggcgacg gttcggccgc   49980
cgtgcacagc cggcgcgagg tggacgacga cctcgccgcg cgcctccacc ggctggcccg   50040
gtcgctcggc gtcagcccgg cggcgctctt ccacctcgcg tgggcgcggg tgctcggcgc   50100
cgtgtcgggc cgggacgacg tcgtcttcgg cacggtcctg ttcgggcgga tgaactccgg   50160
cgccgccgcc gaccgcgtgc agggcttgtt catcaacacg ctcccggtgc gcgtgcggct   50220
cgccgccggc agcaccccgcg acgccctgac cgggctgcgg gaccagctgg ccgggctgct   50280
ggtgcacgag cacgcgccgc tcgcgctggc gcagcgcgcg gccggcatca ccgacggcag   50340
cccgctgttc gcgtcgatct tcaactaccg ccacaaccag gacgacccgg cggcgtcggc   50400
cgggctcgag ggcatccgca cggtctacag cgccgagcac accaactacc gctcgacgc   50460 ctcgatcgac gtcaccggcg accgcttcgc catcaccgtg aacgcggtgg cgcccgcgga   50520
cgccgcgcgg atcgctgagc tgatgcacac ctgcctcggc cacctcgcgg acgtgctcga   50580
agacgcgccg gagacgccgc tgtcgtgggt cagcccgctg agcgcggagg atctcggccg   50640
catcgtgggc gactggaacg agacgcggcg cgcggtcacc cgcgcgtccg tgccggagct   50700
gttcgccaag caggtggccg ccacgccgga cgcgatcgcg gtggcgggcg agggtgtgtc   50760
gtggtcctat cgcgagctcg atgtgcgctc ggatgcgctg gcccggagtc tggtggcggc   50820
```

```
cggtgtgggt atcgagtcgc cggtggtggt ggcgctcgat cggtctccgg aggtgccgac    50880
ggcgttcctc gcggtggcga aggccggcgg tgtgttcgtc ccggtggact tgtcgtggcc    50940
ccaggcgcgt gtcgatgcgg tgatcgccga ctgcgccgcg cgggtggcgg tggccgaccg    51000
gccgatgacc gggctgacgg ttgtgcccgc cgacgcggcc ggcgacccgg ctgccgagtt    51060
gccgccccgc cccttgccgg gtgcggaggt ctaccggatg tacacctccg gctcgacggg    51120
ccggcccaag ggtgtggtga ccacccacca gaacctggtg gatctggcga ccgacacgtg    51180
ttggggtccg accccgcggg tgcttttcca cgccccgcac gccttcgacg cgtcgtcgta    51240
cgagatctgg gtgccgttgc tgaatggcgg cacggtcgtg gtcgcgccgg ggcggagcat    51300
cgatgccgcc gtgctcggcg agctgatccg ggcgcatgag ttgacgcacg tgcacgtcac    51360
cgcgggcctg ctgcgggtgc tggacccgtc gtgcttcgcg gggctgaccg aggtgctcac    51420
gggcggcgat gcggtgtcgg ccgaggcggt gcgccgggtg atggaggcga acccgggcct    51480
gcgggtacgt cagctgtacg gcccgaccga ggtgacgctg tgcgccacgc agcaggtgct    51540
cgatggcacg ggcgtgccga tcgggcggcc gttggacaac accgcgtgt atgtcctgga    51600
tgacttgctg cagccggtcc cggtcggtgt gaccggcgag ctgtatgtgg ccggtgccgg    51660
cttggcgcgc ggctatgcgg gcatgcccgg gttgacggcc gagcggttcg tcgccgaccc    51720
gttcagcagc ggcggtcgcc tctaccgcac gggtgatctg gtgcggtgga ccgatgacgg    51780
tgtgctggtg ttcgcgggcc gggccgatga tcaggtgaag attcgtggct atcgggtgga    51840
gccgggcgag gtcgaggctg tcttggccgc gcatccggac gtggctcagg tggcagtggt    51900
cgtccgggag gacaccccag gggataagcg gctggtcgcc tacgtcgtcg gcggcgatgt    51960
cgaggcgtat gcgcaggagc gccttccggg ctacctggtc ccgtcggcct tcgtccatct    52020
ggacgcgctg ccgctgacca gcaaccagaa ggtcgaccgg gccgcactgc ccgcgccgtc    52080
cgtggagtcc ggcgcgggcc gggcgcccgc cgacgcgcgt gaagagctga tgtgtgccgc    52140
gtttgccgag gtgctcgacc tggatcgggt cggtgtcgac gacgacttct tcgctttggg    52200
tgggcattcg ctgttggtgg tgcggttggt gggccgtatt cggcaggtgt cggggtgga    52260
ggtgtcggct cggctggtct tcgatgcgcg gactccggcc ggtgtggtgg cccgcttgtc    52320
cgagggcgga acgcccgggg aggcggtgcg ggcgcgggtg cgtcccgcgc gggtgccgtt    52380
gtcgttcgcg caacgccggt tgtggttcct gtcccagctg gacggcacga gcacgaccta    52440
caacatcccg gtcgcgctgc aactcgacgg cccgctcgat cgggacgcct tcaccgcggc    52500
actgcacgat gtggtcgccc ggcacgaggt gctgcgtacc gtcttcaccg tcgccgatgg    52560
cgagccgtgg caaacacatcc tcgacacgcc gtcggtgagc gtccccgtca tcgaggtgcc    52620
cgccgacggg cttccggagg cggtggccgc ggcggccgcg cacaccttcg acctgagccg    52680
ggagatcccg ctccgggcgg tgctgctcgc caccggcgcc gaccggcacg tgctggtgct    52740
ggtcgtgcat cacatcgccg ccgacggctg gtcgatgcag cccctcgccc gggacctcgc    52800
cgtcgcctac gccgcccgga tccggggcga ggcgccggcc tggaccgccc tgcccgtcca    52860
gtacgccgac tacgccctgt ggcagcgcga cgtgctcggc tccgagcacg acccggacag    52920
cgccatctcc cagcaggtcg cccattggcg gcgacagctc gccggagccc cgacgagct    52980
accgctgccc gccgaccacc ccgtcccgc cgaggccacc taccgcggcc acaccgtgga    53040
gttcaccgtg cccccggccg tgcaccacca actcgccgaa ctcgcccgcc gcaacggcgt    53100
caccgtcttc atgaccgtgc aaaccgccct cgccgtcctc ctgtccaaac tcggcgccgg    53160
```

-continued

| | | | | | |
|---|---|---|---|---|---|
| caccgacatc | cccatcggcg | tcgccgtcgc | cggacgcacc | gaccccaccc | tcgacaacct | 53220 |
| catcggcttc | ttcgtcaaca | ccctcgtcct | acgcaccgac | ctgaccggca | accccaccat | 53280 |
| caccgacctg | ctgcaccgca | cccgcgacac | cacccrgcac | gccttcaccc | accaagacgt | 53340 |
| cccctrcgaa | aaactcgtcg | aagacctcgc | acccaccccg | tccctcgccc | gccacccrct | 53400 |
| cttccaggtc | atgatgaccc | tgcagagcac | cgggcgggcc | ggcgaggcgg | ccgagctgcc | 53460 |
| cggcctggag | acggcggtgc | tgtcgccggg | cggcgtcgcc | gccaaggtcg | acctcgacct | 53520 |
| gagcctgagc | gaggcgtacg | acgacgacgg | ccgcccggcg | ggtctcgccg | gaacgctcgt | 53580 |
| cgcggcggcc | gacctgttcg | agcacggcac | cgccgagcgg | atcgccggtt | acctcgcgcg | 53640 |
| gctgctcgcc | gtgctgcccg | ccgatcccgg | cgcccggctc | ggcgacgtgg | acctgctcga | 53700 |
| cggcgaggag | cggcggctgg | tcctcaccgg | ctggaacgac | acgacggcgg | ccgtgccggc | 53760 |
| ggtggcggtg | cccgagctga | tcgagcggcg | tgccgccgcc | gaaccggagg | ccggcgccgt | 53820 |
| ctggtgcggc | gacacgcacc | tgcggtacgc | cgagctgaac | gcccgcgcga | accgcctcgc | 53880 |
| ccggctgctc | gtggagcgcg | gggcgggacc | cgagtcgatc | gtcgcggtct | gcctggaacg | 53940 |
| ctcggccgac | ctcgtcgtca | cgctgctggc | cgtgctgaag | accggggccg | cctacctgcc | 54000 |
| gatcgatccc | ggatatccgg | ccggccggat | cgcctacatg | ctcgccgacg | cccgccccgc | 54060 |
| gctgctcgtc | acgagcccgg | cggtcgcctc | cggtgacagc | ctcccggacg | gtggcgcgca | 54120 |
| acggatcgtc | ctcggcgatc | cggacaccgc | ggcggccctc | gacggcctcg | ccggcaccga | 54180 |
| cctgctcgtc | tcggagcggc | gcggcgtcac | gcacccggca | catccggcgt | acgtcatcta | 54240 |
| cacctccggg | tcgaccgggc | gccccaaggg | tgtcgtcgtg | ccgcacgggg | ccctcacgaa | 54300 |
| tttcgtggcg | gcgatgagcg | accggctcgc | gctgggcgcc | ggcgaccggc | tgctcgcggt | 54360 |
| caccacggtc | gccttcgaca | tccacgtcct | ggagctctac | gtgccgctgg | tcggcggcgc | 54420 |
| cggagtggtc | gtcgccgagg | acgccgtggt | gcgcgacccg | gccgcggtcg | ccgcgctcct | 54480 |
| cgaccggcac | gccgtgacga | tcgtgcaggc | caccccggcg | ctgtggcagg | cgctgctcgc | 54540 |
| cgggcacgcc | gacgccgtcc | gcgacgtgcg | gctgctcgtc | ggcggcgagg | cgctgccgcc | 54600 |
| cgcgctcgcc | ggccggatgg | ccgcggccgg | tcgcggtgtc | accaacctgt | acggcccgac | 54660 |
| cgaggtcacc | gtgtgggcga | ccgtcgccga | cctcggcgcg | agcccggccg | ggccggtgcc | 54720 |
| gatcggcacg | cccctgcgca | acacccgcgc | cttcgttctc | gacgacgcgc | tgcgcccggt | 54780 |
| gccgccgggc | gtgccgggcg | agctctacct | cgccggcgat | cagctcgcgc | ggggctacca | 54840 |
| cggccgggcc | ggcctgaccg | ccgagcgctt | cgtggccgac | ccgttcggcc | gcggtgagcg | 54900 |
| gatgtaccgc | accggcgacc | gggtccggtg | gacccgcggc | ggcagcctgg | agttcctggg | 54960 |
| ccgcgtcgac | gaccaggtca | agatccgcgg | tttccggatc | gagctgggcg | aggtcgaggc | 55020 |
| ggcgcttgcc | gcgttcgggc | cggtggcccg | ggcggccgcc | gccgtccgcg | aggacgtgcc | 55080 |
| gggcgaccgc | cggctcgtcg | gctatgtcgt | gccggccgcc | ggcgagccgg | agcccgaccc | 55140 |
| ggcggcggtc | cgcgcgcacg | tcgccgccca | gctgccccgcc | tacatggtcc | cgtcggcggt | 55200 |
| cgtggtcctg | cccgacctgc | cgctgaccgc | gaacggcaag | ctcgaccgca | aggcgctgcc | 55260 |
| ggcacccgac | tacggcgccg | cctccgccgg | ccgggcaccg | gccgacgagc | gcgaggcgct | 55320 |
| catctgcgcg | gtgttcgccg | agacgctcgg | cgtgaccgac | gtcgcagccg | atgccgactt | 55380 |
| cttcgccctg | ggcggccatt | cgctgctggc | cgtgtcgctg | gtcgaacggt | tgcgcgagca | 55440 |
| cggcatcgcg | gttccggtcc | gcgccctgtt | ccagtcgggc | accccgagg | gcctggccgc | 55500 |
| cgcggcccgc | gccgagggcc | cggacgagcc | ggccgtgccg | gccaacggca | tcccggacgg | 55560 |

```
cgccaccgcg ctcacgccgg cgatgctcac cctcgtcgac ctcgacgccg aggagatcgc   55620
ccgggtggtc gccgccgtgc ccggcggggc cgcgaacgtg gccgacgtct atccgctcgc   55680
gccgctgcag gaggggctgc tcttccacag cctgatggac ggcggcgacg acgtgtacgt   55740
gctgccggcc gtcctcggat tcgattcgcg gtcccgcctc gacgcgttcc tggccgcgct   55800
gcaacacgtg atcgaccggc acgacacgta ccggaccgcg gtggtgcacg acggcctgcg   55860
cgagccggtg caggtggtct ggcgccgggc cacgctgccg gtcgaggagg tgaccctgac   55920
cgcgggcgcc gacccggtgc aggaactgct cgccaccgcg ccggtcgagt tcgcgctcga   55980
ccgggccccg ctgctgcggg tgcgctgcgc ggcccggccg gacggcggcg gatggctggc   56040
gctgctccag atccaccacc tcgtccagga ccacgccacg ctcgacgcga tgctcgccga   56100
gatccaggcc ttcctcgccg gccgcggcgg cgagctcgcc gcgcccgagc cgttccgcgg   56160
ctacgtcgcc cggggcccgg ctgccggcgc gccggccgag caccgggcgt acttctcccg   56220
gctgctcggt gacgtcaccg agagcaccgc cccgtacggg ctgaccgacg cgcgggacgc   56280
gcggccgacc ggaaaggccc atcgcgaggt cgaccggcgg ctggccgccc gcgtgcgggc   56340
cacggcgagc gagctgggcg tgagcccggc gaccgtgttc catctcgcct gggcgcgggt   56400
gctgggcacg cttgccggcc gcgacgacgt cgtcttcggc accgtcctgc tgggacggct   56460
cggcgccggc gcccggtccg ggcgagccct cggcccgttc atcaacaccc tgccggtgcg   56520
ggtgcgcctc gccgccgccg gcagccgcga gacgctggcc gggctgcgcg cccagctggc   56580
cgagctgatc ggtcacgagc acgccccgct gacgctggca caggccgcga gcggcgtgcc   56640
cggcgggacg ccgctgttca cctcgatcct caactaccgg caggggccgc ccgccggcga   56700
cgacaccggc gacgaggaga tcgagggcat cgagctgctc tccaccgagg aacgcagcaa   56760
ctacccggtg gccgtctccg tcgacgacga cggttcgggc ttccggctca ccgtcgacgc   56820
ggcccagccg gccgcaccgg accgcgtcgc cgagctgctg cacacctgcc tgcaccggct   56880
caccgacgcg ctcgcgggca cgcccgacgt ggagccggcg cggatcgacg tgctcggcga   56940
ggcggagcgc cgggaggttc tccggacgcc gaacgccacg gcccgcgacg tggcggcggc   57000
gacgctgccc gcgatcgtcg gcgagtgggc gcggaccacg cccggcgcga ccgcggtcac   57060
cgccgagaac gaccggctca cgtacgccga gctggacgct cgcgccaacc gcctggcccg   57120
ctcgctgatc gcccgcgggg tcggtcccgg tgccgtcgtc ggcatgctcc tgccccgctc   57180
gccgggcctg gtggtggcga tgctggcgat cgtcaaggcc ggcggcgcct acctgccgct   57240
cgatcccggc tatccggcgc cccggctggc ccggatggtc gaggacgccg cgccggcgct   57300
gctgctggcc acgccggca ccgcggacgc cgtgcccgcc gggccgcagc gactgctgct   57360
ggacgacccc ggcaccgcgg cggagctggc ccggctggac ggcgacccga tccgcgacga   57420
ggagcgcacc caccccgctgc gccccgggca cccggcgtac ctgatgttca cctccggatc   57480
gacgggacgc ccgaagggcg tgctggtgcc gcacgccggc atcgaccgca tggtccgccg   57540 ctccaccctgc cttcagctgg caccggacga cgtcctgccg cacctctcgt cggtgtcgtt   57600
cgacgcggcc accttcgaga tctggggcgc gctgctcaac ggcgccaccc tcgccgtcgc   57660
accggcggag acgctctcgg tggccgagct gcgggccttc ctcgcggacc ggggcgccac   57720
caagctgttc ctcaccaccg gcctgctgca cgaggtgatc gacgccgacg tgaccgccct   57780
cgccggcctg aaggcggtct acaccggcgg tgacgtgctc tccccggcgc actgccggtc   57840
gcttctcgac cgggtgcccg gcctcgagct ctacaacgcc tacggcccga ccgagaacac   57900
```

```
caccatcacc acccttcatc gcgtacgccc ggaggacctc gacgcgggca cgggcgtacc   57960
gatcggcgtg cccatctccg acacccgggt gtacgtgctc gacgacgcgc tgcggccggt   58020
gcccgtgggg gtcgccggtg agctctacac ctccggcatc gggctggcgc acggctacgc   58080
cggacgaccg gcgccgaccg cggagcgctt cgtggcgtgc ccgttcgcac ccggtgagcg   58140
gatgtaccgc accggcgacc tggtgcgctg gaccgccgac gggcgcctgc tgttcgccgg   58200
ccgcgccgac aaccaggtca agatccgggg cttccgggtg gagccgggcg agctcgagac   58260
ggtcctgtcc ggacatccgg ccgtggcacg ggccgcggtg ctggcgcgcg aggacacgcc   58320
cggcgccaag cggctggtcg catacgtcgt gccggcccgg ccggacgagg acggggacgc   58380
gctggccgag tccgtgcgcg cctacgccgc ccggcaggtg cccgactatc tgatgcccgc   58440
cgcgacggtg gtgctcccgg acctgccgtt gaccagcagc ggcaaggtcg accgggccgc   58500
gctgccggcg ccggacgtgc cgggcgggcc gggccgcgcc gccggcacgc tcaccgagga   58560
gatcctctgc ggcgtcttcg cccaggtgct cgggctgccc acggtcggcg tcgacgacga   58620
cttcttcgcc agcggcggcc attcgctgct ggccacccgg ctggtcagcc ggctgcgtgc   58680
cgtcttcggg gccgagctgc cgatccgggc cgtcttcgag gcgccgacgc cggccacgct   58740
ggccacccgg ctcggcgcat ccgcgccgcg gcgactcgcg ctcggcgaac gcgcccggcc   58800
ggagaacgtg cccctgtcgt acgcccagcg gcggctgtgg ttcctcgacc gcctggaggg   58860
acaggacggc acctacacca tcccgctcac cgtgcggctc gacgggccgg tcgaccgggc   58920
ggcgctcgcc gcgccctgc gcgacgtcct ggagcgccac gaggtgctgc ggaccgtctt   58980
cccgctcgtg gacggcgaac ccgtccagcg ggtgctgccg gtgcacgaca ccggcttcac   59040
gctcggcgga ggtgacgtcg cggccgccga cctcggcgcc gcggtcgccg aggccacggc   59100
cggcaccttc gatctggccg ccgagatccc ggtgcgcgcc tggctgttcc gcgccgggcc   59160
cgaggaccac accctcgtgc tgctggtgca ccacgtcgcc ggcgacggct ggtcgatgac   59220
gccgctggcc cgcgacatcg ccaccgccta cgacagccgc cgcgagagcc gggcgccgca   59280
atgggagccg ctgcccgtgc agtacgccga ctacgcgctc tggcagcgcg aactgctcgg   59340
cgccgaggac gatccggaga gtttgctgtc gcggcagctg gcctactggc gggacgcgct   59400
cgacggcgta ccggaggagc tggacctccc ggccgaccgg ccgcgcccgg ccgaggccac   59460
gcaccgggga cacgaggtgc ccgtgcgggt gccggccgag gtgcaccggc gcctggccga   59520
gctggcccgg tccgagggcg tgaccgtgtt catggtgctg caggccgcct tcggcacgct   59580
gctgtcccgc ctcggcgccg gcgccgacat cccgatcggc acgcggtcg ccggccgcac   59640 cgaccaggcc ctcgacgagc tcgtcggggtt cttcgtcaac acgctggtga tccgggccga   59700
cctgtccggc gaccccacct tccgggagct gctcggccgg gtgcgcgcca ccggcctgtc   59760
cgcctacgag caccaggacg tcccgttcga gcggctcgtc gaggtgctgg caccggcccg   59820
atcgctcgcc cggcacccgc tcttccaggt catgctcacg ctgcagaaca ccggccgcgc   59880
ggacgccggc gaccaggccg tcccgccggc cgccggatcg gccgcggcca gttcgacct   59940 cgagatcagc atcgcggaga cgttcgccgc cgatggcgag ccggccgggc tcagcggcgt   60000
tctcatcgcc gccgccgacc tgttcgagcc ggccaccgcg gccgcgttcg ccgaacggct   60060
ggcccgcgtg ctggccgcgg ccggcgccga tccgcggctg cgggtcagcc aggtcgacat   60120
cctcagcgcc gaggagcgcg aggccgtcct gtccggcggc aacggcggca ccgcgccggt   60180
tcccgtcacc accgtcccgg cgctcttcgc cgagcaggcc cgccggaccc cgggcgcggt   60240
ggcggcgctg agcgagggga tgtcgctcac ctacgccgat ctcgccgccc gcgtgaaccg   60300
```

```
gctcgcccgg cacctggtga gcctcggcgc cggaccggag accgtcgtcg gtatcgccat   60360
gagccgcggc ctcgacatgc tggtggcggt cctcgcggtc gggcaggccg gcgccgccta   60420
cctgcccgtc gacccgtcct acccggacga gcgcaaggag ttcatgctca ccgacgccgg   60480
cgccgcgtat gtgctcacct tggcctcgga cgccgaccgc gtgccgccgg aaccccggc    60540
cgccgccgtg gtcctggacg agcccgtgac ggccgcgcgg atcgccgggc tcgatccggc   60600
cgacctgacc gacgccgacc gggtggcgcc gctgctgccg gcccaccggg cgtacgtcat   60660
ctacacctcc ggatccaccg gccggcccaa gggtgtcgcc gtcgagcacc gcaccgtggt   60720
caacctgctg tcctgggcgg ccgggcggtt cggcggcgcc gacttcgccc ggacgctcgc   60780
cgccacctcg ctcaacttcg acgtctcggt cttcgagatc ttcgggccgc tggtgtccgg   60840
cggcagcatc gagatcgtca ccgacctgct cgccctggcc gacccggcct ccccggcctg   60900
ggaggccagc ctggtcagcg gcgtgccgtc ggcgttctcg cgggtcctcg accggggcga   60960
catcgccgcg cgcacccgca gcgtggtgct ggccggcgag gcgctgaccg ccgacgtggt   61020
gaacgccacc cgtgccgccc tgcccggtgt ccgggtggcc aacatctacg gccgaccga   61080
ggcgaccgtc tactcgaccg cctggcacac cgaccgggac gtgaccggcg gcgccgcgcc   61140
gatcgggcgg ccggtcacca acacccgcgc ctacgtcctc gacgaccgtc tcacgccggt   61200
gccgccgggc gtggtgggcg agctctacct ggccggcgcc cagctggccc gcggctatct   61260
gggccggccc ggcctgaccg gcgagcgctt cgtggcctgc ccgttcggcc gggcgggga    61320
gcgcatgtac cgcaccggcg accgggtccg gtggaacgcc gacggcgacc tggtcttcgc   61380
cggccgggcc gacgaccagg tcaagatccg cggcttccgt atcgagccgg gcgaggtgca   61440
ggccgtcgtg gcgcgccagg ccggcgtggc ccgggcggtg gtgctggccc ggagcgactc   61500
gcccggcgac gcccgcctgg tcgcgtacgt cgtgccggcc gaccgggacg ccgaccgccg   61560
ggcgctgggc gccaccgtcc gctcggacac cgcgcgcgct ctgccggcgt acctggtgcc   61620
ggcggccgtg gtggtcctcg acgagctgcc cgtcacggcc aacggcaagc tcgatcgccg   61680
tgcgctgccc gcgcccggcc tggccgaggc gggcagcggc cgcgggccgg tcacccaccg   61740
cgaggaggtg ctctgcgagg tcttcgccca ggtgctcggc ctgccctcgg tcggcgtgga   61800
cgacgacttc ttcgcgctcg gcgggcactc cctgctggcc gtctcgctgg tggagcagct   61860
gcgccgccgc ggcgtgacgg tcgggggtgcg cgcgctcttc cagacgccca cggtcgccgg   61920
cctggccgag gcggccgcgc ccaccacggt cgccgttccg cccaacctca tccccgagga   61980
cgcgcggcac atcacgcccg gcctgctgcc gctcgtggag ctggagcagg ccgagatcga   62040
ccaggtcgtg gccactgtgg acggcggcgc cgccaacgtg gccgacatct atccgctcgc   62100
gccgctccag cagggcatgc tcttccacca cctcatggcc ggcgacgacg gcgaggacgt   62160
ctacatcatg cccgcggtcg tggagttcga ctcggcggac cgcttcggcg ccttcgtcga   62220
cgccctccag cacgtgatcg accgcaacga cgtctaccgc accggcgtgg tctgggacgg   62280
cctgcgcgag ccggtgcagg tggtctggcc ccgggcgccc ctgccccgtga ccgaggtgac   62340
gctcgatccg gccggcggcg atcccgccgc ccagctgcac gccgccgccg gcgcccggat   62400
ggacctgaac cggcgccccc tgctcgacct ccacgtggcc gcccgccccg aggacggcca   62460
acggctggcc ctgctgcggg ttcaccacat ggtgcaggac cacatggggc tcgaggtgct   62520
cctcggcgag gtgcaggcgt tcctggccgg ccgcggcgac gagcttcccg atccgctgcc   62580
gttccgcgac ttcgtggcgc agacccgcgg cggggtgccg gaggccgagc accggcggtt   62640
```

```
cttcgccggg ctgctgggcg acgtcaccga gcccaccgcg ccgtacggcc tgctcgacgt   62700
gcaccgcgac ggcgtcggcc tggtgcgcca ggaacgcccg ctcgacggtg aggtggtggc   62760
ccggctccgc gccgtggccc gccggctcgg ggtgagcccg cgaccgtca tgcacgtcgc    62820 ctgggcgcgc gtgctcggcg tgatctccgg ccgcgacgac gtggtcttcg gcacgctgct   62880
gctgggccgg ttcagcaccg cgccgaccg ggtgcccggc ccgttcatca acacgcttcc    62940
ggtgcgggcc cggctcggcg gcacgggcgc cgcggcggcg gtggcggaga tgcgccggct   63000
gctggccgag ctgctcgagc acgagcacgc gccgctgacc acggcgcagc aggccagcgg   63060
actctccgga aacctcccgc tgttcacggc gctgttcaac tatcggcaca acacgtcgcc   63120
gggtgcggac ccgtcgcccg cggccggccc gaccgagggc atccgcccgg tctccatgcg   63180
ggagcgcacc aactatccga tctcggtggc ggtggacgac gacggcgagg gcctcggcgt   63240
ggcggtcaac gcgatcccgc cggtgcggcc ggaggcggtg tgcgagctcg tggcgaccgc   63300
gaccgagagc ctgacctcgg cgctggagct gttcctcgac ggcggtccgg acaccgcggt   63360
cggcgagctc gacgtgctgc cgccggggga gcggtcgcgg ctgctggtgg agtggaacga   63420
cacggctcgt ccggtggtgg agtcgtcggt gccggcgttg ttcgccgagc gggtggcggc   63480
cgcgccggat gcggtcgcgg tggtgggcga gggtgtgtcg tggtcctatc gcgagcttga   63540
ccgtcgctcg gatgtgctgg cgcggagtct ggtggcggcg ggtgtgggcc tggagtcgcc   63600
ggtggtggtg gccctcgaac ggtccgccga cgtgctgacc gcgtttctcg ccgtcgcgaa   63660
ggccggcggt gtcttcgttc cggtggactt gtcctggccg cagacgcgta tcgatgcggt   63720
gatcgcggac agccggccgg ttctggtgtt ggacagcgtg gatctgccgg ccgcggaggc   63780
cgacctgccg cgggtgccgg ccggtgcggg cgtgtatcgg atgtacacct cgggttccac   63840
gggccggccc aagggtgtgg tgaccaccca ccagaatctg gtggatctgg cgaccgacac   63900
gtgttgggga tcgacgccgc gggtgttgtt ccacgcccg cacgccttcg acgcgtcgtc    63960
gtacgaaatc tgggtgccgt tgttgaatgg cggcacggtc gtggtggccc cgcggcgcag   64020
catcgacgcc accgtcctga gggacctggt ccgcgggcat gagttgacgc acgtgcatgt   64080
gaccgcgggc ctgttgcggg tgctggaccc gtcgtgcttc gcggggctga ccgaggtttt   64140
gaccggcggg gatgccgtgt cggcggaggc ggtgcgccgg gtcaaggaag cgaacccggg   64200
tctgcgggtg cgccagttgt acggcccgac cgaggtgacc ttgtgcgcca cgcagcatct   64260
gctggatgac ggggtgccga tcgggcggcc gttggacaac acccgcgtct acgttctcga   64320
cgacctcctg cggccggtcc cgacgggtgt ggtggggag ctgtatgtgg ccgggtcggg    64380
tctggcgcgt ggctatgcgg gcatgccggg tttgacggcc gagcgatttg tcgccgaccc   64440
gttctcggtg ggtggtcgcc tctaccgcac cggtgatctg gtccggtgga ccgacgacgg   64500
tgtgctgcac ttcgccgggc gggccgatga tcaggtgaag atccgcggct atcgggtgga   64560
gccgggcgag gttgaagcgg ttctggctca acaccccgac gtcagccagg tcgcggtcgt   64620
cgtccgagag gacgcgccag gggataagcg gctggtcgcc tatgtcgtcg gcggggatgt   64680
cgaggcgtat gcgcaggagc gccttccggg ctacatggtt ccgtcggcct tcgtccatct   64740
ggaagcgctg ccgctgaccg cgaaccagaa ggtcgaccgg gccgccctgc ccgcgcccga   64800
gcgggagacg acgacaccgg gtaaggcacc cgccccgga ccgctcggca acctcgagga    64860
gtcgatgtgc caggcgttcg ccgaggtgct cggcctcgac agcgtcggcc cggacgacga   64920
cttcttcgcc ctgggcggcc actcgctgct cgccgtcgcg ctcgtgcagc ggctcaaggc   64980
acgcggtgtc gccgtcacgg tgcaggacat catggccgcg cccacggtct cggagctgat   65040
```

```
gggctcgctg agcatgtcgt cgatccggga ctccctcggc acgctcctgc cgatccggcg  65100
caccggcgag ctgccgccgc tgttctgcgt ccatccggcc ggcgggctca gctggtgcta  65160
cctgccgctg gccggcacg tgccggccga ccgcccgatc tacggtctgc aggcgcgcgg  65220
cgccgacggc cgggagccgc tcgcaccgtc gctgcgcgag atggccgccg actacgtgag  65280
ccggatgcgc gccgtgcagc ccgaggggcc gtaccacgtg ctcggcttct ccttcggcgt  65340
ggcgcccgcg cacgagatcg ccgtccagct gcgcgagcag ggcgccgagg tcgtgctggt  65400
gctcatggac tcctatccca tggaggatgc ggagtccggc gagcaggcgg ccgacgagga  65460
ggagctgccg tgggaggagc tcatcgaggc cgagttcggc cgggtgctcg gcggcttctc  65520
ccgcgacgaa ctggcggcct tcgccgccgt cttccgcaac aacaccaaga ttcgcgcacg  65580
ccaccggctg ggccgcttcg acggggacgc cctgctgatc gcctcgaccg acagcgcacc  65640
cgacggcgag tccaacacct ggcggtgggc gccgtacatc accggtgaga tcacccaggt  65700
ggtgctcccc tgcgagcaca ccgacctggt acgccccgac atgctcgcgc tgctctggcc  65760
ggccgtcgag gcgtggcagg ccgggcggca ccgaccttag tcaccacagc gtcgagagga  65820
ccgacatgca gaagatcccg ctcgtgtgtg tgccgttcgc cggtgccggc gcctcgttct  65880
tccacccgtg ggccgagctc gccgggccgg accggccgat cgtcgcgctc cagcttccgg  65940
gccgggagtg gcggctgctc gacgaaccgt acgcggacgt cgtcgcggcg gccgcggacc  66000
tggcgctcac cgtcgccgac gaggtgggcg cgggggggccg ggtggcgctc ttcgggcaca  66060
gcctcggcgc cgtcctcgcg tacgagatag cgcacgcgct ggtgcgcgac ggcgaggtgg  66120
gcgtggagcg gctcttcgtc agcggctcgc ccgatccctg gaccccctcgc accaaccggg  66180 cgagcggcct ggacgacgag gagttcctgc tgcgggtgcg cgagttcgcc ggttacgacc  66240
acgaggcgct cgccgatccg gacatgcgcg agctgatcct gccgcgcgtg cgcgccgacg  66300
tcgagatgca cgagagctac gtggcgggca gcgccgatcc gctgcccgca cccgtcaccg  66360
cgctgcacgc ccgcgacgac gcgctggtct ccgccgagca gacggccggg tggagcaagg  66420
ccaccagcgg cccgttccag ctggtcgagg tggacggcgg ccacatgtac ctcaccgagg  66480
acccggccgg cctgctgcgc ctgatcgccg ccgacctgga ccgtgactga acccgaggag  66540
aacccgtgcg cttgaccggc aagaccgcca tcgtcaccgg cgcggccgc ggcctcggcc  66600 gcgcctgcgc cgtggccttc gccgccgagg gagccgacct ggtgctcctg gaccgcgcgg  66660
ccgacctgcc gggggtgccc tatccgctgg gcaccgtggg ccagctggag cacaccgccg  66720
acctctgccg caagcagggc gccgcggtgc tcaccgtccg ggcggacgtg cgcgacctcg  66780
cggcgctcac cgcggcggcc gatcgggcga tcgaccgctt cggcggcatc gacgtgctcg  66840
tcaacaacgc gggcatcgcc gcgccgtccg gaaaggtcac ccacgagatc accgaggacg  66900
agtggcagct gatgatcgac gtcgaccctct ccggcgcgtg gcgcatgacg gcggcggtcg  66960
gccggcacat gaccgagcgc cgctcgggca gcatcgtcaa catcgcctcg acggccggtc  67020
aggtcggcta ccggcacttc gccggctacg tcgccgccaa gcacggcatc gtcgggctca  67080
cccgggccgc cgcgctcgac tacgcgccag cgaaggtgcg ggtcaacgcc gtctgcccgg  67140
gttcggtgcg cgacgatccg cagttcgagg gccggatgct gtcggagatc gcccggtcgc  67200
tcgacgtgcc ggtcgccgag cacgagcaga ccttcctgca ggcgcagccc atgaacgccc  67260
tcatcgagcc ggacgacgtc gccaacgccc cgatctggct cgcctccgac gaatcgcgcc  67320
aggtcaccgg ctccgtcgtc acggtcgacg gcggattcac cacgcgctga acggggagaa  67380
```

```
gacgtgccca agtcccagcc cgccaccaga accgcggcgc ccggcgccgc cgagtgccac    67440
gcgcttgccg tgcgcctggc cggaccgatc gacccgcgcg cgatcgagcg gcggctcgcc    67500
gcccgcatgc cgttctggca cgagcacgtg cgggcccggc cgggcgatga ggccgcgctg    67560
cgccgccgcg agcgcgaact cgcccgcccg gtgccgccgg agcccggtgc gcgggcggtg    67620
ctgctcgcct acgcggacgg ctcggccgac ctggtgctgg tggcccgccg cgaccgcctg    67680
gaccgcgacg cgctgatcgc cctggcccgc ccggagcggg cgccgcgcgg cgcaaaccg    67740 gcggaaccgg acgcgccgcc gccctcggcc gcgcccgcct ggggcctggg cgacggcggc    67800
ccggacgacc ggtgggccga gctgcgcgtg ccggcgcgcg gcccggccga cccggcgcgc    67860
tggcccgccg cgctcgccaa ggtcctcgcc cggtacgagc cgggcgcggc tgcgggctcg    67920
ggcgcggcgc cgggcttggg cgcggcggcg ggctcgggtg tggcggcggg ctccagcgcc    67980
gcctcgggct ccggcgccgc cgcggtcccc ggcccggtgg cgctggcctt cgacggcgac    68040
ctcgccccgc cggacgagta cgtgcccttc ctggcgccca cccacccgct caccgtgcag    68100
gtctcccgga cgcccggcgg cggcaccgag ctgcggtgcc gccaccggct cggcgcggtc    68160
tcgccggccg ccgccgaagc gttcgcccgg atgctggccg cggcacacgg cgagccgccg    68220
gccgatgacg gcgcgaccgc cgagcccacg ccgccggccg cacccgcacc cgcacccgca    68280
cctgcgcccg cgccgccggc tgcggctcgc acgctgaccg ggctcttcgc cgagcaggtc    68340
gccgctcgtc ccacggccgt cgccgtctcg gacgatcggg gtcggcacac ctaccgcgag    68400
ctcgacgagt ggtccggccg gctggcccgg gggctgcgga aggccggcgt gcgcgacggc    68460
gacgcggtcg gcgtctgcct cgaccgctcg gccgagctcg tcgccgtgct cctcgcggtc    68520
ctcaaggccg gcgccgccta tgtgccgctc gacgcggcgt accggccgga ccgcatcgcc    68580
tacaccgtcg gcgacgccgg cctcgcggtc gtggtcacca cctcggcgga ctttcccgac    68640
gtggacggtg tgcggctgct cgcgccggag agcctcgccg aggccggcga cgacccgggc    68700
atcccgctcg ccaccccggc cggcccggag cggccggcct atgtcatcta cacgtccggt    68760
tccacgggcc ggcccaaggg cgtggtcgtc ccgcacgcca acgtgtccgc gctgctcgac    68820
gccacgcgcg aggagtacgc gctcggcccc ggcgacgtgt ggaccttctt ccactcggcc    68880
gccttcgact tctccgtctg ggagatctgg ggctgcctgc tcaccggcgg ccacctcgtc    68940
gtcgtcccgt actgggtgtc ccgctcgccg gagcagttcc acgacctgct cgccgagcgc    69000
ggcgtcaccg tgctcaacca gacgccgtcc agcttcacgc agctcgtggc cgccgaccgc    69060
ggggcggagc gcgacctcgc cgtacgcctg gtgattttcg gtggtgagcc gctcgacgcc    69120
cggacggtgc tgccctggct ggaccgccgt cccgaggcgc gctgccggct ggtcaacatg    69180
ttcggcatca ccgagaccac cgtgcacgtc acggcggtca cgtcacgcg cgcggccgcg    69240 ctcgccggct cccggtcggt cggccgcccg ctgcccggct gggccgtgcg cgtgctcgac    69300
gagcagcgcc gcgaggtgcc gccgggcgtg ccgggcgaga tctacgtggg cggcgccggc    69360
gtggcgatcg gctacctcaa ccgcccggag ctgaccgccg agcggttcgt caccggcccg    69420
gacggccggg gctggtaccg ctccggcgac cgcggccggc tgctgcccga cggcaccctg    69480
gaacacctgg gccggctcga cgaccaggtc aagctgcgcg gcttccggat cgagctggac    69540
gagatccggg gcgtgctcac cgagtgcgcc gggtggcgg cggccgcggt cgtcatccgg    69600
cgctccactc cggacgatcc ggcgaccgcg cggctcgacg cgtacgtggt cgccgaggcc    69660
ggcgccacgc cgccggtggc cgagcacgcg gcccggatgc tgccggccta catgtgcccg    69720
gcgaccttca cgttcctgga cgcgctgccg atgacgccga acggcaaggt ggacaaggcc    69780
```

```
gccctgcccg agcccgcgcg cccggccgcc gacgctgcgg cgacgccggc cggcccgggt    69840
gaggacgggc tcgcgggcga cctggccgac gtgtggcagc aggtcttcgg ctgcccggtg    69900
accgtctcgg acaacttctt cgacctcggc ggcaactcgc tgctcgccgt gcggatggcc    69960
gcgctgatgc gccgccgcgg cctgccccgg ctgcatccgc gcaccctcta cctgcacccc    70020
accgtgcgcg gcctcgcgga cgcgttgcgc tcggcctgac agtcccctcg cccccctcgag   70080
aagtacggga gaagcaccat gcgaaacctg cgtcggacca ccggcatcgg actgctcgcg    70140
ctgctgagcg tggcggcgtg cagctcgacc cccgcggcga gcgagccccc gccgtccgcg    70200
gcgccgccct cggccgtgac ggccaccggc ccggcggccg agaaggccgt caagtcgggc    70260
acccagacct atcaccaggc gctcgacgcc ttcgtcgcgg cgagcaacaa gggcacgacc    70320
gacaccaccg agatcggcaa gtacgcgtcc ggccgggcgc tgatgacctt ccagggcatc    70380
ctcgcctcct accagcagca gggcgtgcac accagcggcg agccgcgcat cgacgagccg    70440
gtcgtcaccg ggctcacccc gccggccgac cccaccggcg tccagctgcg cggctgcatc    70500
gacatcagcg cctggccgct gacgaaggcc gacgggaccc cggccgacaa ggtgggcggg    70560
cagcagggca gcgggcccag cgcgatcctg gcgaacgtcg cccgctcggg tgccacctgg    70620
caggtgaccg agctggccat ccagggaccc tgcgcggcgt gaccgtccgg cgatggctac    70680
cggccgggct cacggtcctg gcgttcgccg ccggcttctg gcagaagctg ccctgccagg    70740
ccgctggctg gccggacgac accgcgacgc tgttcggccg ctactgctac agcgacgtgc    70800
cgattctctt ccgggagcgc ggccttttcg acggcatttt cccgtacgag tccgggccgg    70860
gcgcccagcc gctggagtac ccggtcctca ccggctacct gatggacgcc acggcccggc    70920
tcgttcgcgc gatcctgccc ggcgcggacg tggccgtcgc ctcccgggcg tacttcctca    70980
cgacggtcct ggtgctgctc gccctcgcgg tcctgaccgt gtgggcgacc ggtgcggtgc    71040
tgcgccgcac cggcgggcgg ccgggcgacg cgctgctggt cgccgccgca ccggtgctga    71100
tcctggccgg cacggtgaac tgggacctgc tcgcggtcgc ggcggcggtg ctcgcgatcc    71160
tcgcctggga acgggaccgc ccgctgctgg ccggcgtgct gatcgggctg ggcacggcgg    71220
ccaagctgtt cccgctggtg ctgctcggcc cggtgctgct gctctgcctc cggcagcggc    71280
ggatgcggcg gttcgcccgc gtggccgccg gtgccgccgg ggcctggctt ctggtcaacc    71340
tgccggtggt cgcgctgcaa ccggacggct ggatggagtt ctggcggttc aacgccgggc    71400
gcggggccga gttcgggtcg ctctggttcg cgctggacgg gctcggcctg cacatgccgg    71460
cggtgaacgc cgtcgccctg gcgacgttcg gcgtgctgct ggccgggatc gcggtgctgg    71520
ctctgcggtc gcgccggccg ccggacctgg cgcaactcgc ctgcctggcc gtcggcgcgt    71580
tcctgctgac caacaaggtc tactcgccgc agtacgcgct ctggctcctg ccgctcgtgg    71640
tgatcgcccg tgggcgggtc ccggcggtgg cggtggtgcg cgactgggcc gtctggcagg    71700
ccgccgaggt gctctactgg ctcgcggtgt ggagctggct cgccggttcg ctgaccgacg    71760
agcggcagta cgcctgggca accgtcctgc gcgtgctcgc cacggcgtac gtctgtggtc    71820
aggtggtgtg ggacgtgctc gccgcccctc gcccgcaccg gccggcgccg cccccggcgg    71880
tcgccgagcc ggcccacccg ggctgacccg ggcaacgaga gatcccctcg ccgccggcgg    71940
cgagggggatc tctgttcgtg tgctcagtcg gcggcgaccc acgtgaggcc gttgccggaa    72000
ggggtcagcc cgcccctcgaa cagcggctgc tcctgcgtgc cctccgggcc caggatcgcg    72060
ccggcctgga tctgcgagcc ttcgaacatg gcctgcgcca cgacgctcga cccgcgcagg    72120
```

```
aagccggtgc cgccctcctc gaggccggcc accgcctggc ccagctccgc ggtctgccgg   72180
gagtgccgcc gcaccagctc ggtggagccg gtcagccgcgt cctcgccgga ggcgatgccg   72240
ccgaccaact cggtgaacga ctccatggcc ggtgcgctgc tctcggtcac cttgcgggcg   72300
gcccagaagt acgagctctc atcgacgtgc atgtcgtaga agctcaccag gaagtcgtgg   72360
aagacgccga actcgcgccg gtagcgctgc tcgaactcgg tgaaggcgcg gtcctcgtcc   72420
accgtgccgg ccagcacgct gttgatggag cgggccgcga gcaggccgct gtaggtcgcc   72480
aggtgcacgc cggaggagaa caccgggtcg atgaagcagg cggcgtcgcc gaccaggcac   72540
atgcccggcc gccagtacga ggtgctggag taggagtagt ccttgcggac ccggatctgg   72600
ccgtagtcgc cctcggtgac ccgggtggcg tcaccgagga agtcggcgat catcgggcac   72660
tcggcgatca gctcgaacag cgccttctcc tggtcgccct gcaccttgtg tgccatctcc   72720
cggcggacca ccgcgccgac gctggtcagc gtctcgctga gcgggatgta ccagaaccag   72780
ccggagccga aggcgacgca gaggatgttg cggagttcg gcgcgggcag ccgccggccg   72840
ttctcgaagt agccgaagag cgcgaggttg cggaagaacg gcgagtattc gcgggtgccg   72900
ccgaccgtcg tgtgcagggt gctgcggttg cccgaggcgt cgacgacgaa gcgcgccagc   72960
gcggtgcggg tctgcccgtc ctgggtgaaa cggacgccgc ggacccgctc gtcgtcggcg   73020
atcgcctcgg tcaccgggtg gttctcccgg acgtcgacgc ccagccggcg cgcgttctcc   73080
agcaggatct ggtcgaaccg gcggcgctcc acctggaacg cgtgcgaggt cggcccggcc   73140
atccggggcg aggtggcgaa ggtgaacgtc cacggctcgg tactggtgcc ccacttgaac   73200
gtgccgccgt gcttgcgcat gaacccggcc ttggcgatct cgtcgccgac cccgagcagg   73260
ttgcagacac cgtgcacggt ggacggcagc agcgattcgc cgatctggta ccgcgggaac   73320
ttctcccgct ccagcagcag caccttggcg ccctgcttgg cggtcagcgc cgcggccgtg   73380
gaaccgcccg gcccgccgcc gaccacgatg acatcgaact cttccggttg agcagccacg   73440
aatcctcctc agcgaccatc tgagctgcat gatggttgcc gcgggccgct gtgcgccacg   73500
tgtccgccca cccgcggcgt tcgaccgcgg atgtcgccgg tcgcacgctc gcgcgggccg   73560
ggtcagctcc cctcgaccag ccggttctcc caggcccagg ccgccacgcc gacccggttg   73620
cgtacgccca atttggactg gatcgtggag gcgtgcccct tcaccgtgct cagcgagatg   73680
aagagatcgg ccgcgatctc ctggttcgtg cggccgcggg cgatcgcccg cgccacctcg   73740
agctcgcggt cggagagggg aatgggctcg gagccggccg gcgccgccga ggcgttcagg   73800
tggttcagca gccgcacggt gaccgacggc gagaccagcc cgtcgcccctt gtgcgccgcc   73860 cggacggcct ccaccagcag tgtcgggccg gcgtccttga ggatgaagcc gaccgccccg   73920
ccgcgtagcg cgccgtagac gtattcgtcc gagtcgaacg tggtgaccac gatgaccgc   73980 agaggattga ccacgccggg gccggccagc gagcgggtca cctcgatgcc gtcgatgcgg   74040
ggcatgcgga tgtccaccag gcacacgtcc ggccgcagct tgcgcgcctg tgcgaccgcg   74100
tccacgccgt cgacggcctc ggccaccacc tcgatgtcgg gctcgtcctc gaggatcagg   74160
cgcaggccac tgcggatcat cgcctgatcg tcggcgatca ggacacggat cgtcatcgtc   74220
gctccctcgg tgggttgggc agggtggccg cgaccgacca gccgccgccg gacgggggc   74280 ccgtgctcag cgtgccgccg aggctctcca cccgctctcg catgccgacc agaccgtacc   74340
cgccgcggtg gtgcaaccgc ggtggggccg ccgccgcgtc gttggtgacc tcgaccctga   74400
tctcgtcggc ctgctccacg gtcacggtca cggtcacgtt gggtgcgtgc ggcgcgtgcc   74460
gggcgacgtt ggtgagcgcc tcgcggacga tccggtagac cgtggtggtc acctcgatcg   74520
```

```
gccactgctt catgccgtcg ggagtggtga gccgcaccgg gccgccctgc cgggagaagc   74580
gctcgacaag cgtgctcagc tcctcgggct ccggtgccga cggtgggccg tcgtcggcgt   74640
cgcgcagcag gcccacgacc cggcgcatgg ccgcgagggc ctcggtgccg gccgtttcga   74700
tgaccgccag ccgctcgggc acgcgcccgg cgtcgcgccg cgcgagcacc tgggcggcct   74760
gggtctgcag gatcatgccg gtgatgtggt gcgcgaccac gtcgtgcagc tcccgggcca   74820
gttcgaggcg ttcctcctgg cggatgcgct cggcgttcgc gcgggcccgg ccgtccaccg   74880
tccgcagcga caacccggtg gccgtgccgc ccagccaggt gaggatgttc agccaggtca   74940
ccggcgccgg gccggcgtcc caggtcgcgg cggccacctg gctgagggcg accacgccga   75000
gggcggcgcc gcccacggcg aaggcgggga tcgtgggtgc ggcccgcacc gccgagccgg   75060
tgaggacggc cagggccagc gccatggccg ggccgggctc ggccggcatg tgcagcacgg   75120
ccgccgtgac gacggcgccc gccgcgatcg tgagcccggc cgcggcgcac ggcaccgggc   75180
cgcgccgccg gatcagggcg agcaggcaga cgagcgtcgc ggccgcgccg ccgatcaacc   75240
agtaggccag gccccagctc tgcgcgacgg cgacggcctc gacgacgacg gcggccacga   75300
agaggacggc cagccccgcg tcggccacca tggtggtcgt cctgtccgcc gtccgcacgg   75360
atccaagggt acggatgccg gcgccgtcgc cggcggcggg accggttgcg gccgcgatgt   75420
tcatgccgcc caaggatagg ggcgaatcgg gcgccgccaa ggggtcaaaa gtagggtgac   75480
gcccgaaatc aaccttctt agggcggtac cggtccgcgg ggcgctcccc gacgatgaag   75540
gccatgtctc acgagcgctc cactcccgtt ctgcaggccg agggcctgac gaaacgctac   75600
ggccggcgga gggccctgac cgactgcacg ctctccgttc cctccggacg ggtgatcgcg   75660 ctggtcgac cgcgcggctc gggcaagtcc acactgctgc agctgtgctg cgggatggtc   75720
gcgccgagcc ggggccggat ccgggttctg ggggagcgcc cggacgcggg cgcggcgcac   75780
ctggcgcggg tgggatacgt accgcgggag ccggcggtgt acggctcgtt cacggtggaa   75840
gaccacctca cgatgggcgc gcggctcaat ccgcggtggg accggcggct ggccgaccgg   75900
cgcatcgcct cggccggcat tccgcgtacc cggcgcgcgg accggctctc cgccggccag   75960
cgggccgagc tggcgttgac cctggccggc ggcaagcgcc cggagctgct cgtgctcgac   76020
gagcccggcg cggtgctgga tcgccggccc cgcgcctcgt tcctgcgcgg cgtgctcgac   76080
ttcgtcgccg agatcgacgc gagcgtgctg atctccggtc acccgtccgg agaggtggag   76140
cggctctgcg accacctgat cgtgctgtcc gactcccggg tgctcgtcgc cggcgacgtc   76200
cgggacctgc tcgcccggca ccaccgcatc atcgcgccgc gcggcgagct ggaccgcctg   76260
ccgccgggga tggagcccat ctgggtggag gacttcggct cgtacagcgg gggagtggtg   76320
cgggccgagg tggacctgcc ccggcggccg tggacggtgg agcgggtcga gctcgaggag   76380
ctggtgctca gctatctgag ccgggcctcg gcgcgcgccg cgctcgccgg ctgcctgatc   76440
gcgcccggtc agccggggag ctgacgggcg ctcaggtcca gcagccggct ggtgcgtacc   76500
cggtcggcgg ccatctcgaa gagctggtgc tccacgtgct cgcgctcggc cacgctcagc   76560
acggcctcgc cgccgagccg gccggccagc ccgtccagga cggccagcag cgccggccgg   76620
tggagccggc caccgcgcgc ccacaccccg agggcgcagg ccgcggccag cagcacggtg   76680
taccggtcgg ccagcgcgaa ggcggccggg ttggcgtcga tcgtgatgtc ggccggcccc   76740
agctcccggc aggcgtcccg caggccggtc agctcccggt ggaaccgctc ggcgaaccgg   76800
ccgaccgggc cctcgtcgtg ccacgagtcg tgcaggacgc cggccagcgg gtcgccacgc   76860
```

```
atgccgctga ccagccggga gaagtccaac ggggacagct cgccgccgag ggtgaacacg  76920
ttgtccggcg gcggctcctc ggccgtccac gaccggcggg ccagccgggg caggtgcggc  76980
agcagcatca ccaggcaggc cgcgcgggac acgtgcgcga aggaggcggg cgcggcgtcg  77040
cggaccagct tctggaacat cgcgtacggg ccctgccgca gataaccctg cgcgcccagc  77100
accgagcgca gatcgtcgat cgcgtccagc acgatctgcg cggtcaggta cttcacggcg  77160
ggcgcgtaac cggccgtggc ctccggcagc aggtgcagcc cccgcaggcc cacgcccgag  77220
aagacgtcga cggtgagcag ggcagcatag gcgcgcgcga tggtggtgcg cacgtacggc  77280
aggtcggcga cggcggcccc gtacagccgg cgctccatcg ccatctcggt ggccagccgc  77340
accgcgctgt ccagcgggcc caccagcagg gccggcgaca ccatccgggt gacctgatag  77400
gcccgcagcg ccacctcgat gccgtgtccc tgttcgccca acagcgcgga ggacggcacc  77460 ggcagtcgt cgaagaccag cccgcccagg tcgatgccgc gcatcccgct gcccggatac  77520
cgcgggcggt ccaccgcccg cgcggccggc agctcgtcgc gcaccagcag gaactggctg  77580
tgcgaccggc tgccgcgcgc ctcgccggtg cgggcgaaca gcaccatcgc ctcggcccgg  77640
cgcaggttcg tcacgatctc cttgtgcccg gacagcaccc atccgccgcc ggcgggcgg   77700 gccgcgcact cggcggcgga gaagtcggtg ccgtgcgcga gctcgtggaa cgcggccgcg  77760
atgcgcttgt tggccagcag caggccggcc gccggcgcc gttgctcctc gttgccggcg   77820
caccacacgt tcaccgaggc gatgagcgag ctgaagccgt agcccagccc caggcacggg  77880
tcgcgccgcc agaccgcgcg cagcacctcg gccagccggt cggcgcgggc cagccggccg  77940
ccgtacgcca ccggcacgaa ctcggcgttg agctgatagc ggtcgagcag ccgctcgccc  78000
tcggccagca tctcctgccg ctcgtcggcg gcgagcacgg ccgcatagcc gaccgggttg  78060
ccggggtcgc gggcgtcgcc gagcagcttc tcgagcgccg cggcggtcac cggccgtcct  78120
ccgcccggac ggtgccggcg ggcggccgca gggccgtgcc gaacgggtc accggttcac   78180 cggtgcgtgc ggccgccgcg accgcgcgg ccagcagccg gtcggcgccg tcgtcgtgcg   78240
ggccgggatc gggcgccggc gcccgcagca cccgggccag ctcccggcgc acggcacgca  78300
gcgcggccag cacccacagg ccgtccgccc agagcgggtc cgcggtgtgc cggccctccg  78360
ccgaggtcca cagcagcagg cacgccgcgc ccgcgtagca ccactcgtag gcggcggcca  78420
gctcgtggcc caccatggac ggccgggccg agggcccgag ctcggtcatc tgcccgcaga  78480
tccgccgcgc ctcgccggcc agcgcggccg cgtgccgggc cagccccgcc gggccacccc  78540
ggacggcggc cgacacggcg agcgccggca gcgcctgcac caccgagcac ccgtggcggg  78600
agagcagggt cagggcgccg cggtccagcg gcggtggcgg ctgaccggcc gcgctcgcct  78660
cggccagccc ctcggcggag acggcgccgg ccgcgaagcc ggccgcgagc cgcgggaact  78720
ggtgcgccag cgccgtgcgg acgaccgggg tgctgccgtc gaacaccgcg accacgtggt  78780
ggtcgcgcac cagcttgggg aacatgccgt gctcgtactc gtcacgcagg aaggaccgcg  78840
agccgagcag ttcggccagc tcacgcagca cgcggtccac caccgtgggc acgtacgcct  78900
tgacgatcgc cgacgtcacg ctcatctcgg ccgtgaggct gtgcaccgag cgcgtgccga  78960
cgacggcggt cgcctcggcc gcggcgagca gggcggcgca gcgcgccaga atcccggccg  79020 ggtgccccg gtcgagcagc ggccgccgca tgatcatccg ctgggccacg aagcgggcgg   79080
tcagccgcag cgcgcggtcg ccggcgccca gcgacagccc ggcgcacatg gtgcgggtca  79140
gctgcagcga gcgcagcacc gtctccagcc gcttccggc ccgcccgagc agggccgtgc    79200
cgggcaggcc ggcgtcctcg aacgcgatgc cggagatgtc gatgccccgc accccgtgcg  79260
```

```
tggccacctt gggccggggc agccacgtgc cggggcgag cgcctccttg tcgaccagga    79320
acaggctctg cccgcgggcg tcgccggccc ggccggtgcg ggccagcacg gtgaggtatc    79380
gggcccgggt cgcgttgttg atcgccact tgagaccgcg cagccggtag ccggcgtcgt    79440
ggggcagggc cgtggtcgtg ccgtgcagca ggtcggcgcc gtggtcgggc tcggagagcg    79500
cccatgcgac cggggtgccg gcgagcaccg cggcggcaag cgtcgcgcgc tggccgtcgt    79560
caccggccag ccagaccggc gccgacccga ggtaggtctt gccgtgcgcg acggccgcgc    79620
tcaggtcgcg ccgggcgacc gcacgccaca ggtgcaggag ccgctcgtgg tcgccggggg    79680
caccgcccca ctccggcggt acgtaccagg attgcagacc gaaggagttc agccggtcgt    79740
gcagccgggc cggaactcc tcggcgatgt cgcgggcggc cgtctcggcg tcccatgcgt    79800
cctcggggcc gagcaggtcg tccaggcgca cctccgcggg tggcgccagc gggcgtacgg    79860
tcatcggccc gcgcccgcct gcaccggccg cagcgccggc tcgagctcgg cgtgcagcgc    79920
cgtgatgccg ccggccagga accgctcgcg gaccgcggtc cggcggatct tgccgctcgt    79980 ggtccgcgc accgtgccgc gccgcaccag cagcacgttg cgtaccggca cgccgaagga    80040
gacggtgagc cggcggctga cggcgctcgc cacccgcggg agctcgtcga gcggcgtgcg    80100
cggatgcacc tcctgcacca gcacgatccg ctcgtcgggc gccggcaccc cgaacgccgc    80160
cccgatctgg tggtccaccg cgtcgtgcgc ggcccgggcc tcccgctcga ggtcgtgcgg    80220
ggccaggttg cggccgtgca cgatgagcag ctccttgagg cgtccggtga ggaacagctc    80280
gcctccggtc agcgcaccca ggtcacccgt tcgcacccag ccgccgtcct ggccgtcgcc    80340
cgcgggcctg gcgtcgaaga tgccggggtt gagctcggtc ctgccccagt agccggcgcc    80400
cgcgccgggc ccgcgcagcc agatctcgcc gaccccgccc tcgggcagcg gccgtagccc    80460
gtccgggtcg acgatgagca cctcgaagtc gggcacccgg ccgacacccg gtatctcccg    80520
ggccgcggcg gggtcggccg ggcgcagggc cggcgacgcg gcgtcctcca gcgcgcgagg    80580
gtcggcggga agaaagaccg ccggcgcctc gaagaccttc gtcgacacgt acgcggtgaa    80640
ctcggccatg ccgtagcagg ggttcaccgc gtgggtgtgc aggccgaagg gggcgaagcg    80700
ctcggtgaac gcccggacgg tggccggggtt gaccggctcc gatccgttgt agagcgtgcg    80760
gatgcgggac aggtcgaggc cggcgatctg ctcgtcccgc acggcgcgca cgcacaggtc    80820
gtacgcgaag ttgggcgcgg cggagatggt gacccggtag cggtccatca tccgcagcca    80880
gtccgccggc cggcggacga aggccgtcgg cgacatcagc acgacgccgg cgccgttcag    80940
caggcccgcg gtgagcatgg cgaacaggcc catgtcgtgg tgcagcggca gccagctgcc    81000
gaacacgtcg tcgctgttgt gcccgctgct gcggtcgaac gcgcggaggt tggccagcac    81060
ggcccggtgg ctgagcatca cgcccttggg cgagccggtg gagcccgagc tgtactgcag    81120 gacgccagc gagtccggcc ggggcccgcg ggcggggcgg atcgcttccg ccgcgagggg    81180
cggaagcgca ccgaccggca ggccggacag gccgcgctcg cgcaggacgg cggtgagcgg    81240
cgccgcgtcg tcgcgttga cgacggcag ggcgggggag cagtcggccg cgatgccgac    81300
ggtgcgctcg gaggcgccgg acgaccctcc gggcgggggc gccggcacgg cgaccaggcc    81360
ggcgtagagg cacgccaggt agagctcgac gaactcggcg ccgtgggca gggcgatgag    81420 gatgcgctcc ccggccggga accgggcggc gagccaggcc gccgcgccg cggcgcgcg    81480 gtcgagctcg gcgtacgtga gggtgacggg ctcggcgtcc gggtcgccgg ggagcaccac    81540
gagggcgggc tcgccggggc gcgcgatcgc ctgcgcccgg aaggcgtcgg gaacggtggg    81600
```

```
ttgggtggcg gcgtcgatga ccatggcaac tgcctctccg gaagggtccg ccagggccgc   81660
gacgccgccg gcgggtcgcg ctcagctctg cggttgcttc tgcttctcca tcgccgcgat   81720
caggctcttg ggccgcatgt cggtccagga cttctcgatg tagtcgaggc agtcctgccg   81780
tccggcctcg ccgaacaccg tcgtccagcc gtcgggcacg tcggcgaaga ccggccagag   81840
tgagtgctgt ccctcgtcgt tgaccaggac caggtagttg gcgtcgggat cttcaaacgg   81900
attgggcaca gcgtcgcctc catcgaacgg atcggatgac ggtggtcagg agccgcacgg   81960
ccggcggttg gcgccaccgc cagcactatg gccgagactc ggaacggccg acaagcgtgc   82020
acgggctgtg cgactgcgcc gccggcgcgg ttggacagcg gtcagagcgg gccgcggccg   82080
gcccgcagga gcatgagcgc gatggtcgtg ccatcctcgc cgagcgcggc gcggaagcgc   82140
tggatgacct cctgctcccg ggagagcacc acccgggttc cgccggaggc cagccggatg   82200
gagccgatct tctgcgagat cgaggcccct tcctgccaca gccgcatgat ggcggcgtcg   82260
atctcgtcga tgcggttccg caggaccggg atgtccgcct ccggcacggc ctcgccgtgc   82320
tcggccggcg gtgcgcccgg cgccacgacc tgaatgacgt tctccaccat cgccgtctcc   82380
tgtgagcttg tcggtggtga ctcggggtgg gcagccggga cgttaacacc gccgcgcggc   82440
cgtccgggcg cgtgcgactg aggccgtccg tcagtcgaac gcacgctttc gtgcgcactg   82500
cccaaccagg ccgaacggct cctacagtcg ccgtcgatcg cagtcggtgt aacaccgtcg   82560
aaacgccgga ggatgccttg gccgccgtgg atgtcccgag ggtgcgcccg cccggtgccg   82620
cgcccgcgcc gcggcgtcgc cggtggcggt tctggcagtc gccggacggc cagccggcgt   82680
gggcccgccc ggcgctgctg ggcatcgcgg cgctggcggc cgtgctgtac acggcgaacc   82740
tcgcccgcag cggctacccc atgtactacg ccgtggcggt gaagagcatg tcggtgagct   82800
ggccggcgtt ctggaccggc gcgttcgacc cggccgcctc gatcacgatc gacaagctcg   82860
ccggcgcctt cgtcccgcag gcgctctccg cccgcgtctt cggcttccac cagtggtccc   82920
tggccctgcc gcaggccgtc gagggggtca tcgccgtgct ggtcctctac cgggcggtgc   82980
ggcgctggca cgggcccggc gccgggctgg ccgcggccgg gctgttcgcc acgacgccga   83040
tcgtgtcctc gatgttcggc cactccatgg aggacggtgc gctgacgctc tgcctggtgc   83100
tcgcggccga cgcgttcggc gcggcggtga cccgcggcag cccggcccgg ctggcgctcg   83160
cgggcgcctg gatcgggctc ggcttccagg cgaagatgat gcaggcgtgg ctggtgctgc   83220
cggccctggt cgtcacctat ctcgccggcg caccggtgcg ggcgcgggcc cgggtcgtcc   83280
atgtcgcggc ggcggtggcg gcgaccctgg cggtctcgct gctctgggtg ctggcgctga   83340
ccctgctgcc cggctcgcac cggccgtggg cggacggcac cacctccggc aacgccttcg   83400
ccatggtgtt cggctacaac ggtttcgacc gggccggcat ccacgtgccg ggcgcgctga   83460
cgaccggctt caccgacggc ggggccgcgg ccggcggttc ctggacggcg cttgccgcgg   83520
atcgcctcgc cacccagatc gggtggtggt accgctggc gctgaccggc ctgctgctcg   83580
gcctggcccg gtggcgcacc gcgcgcgccg gcctcctgtt ctgggactg tggttgctga   83640 cggccgcggt ggtgctcagc cggatcacca ttcagcacaa cgcctacctg gccgtgctgg   83700
ccccgccgct ggcggcgctc cggcggcgcc gcgcggtgca gctctggcgc acgcaccgcg   83760
acggcacggc gccctggctg ctgccgcgcg tcgtggtcgt ccaggccggc tggaccctgt   83820
ggctggccac ccgctatccc tcgttcctgg ccgggctgac gtggacggcg ccgatcgccg   83880
ccgtcctggc cgtggtggtg ctgccgcgc ggccgacggc ccgcggccg gccgtcgtcg   83940 tggtggtcgc cggcctgctg gcggtgccgg tcgcgtgggg cgcctcggtg ctgaacccgc   84000
```

```
gatacgccgg cacgtcgttc gaggccggtg cggggccgag cgggccggtg ggcgtgcggc   84060
tcgacgacga caccaccgac cggctgacgc cgggcctgcg caggctcgac gactatctcg   84120
cggcccaccg cgacggccgc acctacctgg cggccacgtc ctcgtggcgc acggccggcc   84180
ggctcatcgt cccgaccggg cactcctacc tgccgctcgg cggcttcagc ggagcggcgc   84240
cgttcccgtc gctggccggc gtgcagcgcc tggtccgcga cggcgagctg cgctacttcg   84300
tcctcggcgg cccggagggc ctcggcggcg aggccaccga ggcgtaccgc atcaccggct   84360
gggtcctcga gacgtgcgcc accgtgccgc cggccgagca cggcgccgat ccggatctca   84420
cggtcctgcg atgcgacaag ccctgacaac cgacgtagca cgacgaaccc gggaggaaca   84480
gtggacaacg gcaccttcac cgatctgcgc atcgaccaca tcgaattcgc ggtcgcggac   84540
gtcgaatccg ccagcgcccc gtttacggag ggctacggct tctcggtgta cggcgggacc   84600
ggcgacgcgc acgcgccggt gcggcgggtg gcgctgggac gcgacgacat ccggctcgtg   84660
ctgaccgcgg cgcccggcgg ggaccatccg gccatggcct acgtcgagca gcacggcgac   84720
ggtgtgtcgg ccatcgcgct cagcacgaga cgcgcccacg cggcgttcac cgaggcggtg   84780
cggcgaggcg ccgtcggggt atccgccccg gtcaccggca acggcgtgac cgtcgcgacc   84840
atccgcggct tcggtgacgt cctgcacacc ttcgtcgagc gggcgccggg cgcggacccc   84900
cggaccctgc ccggcctgga gctgcggcgg cccagcccca cccggttcga ctcgggcctg   84960
caggcgatcg accacatcgc cgtctgcctc gagccgggga ccctcgaccc gaccgtcgac   85020
ttctaccgcg acgtcctcga cttcgagatg atcttcgagg agcgcatcct ggtgggccgg   85080
caggcgatgg actccaaggt ggtgcagagc cgctcgggcg gtgtgacgct caccctcatc   85140
gagcccgaca cgtcgctcga gcagggccag atcgacacct tcctgaagaa ccacggcggg   85200
ccgggcgtgc agcacctcgc gttcatcacc gacgacgtgc tgcgctcggt cggccggatg   85260
tccgagcacg gcgtcgagtt cctgcacacc ccggactcgt actacggccg gctaccgggg   85320
cgcatcccgc aggccgggca cccgatccag gcgctgcgcg acctgaacgt gctcgtcgac   85380
caggaccacg acgggcagct gttccagatc ttcacgaagt cggtgcaccc ccgcgggacg   85440
atcttcatgg aggtgatcga gcgaatgggc gctcgcagct tcggcagcgg caacatcaag   85500
gcgctgtacg aggcggtcga gctcgacatg tccaagcaga gcgcctgagc cgccgatgga   85560
gtcgccggca acccacgcgg aactggtgat cgggaccgtc ctgctcgaca tcgcgctggt   85620
gctcgcggcc ggtgccctgc tcggccggtg ggtgcggcgg ctgcgccagc ccgcggtgat   85680
cggggagatc ctcgcgggca tcgcgctcgg cccgagcctg ctcggcctgc tgccgggcaa   85740
cccgacggcc tggctcttcc cggccgaggc ccggccgtac ctgtccgcgg tggcccagat   85800
cggcctggcc ctgttcacgt tcctgatcgg ctgggagttc aacccggcga ctctggcccg   85860
gcaccgcggc accgccgccg cggtgtcgat cggctccatc gcggtctcgt tcggcctcgg   85920
catcgcgctg gccacggtgc tgcatccccg gcacgacacg accgggggcg ggaaggtcgg   85980
cttcaccgag ttcgcgctct tcctgggcgt ggccatgtcg atcaccgcgt tcccggtgct   86040
ggcccggatc ctcgcggagc ggcgcctcac cggcacgcgg gtgggcagca tcgcgctggt   86100
cagcgccgcg atcgacgacg tggtggcctg tgtcctgctg gccctggtga cggccatcgc   86160
cacggcgagc gggccggtcc agctcgtacg catcctcgcc ctgctggccg tcttcctggt   86220
ggtgctggtg acggtcgtac ggccgctgct ggtcttgctg gcgcggcggc cgtccgcgtc   86280
gtatcttctg gtggcggtgg tcgcggtcgt gctgctctcg gcatatgcga ccacctggat   86340
```

-continued

```
cggcctgcac gcgatcttcg gcgcgttctg cgccggcctg gtcatgcccc gggagccggc    86400
ggcggcgctg cgtgagcggg tgcggcagcc gctggaacac gtaagcgtgg tgctgctgcc    86460
ggtgttcttc atcgtcaccg gcctcggcgt cgacatcggc gcgctcaccg cggcgaacat    86520
cctcgaactc gccgcgatca tcgtgatcgc ctgcgccggc aagctggccg gcgcgatcgt    86580
gccggcggtg tcgctcggca tgtcgtggcg ggacgccaga accctcggcc tgctcgtcaa    86640
cacgcgcggc ctgaccgagc tcgtcgtgct caacgtcggt ctgcagctcg ccgtgctgga    86700
cggccagatg ttcacgatga tggtgctgat ggcgctggtg acgaccgccc ttgcgggccc    86760
gctgatcgga tcgccccgga caccggcggc cggcgcaccg gctcaggcgc tcccggccga    86820
accgcggacg cggcgggcgg cgtaggcccg gcgcatcttg atgtagttgc cgcatccggc    86880
catcgagcac cagcgccgcg cctggttgcg ggaggcgtcg tagtaggccc accggcaggt    86940
gtcccggtcg cagaccttca gccgggtcca cacctgcagc tcggcgcact gccggaccgc    87000
gtcgatcagc ccgccagggg cacggtcgaa cggcgtgccc ccggccggca gcaggcgcgg    87060
cgcgccgccg gccaggctca gccgcacggg aacggcggcc aggatctcct ccaggcggcg    87120
cagcgcggcc gggtcggcgg gatggccggc gtggcccagc agcacctggc gaaggccctc    87180
acgaagcgcg acggcccgtg ccaggtcggc cgggcgcacc ctcgcgccgg gggcgagcag    87240
gctttccccg ccagccacg cccgaagggc gtccggggtg ctcagcgact cgtcgtcgac    87300
ctgaggctca taggtgttga cgaaatcgcg caacagccgg gcaggggatg gcactgcggc    87360
ctcgtcactc accgttgacc tccttggtgg cgacagcgta gcgccttgac aggcgcgcga    87420
accgcctgga acgatccgct ttcacaccag caaaactact ttggtggtgt gaagaggcgc    87480
gaaggagcgg atcgtggcca ccacgctgag ggacgtggca cggctcgccc gggtgtcggt    87540
gaagacggtc tccaacgtcg tcaacgacca cccgcacgtc agcgacgacg tgcgccgccg    87600
ggtcgagacg gcgatccggc agctgggcta ccgtcccaac ctcgtcgccc gcgccctgcg    87660
cagcggccgc ggcagcggac tgctcgccct ggcgatgccg ggcgccggcg cgccgcagtc    87720
gcccgccctg atcgaggaga tcatccggcg ggcggccccg ctcggattcc gggtcctcat    87780
cgagccgctc gagtcgtcac ggccgaggcc gccggccccc ggcgtcgacg cccggctgct    87840
gaacgcggag gcgccggccc ccgagctggt ggacgcccag gcggccacgg gcaccccgct    87900
ggtgctgctg accggcaccc ccgatccgcg atacgactgc gtcggccgg acgccgcccg    87960
cgcggccgag gacgcggtgg accacctgcg ccgtctcggc cggcgccgcg tcgccaccat    88020
cggcggctcg ctctccaccg gtccggccgg ctccggctcc gacttcggtt ccggctccgg    88080
ttccggctcc ggctccggtt ccggctccgg ctcgggctcc ggctcgggct cgggctccgg    88140
ctcgggctcc ggcttcggct cgggctccgg cttcggctcg gctccgcgg agggctaccg    88200
ggccgcacgg cagttgttag gccacgaaga tcgcccggac gcgatcgtct gcggcagcgt    88260
gcggctggcg gtcggcgtga tccgggccgc cgccgacgcc ggcctgcggg tgcccgagga    88320
cgtcgccgtg atcggcatcg gcgacggcga ggagggccgc tacacgcggc cggccctgac    88380
cacggtcgcc accgacccgg cgttcatcgc cggcaaggcg c    88421
```

<210> SEQ ID NO 2
<211> LENGTH: 333
<212> TYPE: PRT
<213> ORGANISM: Actinoplanes sp.

<400> SEQUENCE: 2

Met Ser Trp Arg Gln Phe Arg Trp Gln Ala Leu Ala Gly Ala Val Ala

```
                1               5                  10                 15
        Leu Val Pro Leu Val Ala Tyr Leu Ile Val Thr Ser Leu Asp Ile Arg
                        20                  25                 30

Arg Ala His Asp Arg Tyr Gln Ala Gln Cys Ala Ser Ile Gly Asn Cys
                        35                  40                 45

Ala Glu Ala Met Leu Gln Phe Gln Asn Asp Phe Arg Thr Arg Leu Leu
                50                  55                  60

Leu Leu Ala Ile Leu Ala Ala Ile Pro Gly Ile Leu Gly Val Phe
        65                  70                  75                     80

Trp Gly Ala Pro Leu Val Ala Arg Glu Leu Glu Thr Gly Thr His Arg
                            85                  90                 95

Leu Val Trp Asn Gln Ser Val Thr Arg Arg Trp Leu Ala Val Lys
                        100                 105                110

Val Leu Phe Val Gly Val Ala Ala Met Ala Val Ala Thr Leu Val Ser
                        115                 120                125

Thr Leu Leu Thr Trp Ala Ser Ser Pro Val Asp Ala Val Ser Gln Asp
                130                 135                 140

Arg Phe Gly Ala Leu Val Phe Asp Ala Arg Asn Ile Val Pro Val Ala
        145                 150                 155                    160

Tyr Ala Ala Phe Ala Leu Val Leu Gly Thr Val Ile Gly Leu Leu Val
                            165                 170                175

Arg Arg Thr Ile Pro Ala Met Ala Leu Thr Met Leu Val Phe Ala Val
                        180                 185                 190

Val Gln Phe Thr Val Pro Ala Leu Ala Arg Pro His Leu Met Ala Pro
                        195                 200                 205

Glu Thr Gln Thr Arg Gln Met Thr Leu Gln Glu Phe Gly Glu Val Arg
                210                 215                 220

Gly Phe Gly Asp Glu Pro Thr Val Asn Gly Leu Ser Ile Arg Gly Ala
        225                 230                 235                    240

Trp Val Thr Ser Thr Ser Pro Leu Leu Thr Ala Asp Gly Thr Arg Leu
                            245                 250                255

Asp Lys Ala Thr Tyr Arg Lys Cys Val Thr Asp Pro Pro Ala Val Ser
                        260                 265                 270

Gly Gly Ala Pro Gly Val Gly Gly Thr Val Ala Cys Leu Ala Asp Leu
                        275                 280                 285

Asp Leu His Val Glu Val Ala Tyr Gln Pro Asn Asp Arg Tyr Trp Thr
                290                 295                 300

Phe Gln Trp Ile Glu Ser Ala Leu Tyr Leu Ala Leu Gly Gly Leu Leu
        305                 310                 315                    320

Leu Ala Val Gly Leu Trp Arg Ile Arg Arg His Val Ile
                            325                 330

<210> SEQ ID NO 3
<211> LENGTH: 304
<212> TYPE: PRT
<213> ORGANISM: Actinoplanes sp.

<400> SEQUENCE: 3

Met Pro His Glu Asp Ser Ser Pro Val Leu Gln Ala Glu Gly Leu Thr
1               5                  10                  15

Lys Arg Tyr Gly Arg Arg Thr Ala Leu Gln Asp Cys Asn Leu Thr Ile
                20                  25                  30

Pro Arg Gly Arg Val Ile Gly Leu Val Gly Pro Asn Gly Ala Gly Lys
            35                  40                  45
```

-continued

```
Ser Thr Leu Leu Gln Leu Ala Cys Gly Leu Ile Thr Pro Ser Glu Gly
    50                  55                  60

Ser Leu Arg Val Leu Gly Glu Thr Pro Ala Ala Asn Ala Gly His Leu
65                  70                  75                  80

Ala Lys Val Gly Phe Val Ala Gln Asp Thr Pro Val Tyr Ser Asn Phe
                85                  90                  95

Thr Val Gly Asp His Leu Lys Met Gly Ala Lys Leu Asn Pro Thr Trp
            100                 105                 110

Asp Gln Ala Leu Ala Glu Arg Val Ala Gln Val Gly Leu Asn His
            115                 120                 125

Gly Gln Lys Ala Gly Arg Leu Ser Gly Gly Gln Arg Ala Gln Leu Ala
    130                 135                 140

Leu Thr Leu Ala Ala Ala Lys Arg Pro Glu Leu Leu Met Phe Asp Glu
145                 150                 155                 160

Pro Ala Ala Ala Leu Asp Pro Leu Ala Arg Asp Gly Phe Leu Gln Asn
                165                 170                 175

Leu Leu Glu Phe Val Thr Glu Leu Asp Ala Ser Ala Ile Leu Ser Ser
            180                 185                 190

His Leu Leu Gly Asp Val Glu Arg Val Cys Asn Tyr Leu Ile Val Leu
    195                 200                 205

Cys Ala Ser Arg Val Gln Val Ala Gly Asp Val Pro Asp Leu Leu Asn
    210                 215                 220

Thr His Tyr Arg Ile Val Ala Pro Arg Gly Glu Leu Asp His Pro Pro
225                 230                 235                 240

Ala Gly Leu Glu Val Ile Arg Ala Gln His Ala Asp Arg Tyr Thr Thr
                245                 250                 255

Ala Val Val Arg Gly Asp Gly Ser Arg Pro Ser Thr Trp Thr Ile Glu
            260                 265                 270

Pro Ile Gln Leu Glu Glu Leu Val Leu Ala Tyr Met Thr Arg Ala Met
            275                 280                 285

Gly Val Thr Gly Glu Pro Leu Met Ala Ala Ser Gly Glu Val Val Arg
    290                 295                 300
```

<210> SEQ ID NO 4
<211> LENGTH: 336
<212> TYPE: PRT
<213> ORGANISM: Actinoplanes sp.

<400> SEQUENCE: 4

```
Met Ser Trp Arg Gln Phe Arg Gly Gln Ala Val Val Gly Val Val Val
1               5                   10                  15

Leu Ala Leu Leu Ala Ala Tyr Leu Val Tyr Leu Gly Val Asp Ile Arg
            20                  25                  30

Gly Ala Tyr Asp Asp Tyr Arg Ala Gln Cys Pro Ala Gly Gly Asp Cys
        35                  40                  45

Ala Gly Pro Leu Gly Gln Phe Ser Leu Asp Tyr Glu Asn Thr Leu Leu
    50                  55                  60

Tyr Leu Ala Gly Val Leu Ala Leu Val Pro Gly Leu Leu Gly Met Phe
65                  70                  75                  80

Trp Gly Ala Pro Leu Ile Thr Arg Glu Leu Glu Asn Gly Thr Gln Arg
                85                  90                  95

Leu Val Trp Asn Gln Ser Val Thr Arg Arg Trp Leu Leu Ile Lys
            100                 105                 110

Leu Leu Val Val Gly Leu Ala Cys Met Val Val Ala Gly Val Pro Ser
    115                 120                 125
```

```
Leu Leu Leu Thr Trp Ala Ala Pro Val Asp Asn Val Ala Asp Asn
        130                 135                 140

Arg Phe Ser Thr Val Met Phe Gly Ala Arg Phe Leu Pro Pro Ile Ala
145                 150                 155                 160

Tyr Ala Ala Phe Ala Phe Val Leu Gly Thr Leu Ile Gly Leu Leu Val
                165                 170                 175

Arg Arg Thr Val Pro Ala Met Ala Leu Thr Leu Val Ala Phe Val Ile
                180                 185                 190

Phe Gln Phe Leu Val Pro Asn Leu Val Arg Pro His Leu Met Pro Ala
            195                 200                 205

Lys His Leu Val Lys Pro Met Thr Val Ser Ala Ile Asn Glu Ala Lys
        210                 215                 220

Ser Leu Gly Ser Ile Thr Gly Ala Pro Val Leu Asn Gly Leu Ser Ile
225                 230                 235                 240

Ser Gln Gly Trp Ile Thr Asp Val Ser Ala Leu Lys Thr Ala Asp Gly
                245                 250                 255

Arg Ser Leu Asp Ala Lys Thr Phe Asp Asn Cys Tyr Met Asn Ala Pro
            260                 265                 270

Lys Thr Gly Ala Thr Glu Gly Pro Tyr Gly Asp Val Ala Val Cys Leu
        275                 280                 285

Ala Lys Leu Asp Leu His Val Asp Ile Ala Tyr Gln Pro Trp Asn Arg
290                 295                 300

Tyr Trp Ala Phe Gln Phe Leu Glu Ser Gly Phe Tyr Val Leu Leu Ser
305                 310                 315                 320

Gly Leu Leu Ile Gly Ala Ala Val Trp Arg Val Gln Arg Arg Pro Ser
                325                 330                 335

<210> SEQ ID NO 5
<211> LENGTH: 283
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will contain a
      methionineresidue at this position

<400> SEQUENCE: 5

Val Arg Ser Ala Val Val Gly Thr Gly Leu Ile Gly Thr Ser Val
1               5                   10                  15

Gly Leu Ala Leu Thr Gln Arg Asp Ile Thr Val His Leu Leu Asp Ala
                20                  25                  30

Asp Pro Ala Ala Arg Ala Ala Ala Leu Gly Ala Gly Ile Ala
        35                  40                  45

Gly Glu Pro Arg Thr Arg Val Asp Val Ala Val Ile Ala Val Pro Pro
    50                  55                  60

Ala Ala Val Ala Pro Val Leu Ala Asp Leu Gln Arg Arg Gly Thr Ala
65                  70                  75                  80

Arg Val His Thr Asp Ala Ala Ser Val Lys Val Leu Pro Ser Arg Gln
                85                  90                  95

Ile Glu Val Leu Gly Cys Asp Ala Ser Ser His Val Gly Gly His Pro
                100                 105                 110

Leu Ala Gly Ser Glu Arg Ser Gly Pro His Ala Ala Arg Gly Ser Leu
            115                 120                 125

Phe Glu Gly Arg Pro Trp Val Leu Ser Pro Gly Arg Arg Ser Ser Thr
```

-continued

```
            130                 135                 140
Ala Ala Val Asp Gly Ala Leu Ala Val Val Ser Ala Cys Gly Ala Thr
145                 150                 155                 160
Pro Val Leu Met Ser Ala Glu Glu His Asp Arg Ala Val Ala Leu Val
                165                 170                 175
Ser His Val Pro His Leu Val Ala Gly Leu Leu Ala Ala Arg Met Leu
            180                 185                 190
Asp Gly Thr Pro Ala Gln Leu Gly Leu Ala Gly Gln Gly Val Arg Asp
        195                 200                 205
Thr Thr Arg Ile Ala Gly Gly Arg Ala Ala Leu Trp Thr Glu Ile Leu
    210                 215                 220
Ala Ala Asn Ala Gly Ala Val Ala Asp Val Leu Asp Asp Leu Ser Ala
225                 230                 235                 240
Glu Leu Ala Ala Thr Ile Ser Ala Leu Arg Glu Leu Glu Ala His Pro
                245                 250                 255
Gly Arg Ala Glu Ala Leu Ala Ala Leu Thr Gly Met Leu Gln Arg Gly
            260                 265                 270
Val Asp Gly Arg Asp Arg Ile Ala Ala Ser Pro
        275                 280

<210> SEQ ID NO 6
<211> LENGTH: 336
<212> TYPE: PRT
<213> ORGANISM: Actinoplanes sp.

<400> SEQUENCE: 6

Met Glu Ser Leu His Ile Ala Ser Ala Arg His Glu Pro Asp Arg His
1               5                   10                  15
Asp Glu Thr Gln Met Asn Thr Pro Ser Met Met Arg Val Glu Trp Leu
            20                  25                  30
Pro Val Asp Ser Leu Glu Met Leu Asp Ser Pro Arg Leu Ala Gly Glu
        35                  40                  45
Asp Pro Arg His Thr Gln Met Leu Ala Ser Leu Asp Ala Glu Leu Pro
    50                  55                  60
Pro Ile Ile Val His Arg Ala Ser Met Arg Val Ile Asp Gly Ala His
65                  70                  75                  80
Arg Leu Gly Ala Ala Arg Leu Arg Gly Asp Glu Leu Ile Lys Ala Ala
                85                  90                  95
Met Phe Glu Gly Ser Glu Gln Glu Ala Phe Val Leu Gly Val Lys Ala
            100                 105                 110
Asn Ile Ala His Gly Leu Pro Leu Ser Thr Ala Asp Arg Thr Arg Ala
        115                 120                 125
Ala Glu Arg Ile Ile Glu Ser His Pro Ser Trp Ser Asp Arg Thr Ile
    130                 135                 140
Ala Ala Ser Ser Gly Leu Ser Ala Arg Thr Val Gly Asn Ile Arg Arg
145                 150                 155                 160
Arg Leu Glu Leu Ser Gly Asp Ile Gly Gln Gly Ser Arg Thr Arg Val
                165                 170                 175
Gly Arg Asp Gly Arg Val Arg Pro Leu Asp Asn Ser Glu Gly Arg Leu
            180                 185                 190
Lys Ala Val Ser Tyr Ile Gln Gln Pro Asp Ala Ser Leu Arg Glu
        195                 200                 205
Ile Ala Lys Asn Ala Gly Val Ser Pro Ser Thr Ala Arg Asp Val Arg
    210                 215                 220
```

```
Asn Arg Leu Gln Arg Gly Glu Asp Pro Leu Pro Gly Pro Arg Arg Thr
225                 230                 235                 240

Gly Gly His Arg Asp Asp Ile Ser Phe Asp Lys Glu Asn Thr Ile Arg
            245                 250                 255

Leu Leu Glu Pro Thr Val Arg Ser Ile Leu Gln Gly Leu Lys Asn Asp
        260                 265                 270

Pro Ser Leu Arg Phe Thr Glu Ser Gly Arg Asn Leu Leu Arg Trp Val
    275                 280                 285

Leu Ala Arg Thr Val Gln Asp Asp Glu Trp Lys Asp Met Leu Asp Ala
290                 295                 300

Val Pro Ser His Cys Thr Tyr Val Leu Ala Asn Val Ala Arg Arg Cys
305                 310                 315                 320

Ser Gln Glu Trp Leu Glu Phe Ala Glu Thr Leu Glu Lys Asn Ala Ala
            325                 330                 335

<210> SEQ ID NO 7
<211> LENGTH: 444
<212> TYPE: PRT
<213> ORGANISM: Actinoplanes sp.

<400> SEQUENCE: 7

Met Ser Ile Leu Arg Glu Ala Pro Gly Thr Gly Arg Val Leu Arg Arg
1               5                   10                  15

Glu Asp Leu His Gln Ser Leu Ser Asp Pro Leu Leu Asp Thr Met Asn
            20                  25                  30

Phe Leu Asn Glu Val Thr Ala Arg Tyr Pro Arg Ala Val Ser Phe Ala
        35                  40                  45

Pro Gly Arg Pro Phe Asp Gly Phe Asp Val Glu Gln Ile Phe Arg
    50                  55                  60

Gly Ile Arg Gly Tyr Leu Glu His Leu Ala Gly Gln Gly Arg Ser Pro
65              70                  75                  80

Ala Glu Ile Arg Asp Ala Val Phe Gln Tyr Gly Pro Ala Ala Gly Arg
                85                  90                  95

Ile Arg Glu Val Ile Ala Gln Trp Leu Arg Arg Asp Glu Gly Ile Asp
            100                 105                 110

Val Ala Pro Glu Ser Ile Val Val Thr Val Gly Ala Gln Glu Ala Met
        115                 120                 125

Leu Leu Ala Leu Arg Ala Leu Ile Arg Asp Glu Arg Asp Ala Leu Phe
130                 135                 140

Val Ala Ser Pro Cys Tyr Val Gly Ile Thr Gly Ala Ala Arg Leu Leu
145                 150                 155                 160

Asp Ile Asp Pro Val Pro Val Ala Glu Arg Glu Asp Gly Phe His Pro
                165                 170                 175

Glu Asp Leu Ala Arg Ala Val His Ala Glu Leu Ser Arg Gly Arg Arg
            180                 185                 190

Pro Arg Ala Phe Tyr Val Val Pro Asp His Thr Asn Pro Ser Gly Ala
        195                 200                 205

Thr Met Pro Leu Glu Ala Arg His Ala Leu Leu Asp Leu Ala Gly Glu
    210                 215                 220

Leu Gly Leu Leu Val Ile Glu Asp Ser Pro Tyr Arg Leu Val Ser Pro
225                 230                 235                 240

Gly Gln Gln Leu Pro Ser Leu Lys Ala Leu Asp Pro Gly Arg His Val
                245                 250                 255

Val His Leu Gly Ser Phe Ser Lys Thr Leu Phe Pro Gly Ala Arg Val
            260                 265                 270
```

```
Gly Phe Ala Ile Ala Asp Gln Pro Val Ser Asp Ala Ala Gly Gly Ala
            275                 280                 285

Gly Leu Leu Ala Asp Glu Leu Ala Lys Val Lys Ser Met Val Thr Val
            290                 295                 300

Asn Thr Ser Pro Leu Ser Gln Ala Ala Val Ala Gly Met Leu Leu Ala
305                 310                 315                 320

Ala Gly Gly Thr Ala Ala Glu Ala Ser Ala Glu Ser Ser Ala His Tyr
                    325                 330                 335

Gly Ala Ala Met Arg Arg Thr Leu Asp Arg Leu Glu Glu His Leu Pro
            340                 345                 350

Ala Ser Phe Arg Ala Arg Thr Gly Val Arg Trp Asn Arg Pro Ser Gly
            355                 360                 365

Gly Phe Phe Leu Ala Val Asn Val Pro Phe Thr Ala Asp Asn Ala Ala
            370                 375                 380

Leu Ser Arg Ser Ala Glu Asp His Gly Val Ile Trp Thr Pro Met Ser
385                 390                 395                 400

Tyr Phe Tyr Pro Ala Gly Gly Glu Gln Gly Ile Arg Leu Ser Ile
                    405                 410                 415

Ser Tyr Leu Thr Pro Glu Glu Ile Asp Glu Gly Val Lys Arg Leu Ala
                    420                 425                 430

Gly Phe Ile Thr Thr Glu Ile Ala Ala Leu Arg Pro
            435                 440

<210> SEQ ID NO 8
<211> LENGTH: 356
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 8

Val Thr Ala Thr Ala Leu Leu Pro Leu Thr Leu Ala Asp Tyr Glu Gln
1               5                   10                  15

Leu Ala Gln Ala Arg Met Glu Pro Pro Val Trp Asp Phe Ile Ala Gly
                20                  25                  30

Gly Ala Gly Glu Glu Leu Thr Leu Ala Ala Asn Thr Ala Ala Phe Ala
            35                  40                  45

Pro Pro Arg Leu Arg Pro Arg Val Leu Thr Gly Ala Gly Ala Pro Asp
        50                  55                  60

Thr Gly Thr Thr Ile Leu Gly Arg Arg Trp Ala Ala Pro Ile Gly Val
65                  70                  75                  80

Ala Pro Leu Gly Tyr His Thr Leu Val Asp Pro Ala Gly Glu Val Ala
                85                  90                  95

Thr Ala Ala Ala Gly Ala Ala Gly Leu Pro Leu Val Val Ser Thr
            100                 105                 110

Phe Ser Gly Arg Thr Val Glu Asp Ile Ala Ala Ala Thr Thr Ala Pro
            115                 120                 125

Arg Trp Leu Gln Val Tyr Cys Phe Arg Asp Arg Ala Val Thr Ala Ala
        130                 135                 140

Leu Val Thr Arg Ala Val Arg Ala Gly Phe Glu Ala Leu Val Leu Thr
145                 150                 155                 160

Val Asp Ala Pro Arg Leu Gly Arg Arg Leu Arg Asp Ile Arg Asn Asp
```

-continued

```
                        165                 170                 175
Phe Arg Leu Pro Pro Gly Val Ala Pro Ala Asn Leu Thr Gly Asp Gly
                180                 185                 190

Phe Ala Ser Pro Ser Gly His Ala Leu Gly Ala Phe Asp Ala Ala Met
            195                 200                 205

Asp Trp Thr Val Val Ala Trp Leu Arg Glu Leu Ser Gly Leu Pro Val
        210                 215                 220

Leu Leu Lys Gly Val Leu Thr Ala Asp Gly Ala Arg Arg Ala Leu Asp
225                 230                 235                 240

Ala Gly Ala Asp Gly Ile Val Val Ser Asn His Gly Gly Arg Gln Leu
                245                 250                 255

Asp Gly Val Pro Ala Thr Leu Asp Val Leu Pro Glu Val Val Ala Ala
            260                 265                 270

Val Ala Gly Arg Cys Pro Val Leu Leu Asp Gly Gly Val Arg Arg Gly
        275                 280                 285

Arg Asp Val Leu Leu Ser Leu Ala Leu Gly Ala Asp Ala Val Leu Val
    290                 295                 300

Gly Arg Pro Val Leu Tyr Gly Leu Ala Val Gly Gly Thr Ala Gly Val
305                 310                 315                 320

Arg His Val Leu Asp Ile Leu Ala Gly Glu Leu Thr Asp Asp Met Ala
                325                 330                 335

Leu Ala Gly Val Ala Ser Pro Ala Asp Ala Gly Ala Asp Leu Ala Gly
            340                 345                 350

Pro Val Ala Pro
        355
```

<210> SEQ ID NO 9
<211> LENGTH: 640
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine at this position

<400> SEQUENCE: 9

```
Val Ala Thr Ile Asp Gly Pro Asp Leu Gly Val Ile Gly Leu Arg Val
1               5                   10                  15

Asp Gly Leu Ile Pro Met Gln Lys Val Arg Pro Gly Thr Val Arg Arg
            20                  25                  30

Ile Leu Pro Tyr Ala Lys Lys His Arg Trp Ser Leu Ala Val Ala Leu
        35                  40                  45

Leu Met Thr Val Val Asp Ala Ala Leu Thr Val Ala Asn Pro Leu Leu
    50                  55                  60

Leu Lys Gln Ile Ile Asp Arg Gly Ile Val Ala Gly Arg Leu Asp Val
65                  70                  75                  80

Val Val Gly Leu Ser Leu Val Val Ala Gly Leu Ala Leu Val Asn Val
                85                  90                  95

Ala Ala Ile His Val Gln Thr Leu Ala Ser Gly Arg Val Gly Gln Gly
            100                 105                 110

Leu Ile Tyr Asp Leu Arg Thr Lys Val Phe Ala His Val Met Arg Gln
        115                 120                 125

Pro Leu Ala Phe Phe Thr Arg Ala Gln Thr Gly Ser Leu Val Ser Arg
    130                 135                 140
```

-continued

```
Leu Asn Thr Asp Val Val Gly Ala Glu Gln Ala Met Thr Ser Met Ile
145                 150                 155                 160

Thr Gln Thr Val Ser Thr Val Leu Thr Val Leu Val Ile Gly Ala
            165                 170                 175

Met Phe Tyr Leu Ser Trp Ala Ile Ala Leu Val Ala Leu Val Leu Ile
            180                 185                 190

Pro Leu Phe Phe Leu Pro Gly Lys Leu Ile Ala Gly Arg Leu Glu Arg
            195                 200                 205

Leu Ala Arg Gly Gly Met Gln Val Asp Ala Glu Leu Gly Ser Met Met
    210                 215                 220

Asn Glu Arg Phe Asn Val Ser Gly Ala Met Leu Val Lys Leu Tyr Gly
225                 230                 235                 240

Arg Pro Glu Ser Glu Glu Thr Ala Phe Ala Gly Arg Ala Arg Val
            245                 250                 255

Arg Asp Ile Ala Ile Ser Met Gly Val His Ala Arg Leu Leu Phe Ile
            260                 265                 270

Ile Ala Thr Leu Leu Thr Thr Val Thr Ala Met Val Tyr Gly Phe
    275                 280                 285

Gly Gly Ala Leu Val Ile Asp Gly Thr Leu Gly Ile Gly Thr Leu Val
    290                 295                 300

Ala Met Val Ala Leu Leu Ala Gln Leu Tyr Gly Pro Val Asn Gln Leu
305                 310                 315                 320

Thr Asn Ile Gln Val Asp Val Thr Ala Leu Val Ser Phe Asp Arg
            325                 330                 335

Val Phe Glu Val Leu Asp Leu Asp Pro Leu Val Lys Glu Arg Pro Gly
            340                 345                 350

Ala Arg Ala Leu Pro Ala Ala Glu Pro Gly Arg Ser Ala Ala Pro Asp
    355                 360                 365

Ile Glu Phe Asp Asn Val Val Phe Arg Tyr Pro Gly Ala Asp Glu Val
    370                 375                 380

Ser Leu Ala Ser Leu Glu Thr Val Ala Gln Arg Ser Ser Asp Gly Thr
385                 390                 395                 400

Ala Glu Arg Pro Val Leu Asn Gly Ile Ser Phe Leu Ala Pro Ala Gly
            405                 410                 415

Lys Leu Thr Ala Leu Val Gly Pro Ser Gly Ala Gly Lys Thr Thr Ile
            420                 425                 430

Thr His Leu Val Pro Arg Leu Tyr Asp Thr Thr Ser Gly Thr Val Arg
    435                 440                 445

Ile Ala Gly His Asp Val Arg Asp Leu Thr Leu Arg Ser Leu Ser Glu
    450                 455                 460

Ser Ile Gly Val Val Thr Gln Asp Ala His Leu Phe His Asp Thr Ile
465                 470                 475                 480

Arg Ala Asn Leu Leu Tyr Gly Arg Pro Asp Ala Gly Glu Arg Asp Leu
            485                 490                 495

Val Ala Ala Cys Glu Ala Ala Arg Ile Trp Glu Met Val Ser Ser Leu
            500                 505                 510

Pro Asp Gly Leu Asp Thr Val Val Gly Asp Arg Gly Tyr Arg Leu Ser
    515                 520                 525

Gly Gly Glu Lys Gln Arg Leu Ala Leu Ala Arg Leu Leu Lys Ser
    530                 535                 540

Pro Pro Val Val Leu Asp Glu Ala Thr Ala His Leu Asp Ser Glu
545                 550                 555                 560

Ser Glu Ala Ala Ile Gln Arg Ala Leu Asp Thr Ala Leu Ala Gly Arg
```

```
                         565                 570                 575
Thr Ser Leu Val Ile Ala His Arg Leu Ala Thr Ile Leu Asp Ala Asp
                580                 585                 590

Gln Ile Leu Val Ile Asp Asp Gly Arg Val Val Glu Arg Gly Thr His
            595                 600                 605

Asp Glu Leu Ile Ala His Gly Gly Leu Tyr Ala Glu Leu Tyr Arg Thr
        610                 615                 620

Gln Phe Ala Gly Gln Arg Thr Glu Glu Arg Gln Pro Ala Val Pro Ser
625                 630                 635                 640

<210> SEQ ID NO 10
<211> LENGTH: 271
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 10

Val Ser Ala Ala Gly Ser Gly Phe Val Thr Thr Asn Gly Val Arg Leu
1               5                   10                  15

Ala Tyr Arg Arg Ser Gly Ala Gly Glu Pro Val Leu Met Ile Met Gly
            20                  25                  30

Ser Gly Ser Ala Gly Gln Thr Trp Thr Val His Gln Thr Pro Ala Leu
        35                  40                  45

His Glu Ala Gly Tyr Ser Thr Val Val Phe Asp Ser Arg Gly Ile Pro
    50                  55                  60

Pro Ser Asp Val Pro Ala Gly Lys Tyr Ser Leu Ala Asp Met Thr Ala
65                  70                  75                  80

Asp Thr Arg Gly Leu Ile Glu Ala Leu Asp Leu Ala Pro Cys Arg Ile
                85                  90                  95

Val Gly Thr Ser Leu Gly Ala Met Ile Ala Gln Glu Leu Ala Val Asp
            100                 105                 110

His Pro Glu Leu Val Arg Cys Ala Val Leu Ile Ala Thr Leu Ala Arg
        115                 120                 125

Pro Asp Ala Ala Arg Ala Ala Gln Asn Gln Ala Asp Ile Asp Leu Leu
    130                 135                 140

Glu Ser Gly Val Thr Leu Pro Ala Ala Tyr Glu Ala Thr Ala Val
145                 150                 155                 160

Phe Lys Met Phe Ser Pro Ala Thr Leu Asn Asp Val Ala Val Arg
                165                 170                 175

Glu Trp Leu Asp Ile Phe Glu Leu Ser Gly Thr Gly Val Ser Ala Gly
            180                 185                 190

Gly Gln Ala Trp Ala Glu Leu Thr Gly Asp Arg Arg Ala Ala Leu Arg
        195                 200                 205

Ser Val Thr Ala Pro Cys Arg Val Ile Ser Phe Ala Asp Asp Leu Ile
    210                 215                 220

Thr Pro Pro His Leu Ala Ala Glu Val Ala Glu Ala Ile Pro Asp Cys
225                 230                 235                 240

Asp Leu Val Glu Ile Ser Arg Cys Gly His Leu Gly Tyr Leu Glu Arg
                245                 250                 255

Pro Asp Ala Val Asn Ala Ala Ile Leu Glu Phe Leu Asp Ser His
            260                 265                 270
```

<210> SEQ ID NO 11
<211> LENGTH: 529
<212> TYPE: PRT
<213> ORGANISM: Actinoplanes sp.

<400> SEQUENCE: 11

```
Met Gly Asn Ala Asp Gln Pro Arg Tyr Leu Arg Ser Asn Val Ile Ala
1               5                   10                  15

Glu Pro Leu Val Asp Arg Phe Tyr Ala Trp Leu His Thr Val Ala Pro
            20                  25                  30

Val Pro Ala Ser Met Asn Leu Ala Phe Leu Gln Val Pro Leu Leu Glu
        35                  40                  45

Ser Tyr Leu Gln Ser Pro Pro Val His Val Ala Ala Ser Thr Asn Pro
    50                  55                  60

Lys Met Arg Gly Gly Tyr Phe Val Ala Val Glu Ser Arg Ser Asp
65                  70                  75                  80

Glu Val Ala Glu Leu Leu Lys Thr Ile Lys Asn Glu Arg Ala Asp Met
                85                  90                  95

Leu Gly Phe Ala Ala Val Ala Glu Ala Glu Asp Leu Ile Arg Glu
            100                 105                 110

Asn Ala Val Gly Tyr Asp Leu Thr Pro Leu Tyr Pro Arg Leu Pro Ala
        115                 120                 125

Ala Leu Asn Gly Leu Val Glu Ile Ala Tyr Asp Thr Ser Asn Gln Pro
    130                 135                 140

Ser Leu His Phe Leu Glu Pro Leu Leu Tyr Arg Ser Pro Ala Tyr Asp
145                 150                 155                 160

Glu Arg Arg Gln Ser Val Gln Leu Ser Leu Asp Asp Gly Val Glu Arg
                165                 170                 175

Pro Phe Ile Leu Ser Thr Pro Arg Leu Pro Arg Ala Gly Val Leu Asp
            180                 185                 190

Leu Pro Leu Pro Leu Arg His Pro Gly Leu Thr Glu Leu Phe Asp Ala
        195                 200                 205

Arg Val Arg Pro Thr Ser Leu Asn Arg Leu Arg Glu Ala Leu Glu Leu
    210                 215                 220

Asp Asp Ala Gly Ala Ala Ala Leu Asp Ala Leu Leu Thr Asp Glu Pro
225                 230                 235                 240

Ser Leu Ser Pro Asp Arg His Ile Glu Ser Gly Arg Val Arg Tyr
                245                 250                 255

Tyr Gly His Ala Cys Val Val Met Gln Thr Glu Gln Ala Ala Val Val
            260                 265                 270

Thr Asp Pro Phe Ile Ser Thr Asp Asn Arg His Gly Asp Arg Tyr Thr
        275                 280                 285

Leu Asp Asp Leu Pro Asp His Ile Asp Leu Val Leu Ile Thr His Gly
    290                 295                 300

His Gln Asp His Ile Val Leu Glu Thr Leu Leu Gln Leu Arg Gly Arg
305                 310                 315                 320

Ile Gly Thr Val Val Pro Arg Thr Ser Arg Gly Asn Leu Pro Asp
                325                 330                 335

Pro Ser Ile Ala Leu Tyr Leu Arg Arg Ile Gly Phe Thr Val Val Glu
            340                 345                 350

Val Glu Glu Phe Asp Glu Val Pro Phe Pro Gly Gly Thr Val Thr Ala
        355                 360                 365

Thr Pro Phe Leu Gly Glu His Ala Asp Leu Asp Ile Arg Gly Lys Ser
    370                 375                 380
```

```
Thr Tyr Phe Val Arg Met Ala Gly Arg Thr Ile Phe Ile Gly Ala Asp
385                 390                 395                 400

Ser Ser Gly Ile Asp Pro Val Leu Tyr Arg Tyr Ile Arg Asp His Val
            405                 410                 415

Gly Gln Val Asp Met Ala Phe Leu Gly Met Glu Cys Asp Gly Ala Pro
            420                 425                 430

Leu Asn Trp Leu Tyr Lys Gly Leu Leu Thr Lys Pro Val Asn Lys Lys
            435                 440                 445

Met Ser Ala Ser Arg Arg Leu Ser Gly Ser Asn Ala Glu Gln Ala Gly
    450                 455                 460

Ala Ile Met Thr Glu Leu Gly Ala Thr Ala Gly Tyr Ile Tyr Ala Met
465                 470                 475                 480

Gly Glu Glu Ser Trp Gln Gly His Val Met Ala Thr Thr Tyr Asn Glu
                485                 490                 495

Asp Thr Tyr Gln Leu Lys Gln Ile Asp Glu Phe Leu Ala Trp Cys Ala
            500                 505                 510

Asp Arg Gly Phe Thr Ala Glu His Leu Phe Asn Lys Arg Glu Trp Arg
            515                 520                 525

Trp

<210> SEQ ID NO 12
<211> LENGTH: 90
<212> TYPE: PRT
<213> ORGANISM: Actinoplanes sp.

<400> SEQUENCE: 12

Met Ser Glu Thr Asp Leu Ser Ala Ala Arg His Thr Pro Glu Gln Ile
1               5                   10                  15

Arg Ser Trp Leu Ile Asp Arg Ile Ala Tyr Tyr Val Met Leu Pro Thr
            20                  25                  30

Gln Glu Ile Glu Pro Asp Val Ser Leu Ala Glu Tyr Gly Leu Asp Ser
        35                  40                  45

Val Tyr Ala Phe Ala Leu Cys Gly Glu Ile Glu Asp Thr Leu Gly Ile
    50                  55                  60

Pro Ile Glu Pro Thr Leu Leu Trp Asp Val Asp Thr Val Ala Thr Leu
65                  70                  75                  80

Thr Ala His Leu Ala Asp Arg Val Asn Arg
                85                  90

<210> SEQ ID NO 13
<211> LENGTH: 1051
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard codon. It is
      expected that the biosynthesized protein will have a formylmethio-
      nine residue at this position

<400> SEQUENCE: 13

Val Pro Thr Pro Asp Leu Arg Pro Leu Thr Pro Ala Gln Leu Ala Val
1               5                   10                  15

Trp His Ala Gln Gln Leu Ala Pro His Ser Pro Val Tyr Gln Val Gly
            20                  25                  30

Glu Phe Val Glu Ile Asp Gly Glu Cys Asp Pro Asp Leu Leu Val Ala
        35                  40                  45
```

-continued

```
Ala Leu Arg Gln Val Met Gly Glu Ala Glu Ser Ala Arg Leu Arg Phe
 50                  55                  60

Arg Val Ile Asp Gly Thr Pro Trp Gln Tyr Val Ala Glu Asp Gly Asp
 65                  70                  75                  80

Asp Pro Ile Gln Val Val Asp Leu Gly Ala Ala Asp Pro Arg Ala
                 85                  90                  95

Ala Ala Leu Gly Arg Met Ala Ala Asp Leu Asp Arg Pro Gly Asp Leu
                100                 105                 110

Arg Asp Gly Pro Leu Val Glu His His Val Tyr Leu Leu Gly Glu Gly
            115                 120                 125

Arg Val Ile Trp Tyr His Arg Ala His His Ile Val Cys Asp Gly Gly
        130                 135                 140

Ser Leu Gly Ile Val Ala Ser Arg Val Ala Gly Val Tyr Ser Ala Leu
145                 150                 155                 160

Ala Ala Gly Gly Asp Val Arg Pro Gly Ala Leu Pro Pro Leu Ser Val
                165                 170                 175

Leu Leu Ser Ala Ala Asp Ala Tyr Glu Arg Ser Gly Asp Arg Asp Arg
                180                 185                 190

Asp Arg Glu His Trp Arg Ser Ala Leu Ala Gly Leu Pro Ala Glu Leu
            195                 200                 205

Leu Ala Gly Ala Gly Arg Pro Arg Pro Leu Pro Gly Pro Pro Val Arg
210                 215                 220

His Glu His Asp Leu Ser Ala Ala Glu Ala Gly Arg Leu Arg Ala Gly
225                 230                 235                 240

Ala Arg Arg Leu Arg Thr Ser Val Ala Gln Ala Gly Ile Ala Ala Ala
                245                 250                 255

Ala Leu Tyr Gln His Arg Leu Thr Gly Ala Arg Asp Val Leu Val Ala
                260                 265                 270

Val Pro Val Ala Gly Arg Thr Thr Arg Pro Glu Phe Asp Val Pro Gly
            275                 280                 285

Met Thr Ser Asn Val Val Pro Val Arg Leu Ala Val Thr Pro Ala Thr
        290                 295                 300

Thr Val Gly Glu Leu Leu Arg Asp Val Ala Arg Gly Val Arg Asp Gly
305                 310                 315                 320

Leu Arg His Gln Arg Tyr Pro Tyr Pro Asn Ile Val Asp Asp Leu Gly
                325                 330                 335

Leu Ala Asp Arg Ala Ala Leu Arg Pro Val Thr Val Asn Ala Leu Ala
                340                 345                 350

Leu Gly Arg Pro Leu Arg Phe Gly Ser Ala Val Gly Val Arg Ser Gly
            355                 360                 365

Leu Ser Ala Gly Pro Val Asp Asp Val Thr Ile Gly Leu Tyr Glu Lys
        370                 375                 380

Val Ser Gly Gly Gly Met Gln Thr Ile Ala Glu Leu Asn Pro Gly Arg
385                 390                 395                 400

Thr Asp Arg Pro Asp Ala Ala Glu Val Ser Arg Trp Phe Arg Thr Leu
                405                 410                 415

Leu Arg Gly Leu Ala Glu Ser Asp Ala Gly Asp Pro Val Ala Arg Ile
                420                 425                 430

Asp Ile Val Asp Glu Pro Glu Arg Arg Leu Leu Asp Glu Trp Asn
            435                 440                 445

Ala Thr Ala Ala Pro Ser Ser Asp Thr Val Leu Ala Arg Phe Glu Glu
450                 455                 460

Gln Ala Ala Arg Thr Pro Glu Ala Pro Ala Val Val Cys Gly Asp Val
```

-continued

```
465                 470                 475                 480
Thr Val Thr Tyr Ala Glu Leu Glu Ala Gly Ala Asn Arg Leu Ala Arg
                485                 490                 495
Val Leu Arg Ala Arg Gly Ala Gly Pro Glu Ser Val Val Ala Leu Cys
            500                 505                 510
Leu Pro Arg Gly Pro Glu Val Val Thr Gly Ile Leu Ala Ala Trp Lys
            515                 520                 525
Ala Gly Ala Ala Tyr Leu Pro Val Asp Thr Glu Leu Pro Ala Glu Arg
            530                 535                 540
Val Ala Tyr Leu Leu Gly Asp Ser Ala Ala Val Arg Leu Gly Thr
545                 550                 555                 560
Ala Glu Thr Leu Ala Ala Leu Pro Asp Gly Pro Ala Ala Asp Val Asp
                565                 570                 575
Val His Ala Pro Glu Ile Ala Arg Glu Ser Pro Ser Pro Leu Arg Leu
            580                 585                 590
Glu Pro Leu Pro Asp Gln Leu Ala Tyr Val Ile Tyr Thr Ser Gly Ser
            595                 600                 605
Thr Gly Leu Ser Lys Gly Val Gly Val Ser His Gly Gly Leu Ala Asn
            610                 615                 620
Tyr Val Gly Trp Ala Ser Val Leu Tyr Gly Gly Leu Ser Ala Pro Leu
625                 630                 635                 640
His Ser Ser Leu Ala Phe Asp Leu Thr Val Thr Ser Val Phe Val Pro
                645                 650                 655
Leu Val Cys Gly Gly Ser Val Val Ser Ala Ala Gly Gly Gly Arg
            660                 665                 670
Gly Leu Ala Ser Leu Leu Ala Ala Gly Asp Gly Phe Ser Leu Val Lys
            675                 680                 685
Val Val Pro Gly His Leu Arg Leu Leu Ala Glu Leu Val Pro Ala Gly
            690                 695                 700
Glu Met Ala Ala Val Gly Ser Leu Val Ala Gly Gly Glu Val Leu Ala
705                 710                 715                 720
Gly Gly Asp Val Arg Glu Trp Leu Ser Arg Val Pro Gly Ser Val Val
                725                 730                 735
Val Asn Glu Tyr Gly Pro Thr Glu Thr Val Val Gly Cys Ser Val Phe
            740                 745                 750
Ser Val Ala Ala Gly Asp Val Gly Asp Val Val Pro Val Gly Arg
            755                 760                 765
Pro Val Ala Asn Thr Arg Leu Phe Val Leu Asp Glu Gly Leu Arg Pro
            770                 775                 780
Val Pro Ala Gly Val Ala Gly Glu Leu Tyr Val Ala Gly Ser Gln Val
785                 790                 795                 800
Ala Arg Gly Tyr Val Gly Arg Ser Gly Leu Thr Ala Ser Arg Phe Val
                805                 810                 815
Ala Cys Pro Phe Gly Val Gly Glu Arg Met Tyr Arg Thr Gly Asp Val
                820                 825                 830
Val Arg Leu Ala Gly Gly Asp Leu Val Phe Val Gly Arg Val Asp Glu
            835                 840                 845
Gln Val Lys Ile Arg Gly Tyr Arg Val Glu Pro Asp Glu Val Arg Leu
            850                 855                 860
Val Val Ala Gly His Pro Arg Val Ala Gly Ala Val Val Ala Arg
865                 870                 875                 880
Pro Asp Ala Val Gly Glu Arg Gln Leu Val Ala Tyr Val Val Ala Ala
                885                 890                 895
```

-continued

Gly Glu Pro Ala Gly Leu Ala Glu Ser Val Arg Ala His Val Ala Glu
            900                 905                 910

Arg Leu Pro Glu Tyr Met Val Pro Ala Ala Val Val Thr Leu Asp Glu
            915                 920                 925

Ile Pro Leu Thr Val Asn Gly Lys Val Asp Arg Ala Ala Leu Pro Glu
            930                 935                 940

Pro Gly Pro Val Ala Thr Gly Asn Ala Asp Arg Glu Pro Thr Thr Glu
945                 950                 955                 960

Arg Glu Ser Leu Leu Cys Gly Ala Phe Ala Asp Val Leu Gly Ile Glu
            965                 970                 975

Arg Val Gly Val Asp Asp Phe Phe Ser Leu Gly Gly His Ser Leu
            980                 985                 990

Leu Ala Thr Ser Leu Val Ser Arg Val Arg Leu Val Leu Gly Glu Glu
            995                 1000                1005

Leu Pro Ile Glu Glu Leu Phe Ala Thr Pro Thr Pro Ala Glu Leu
        1010                1015                1020

Ala Ala Trp Leu Gln Arg Asn Ala Asp Arg Pro Gln Pro Ala Arg
        1025                1030                1035

Pro Ala Leu Arg Pro Met His Glu Arg Glu Thr Thr Ala
        1040                1045                1050

<210> SEQ ID NO 14
<211> LENGTH: 4999
<212> TYPE: PRT
<213> ORGANISM: Actinoplanes sp.

<400> SEQUENCE: 14

Met Thr Pro Met Ser Tyr Ala Gln Arg Arg Leu Trp Phe Gln Leu Arg
1               5                   10                  15

Val Glu Gly Pro Asp Ala Thr Tyr Asn Ser Pro Ala Val Leu Arg Leu
            20                  25                  30

Thr Gly Glu Leu Asp Thr Ala Ala Leu Glu His Ala Leu Arg Asp Val
        35                  40                  45

Leu Glu Arg His Glu Val Leu Arg Thr Val Tyr Pro Asp Val Gly Gly
    50                  55                  60

Glu Pro Arg Gln Arg Val Val Arg Pro Asp Asp Met Val Trp Glu Leu
65                  70                  75                  80

Pro Thr Thr Arg Val Ser Gly Ala Gly Ala Gly Asp Asp Arg Leu Val
                85                  90                  95

Thr Leu Asp Glu Leu Pro Trp Asp Arg Pro Val Leu Asp Leu Pro Ser
            100                 105                 110

Pro Ala Pro Ala Gly Arg Glu Pro Asp Gly Glu Ile Thr Val Asp Glu
        115                 120                 125

Leu Pro Gly Ala Ile Ala Arg Val Ala Ala His Pro Phe Asp Leu Ser
    130                 135                 140

Ile Glu Ile Pro Val Arg Ala Arg Leu Phe Ala Leu Gly Pro Arg His
145                 150                 155                 160

His Val Leu Val Val Leu His His Ile Ala Thr Asp Gly Ser Ser
                165                 170                 175

Gly Gly Pro Phe Ala Arg Asp Leu Ala Ala Ala Tyr Arg Ala Arg Arg
            180                 185                 190

Thr Gly Thr Ala Pro Gln Trp Ala Pro Leu Pro Val Gln Tyr Ala Asp
        195                 200                 205

Tyr Ala Ala Trp Gln Gln Glu Leu Leu Gly Ala Glu Asp Asp Pro Asp

-continued

```
            210                 215                 220
Ser Val Ile Ser Arg Gln Leu Ala His Trp Gln Glu Arg Leu Ala Gly
225                 230                 235                 240

Met Pro Val Glu Leu Asp Leu Pro Ala Asp Arg Pro Arg Pro Ala Glu
                245                 250                 255

Pro Gly His Gly Gly His Thr Lys Ala Leu Ser Leu Pro Pro Ala Val
                260                 265                 270

His Arg Gly Leu Ala Thr Leu Ala Arg Arg Arg Ala Thr Leu Gln
                275                 280                 285

Met Val Val Gln Thr Gly Val Ala Ile Leu Leu Ser Lys Leu Gly Ala
290                 295                 300

Gly Arg Asp Val Pro Leu Gly Ile Pro Val Ala Gly Arg Thr Asp Ala
305                 310                 315                 320

Ala Leu Asp Asp Leu Ile Gly Phe Phe Val Asn Thr Leu Val Val Arg
                325                 330                 335

Ala Asp Leu Ser Gly Asp Pro Thr Val Ala Asp Ala Leu Gly Arg Val
                340                 345                 350

Arg Gly Gly Ala Val Ala Ala Leu Ala Asp Gln Asp Val Pro Phe Asp
                355                 360                 365

Lys Leu Val Glu Arg Leu Ala Pro Ala Arg Val Leu Gly Arg His Pro
                370                 375                 380

Leu Phe Gln Val Met Val Ala Pro Leu Asp Asp Gly Thr Pro Ile Asp
385                 390                 395                 400

Leu Asp Gly Val Arg Gly Glu Pro Leu Thr Ile Gly Arg Ser Gly Ala
                405                 410                 415

Lys Phe Asp Val Glu Val Met Thr Gly Glu Val Arg Ala Ala Asp Gly
                420                 425                 430

Ala Pro Ala Gly Ile Arg Gly Ile Leu Thr Leu Ser Ala Asp Leu Phe
                435                 440                 445

Asp Glu Ala Thr Ala Gly Arg Met Ala Ala Gly Leu Val Arg Val Leu
                450                 455                 460

Thr Ala Met Ala Glu Ala Pro Glu Arg Arg Leu Ser Gly Ile Glu Val
465                 470                 475                 480

Leu Ser Pro Gly Glu Arg Ser Arg Leu Leu Val Glu Trp Asn Asp Thr
                485                 490                 495

Ala Arg Pro Val Val Glu Ser Ser Val Pro Ala Leu Phe Ala Lys Arg
                500                 505                 510

Val Ala Ala Thr Pro Asp Ala Thr Ala Val Val Gly Glu Gly Val Ser
                515                 520                 525

Trp Ser Tyr Arg Glu Leu Asp Arg Arg Ser Asp Val Leu Ala Arg Arg
530                 535                 540

Leu Val Ala Ala Gly Val Gly Val Glu Ser Pro Val Val Ala Leu
545                 550                 555                 560

Glu Arg Ser Pro Glu Val Leu Ser Ala Phe Leu Ala Val Ala Lys Ala
                565                 570                 575

Gly Gly Val Phe Val Pro Val Asp Leu Ser Trp Pro Gln Ala Arg Val
                580                 585                 590

Asp Ala Val Val Ala Asp Cys Ala Ala Arg Val Ala Val Ala Asp Arg
                595                 600                 605

Pro Met Ser Gly Leu Thr Val Val Ser Ala Gly Leu Gly Gly Asp Ser
                610                 615                 620

Ala Val Val Ser Ala Asp Leu Thr Ala Asp Arg Ala Val Val Leu Pro
625                 630                 635                 640
```

-continued

```
Ser Arg Pro Val Pro Gly Ala Ala Val Tyr Arg Met Tyr Thr Ser Gly
            645                 650                 655
Ser Thr Gly Arg Pro Lys Gly Val Val Thr Thr His Gln Asn Leu Val
        660                 665                 670
Asp Leu Ala Thr Asp Thr Cys Trp Gly Pro Thr Pro Arg Val Leu Phe
    675                 680                 685
His Ala Pro His Ala Phe Asp Ala Ser Ser Tyr Glu Ile Trp Val Pro
690                 695                 700
Leu Leu Asn Gly Gly Thr Val Val Ala Pro Gln Arg Ser Ile Asp
705                 710                 715                 720
Ala Thr Val Leu Lys Asp Leu Ile Arg Ala His Asp Leu Thr His Val
            725                 730                 735
His Val Thr Ala Gly Leu Leu Arg Val Leu Asp Pro Ser Cys Phe Ala
        740                 745                 750
Gly Leu Thr Glu Val Leu Thr Gly Gly Asp Ala Val Ser Ala Glu Ala
    755                 760                 765
Val Arg Arg Val Lys Asp Ala Asn Pro Gly Leu Arg Val Arg Gln Leu
770                 775                 780
Tyr Gly Pro Thr Glu Val Thr Leu Cys Ala Thr Gln His Leu Leu Asp
785                 790                 795                 800
Asp Gly Val Pro Ile Gly Arg Pro Leu Asp Asn Thr Arg Val Tyr Val
            805                 810                 815
Leu Asp Asp Leu Leu Gln Pro Val Pro Val Gly Val Thr Gly Glu Leu
        820                 825                 830
Tyr Val Ala Gly Ala Gly Val Ala Arg Gly Tyr Ala Gly Met Pro Gly
    835                 840                 845
Leu Thr Ala Glu Arg Phe Val Ala Asp Pro Phe Asn Thr Gly Gly Arg
850                 855                 860
Leu Tyr Arg Thr Gly Asp Leu Val Arg Trp Thr Asp Gly Val Leu
865                 870                 875                 880
His Phe Ala Gly Arg Ala Asp Asp Gln Val Lys Ile Arg Gly Tyr Arg
            885                 890                 895
Val Glu Pro Gly Glu Val Glu Ala Val Leu Ala Gln His Pro Asp Val
        900                 905                 910
Ser Gln Val Ala Val Val Arg Glu Asp Thr Pro Gly Asp Lys Arg
    915                 920                 925
Leu Val Ala Tyr Val Val Gly Gly Asp Ile Glu Ala Tyr Gly Gln Glu
    930                 935                 940
Arg Leu Pro Gly Tyr Met Val Pro Ser Ala Phe Val His Leu Asp Ala
945                 950                 955                 960
Leu Pro Leu Thr Ser Asn Gln Lys Val Asp Arg Ala Ala Leu Pro Ala
            965                 970                 975
Pro Ser Met Glu Ser Gly Ala Arg Ala Pro Ala Asp Ala Arg Glu
        980                 985                 990
Glu Leu Val Cys Ala Ala Phe Ala  Glu Val Leu Gly Leu  Asp Arg Val
    995                 1000                1005
Gly Val  Asp Asp Asp Phe Phe  Ala Leu Gly Gly His  Ser Leu Leu
    1010                1015                1020
Ala Val  Ser Leu Val Glu Asp  Leu Arg Gln Arg Gly  Leu His Val
    1025                1030                1035
Ser Val  Arg Ala Leu Phe Ala  Thr Pro Thr Pro Ala  Ala Leu Ala
    1040                1045                1050
```

-continued

| | | | | | | | | | | |
|---|---|---|---|---|---|---|---|---|---|---|
|Val|Ser 1055|Thr|Val|Ala|Ala 1060|Pro|Ile|Glu|Val 1065|Pro|Pro|Asn|Leu|Ile|
|Pro|Gln 1070|Gly|Gly|Ala|Arg 1075|Glu|Leu|Thr|Pro 1080|Asp|Met|Leu|Pro|Leu|
|Val|Asp 1085|Leu|Thr|Gly|Glu 1090|Glu|Leu|Ala|Thr 1095|Ile|Val|Ala|Ala|Val|
|Pro|Gly 1100|Gly|Ala|Ala|Asn 1105|Ile|Ala|Asp|Ile 1110|Tyr|Pro|Leu|Ala|Pro|
|Leu|Gln 1115|Glu|Gly|Ile|Phe 1120|Phe|His|His|Leu 1125|Met|Thr|Glu|Gly|Asp|
|Thr|Ala 1130|Asp|Val|Tyr|Ala 1135|Leu|Pro|Tyr|Leu 1140|Leu|Arg|Val|Gly|Thr|
|Arg|Glu 1145|Gln|Leu|Asp|Ala 1150|Phe|Leu|Gly|Ala 1155|Leu|Gln|Gln|Val|Val|
|Asp|Arg 1160|His|Asp|Val|Tyr 1165|Arg|Thr|Ala|Ile 1170|Ala|Trp|Gln|Asn|Leu|
|Arg|Glu 1175|Pro|Val|Gln|Val 1180|Val|His|Arg|His 1185|Ala|Thr|Leu|Pro|Val|
|Thr|Glu 1190|Val|Thr|Pro|Asp 1195|Gln|Leu|His|Ala 1200|Ala|Thr|Gly|Gly|
|Arg|Leu 1205|Pro|Leu|Asp|His 1210|Ala|Pro|Leu|Leu 1215|Ser|Val|His|Ile|Ala|
|Pro|Glu 1220|Pro|Asp|Gly|Gly 1225|Trp|Leu|Ala|Leu 1230|Leu|Arg|Met|His|His|
|Leu|Val 1235|Gln|Asp|His|Thr 1240|Ala|Leu|Asp|Ile 1245|Val|Leu|Asp|Glu|Ile|
|Arg|Thr 1250|Ile|Leu|Ala|Gly 1255|Ala|Thr|Asp|His 1260|Leu|Pro|Pro|Pro|Val|
|Pro|Phe 1265|Arg|Asn|Phe|Val 1270|Ala|Arg|Ser|Arg 1275|Arg|Gly|Ala|Ala|Glu|
|Ala|Ala 1280|His|Arg|Asp|Tyr 1285|Phe|Thr|Gly|Leu 1290|Leu|Gly|Asp|Val|Thr|
|Glu|Thr 1295|Thr|Ala|Pro|Tyr 1300|Gly|Leu|Thr|Asp 1305|Val|His|Gly|Glu|His|
|Ser|Gly 1310|Val|Arg|Arg|Gly 1315|Arg|Leu|Ala|Val 1320|Ser|Ala|Gly|Leu|Ala|
|Gly|Arg 1325|Val|Arg|Glu|Thr 1330|Ala|Arg|Asp|Arg 1335|Gly|Val|Ser|Pro|Ala|
|Thr|Leu 1340|Phe|His|Leu|Ala 1345|Trp|Ala|Arg|Val 1350|Leu|Ala|Ala|Val|Ser|
|Gly|Arg 1355|Asp|Asp|Val|Val 1360|Phe|Gly|Thr|Val 1365|Leu|Leu|Gly|Arg|Met|
|Asp|Ala 1370|Gly|Pro|Gly|Ala 1375|Asp|Arg|Val|Pro 1380|Gly|Leu|Phe|Met|Asn|
|Thr|Leu 1385|Pro|Val|Arg|Val 1390|Arg|Leu|Gly|Gly 1395|Arg|Thr|Val|Asp|Glu|
|Ala|Leu 1400|His|Gly|Met|Arg 1405|Ala|Gln|Leu|Ala 1410|Asp|Leu|Leu|Thr|His|
|Glu|His 1415|Ala|Pro|Leu|Val 1420|Leu|Ala|Gln|Gln 1425|Ser|Ala|Gly|Leu|Pro|
|Gly|Gly 1430|Ser|Pro|Leu|Phe 1435|Thr|Ser|Leu|Phe 1440|Asn|Tyr|Arg|His|Asn|
|Ala|Thr|Asp|Ile|Glu|Arg|Ser|Gly|Thr|Gly|Ile|Asp|Gly|Val|Glu|

-continued

|  |  |  |
|---|---|---|
| 1445 | 1450 | 1455 |

Ala Leu Pro Thr Gly Asp Pro Ser Asn Tyr Pro Leu Asp Val Ser
    1460                1465                1470

Val Asn Gln Ser Pro Leu Gly Phe Glu Leu Val Val Glu Ala Thr
    1475                1480                1485

Glu Pro Ala Asp Pro Asp Gln Leu Cys Arg Leu Leu His Ala Cys
    1490                1495                1500

Leu Asp Asp Leu Ile Ala Ala Leu Asp Glu Gln Pro Gly Arg Ala
    1505                1510                1515

Leu Gly Thr Leu Asp Val Val Ala Gly Arg Glu Arg Asp Leu Leu
    1520                1525                1530

Leu Asp Gly Trp Asn Ala Thr Ala Val Pro Ala Gln Pro Ala Leu
    1535                1540                1545

Val Pro Glu Leu Phe Thr Ala Gln Ala Ala Arg Thr Pro Thr Trp
    1550                1555                1560

Pro Ala Leu Val Thr Ala Gly Ala Glu Met Ser Tyr Ala Glu Leu
    1565                1570                1575

Glu Glu Arg Ser Asn Arg Leu Ala Arg Trp Leu Ala Gly Arg Gly
    1580                1585                1590

Val Gly Ala Asp Asp Arg Val Ala Leu Met Met Arg Arg Gly Pro
    1595                1600                1605

Glu Leu Met Val Ala Ile Leu Ala Val Leu Lys Ala Gly Ala Ala
    1610                1615                1620

Tyr Leu Pro Val Asp Pro Asp Leu Pro Arg Asp Arg Val Asp Tyr
    1625                1630                1635

Leu Leu Ala Asp Ala Ala Pro Ala Phe Val Leu Ala Glu Arg Ala
    1640                1645                1650

Thr Ala Pro Trp Val Pro Val Ala Gly Gly Ile Pro Val Leu Val
    1655                1660                1665

Val Asp Ala Pro Ala Val Ala Ala Glu Val Ala Ala His Ser Gly
    1670                1675                1680

Glu Ala Val Thr Asp Arg Asp Arg Arg Ala Ala Leu Arg Gly Gly
    1685                1690                1695

His Leu Ala Tyr Val Ile Tyr Thr Ser Gly Ser Thr Gly Arg Pro
    1700                1705                1710

Lys Gly Val Leu Ile Thr His Asp Gly Leu Ala Asn Leu Thr Leu
    1715                1720                1725

Asp His Gly Arg Phe Gly Leu Gly Pro Gly Ala Arg Val Ala Gln
    1730                1735                1740

Phe Ala Ser Pro Gly Phe Asp Met Phe Val Asp Glu Trp Ser Met
    1745                1750                1755

Ala Leu Leu Ala Gly Ala Ala Leu Thr Phe Val Pro Pro Glu Arg
    1760                1765                1770

Arg Leu Gly Ala Asp Leu Ala Ala Phe Leu Ala Glu Tyr Gly Val
    1775                1780                1785

Thr His Ala Thr Leu Pro Pro Ala Val Val Gly Thr Pro Asp Gly
    1790                1795                1800

Val Leu Pro Pro Ser Phe Val Leu Asp Val Gly Asp Val Leu
    1805                1810                1815

Pro Gly Asp Leu Ala Arg Arg Trp Leu Arg Asp Gly Arg Val Leu
    1820                1825                1830

Phe Asn Ser Tyr Gly Pro Thr Glu Thr Thr Val Asn Ala Ala Thr
    1835                1840                1845

-continued

```
Trp Arg Ala Glu Ala Gly Asp Trp Gly Ser Val Ala Pro Ile Gly
1850                1855                1860

Thr Pro Val Pro Asn Leu Arg Ala Tyr Val Leu Asp Gly Trp Leu
    1865                1870                1875

Arg Pro Val Pro Val Gly Ala Asp Gly Glu Leu Tyr Val Ser Gly
    1880                1885                1890

Ala Gly Leu Ala Arg Gly Tyr Leu Asn Arg Ala Gly Leu Thr Ala
    1895                1900                1905

Glu Arg Phe Val Ala Cys Pro Phe Glu Pro Gly Glu Arg Met Tyr
    1910                1915                1920

Arg Thr Gly Asp Val Val Arg Trp Thr Ala Glu Gly Arg Leu Val
    1925                1930                1935

Phe Ala Gly Arg Ser Asp Asp Gln Val Lys Ile Arg Gly Phe Arg
    1940                1945                1950

Ile Glu Pro Gly Glu Val Glu Ala Val Leu Ala Ala Gly Pro Gly
    1955                1960                1965

Val Ser Gln Ala Ala Val Ile Val Arg Glu Asp Val Pro Gly Asp
    1970                1975                1980

Lys Arg Leu Val Ala Tyr Val Val Gly Gly Asp Val Glu Ala Leu
    1985                1990                1995

Arg Ser Tyr Ala Gln Gln Arg Leu Pro Gly Tyr Met Val Pro Ser
    2000                2005                2010

Ala Phe Val Glu Leu Asp Arg Leu Pro Leu Thr Val Asn Gly Lys
    2015                2020                2025

Leu Asp Arg Arg Ala Leu Pro Val Pro Asp Leu Ala Arg Gly Thr
    2030                2035                2040

Gly Ser Gly Arg Pro Ala Gly Thr Pro Arg Glu Gln Leu Leu Cys
    2045                2050                2055

Ala Gly Phe Ala Ala Val Leu Gly Val Asp Asp Val Gly Ala Asp
    2060                2065                2070

Asp Asp Phe Phe Ala Leu Gly Gly His Ser Leu Leu Val Val Ser
    2075                2080                2085

Leu Val Glu Trp Leu Arg Arg Arg Gly Val Ser Val Pro Val Arg
    2090                2095                2100

Ala Leu Phe Thr Thr Pro Thr Pro Ala Gly Leu Ala Glu Ala Val
    2105                2110                2115

Gly Asp Gly Ala Val Val Pro Pro Asn Leu Ile Pro Glu Gly
    2120                2125                2130

Ala Ala Glu Leu Thr Pro Glu Met Val Pro Leu Ala Asp Leu Thr
    2135                2140                2145

Ser Glu Glu Leu Ala Ile Val Ala Ser Val Pro Gly Gly Ala
    2150                2155                2160

Ala Asn Val Ala Asp Val Tyr Pro Leu Ala Pro Leu Gln Glu Gly
    2165                2170                2175

Ile Phe Phe Pro Val Ala Thr Gly Pro Gln Cys Tyr Ala Thr Val
    2180                2185                2190

Gly Ser Ser Leu Pro Asp Asp Gly Gly Ser Ala Pro Cys Ser Arg
    2195                2200                2205

Phe Arg Arg Arg Cys Val Ser Thr Ser Val Val Trp Gln Gly Leu
    2210                2215                2220

Arg Glu Pro Val Gln Val Val Trp Arg His Ala Arg Leu Pro Val
    2225                2230                2235
```

-continued

```
Glu Glu Val Val Leu His Glu Gly Ala Asp Pro Val Glu Gln Met
    2240            2245            2250

Met Ala Leu Ala Gly Gly Trp Met Asp Leu Thr Arg Ala Pro Leu
    2255            2260            2265

Ile Asp Val His Ile Ala Ala Gly Pro Gly Gly Asp Arg Trp Leu
    2270            2275            2280

Ala Val Leu Arg Ile His His Leu Val Gln Asp His Thr Ala Leu
    2285            2290            2295

Glu Thr Leu Leu Asp Glu Leu Gln Ser Phe Leu Glu Gly Arg Gly
    2300            2305            2310

Gly Glu Leu Ala Glu Pro Val Pro Phe Arg Glu Phe Val Ala Gln
    2315            2320            2325

Ala Arg Leu Gly Val Pro Arg Glu Glu His Glu Arg Tyr Phe Ala
    2330            2335            2340

Glu Leu Leu Gly Asp Ile Thr Glu Thr Thr Ala Pro Tyr Asp Leu
    2345            2350            2355

Thr Asp Val His Gly Asp Gly Thr Gly Tyr Asp His Gly Ala Leu
    2360            2365            2370

Pro Leu Asp Ala Thr Val Ala Ala Arg Val Arg Glu Ala Ala Arg
    2375            2380            2385

Thr Leu Gly Val Ser Pro Ala Thr Leu Phe His Leu Ala Trp Ala
    2390            2395            2400

Arg Val Leu Gly Thr Leu Ala Gly Arg Asp Asp Val Val Phe Gly
    2405            2410            2415

Thr Val Leu Phe Gly Arg Met Asn Ser Gly Ala Gly Ala Asp Arg
    2420            2425            2430

Val Ser Gly Leu Phe Ile Asn Thr Leu Pro Val Arg Val Arg Leu
    2435            2440            2445

Gly Ala Pro Thr Gly Asp Ala Leu Gly Asp Leu Arg Asp Gln Leu
    2450            2455            2460

Ala Glu Leu Leu Val His Glu His Ala Ser Leu Ala Ser Ala Gln
    2465            2470            2475

Lys Ala Ser Gly Leu Pro Gly Gly Ser Pro Leu Phe Thr Ser Ile
    2480            2485            2490

Phe Asn Tyr Arg His Asn Gln Val Ser Ala Glu Arg Glu Thr Ala
    2495            2500            2505

Ala Leu Pro Gly Ile Arg Val Leu Ala Ala Arg Asp Ser Thr Asn
    2510            2515            2520

Tyr Pro Leu Thr Val Ala Val Asp Asp Asp Gly His Gly Phe Thr
    2525            2530            2535

Leu Val Val Glu Val Ala Ser Thr Val Asp Ala Ala Gly Val Cys
    2540            2545            2550

Glu Leu Leu His Thr Ala Val Asp Asn Leu Ile Ala Ala Leu Thr
    2555            2560            2565

Asp Arg Pro Gly Gly Pro Leu Ala Glu Val Asp Ile Leu Glu Arg
    2570            2575            2580

Gly Leu Arg Asp Arg Leu Leu Thr Ala Trp Asn Glu Ala Arg Glu
    2585            2590            2595

Pro Ala Pro Pro Val Thr Leu Pro Asp Leu Phe Asp Arg Gln Ala
    2600            2605            2610

Arg Arg Thr Pro Glu Ala Val Ala Leu Thr Ala Asp Gly Val Ser
    2615            2620            2625

Leu Thr Tyr Arg Glu Leu Ser Glu Arg Ala Asn Arg Ile Ala Arg
```

-continued

| | 2630 | | | | 2635 | | | | 2640 | | |
|---|---|---|---|---|---|---|---|---|---|---|---|
| Leu | Leu | Thr | Ser | Arg | Gly | Ile | Gly | Pro | Glu | Ser | Leu | Val | Gly | Val |
| | 2645 | | | | | 2650 | | | | 2655 | | |
| Val | Leu | Pro | Arg | Ser | Ala | Asp | Leu | Val | Val | Ala | Leu | Leu | Gly | Val |
| | 2660 | | | | | 2665 | | | | 2670 | | |
| Leu | Gln | Ala | Gly | Ala | Ala | Tyr | Val | Pro | Val | Asp | Ala | Asp | Tyr | Pro |
| | 2675 | | | | | 2680 | | | | 2685 | | |
| Ala | Glu | Arg | Ile | Gly | Tyr | Ile | Leu | Gly | Asp | Ala | Gly | Ala | Val | Cys |
| | 2690 | | | | | 2695 | | | | 2700 | | |
| Val | Leu | Thr | Val | Asp | Ala | Thr | Ala | Gly | Ala | Val | Pro | Pro | Gly | Val |
| | 2705 | | | | | 2710 | | | | 2715 | | |
| Pro | Lys | Leu | Val | Leu | Asp | His | Pro | Glu | Thr | Val | Thr | Ala | Leu | Ala |
| | 2720 | | | | | 2725 | | | | 2730 | | |
| Ala | Cys | Asp | Thr | Ala | Pro | Leu | Gly | Glu | Ala | Glu | Arg | Ala | Gly | Glu |
| | 2735 | | | | | 2740 | | | | 2745 | | |
| Leu | Leu | Pro | Glu | His | Pro | Ala | Tyr | Val | Ile | Tyr | Thr | Ser | Gly | Ser |
| | 2750 | | | | | 2755 | | | | 2760 | | |
| Thr | Gly | Thr | Pro | Lys | Gly | Val | Leu | Ile | Pro | His | Arg | Asn | Val | Val |
| | 2765 | | | | | 2770 | | | | 2775 | | |
| Glu | Leu | Phe | Ala | Ala | Thr | Arg | Gly | Ser | Phe | His | Phe | Gly | Glu | Gly |
| | 2780 | | | | | 2785 | | | | 2790 | | |
| Asp | Val | Trp | Ser | Trp | Phe | His | Ser | Val | Ala | Phe | Asp | Phe | Ser | Val |
| | 2795 | | | | | 2800 | | | | 2805 | | |
| Trp | Glu | Leu | Trp | Gly | Ala | Leu | Leu | His | Gly | Gly | Arg | Val | Val | Met |
| | 2810 | | | | | 2815 | | | | 2820 | | |
| Val | Pro | Phe | Ala | Val | Ser | Arg | Ser | Pro | Arg | Asp | Phe | Trp | Glu | Leu |
| | 2825 | | | | | 2830 | | | | 2835 | | |
| Leu | Val | Arg | Glu | Arg | Val | Thr | Val | Leu | Ser | Gln | Thr | Pro | Ser | Ala |
| | 2840 | | | | | 2845 | | | | 2850 | | |
| Phe | Tyr | Gln | Leu | Ala | Ala | Ala | Asp | Asp | Thr | Pro | Asp | Ala | Leu |
| | 2855 | | | | | 2860 | | | | 2865 | | |
| Arg | Val | Val | Phe | Gly | Gly | Glu | Ala | Leu | Asp | Pro | Gly | Arg | Leu |
| | 2870 | | | | | 2875 | | | | 2880 | | |
| Ala | Gly | Trp | Arg | Glu | Arg | Pro | Asp | Gly | Pro | Arg | Leu | Val | Asn |
| | 2885 | | | | | 2890 | | | | 2895 | | |
| Met | Tyr | Gly | Ile | Thr | Glu | Thr | Thr | Val | His | Val | Thr | His | Gln | Asp |
| | 2900 | | | | | 2905 | | | | 2910 | | |
| Leu | Ala | Pro | Ala | Asp | Thr | Thr | Gly | Ser | Pro | Ile | Gly | Arg | Gly | Ile |
| | 2915 | | | | | 2920 | | | | 2925 | | |
| Pro | Gly | Leu | Ser | Val | Tyr | Val | Leu | Asp | Glu | Ala | Leu | Arg | Pro | Val |
| | 2930 | | | | | 2935 | | | | 2940 | | |
| Pro | Pro | Gly | Val | Ala | Gly | Glu | Val | Tyr | Val | Ala | Gly | Arg | Gln | Leu |
| | 2945 | | | | | 2950 | | | | 2955 | | |
| Ala | Arg | Ala | Tyr | Leu | Gly | Arg | Ala | Ala | Leu | Thr | Gly | Thr | Arg | Phe |
| | 2960 | | | | | 2965 | | | | 2970 | | |
| Val | Ala | Cys | Pro | Phe | Leu | Pro | Ala | Gly | Glu | Arg | Met | Tyr | Arg | Thr |
| | 2975 | | | | | 2980 | | | | 2985 | | |
| Gly | Asp | Arg | Ala | Arg | Trp | Ser | Arg | Gly | Arg | Leu | Gln | Phe | Ala | Gly |
| | 2990 | | | | | 2995 | | | | 3000 | | |
| Arg | Thr | Asp | Asp | Gln | Val | Gln | Ile | Arg | Gly | Phe | Arg | Ile | Glu | Pro |
| | 3005 | | | | | 3010 | | | | 3015 | | |
| Gly | Glu | Val | Gln | Ala | Val | Val | Ala | Ala | His | Pro | Glu | Ile | Ala | Ala |
| | 3020 | | | | | 3025 | | | | 3030 | | |

-continued

```
Ala Ala Val Val Val Arg Glu Asp Val Pro Gly Asp Pro Arg Leu
    3035                3040                3045

Thr Ala Tyr Val Val Pro Ala Gly Pro Arg Thr Ala Pro Ala Ala
    3050                3055                3060

Val Ala Glu Thr Val Arg Arg Phe Ala Ala Asp Arg Leu Pro Ala
    3065                3070                3075

Tyr Met Leu Pro Ser Ala Val Val Leu Asp Ala Leu Pro Leu
    3080                3085                3090

Thr Asp His Gly Lys Leu Asp Arg Arg Ala Leu Pro Ala Pro Gln
    3095                3100                3105

His Thr Gly Ala Ala Ser Gly Arg Ala Pro Ala Thr Val Ala Glu
    3110                3115                3120

Glu Val Leu Cys Ala Ala Phe Ala Glu Val Leu Gly Val Glu Arg
    3125                3130                3135

Val Gly Val Asp Asp Asp Phe Phe Ala Leu Gly Gly His Ser Leu
    3140                3145                3150

Leu Ile Val Ser Leu Val Glu Arg Val Arg Arg Ala Gly Leu Ala
    3155                3160                3165

Ile Pro Val Arg Ala Leu Phe Arg Ser Ala Thr Pro Ala Gly Leu
    3170                3175                3180

Ala Ala Leu Ala Arg Pro Tyr Arg Val Asp Ile Pro Pro Asn Leu
    3185                3190                3195

Val Pro Asp Gly Ala Arg Glu Ile Thr Pro Asp Met Leu Thr Leu
    3200                3205                3210

Ala Ala Leu Thr Glu Ala Glu Ile Ala Thr Val Leu Ala Thr Val
    3215                3220                3225

Pro Gly Gly Ala Val Asn Val Ala Asp Ile Tyr Pro Leu Ala Pro
    3230                3235                3240

Leu Gln Glu Gly Ile Phe Phe His His Leu Met Ala Asp Ala Gly
    3245                3250                3255

Arg Ala Asp Ala Tyr Ala Met Pro Tyr Val Leu His Leu Asp Thr
    3260                3265                3270

Ala Glu Arg Leu Asp Val Leu Leu Gly Ala Leu Gln Arg Val Ile
    3275                3280                3285

Asp Arg Asn Asp Ile Tyr Arg Thr Gly Val Val Ser Ala Gly Leu
    3290                3295                3300

Arg Glu Pro Val Gln Val Val Trp Arg Ser Ala Val Leu Pro Val
    3305                3310                3315

Glu Glu Val Ala Leu Asp Gly Gly His Asp Pro Val Glu Gln Leu
    3320                3325                3330

Leu Ala Ala Ala Gly Glu Glu Phe Asp Leu Thr Arg Ala Pro Leu
    3335                3340                3345

Ile Arg Ala His Val Ala Ala His Pro Asp Gly Gly Arg Leu Leu
    3350                3355                3360

Leu Leu Arg Ile His His Leu Val Gln Asp His Thr Thr Phe Asp
    3365                3370                3375

Val Val Leu Gly Glu Leu Arg Ala Phe Leu Glu Gly Arg Gly Gly
    3380                3385                3390

Glu Leu Ala Glu Pro Val Pro Phe Arg Glu Phe Val Ala Gln Ala
    3395                3400                3405

Arg Leu Gly Val Pro Arg Glu Glu His Glu Arg Tyr Phe Ala Glu
    3410                3415                3420
```

```
Leu Leu Gly Asp Val Thr Glu Thr Thr Ala Pro Tyr Gly Leu Thr
3425                3430                3435

Asp Val His Gly Asp Gly Ser Arg Ala Val Gln Val Ser Leu Pro
3440                3445                3450

Val Ala Glu Ala Leu Ala Val Arg Val Arg Glu Val Ala Arg Thr
3455                3460                3465

Leu Gly Val Ser Pro Ala Thr Val Phe His Leu Ala Trp Ala Arg
3470                3475                3480

Val Leu Ser Val Ile Ala Gly Arg Asp Asp Val Val Phe Gly Thr
3485                3490                3495

Ile Leu Phe Gly Arg Met Asn Ser Gly Ala Ala Ala Glu Arg Val
3500                3505                3510

Pro Gly Leu Phe Ile Asn Thr Leu Pro Val Arg Val Arg Leu Asn
3515                3520                3525

Gly Thr Ser Val Gly Glu Ala Leu Thr Ala Leu Arg Asp Gln Met
3530                3535                3540

Ala Glu Leu Met Ala His Glu His Ala Pro Leu Ala Leu Ala Gln
3545                3550                3555

Arg Ala Gly Gly Val Pro Ala Gly Ser Pro Leu Phe Thr Ser Leu
3560                3565                3570

Phe Asn Tyr Arg His Asn Val Ala Gly Gly Asp Gly Gly Ala
3575                3580                3585

Leu Glu Gly Val Thr Pro Val Leu His Arg Asp Thr Thr Asn Tyr
3590                3595                3600

Pro Val Val Val Ser Val Asp Asp Gly Thr Ser Phe Asp Leu
3605                3610                3615

Val Val Glu Ala Val Ala Pro Ala Glu Ala Gly Arg Val Gly Arg
3620                3625                3630

Leu Met His Glu Cys Leu Ala Glu Leu Val Gly Ala Leu Ala Gly
3635                3640                3645

Ala Pro Glu Thr Pro Leu Ser Arg Val Arg Val Ile Asp Glu Ala
3650                3655                3660

Glu Ile Glu Arg Val Val His Ser Trp Asn Asp Thr Ala Arg Pro
3665                3670                3675

Val Val Glu Ser Ser Val Pro Ala Leu Phe Ala Glu Gln Val Ala
3680                3685                3690

Ala Ala Pro Asp Ala Thr Ala Val Val Gly Glu Gly Val Ser Trp
3695                3700                3705

Ser Tyr Arg Glu Leu Asp Ala Arg Ser Asp Ala Leu Ala Arg Ser
3710                3715                3720

Leu Val Ala Ala Gly Val Gly Val Glu Ser Pro Val Val Ala
3725                3730                3735

Leu Glu Arg Ser Pro Glu Val Leu Ser Ala Phe Leu Ala Val Ala
3740                3745                3750

Lys Ala Gly Gly Val Phe Val Pro Val Asp Leu Ser Trp Pro Gln
3755                3760                3765

Ala Arg Ile Asp Ala Val Val Ala Asp Cys Ala Ala Arg Val Ala
3770                3775                3780

Val Ala Asp Arg Pro Met Ser Gly Leu Thr Val Val Pro Ala Asp
3785                3790                3795

Gln Val Gly Asp Ser Ala Val Val Leu Pro Ala Gly Pro Val Pro
3800                3805                3810

Gly Ala Ala Val Tyr Arg Met Tyr Thr Ser Gly Ser Thr Gly Arg
```

-continued

|  | 3815 |  |  |  | 3820 |  |  |  | 3825 |  |
|---|---|---|---|---|---|---|---|---|---|---|

Pro Lys Gly Val Val Thr Thr His Gln Asn Leu Val Asp Leu Ala
    3830                3835                3840

Thr Asp Thr Cys Trp Gly Pro Thr Pro Arg Val Leu Phe His Ala
    3845                3850                3855

Pro His Ala Phe Asp Ala Ser Ser Tyr Glu Ile Trp Val Pro Leu
    3860                3865                3870

Leu Asn Gly Gly Thr Val Val Ala Pro Gln Arg Ser Ile Asp
    3875                3880                3885

Ala Thr Val Leu Arg Asp Leu Ile Arg Gly His Glu Leu Thr His
    3890                3895                3900

Val His Val Thr Ala Gly Leu Leu Arg Val Leu Asp Pro Ser Cys
    3905                3910                3915

Phe Ala Gly Leu Thr Glu Val Leu Thr Gly Gly Asp Ala Val Ser
    3920                3925                3930

Ala Glu Ala Val Arg Arg Val Arg Glu Ala Asn Pro Gly Leu Arg
    3935                3940                3945

Val Arg Gln Leu Tyr Gly Pro Thr Glu Val Thr Leu Cys Ala Thr
    3950                3955                3960

Gln His Leu Leu Val Asp Gly Val Pro Ile Gly Arg Pro Leu Asp
    3965                3970                3975

Asn Thr Arg Val Tyr Val Leu Asp Asp Leu Leu Gln Pro Val Pro
    3980                3985                3990

Val Gly Val Thr Gly Glu Leu Tyr Val Ala Gly Ala Gly Leu Ala
    3995                4000                4005

Arg Gly Tyr Ala Gly Met Pro Gly Leu Thr Ala Glu Arg Phe Val
    4010                4015                4020

Ala Asp Pro Phe Ser Val Gly Gly Arg Leu Tyr Arg Thr Gly Asp
    4025                4030                4035

Leu Val Arg Trp Thr Asp Asp Gly Val Leu His Phe Ala Gly Arg
    4040                4045                4050

Ala Asp Asp Gln Val Lys Ile Arg Gly Tyr Arg Val Glu Pro Gly
    4055                4060                4065

Glu Val Glu Ala Val Leu Ala Gln His Pro Asp Val Ser Gln Val
    4070                4075                4080

Ala Val Val Val Arg Glu Asp Thr Pro Gly Asp Lys Arg Leu Val
    4085                4090                4095

Ala Tyr Val Val Gly Gly Asp Val Glu Ala Tyr Ala Gln Glu Arg
    4100                4105                4110

Leu Pro Gly Tyr Leu Val Pro Ser Ala Phe Val His Leu Asp Ala
    4115                4120                4125

Leu Pro Leu Thr Ser Asn Gln Lys Val Asp Arg Ala Ala Leu Pro
    4130                4135                4140

Ala Pro Ser Val Glu Ser Gly Val Gly Arg Ala Pro Ala Asp Ala
    4145                4150                4155

Arg Glu Glu Leu Met Cys Ala Ala Phe Ala Glu Val Leu Asp Leu
    4160                4165                4170

Asp Arg Val Gly Val Asp Asp Phe Phe Ala Leu Gly Gly His
    4175                4180                4185

Ser Leu Leu Val Val Arg Leu Val Gly Arg Ile Arg Gln Val Phe
    4190                4195                4200

Gly Val Glu Val Ser Ala Arg Leu Val Phe Asp Ala Arg Thr Pro
    4205                4210                4215

```
Ala Gly Val Val Ala Arg Leu Ser Glu Gly Gly Thr Ala Arg Glu
    4220                4225                4230

Ala Val Arg Ala Arg Val Arg Pro Ala Arg Val Pro Leu Ser Phe
    4235                4240                4245

Ala Gln Arg Arg Leu Trp Phe Leu Ser Gln Leu Glu Gly Pro Ser
    4250                4255                4260

Ala Thr Tyr Asn Ile Pro Val Ala Leu Arg Leu Asp Gly Pro Leu
    4265                4270                4275

Asp Arg Asp Ala Leu Thr Ala Ala Leu His Asp Val Val Ala Arg
    4280                4285                4290

His Glu Val Leu Arg Thr Val Phe Thr Val Ala Asp Gly Glu Pro
    4295                4300                4305

Trp Gln Gln Ile Leu Asp Asp Pro Gln Val Ser Val Pro Val Val
    4310                4315                4320

Glu Val Thr Pro Asp Arg Leu Pro Glu Ala Val Ala Val Ala Ala
    4325                4330                4335

Gly His Arg Phe Asp Leu Gly Arg Glu Leu Pro Leu Arg Ala Val
    4340                4345                4350

Leu Leu Ala Thr Gly Asp Asp Val His Val Leu Val Leu Val Val
    4355                4360                4365

His His Ile Ala Ala Asp Gly Trp Ser Met Arg Pro Leu Ala Arg
    4370                4375                4380

Asp Leu Ala Ala Ala Tyr Ala Ala Arg Ile Asp Ala Thr Ala Pro
    4385                4390                4395

Ala Leu Gly Ala Leu Pro Val Gln Tyr Ala Asp Tyr Ala Leu Trp
    4400                4405                4410

Gln Arg Asp Val Leu Gly Ser Glu His Asp Pro Asp Ser Val Ile
    4415                4420                4425

Ser Gln Gln Val Ala Tyr Trp Arg Arg Gln Leu Ala Gly Val Pro
    4430                4435                4440

Glu Glu Leu Asp Leu Pro Val Asp Arg Ala Arg Pro Ala Glu Ala
    4445                4450                4455

Ser His Arg Gly His Thr Val Glu Phe Ala Val Pro Pro Ala Val
    4460                4465                4470

His His Gln Leu Ala Glu Leu Ala Arg Arg Asn Gly Val Thr Val
    4475                4480                4485

Phe Met Thr Val Gln Thr Ala Leu Ala Val Leu Leu Ser Lys Leu
    4490                4495                4500

Gly Ala Gly Thr Asp Ile Pro Ile Gly Val Ala Val Ala Gly Arg
    4505                4510                4515

Thr Asp Pro Thr Leu Asp Asn Leu Ile Gly Phe Phe Val Asn Thr
    4520                4525                4530

Leu Val Leu Arg Thr Asp Leu Thr Gly Asn Pro Thr Ile Thr Asp
    4535                4540                4545

Leu Leu His Arg Thr Arg Asp Thr Thr Leu His Ala Phe Thr His
    4550                4555                4560

Gln Asp Val Pro Phe Glu Lys Leu Val Glu Asp Leu Ala Pro Thr
    4565                4570                4575

Arg Ser Leu Ala Arg His Pro Leu Phe Gln Val Met Met Thr Leu
    4580                4585                4590

Gln Ser Ala Ser Ala Asp Glu Glu Pro Leu Ala Leu Ala Gly Leu
    4595                4600                4605
```

-continued

```
Arg Val Thr Asp Leu Pro Ala Gly Glu Thr Pro Ala Lys Val Asp
4610            4615            4620

Leu Asp Leu Thr Leu His Glu Val Ala Gly Arg Asp Gly Met His
4625            4630            4635

Ala Thr Leu Leu Gly Ala Ala Asp Leu Phe Glu Gln Glu Thr Val
4640            4645            4650

Arg Ala Leu Ala Asp Arg Leu Leu Arg Thr Leu Glu Ala Met Ala
4655            4660            4665

Ala Ala Pro Asp Asp Arg Leu Asp Arg Ile Glu Val Leu Ser Pro
4670            4675            4680

Gly Glu Arg Ser Arg Leu Leu Val Glu Trp Asn Asp Thr Ala Arg
4685            4690            4695

Pro Val Val Glu Ser Ser Val Pro Ala Leu Phe Ala Glu Gln Val
4700            4705            4710

Ala Ala Ala Pro Asp Ala Val Ala Val Val Gly Glu Gly Val Ser
4715            4720            4725

Trp Thr Tyr Arg Glu Leu Asp Ala Arg Ser Asp Ala Leu Ala Arg
4730            4735            4740

Ser Leu Val Ala Ala Gly Val Gly Val Glu Ser Pro Val Val Val
4745            4750            4755

Ala Leu Glu Arg Ser Pro Glu Val Leu Ser Ala Phe Leu Ala Val
4760            4765            4770

Ala Lys Ala Gly Gly Val Phe Val Pro Val Asp Leu Ser Trp Pro
4775            4780            4785

Gln Ala Arg Val Asp Ala Val Val Ala Asp Cys Gly Ala Arg Ile
4790            4795            4800

Ala Val Ala Asp Arg Pro Met Ser Gly Leu Thr Val Val Ser Ala
4805            4810            4815

Gly Leu Gly Gly Asp Ser Ala Val Val Ser Gly Asp Leu Thr Ala
4820            4825            4830

Asp Arg Ala Val Val Leu Pro Ala Gly Pro Val Pro Gly Ala Ala
4835            4840            4845

Val Tyr Arg Met Tyr Thr Ser Gly Ser Thr Gly Arg Pro Lys Gly
4850            4855            4860

Val Val Thr Thr His Gln Asn Leu Val Asp Leu Ala Thr Asp Thr
4865            4870            4875

Cys Trp Gly Pro Thr Pro Arg Val Leu Phe His Ala Pro His Ala
4880            4885            4890

Phe Asp Ala Ser Ser Tyr Glu Ile Trp Val Pro Leu Leu Asn Gly
4895            4900            4905

Gly Thr Val Val Val Ala Pro Arg Arg Ser Ile Asp Ala Thr Val
4910            4915            4920

Leu Arg Asp Leu Ile Gly Ala His Glu Leu Thr His Val His Val
4925            4930            4935

Thr Ala Gly Leu Leu Arg Val Leu Asp Pro Ser Cys Phe Ala Gly
4940            4945            4950

Leu Thr Glu Val Leu Thr Gly Gly Asp Ala Val Ser Ala Glu Ala
4955            4960            4965

Val Arg Arg Val Lys Asp Ala Asn Pro Gly Leu Arg Val Arg Gln
4970            4975            4980

Leu Tyr Gly Pro Thr Glu Val Thr Leu Cys Ala Thr Gln His Leu
4985            4990            4995

Leu
```

```
<210> SEQ ID NO 15
<211> LENGTH: 4999
<212> TYPE: PRT
<213> ORGANISM: Actinoplanes sp.

<400> SEQUENCE: 15

Met Ile Pro Leu Ser Phe Ala Gln Arg Arg Leu Trp Phe Leu Gly Arg
1               5                   10                  15

Leu Glu Gly Pro Ser Ala Thr Tyr Asn Ile Pro Leu Val Leu Gly Leu
            20                  25                  30

Thr Gly Thr Val Asp Ala Ala Leu Glu Thr Ala Leu Arg Asp Val
        35                  40                  45

Leu Glu Arg His Glu Val Leu Arg Thr Val Tyr Pro Asp Ala Gly Gly
50                  55                  60

Glu Pro His Gln Arg Ile Leu Pro Leu Gly Glu Thr Gly Phe Gly Leu
65                  70                  75                  80

Arg Val Ala Glu Val Thr Asp Gly Glu Leu Asp Ala Val Ala Asp
                85                  90                  95

Ala Thr Gly His Ala Phe Asp Leu Ala Thr Glu Ile Pro Val Arg Ala
            100                 105                 110

Ser Leu Leu Thr Val Glu Pro Gly Arg His Val Leu Ala Leu Val Leu
        115                 120                 125

His His Ile Ala Ala Asp Gly Trp Ser Met Gly Pro Leu Leu Arg Asp
130                 135                 140

Leu Ser Thr Ala Tyr Thr Ala Arg Leu Ala Gly Gly Glu Pro Ala Trp
145                 150                 155                 160

Ser Pro Leu Pro Val Gln Tyr Ala Asp Tyr Ala Leu Trp Gln Gln Glu
                165                 170                 175

Val Leu Gly Ala Gly Asp Asp Pro Glu Ser Leu Leu Arg Glu Gln Val
            180                 185                 190

Gly Tyr Trp Arg Ser Ala Leu Ala Gly Ala Pro Glu Glu Leu Arg Leu
        195                 200                 205

Pro Ala Asp His Arg Arg Pro Pro Val Ser Ser Arg Ala His Met
210                 215                 220

Ala Glu Phe Ala Val Pro Ala Ala His Gly Asp Leu Thr Ala Leu
225                 230                 235                 240

Thr Arg Glu Leu Gly Ala Thr Leu Phe Met Ala Val His Ala Ala Thr
                245                 250                 255

Ala Met Val Leu Ser Gly Leu Gly Ala Gly Asp Asp Leu Pro Ile Gly
            260                 265                 270

Thr Val Val Ala Gly Arg Thr Asp Ala Gly Leu Asp Asp Leu Val Gly
        275                 280                 285

Cys Phe Val Asn Asn Leu Val Ile Arg Ala Asp Leu Thr Gly Asp Pro
290                 295                 300

Thr Phe Ala Asp Leu Leu Arg Gln Val Arg Glu Arg Ala Leu Asp Ala
305                 310                 315                 320

Tyr Gly His Gln Asp Val Pro Phe Glu Lys Leu Val Glu Glu Leu Ala
                325                 330                 335

Pro Ser Arg Ser Leu Ser Arg His Pro Leu Phe Gln Val Ala Val Ala
            340                 345                 350

Val Glu Thr Asp Asp Leu Ile Gly Gly Arg Gly Gly Pro Ala Leu
        355                 360                 365

Arg Leu Pro Gly Leu Gly Ile Glu Val Leu Pro Gly Glu Pro Ser Ala
```

-continued

```
            370                 375                 380
Arg Asp Leu Asp Leu Asp Leu Val Val Arg Glu Thr Phe Asp Ala Glu
385                 390                 395                 400

Gly Arg Pro Ala Gly Leu Thr Gly Ala Leu Ile Gly Ala Ala Gly Leu
                405                 410                 415

Phe Asp Ala Ala Ser Val Glu Arg Leu Ala Ala Leu Leu Ala Arg Ala
                420                 425                 430

Leu Glu Ala Leu Ala Ala Asp Pro Arg Thr Arg Ala Gly Asp Leu Asp
                435                 440                 445

Leu Leu Ser Pro Ala Asp Arg Arg Leu Ile Leu Arg Gly Trp Asn Asp
450                 455                 460

Thr Ala Ala Pro Ala Pro Ala Gly Leu Val Pro Asp Leu Phe Ala Ala
465                 470                 475                 480

Gln Ala Ala Arg Thr Pro Asp Ala Val Ala Val Ala Gly Pro Asp Arg
                485                 490                 495

Glu Leu Thr Tyr Ala Glu Leu Asp Glu Arg Ser Gly Arg Leu Ala Arg
                500                 505                 510

Trp Leu Ile Arg Arg Gly Val Ala Ala Asp Thr Arg Val Ala Leu Val
                515                 520                 525

Leu Glu Arg Ser Ala Glu Leu Pro Val Ala Ile Leu Ala Val Leu Lys
                530                 535                 540

Ala Gly Gly Ala Tyr Leu Pro Ile Asp Pro Ala Gln Pro Pro Arg Arg
545                 550                 555                 560

Ile Ala Asp Ile Val Ala Asp Ala Ala Pro Ala Leu Val Leu Ala Gln
                565                 570                 575

Ala Ser Thr Ala Asp Val Val Ala Asp Ala Ser Pro Ala Leu Val Leu
                580                 585                 590

Ala Pro Ala Ser Asp Gly Val Pro Thr Gly Ala Val Pro Val His Leu
                595                 600                 605

Leu Asp Ser Pro Ala Val Arg Asp Glu Val Ala Gln Cys Pro Ala Gly
                610                 615                 620

Ala Val Thr Asp Ala Asp Arg Arg Gly Val Leu Leu Gly Gly His Ala
625                 630                 635                 640

Ala Tyr Val Ile Tyr Thr Ser Gly Ser Thr Gly Arg Pro Lys Gly Val
                645                 650                 655

Val Val Ser His Asp Ala Phe Ala Asn Leu Val Leu Asp Gln Arg Arg
                660                 665                 670

Leu Gly Ile Gly Pro Gly Ser Arg Val Ala Gln Phe Ala Ser Pro Gly
                675                 680                 685

Phe Asp Met Phe Val Asp Glu Trp Ser Met Ala Leu Leu Ala Gly Ala
690                 695                 700

Ala Leu Val Ile Val Pro Pro Glu Arg Arg Leu Gly Ala Asp Leu Ala
705                 710                 715                 720

Ala Phe Leu Thr Glu Arg Gly Val Thr His Ala Thr Leu Pro Pro Ala
                725                 730                 735

Val Val Ala Thr Leu Pro Glu Glu Ser Leu Pro Arg Ser Phe Val Leu
                740                 745                 750

Asp Ile Gly Gly Asp Ala Leu Pro Asp Leu Ala Arg Arg Trp Leu
                755                 760                 765

Arg Asp Gly Arg Trp Leu Gly Asn Ser Tyr Gly Pro Thr Glu Thr Thr
770                 775                 780

Val Asn Ala Ala Thr Trp Arg Cys Glu Pro Gly Thr Trp Glu Gly Ala
785                 790                 795                 800
```

-continued

Thr Pro Ile Gly Arg Pro Val Ala Asn Leu Arg Ala Tyr Val Leu Asp
            805                 810                 815

Gly Arg Leu Arg Pro Val Pro Val Gly Val Glu Gly Glu Leu Tyr Val
            820                 825                 830

Ser Gly Ala Gly Leu Ala Arg Gly Tyr Leu Asn Arg Ala Gly Leu Thr
            835                 840                 845

Ala Gly Ser Phe Val Ala Cys Pro Phe Glu Pro Gly Glu Arg Met Tyr
            850                 855                 860

Arg Thr Gly Asp Ile Val Arg Trp Asp Ala Arg Gly Arg Leu Val Tyr
865                 870                 875                 880

Ala Gly Arg Ala Asp Asp Gln Ala Lys Ile Arg Gly Phe Arg Val Glu
            885                 890                 895

Pro Gly Glu Val Glu Ala Val Leu Ala Ala Gly Pro Gly Val Asn Gln
            900                 905                 910

Val Ala Val Ile Val Arg Glu Asp Val Pro Gly Asp Lys Arg Leu Val
            915                 920                 925

Ala Tyr Val Val Gly Gly Asp Val Glu Thr Leu Arg Ser Tyr Ala Gln
            930                 935                 940

Gln Arg Leu Pro Gly Tyr Leu Val Pro Ser Ala Ile Val Ala Leu Ala
945                 950                 955                 960

Glu Leu Pro Leu Thr Pro Ser Ala Lys Val Asp Arg Arg Ala Leu Pro
            965                 970                 975

Val Pro Asp Tyr Gly Arg Asp Ala Gly Gly Gly Arg Ala Pro Ala Asn
            980                 985                 990

Ala Arg Glu Glu Val Leu Cys Arg Ala Phe Ala Glu Val Leu Gly Val
            995                 1000                1005

Glu Arg Val Gly Val Glu Asp Asp Phe Phe Ala Leu Gly Gly His
            1010                1015                1020

Ser Leu Leu Val Val Ser Leu Val Glu Arg Leu Arg Arg Gln Gly
            1025                1030                1035

Ile Ser Val Pro Val Arg Ala Leu Phe Thr Thr Pro Thr Pro Ala
            1040                1045                1050

Gly Leu Ala Glu Ala Val Gly Asp Gly Ala Val Val Pro Pro
            1055                1060                1065

Asn Leu Ile Pro Glu Gly Ala Ala Glu Leu Thr Pro Glu Met Leu
            1070                1075                1080

Pro Leu Ala Asp Leu Thr Ala Asp Glu Leu Ala Val Val Val Asp
            1085                1090                1095

Ser Val Pro Gly Gly Ala Ala Asn Ile Ala Asp Val Tyr Pro Leu
            1100                1105                1110

Ala Pro Leu Gln Glu Gly Ile Phe Phe His His Met Met Ala Asp
            1115                1120                1125

Arg Asp Ser Ala Asp Val Tyr Val Thr Pro Thr Val Val Glu Phe
            1130                1135                1140

Asp Ser Arg Asp Arg Leu Asp Gly Phe Leu Ala Ala Leu Gln Gln
            1145                1150                1155

Val Val Asp Arg Thr Asp Val Tyr Arg Thr Ser Val Val Trp Gln
            1160                1165                1170

Gly Leu Arg Glu Pro Val Gln Val Val Trp Arg His Ala Arg Leu
            1175                1180                1185

Pro Val Asp Glu Val Val Leu Arg Asp Asp Leu Asp Pro Val Glu
            1190                1195                1200

-continued

```
Gln Leu Asn Ala Leu Gly Thr Ala Trp Met Asp Leu Ser Glu Ala
    1205                1210                1215

Pro Leu Val Gln Ala Val Val Ala Ala Arg Pro Gly Asp Pro Gln
    1220                1225                1230

Arg Trp Leu Ala Val Leu Arg Ile His His Leu Val Gln Asp His
    1235                1240                1245

Thr Ala Leu Asp Ile Leu Leu Glu Glu Leu Ala Ala Tyr Leu Ala
    1250                1255                1260

Gly Arg Gly Gly Asp Leu Pro Glu Pro Val Pro Phe Arg Glu Phe
    1265                1270                1275

Val Ala His Thr Arg Leu Gly Val Pro Arg Glu Glu His Glu Arg
    1280                1285                1290

Tyr Phe Ala Gly Leu Leu Gly Asp Val Thr Glu Thr Thr Ala Pro
    1295                1300                1305

Tyr Gly Leu Leu Asp Val His Ser Gly Gly Leu Ala Ser Ala Gln
    1310                1315                1320

Ala His Leu Arg Leu Asp Gly Pro Leu Gly Arg Arg Val Ala Ala
    1325                1330                1335

Phe Ala Arg Glu His Gly Val Ser Pro Ala Thr Leu Phe His Leu
    1340                1345                1350

Ala Trp Ala Arg Val Leu Gly Thr Leu Ala Gly Arg Asp Asp Val
    1355                1360                1365

Val Phe Gly Thr Val Leu Phe Gly Arg Met Asn Ser Gly Ala Gly
    1370                1375                1380

Ala Asp Arg Val Pro Gly Leu Phe Ile Asn Thr Leu Pro Val Arg
    1385                1390                1395

Val Arg Leu Gly Ala Pro Val Gly Asp Ala Leu Asp Gly Leu Arg
    1400                1405                1410

Asp Gln Leu Ile Glu Leu Ile Ala His Glu His Ala Pro Leu Ala
    1415                1420                1425

Val Ala Gln Gln Ala Ala Asn Leu Phe Gly Arg Pro Leu Phe Thr
    1430                1435                1440

Ser Ile Phe Asn Tyr Arg Tyr Ala Arg Gly Ala Glu Pro Ala Gly
    1445                1450                1455

Ala Ala Leu Asp Gly Ile Arg Leu Leu Ser Ala Arg Asp Leu Thr
    1460                1465                1470

Asn Tyr Pro Leu Ala Val Ala Val Asp Ala Glu Gly Asp Thr Phe
    1475                1480                1485

Ser Leu Thr Val Asp Ala Val Ala Pro Ala Asp Pro Val Gln Val
    1490                1495                1500

Gly Glu Leu Leu Val Thr Ala Leu Arg Asn Leu Thr Arg Thr Ala
    1505                1510                1515

Glu Asn Ala Pro Gly Thr Pro Leu Ala Ala Val Gly Val Leu Gly
    1520                1525                1530

Glu Asp Glu Leu Ser Arg Val Val Ser Gly Trp Asn Asp Thr Ala
    1535                1540                1545

Arg Arg Val Arg Gln Ala Ser Val Pro Glu Leu Phe Ala Glu Arg
    1550                1555                1560

Val Ala Ala Pro Gly Ala Pro Ala Val Ala Ala Gly Asp Leu
    1565                1570                1575

Arg Trp Thr Tyr Ala Asp Leu Asp Ala Arg Ser Asp Ala Leu Ala
    1580                1585                1590

Arg Ser Leu Val Ala Ala Gly Val Thr Ala Glu Ser Pro Val Val
```

-continued

|  | 1595 |  |  |  | 1600 |  |  |  | 1605 |  |  |
|---|---|---|---|---|---|---|---|---|---|---|---|

Val Ala Leu Glu Arg Ser Ala Asp Val Leu Thr Ala Phe Leu Ala
    1610                1615                1620

Val Ala Lys Ala Gly Gly Val Phe Val Pro Val Asp Leu Ser Trp
    1625                1630                1635

Pro Arg Ala Arg Val Asp Ala Val Ile Ala Asp Cys Ala Ala Trp
    1640                1645                1650

Ile Ala Val Ala Asp Arg Pro Met Thr Gly Leu Thr Val Val Pro
    1655                1660                1665

Ala Asn Arg Ala Gly Asp Pro Ala Val Ala Leu Pro Pro Arg Pro
    1670                1675                1680

Leu Pro Gly Ala Ala Ala Tyr Arg Met Tyr Thr Ser Gly Ser Thr
    1685                1690                1695

Gly Arg Pro Lys Gly Val Val Thr Thr His Gln Asn Val Val Asp
    1700                1705                1710

Leu Val Thr Asp Arg Cys Trp Gly Pro Thr Pro Arg Val Leu Phe
    1715                1720                1725

His Ala Pro His Ala Phe Asp Ala Ser Ser Phe Glu Leu Trp Val
    1730                1735                1740

Pro Leu Leu Thr Gly Gly Thr Val Val Ala Pro Gly Glu Ser
    1745                1750                1755

Ile Asp Thr Gly Val Leu Arg Gln Leu Ile Arg Ala His Glu Leu
    1760                1765                1770

Thr His Val His Val Thr Ala Gly Leu Leu Arg Val Leu Ala Glu
    1775                1780                1785

Asp Pro Ser Cys Phe Ala Gly Leu Thr Glu Val Leu Thr Gly Gly
    1790                1795                1800

Asp Val Val Pro Ala Glu Ala Val Arg Arg Val Leu Asp Ala Asn
    1805                1810                1815

Pro Gly Val Arg Val Arg Gln Leu Tyr Gly Pro Thr Glu Val Thr
    1820                1825                1830

Leu Cys Ala Thr Gln His Val Val Arg Glu Pro Ser Pro Val Leu
    1835                1840                1845

Pro Ile Gly Arg Pro Leu Asp Asn Thr Arg Val Tyr Val Leu Asp
    1850                1855                1860

Gly Leu Leu Gln Pro Val Pro Val Gly Val Thr Gly Glu Leu Tyr
    1865                1870                1875

Ile Ala Gly Ala Gly Val Ala Arg Gly Tyr Ala Asp Met Pro Gly
    1880                1885                1890

Thr Thr Ala Glu Arg Phe Val Ala Asp Pro Phe Thr Ala Gly Gly
    1895                1900                1905

Arg Leu Tyr Arg Thr Gly Asp Leu Val Arg Trp Thr Gly Glu Gly
    1910                1915                1920

Glu Leu Val Phe Ala Gly Arg Ala Asp Asp Gln Val Lys Ile Arg
    1925                1930                1935

Gly Tyr Arg Val Glu Pro Gly Glu Val Glu Ala Val Leu Ala Ala
    1940                1945                1950

Leu Pro Gly Val Ser Gln Ala Ala Val Ile Val Arg Glu Asp Val
    1955                1960                1965

Pro Gly Asp Lys Arg Leu Val Ala Tyr Leu Val Ala Ala Pro Glu
    1970                1975                1980

Thr Val Glu Ala Ala Arg Ala His Ala Glu Gln Arg Leu Pro Ser
    1985                1990                1995

```
Tyr Leu Val Pro Ser Ala Phe Val Gln Leu Asp Ala Leu Pro Leu
    2000            2005            2010

Thr Gly Asn Gln Lys Val Asp Arg Ala Ala Leu Pro Ala Pro Leu
    2015            2020            2025

Gly Phe Glu Ala Gly Ala Gly Arg Ala Pro Ala Asp Ala Arg Glu
    2030            2035            2040

Glu Leu Val Gly Ala Ala Phe Ala Glu Val Leu Asp Leu Gly Arg
    2045            2050            2055

Val Gly Pro Asp Asp Asp Phe Phe Ala Leu Gly Gly His Ser Leu
    2060            2065            2070

Leu Ala Leu Ala Leu Val Glu Arg Leu Arg Arg Gln Gly Leu Gly
    2075            2080            2085

Val Ser Val Arg Ala Val Phe Asp Ala Arg Thr Pro Ala Ala Leu
    2090            2095            2100

Thr Arg Arg Gly Asp Gly Gly Ala Asp Asp Arg Pro Ala Leu Arg
    2105            2110            2115

Ala Gly Ala Arg Pro Ala Arg Leu Pro Leu Ser Tyr Ala Gln Arg
    2120            2125            2130

Arg Leu Trp Phe Leu Ala Gln Leu Glu Gly Pro Ser Ala Thr Tyr
    2135            2140            2145

Asn Ile Pro Val Ala Leu Arg Leu Glu Gly Asp Leu Asp Arg Asp
    2150            2155            2160

Ala Leu Thr Ala Ala Leu Arg Asp Val Val Ala Arg His Glu Val
    2165            2170            2175

Leu Arg Thr Val Phe Thr Val Ala Asp Gly Glu Pro Trp Gln His
    2180            2185            2190

Ile Leu Asp Pro Ala Arg Ala Glu Pro Ala Leu Pro Val Val Asp
    2195            2200            2205

Val Pro Ala Gly Arg Val Glu Glu Ala Val Ala Glu Ala Ala Ala
    2210            2215            2220

Tyr Ala Phe Asp Leu Ala Arg Glu Ile Pro Leu Arg Ala Val Leu
    2225            2230            2235

Leu Ala Pro Gly Asp Gly Thr His Val Leu Val Leu Val Leu His
    2240            2245            2250

His Ile Ala Ala Asp Gly Trp Ser Met Arg Pro Leu Ala Arg Asp
    2255            2260            2265

Leu Ala Thr Ala Tyr Ala Ala Arg Arg Arg Gly Gln Ala Pro Glu
    2270            2275            2280

Ser Glu Thr Leu Pro Val Gln Tyr Ala Asp Tyr Ala Leu Trp Gln
    2285            2290            2295

Arg Asp Leu Leu Gly Ser Asp Ser Asp Pro Ala Ser Leu Ile Ser
    2300            2305            2310

Arg Gln Ile Ala His Trp Arg Glu Arg Leu Asp Gly Val Pro Glu
    2315            2320            2325

Glu Leu Asp Leu Pro Ala Asp Arg Pro Arg Pro Ala Ala Ala Ser
    2330            2335            2340

His Arg Gly His Leu His Ser Ala Glu Ile Pro Ala Asp Val His
    2345            2350            2355

Arg Ser Leu Arg Arg Val Ala Ala Asp His Gly Ala Thr Val Phe
    2360            2365            2370

Met Thr Leu Gln Ala Ala Val Ala Val Leu Leu Ser Arg Leu Gly
    2375            2380            2385
```

-continued

```
Ala Gly Thr Asp Val Pro Ile Gly Thr Val Val Ala Gly Arg Ala
2390                2395                2400

Asp Arg Ala Leu Glu Asn Leu Val Gly Phe Phe Val Asn Thr Leu
2405                2410                2415

Val Leu Arg Thr Asp Leu Thr Gly Asp Pro Arg Leu Thr Asp Val
2420                2425                2430

Leu Gly Gln Val Arg Glu Leu Thr Leu Arg Ala Leu Ala His Gln
2435                2440                2445

Asp Val Pro Phe Glu Lys Leu Val Glu Glu Leu Thr Pro Ala Arg
2450                2455                2460

Ser Leu Ala Arg His Pro Leu Phe Gln Val Met Val Thr Leu Asp
2465                2470                2475

Gly Gly Gly Pro Asp Gly Ala Glu Leu Pro Gly Leu Ala Met Ser
2480                2485                2490

Val Val Pro Thr Gly Ala Val Pro Ala Lys Phe Asp Leu Asp Leu
2495                2500                2505

Thr Phe Thr Glu Thr Phe Asp Ala Ala Gly Glu Pro Ala Gly Leu
2510                2515                2520

Arg Val Asp Leu Ile Ala Ala Ala Asp Leu Phe Asp Ala Gly Thr
2525                2530                2535

Ala Ala Arg Leu Ala Gly Tyr Leu Ser Arg Val Leu Gly Val Leu
2540                2545                2550

Ala Ala Asp Pro Arg Arg Arg Leu Ala Glu Val Asp Pro Leu Glu
2555                2560                2565

Ala Glu Glu Ser Arg Leu Met Leu Ala Ala Gly Glu Glu Pro Ala
2570                2575                2580

Pro Ala Leu Pro Glu Ile Thr Val Ala Ala Leu Val Ala Glu Gln
2585                2590                2595

Cys Ala Arg Thr Pro Gly Ala Val Ala Val Thr Gly Pro Asp Ala
2600                2605                2610

Ser Leu Thr Tyr Ala Glu Leu Asp Glu Arg Ala Ala Arg Ile Ala
2615                2620                2625

Arg Trp Leu Arg Arg His Gly Ala Gly Pro Gly Ala Ala Val Cys
2630                2635                2640

Val Leu Met Glu Arg Ser Ala Glu Leu Val Ala Val Leu Leu Gly
2645                2650                2655

Val Met Arg Ala Gly Ala Ala Tyr Val Pro Val Asp Pro Ala Tyr
2660                2665                2670

Pro Ala Glu Arg Ile Arg Phe Val Val Thr Asp Ala Arg Ala Ala
2675                2680                2685

Cys Val Val Ser Glu Ser Ala Ser Ala Gly Leu Val Pro Asp Gly
2690                2695                2700

Val Pro Cys Leu Ala Ile Asp Asp Pro Ala Ala Ala Glu Pro
2705                2710                2715

Ala Glu Pro Gly Asp Asp Pro Gly Asp Ala Ala Gly Pro Arg Pro
2720                2725                2730

Asp Asp Pro Ala Tyr Ile Ile Tyr Thr Ser Gly Ser Thr Gly Thr
2735                2740                2745

Pro Lys Gly Val Val Val Ser His Arg Asn Val Val Ala Leu Leu
2750                2755                2760

Thr Ala Thr Arg Pro Leu Phe Gly Phe Ala Gly Asp Glu Val Trp
2765                2770                2775

Ser Trp Phe His Ser Val Ala Phe Asp Phe Ser Val Trp Glu Leu
```

-continued

| | | | | | | |
|---|---|---|---|---|---|---|
| 2780 | | 2785 | | 2790 | | |

Trp Gly Ala Leu Thr His Gly Gly Arg Val Val Val Pro Tyr
2795          2800              2805

Ala Val Ser Arg Ser Pro Arg Asp Phe Trp Glu Leu Val Val Arg
2810          2815              2820

Glu Gly Val Thr Val Leu Ser Gln Thr Pro Ser Ala Phe Ala Gln
2825          2830              2835

Leu Met Ala Ala Ala Gly Asp Asp Arg Asp Ala Leu Arg Phe
2840          2845              2850

Val Val Phe Gly Gly Glu Ala Leu Asp Pro Gly Arg Leu Ala Gly
2855          2860              2865

Trp Leu Ala Arg Arg Pro Asp Lys Pro Arg Leu Val Asn Met Tyr
2870          2875              2880

Gly Ile Thr Glu Thr Thr Val His Thr Thr Tyr Gln His Ile Ala
2885          2890              2895

Pro Gly Thr Thr Gly Ser Val Ile Gly Arg Gly Leu Pro Gly Phe
2900          2905              2910

Gly Leu Tyr Val Leu Asp Glu Ala Leu Arg Pro Val Pro Ala Gly
2915          2920              2925

Val Pro Gly Glu Val Tyr Ala Arg Gly Pro Gln Val Ala Arg Gly
2930          2935              2940

Tyr Ile Gly Arg Pro Gly Leu Thr Ala Glu Arg Phe Val Ala Ser
2945          2950              2955

Pro Phe Ala Pro Gly Glu Arg Met Tyr Arg Thr Gly Asp Val Ala
2960          2965              2970

Arg Trp Thr Ala Asp Gly Arg Leu Val Phe Ala Gly Arg Ser Asp
2975          2980              2985

Asp Gln Ile Lys Ile Arg Gly Phe Arg Ile Glu Pro Gly Glu Val
2990          2995              3000

Glu Ala Val Leu Ala Ala Gly Pro Gly Val Ser Gln Ala Ala Val
3005          3010              3015

Ile Val Arg Glu Asp Val Pro Gly Asp Lys Arg Leu Val Ala Tyr
3020          3025              3030

Val Val Gly Gly Asp Ala Glu Thr Leu Arg Ser His Ala Gln Gln
3035          3040              3045

Arg Leu Pro Gly Tyr Leu Val Pro Ser Ala Phe Val Glu Leu Asp
3050          3055              3060

Arg Leu Pro Leu Thr Val Asn Gly Lys Leu Asp Arg Arg Ala Leu
3065          3070              3075

Pro Val Pro Asp Tyr Gly Arg Asp Ala Gly Gly Arg Ala Pro
3080          3085              3090

Ala Asn Ala Arg Glu Glu Val Leu Cys Arg Ala Phe Ala Glu Val
3095          3100              3105

Leu Gly Val Glu Arg Val Gly Val Glu Asp Asp Phe Phe Ala Leu
3110          3115              3120

Gly Gly His Ser Leu Leu Val Val Ser Leu Val Glu Arg Leu Arg
3125          3130              3135

Arg Gln Gly Ile Ser Val Pro Val Arg Ala Leu Phe Thr Thr Pro
3140          3145              3150

Thr Pro Ala Gly Leu Ala Glu Ala Val Gly Asp Gly Ala Val Val
3155          3160              3165

Val Pro Pro Asn Leu Ile Pro Glu Asp Ala Ala Glu Leu Thr Pro
3170          3175              3180

-continued

```
Glu Met Leu Pro Leu Ala Asp Leu Thr Ala Asp Glu Leu Ala Val
    3185                3190                3195

Val Val Ala Ser Val Pro Gly Gly Ala Ala Asn Ile Ala Asp Val
    3200                3205                3210

Tyr Pro Leu Ala Pro Leu Gln Glu Gly Ile Phe Phe His His Met
    3215                3220                3225

Met Ala Asp Arg Asp Ser Ala Asp Val Tyr Val Thr Pro Thr Val
    3230                3235                3240

Val Glu Phe Asp Ser Arg Asp Arg Leu Asp Gly Phe Leu Ala Ala
    3245                3250                3255

Leu Gln Gln Val Val Asp Arg Thr Asp Val Tyr Arg Thr Ser Val
    3260                3265                3270

Val Trp Gln Gly Leu Arg Glu Pro Val Gln Val Val Trp Arg His
    3275                3280                3285

Ala Arg Leu Pro Ile Asp Glu Val Glu Leu His Glu Gly Thr Asp
    3290                3295                3300

Pro Ala Glu Gln Leu Ile Ala Leu Ala Thr Glu Arg Val Asp Leu
    3305                3310                3315

Asp Arg Ala Pro Leu Ile Arg Thr Thr Thr Ala Ala Val Pro Gly
    3320                3325                3330

Ser Gly Arg Trp Leu Ala Leu Leu Arg Ile His His Leu Val Gln
    3335                3340                3345

Asp His Thr Thr Leu Asp Val Leu Leu Gly Glu Leu Arg Ala Phe
    3350                3355                3360

Leu Glu Gly Arg Gly Asp Glu Leu Pro Glu Pro Val Pro Phe Arg
    3365                3370                3375

Glu Phe Val Ala Gln Ala Arg Leu Gly Val Pro Arg Glu Glu His
    3380                3385                3390

Glu Arg Tyr Phe Ala Glu Leu Leu Gly Asp Val Thr Glu Thr Thr
    3395                3400                3405

Ala Pro Tyr Gly Leu Thr Glu Val His Gly Asp Gly Ser Ala Ala
    3410                3415                3420

Val His Ser Arg Arg Glu Val Asp Asp Asp Leu Ala Ala Arg Leu
    3425                3430                3435

His Arg Leu Ala Arg Ser Leu Gly Val Ser Pro Ala Ala Leu Phe
    3440                3445                3450

His Leu Ala Trp Ala Arg Val Leu Gly Ala Val Ser Gly Arg Asp
    3455                3460                3465

Asp Val Val Phe Gly Thr Val Leu Phe Gly Arg Met Asn Ser Gly
    3470                3475                3480

Ala Ala Ala Asp Arg Val Gln Gly Leu Phe Ile Asn Thr Leu Pro
    3485                3490                3495

Val Arg Val Arg Leu Ala Ala Gly Ser Thr Arg Asp Ala Leu Thr
    3500                3505                3510

Gly Leu Arg Asp Gln Leu Ala Gly Leu Leu Val His Glu His Ala
    3515                3520                3525

Pro Leu Ala Leu Ala Gln Arg Ala Ala Gly Ile Thr Asp Gly Ser
    3530                3535                3540

Pro Leu Phe Ala Ser Ile Phe Asn Tyr Arg His Asn Gln Asp Asp
    3545                3550                3555

Pro Ala Ala Ser Ala Gly Leu Glu Gly Ile Arg Thr Val Tyr Ser
    3560                3565                3570
```

-continued

```
Ala Glu His Thr Asn Tyr Pro Leu Asp Ala Ser Ile Asp Val Thr
3575                3580                3585

Gly Asp Arg Phe Ala Ile Thr Val Asn Ala Val Ala Ala Asp Ala
3590                3595                3600

Ala Arg Ile Ala Glu Leu Met His Thr Cys Leu Gly His Leu Ala
3605                3610                3615

Asp Val Leu Glu Asp Ala Pro Glu Thr Pro Leu Ser Trp Val Ser
3620                3625                3630

Pro Leu Ser Ala Glu Asp Leu Gly Arg Ile Val Gly Asp Trp Asn
3635                3640                3645

Glu Thr Arg Arg Ala Val Thr Arg Ala Ser Val Pro Glu Leu Phe
3650                3655                3660

Ala Lys Gln Val Ala Ala Thr Pro Asp Ala Ile Ala Val Ala Gly
3665                3670                3675

Glu Gly Val Ser Trp Ser Tyr Arg Glu Leu Asp Val Arg Ser Asp
3680                3685                3690

Ala Leu Ala Arg Ser Leu Val Ala Ala Gly Val Gly Ile Glu Ser
3695                3700                3705

Pro Val Val Ala Leu Asp Arg Ser Pro Glu Val Pro Thr Ala
3710                3715                3720

Phe Leu Ala Val Ala Lys Ala Gly Gly Val Phe Val Pro Val Asp
3725                3730                3735

Leu Ser Trp Pro Gln Ala Arg Val Asp Ala Val Ile Ala Asp Cys
3740                3745                3750

Ala Ala Arg Val Ala Val Ala Asp Arg Pro Met Thr Gly Leu Thr
3755                3760                3765

Val Val Pro Ala Asp Ala Ala Gly Asp Pro Ala Ala Glu Leu Pro
3770                3775                3780

Pro Arg Pro Leu Pro Gly Ala Glu Val Tyr Arg Met Tyr Thr Ser
3785                3790                3795

Gly Ser Thr Gly Arg Pro Lys Gly Val Val Thr Thr His Gln Asn
3800                3805                3810

Leu Val Asp Leu Ala Thr Asp Thr Cys Trp Gly Pro Thr Pro Arg
3815                3820                3825

Val Leu Phe His Ala Pro His Ala Phe Asp Ala Ser Ser Tyr Glu
3830                3835                3840

Ile Trp Val Pro Leu Leu Asn Gly Gly Thr Val Val Ala Pro
3845                3850                3855

Gly Arg Ser Ile Asp Ala Ala Val Leu Gly Glu Leu Ile Arg Ala
3860                3865                3870

His Glu Leu Thr His Val His Val Thr Ala Gly Leu Leu Arg Val
3875                3880                3885

Leu Asp Pro Ser Cys Phe Ala Gly Leu Thr Glu Val Leu Thr Gly
3890                3895                3900

Gly Asp Ala Val Ser Ala Glu Ala Val Arg Arg Val Met Glu Ala
3905                3910                3915

Asn Pro Gly Leu Arg Val Arg Gln Leu Tyr Gly Pro Thr Glu Val
3920                3925                3930

Thr Leu Cys Ala Thr Gln Gln Val Leu Asp Gly Thr Gly Val Pro
3935                3940                3945

Ile Gly Arg Pro Leu Asp Asn Thr Arg Val Tyr Val Leu Asp Asp
3950                3955                3960

Leu Leu Gln Pro Val Pro Val Gly Val Thr Gly Glu Leu Tyr Val
```

-continued

```
          3965                3970                3975
   Ala Gly  Ala Gly Leu Ala  Arg Gly Tyr Ala  Gly Met  Pro Gly Leu
          3980                3985                3990
   Thr Ala  Glu Arg Phe Val  Ala Asp Pro Phe  Ser Ser  Gly Gly Arg
          3995                4000                4005
   Leu Tyr  Arg Thr Gly Asp  Leu Val Arg Trp  Thr Asp  Asp Gly Val
          4010                4015                4020
   Leu Val  Phe Ala Gly Arg  Ala Asp Asp Gln  Val Lys  Ile Arg Gly
          4025                4030                4035
   Tyr Arg  Val Glu Pro Gly  Glu Val Glu Ala  Val Leu  Ala Ala His
          4040                4045                4050
   Pro Asp  Val Ala Gln Val  Ala Val Val Val  Arg Glu  Asp Thr Pro
          4055                4060                4065
   Gly Asp  Lys Arg Leu Val  Ala Tyr Val Val  Gly Gly  Asp Val Glu
          4070                4075                4080
   Ala Tyr  Ala Gln Glu Arg  Leu Pro Gly Tyr  Leu Val  Pro Ser Ala
          4085                4090                4095
   Phe Val  His Leu Asp Ala  Leu Pro Leu Thr  Ser Asn  Gln Lys Val
          4100                4105                4110
   Asp Arg  Ala Ala Leu Pro  Ala Pro Ser Val  Glu Ser  Gly Ala Gly
          4115                4120                4125
   Arg Ala  Pro Ala Asp Ala  Arg Glu Glu Leu  Met Cys  Ala Ala Phe
          4130                4135                4140
   Ala Glu  Val Leu Asp Leu  Asp Arg Val Gly  Val Asp  Asp Asp Phe
          4145                4150                4155
   Phe Ala  Leu Gly Gly His  Ser Leu Leu Val  Val Arg  Leu Val Gly
          4160                4165                4170
   Arg Ile  Arg Gln Val Phe  Gly Val Glu Val  Ser Ala  Arg Leu Val
          4175                4180                4185
   Phe Asp  Ala Arg Thr Pro  Ala Gly Val Val  Ala Arg  Leu Ser Glu
          4190                4195                4200
   Gly Gly  Thr Ala Arg Glu  Ala Val Arg Ala  Arg Val  Arg Pro Ala
          4205                4210                4215
   Arg Val  Pro Leu Ser Phe  Ala Gln Arg Arg  Leu Trp  Phe Leu Ser
          4220                4225                4230
   Gln Leu  Asp Gly Thr Ser  Thr Thr Tyr Asn  Ile Pro  Val Ala Leu
          4235                4240                4245
   Gln Leu  Asp Gly Pro Leu  Asp Arg Asp Ala  Phe Thr  Ala Ala Leu
          4250                4255                4260
   His Asp  Val Val Ala Arg  His Glu Val Leu  Arg Thr  Val Phe Thr
          4265                4270                4275
   Val Ala  Asp Gly Glu Pro  Trp Gln His Ile  Leu Asp  Thr Pro Ser
          4280                4285                4290
   Val Ser  Val Pro Val Ile  Glu Val Pro Ala  Asp Gly  Leu Pro Glu
          4295                4300                4305
   Ala Val  Ala Ala Ala Ala  Ala His Thr Phe  Asp Leu  Ser Arg Glu
          4310                4315                4320
   Ile Pro  Leu Arg Ala Val  Leu Leu Ala Thr  Gly Ala  Asp Arg His
          4325                4330                4335
   Val Leu  Val Leu Val Val  His His Ile Ala  Ala Asp  Gly Trp Ser
          4340                4345                4350
   Met Gln  Pro Leu Ala Arg  Asp Leu Ala Val  Ala Tyr  Ala Ala Arg
          4355                4360                4365
```

-continued

Ile Arg Gly Glu Ala Pro Ala Trp Thr Ala Leu Pro Val Gln Tyr
4370              4375              4380

Ala Asp Tyr Ala Leu Trp Gln Arg Asp Val Leu Gly Ser Glu His
    4385              4390              4395

Asp Pro Asp Ser Ala Ile Ser Gln Gln Val Ala His Trp Arg Arg
    4400              4405              4410

Gln Leu Ala Gly Ala Pro Asp Glu Leu Pro Leu Pro Ala Asp His
    4415              4420              4425

Pro Arg Pro Ala Glu Ala Thr Tyr Arg Gly His Thr Val Glu Phe
    4430              4435              4440

Thr Val Pro Pro Ala Val His His Gln Leu Ala Glu Leu Ala Arg
    4445              4450              4455

Arg Asn Gly Val Thr Val Phe Met Thr Val Gln Thr Ala Leu Ala
    4460              4465              4470

Val Leu Leu Ser Lys Leu Gly Ala Gly Thr Asp Ile Pro Ile Gly
    4475              4480              4485

Val Ala Val Ala Gly Arg Thr Asp Pro Thr Leu Asp Asn Leu Ile
    4490              4495              4500

Gly Phe Phe Val Asn Thr Leu Val Leu Arg Thr Asp Leu Thr Gly
    4505              4510              4515

Asn Pro Thr Ile Thr Asp Leu Leu His Arg Thr Arg Asp Thr Thr
    4520              4525              4530

Leu His Ala Phe Thr His Gln Asp Val Pro Phe Glu Lys Leu Val
    4535              4540              4545

Glu Asp Leu Ala Pro Thr Arg Ser Leu Ala Arg His Pro Leu Phe
    4550              4555              4560

Gln Val Met Met Thr Leu Gln Ser Thr Gly Arg Ala Gly Glu Ala
    4565              4570              4575

Ala Glu Leu Pro Gly Leu Glu Thr Ala Val Leu Ser Pro Gly Gly
    4580              4585              4590

Val Ala Ala Lys Val Asp Leu Asp Leu Ser Leu Ser Glu Ala Tyr
    4595              4600              4605

Asp Asp Asp Gly Arg Pro Ala Gly Leu Ala Gly Thr Leu Val Ala
    4610              4615              4620

Ala Ala Asp Leu Phe Glu His Gly Thr Ala Glu Arg Ile Ala Gly
    4625              4630              4635

Tyr Leu Ala Arg Leu Leu Ala Val Leu Pro Ala Asp Pro Gly Ala
    4640              4645              4650

Arg Leu Gly Asp Val Asp Leu Leu Asp Gly Glu Glu Arg Arg Leu
    4655              4660              4665

Val Leu Thr Gly Trp Asn Asp Thr Thr Ala Ala Val Pro Ala Val
    4670              4675              4680

Ala Val Pro Glu Leu Ile Glu Arg Arg Ala Ala Ala Glu Pro Glu
    4685              4690              4695

Ala Gly Ala Val Trp Cys Gly Asp Thr His Leu Arg Tyr Gly Glu
    4700              4705              4710

Leu Asn Ala Arg Ala Asn Arg Leu Ala Arg Leu Leu Val Glu Arg
    4715              4720              4725

Gly Ala Gly Pro Glu Ser Ile Val Ala Val Cys Leu Glu Arg Ser
    4730              4735              4740

Ala Asp Leu Val Val Thr Leu Leu Ala Val Leu Lys Thr Gly Ala
    4745              4750              4755

```
Ala Tyr Leu Pro Ile Asp Pro Gly Tyr Pro Ala Gly Arg Ile Ala
    4760            4765                4770

Tyr Met Leu Ala Asp Ala Arg Pro Ala Leu Leu Val Thr Ser Pro
    4775            4780                4785

Ala Val Ala Ser Gly Asp Ser Leu Pro Asp Gly Gly Ala Gln Arg
    4790            4795                4800

Ile Val Leu Gly Asp Pro Asp Thr Ala Ala Leu Asp Gly Leu
    4805            4810                4815

Ala Gly Thr Asp Leu Leu Val Ser Glu Arg Arg Gly Val Thr His
    4820            4825                4830

Pro Ala His Pro Ala Tyr Val Ile Tyr Thr Ser Gly Ser Thr Gly
    4835            4840                4845

Arg Pro Lys Gly Val Val Pro His Gly Ala Leu Thr Asn Phe
    4850            4855                4860

Val Ala Ala Met Ser Asp Arg Leu Ala Leu Gly Ala Gly Asp Arg
    4865            4870                4875

Leu Leu Ala Val Thr Thr Val Ala Phe Asp Ile His Val Leu Glu
    4880            4885                4890

Leu Tyr Val Pro Leu Val Gly Gly Ala Gly Val Val Val Ala Glu
    4895            4900                4905

Asp Ala Val Val Arg Asp Pro Ala Ala Val Ala Ala Leu Leu Asp
    4910            4915                4920

Arg His Ala Val Thr Ile Val Gln Ala Thr Pro Ala Leu Trp Gln
    4925            4930                4935

Ala Leu Leu Ala Gly His Ala Asp Ala Val Arg Asp Val Arg Leu
    4940            4945                4950

Leu Val Gly Gly Glu Ala Leu Pro Pro Ala Leu Ala Gly Arg Met
    4955            4960                4965

Ala Ala Ala Gly Arg Gly Val Thr Asn Leu Tyr Gly Pro Thr Glu
    4970            4975                4980

Val Thr Val Trp Ala Thr Val Ala Asp Leu Gly Ala Ser Pro Ala
    4985            4990                4995

Gly

<210> SEQ ID NO 16
<211> LENGTH: 234
<212> TYPE: PRT
<213> ORGANISM: Actinoplanes sp.

<400> SEQUENCE: 16

Met Gln Lys Ile Pro Leu Val Cys Val Pro Phe Ala Gly Ala Gly
1               5                   10                  15

Ser Phe Phe His Pro Trp Ala Glu Leu Ala Gly Pro Asp Arg Pro Ile
                20                  25                  30

Val Ala Leu Gln Leu Pro Gly Arg Glu Trp Arg Leu Leu Asp Glu Pro
            35                  40                  45

Tyr Ala Asp Val Val Ala Ala Ala Asp Leu Ala Leu Thr Val Ala
    50                  55                  60

Asp Glu Val Gly Ala Gly Gly Arg Val Ala Leu Phe Gly His Ser Leu
65                  70                  75                  80

Gly Ala Val Leu Ala Tyr Glu Ile Ala His Ala Leu Val Arg Asp Gly
                85                  90                  95

Glu Val Gly Val Glu Arg Leu Phe Val Ser Gly Ser Pro Asp Pro Trp
            100                 105                 110
```

-continued

```
Thr Pro Arg Thr Asn Arg Ala Ser Gly Leu Asp Asp Glu Glu Phe Leu
        115                 120                 125

Leu Arg Val Arg Glu Phe Ala Gly Tyr Asp His Glu Ala Leu Ala Asp
        130                 135                 140

Pro Asp Met Arg Glu Leu Ile Leu Pro Ala Leu Arg Ala Asp Val Glu
145                 150                 155                 160

Met His Glu Ser Tyr Val Ala Gly Ser Ala Asp Pro Leu Pro Ala Pro
                165                 170                 175

Val Thr Ala Leu His Ala Arg Asp Asp Ala Leu Val Ser Ala Glu Gln
            180                 185                 190

Thr Ala Gly Trp Ser Lys Ala Thr Ser Gly Pro Phe Gln Leu Val Glu
        195                 200                 205

Val Asp Gly Gly His Met Tyr Leu Thr Glu Asp Pro Ala Gly Leu Leu
    210                 215                 220

Arg Leu Ile Ala Ala Asp Leu Asp Arg Asp
225                 230

<210> SEQ ID NO 17
<211> LENGTH: 274
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It
      is expected that the biosynthesized protein will have a
      formylmethionine residue at this position

<400> SEQUENCE: 17

Val Arg Leu Thr Gly Lys Thr Ala Ile Val Thr Gly Ala Ala Arg Gly
1               5                   10                  15

Leu Gly Arg Ala Cys Ala Val Ala Phe Ala Ala Glu Gly Ala Asp Leu
            20                  25                  30

Val Leu Leu Asp Arg Ala Ala Asp Leu Pro Gly Val Pro Tyr Pro Leu
        35                  40                  45

Gly Thr Val Gly Gln Leu Glu His Thr Ala Asp Leu Cys Arg Lys Gln
    50                  55                  60

Gly Ala Ala Val Leu Thr Val Arg Ala Asp Val Arg Asp Leu Ala Ala
65                  70                  75                  80

Leu Thr Ala Ala Ala Asp Arg Ala Ile Asp Arg Phe Gly Gly Ile Asp
                85                  90                  95

Val Leu Val Asn Asn Ala Gly Ile Ala Ala Pro Ser Gly Lys Val Thr
            100                 105                 110

His Glu Ile Thr Glu Asp Glu Trp Gln Leu Met Ile Asp Val Asp Leu
        115                 120                 125

Ser Gly Ala Trp Arg Met Thr Ala Ala Val Gly Arg His Met Thr Glu
    130                 135                 140

Arg Arg Ser Gly Ser Ile Val Asn Ile Ala Ser Thr Ala Gly Gln Val
145                 150                 155                 160

Gly Tyr Arg His Phe Ala Gly Tyr Val Ala Ala Lys His Gly Ile Val
                165                 170                 175

Gly Leu Thr Arg Ala Ala Ala Leu Asp Tyr Ala Pro Ala Lys Val Arg
            180                 185                 190

Val Asn Ala Val Cys Pro Gly Ser Val Arg Asp Asp Pro Gln Phe Glu
        195                 200                 205

Gly Arg Met Leu Ser Glu Ile Ala Arg Ser Leu Asp Val Pro Val Ala
    210                 215                 220
```

-continued

Glu His Glu Gln Thr Phe Leu Gln Ala Gln Pro Met Asn Ala Leu Ile
225                 230                 235                 240

Glu Pro Asp Asp Val Ala Asn Ala Ala Ile Trp Leu Ala Ser Asp Glu
            245                 250                 255

Ser Arg Gln Val Thr Gly Ser Val Val Thr Val Asp Gly Gly Phe Thr
            260                 265                 270

Thr Arg

<210> SEQ ID NO 18
<211> LENGTH: 891
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V is a non-standard initiator codon. It is
      expected that the biosynthesized protein will have a
      formylmethionine residue at this position

<400> SEQUENCE: 18

Val Pro Lys Ser Gln Pro Ala Thr Arg Thr Ala Ala Pro Gly Ala Ala
1               5                   10                  15

Glu Cys His Ala Leu Ala Val Arg Leu Ala Gly Pro Ile Asp Pro Ala
                20                  25                  30

Pro Ile Glu Arg Arg Leu Ala Ala Arg Met Pro Phe Trp His Glu His
            35                  40                  45

Val Ala Ala Arg Pro Gly Asp Glu Ala Ala Leu Arg Arg Arg Glu Arg
    50                  55                  60

Glu Leu Ala Arg Pro Val Pro Pro Glu Pro Gly Ala Arg Ala Val Leu
65                  70                  75                  80

Leu Ala Tyr Ala Asp Gly Ser Ala Asp Leu Val Leu Val Ala Arg Arg
                85                  90                  95

Asp Arg Leu Asp Arg Asp Ala Leu Ile Ala Leu Ala Arg Pro Glu Arg
            100                 105                 110

Ala Pro Arg Gly Arg Lys Pro Ala Glu Pro Asp Ala Pro Pro Ser
            115                 120                 125

Ala Ala Pro Ala Trp Gly Leu Gly Asp Gly Pro Asp Asp Arg Trp
    130                 135                 140

Ala Glu Leu Arg Val Pro Ala Arg Gly Pro Ala Asp Pro Ala Arg Trp
145                 150                 155                 160

Pro Ala Ala Leu Ala Lys Val Leu Ala Arg Tyr Glu Pro Gly Ala Ala
                165                 170                 175

Ala Gly Ser Gly Ala Ala Gly Leu Gly Ala Ala Gly Ser Gly
            180                 185                 190

Val Ala Ala Gly Ser Ser Ala Ser Gly Ser Gly Ala Ala Ala Val
    195                 200                 205

Pro Gly Pro Val Ala Leu Ala Phe Asp Gly Asp Leu Ala Pro Pro Asp
    210                 215                 220

Glu Tyr Val Pro Phe Leu Ala Pro Thr His Pro Leu Thr Val Gln Val
225                 230                 235                 240

Ser Arg Thr Pro Gly Gly Gly Thr Glu Leu Arg Cys Arg His Arg Leu
                245                 250                 255

Gly Ala Val Ser Pro Ala Ala Ala Glu Ala Phe Ala Arg Met Leu Ala
            260                 265                 270

Ala Ala His Gly Glu Pro Pro Ala Asp Asp Gly Ala Thr Ala Glu Pro
    275                 280                 285

```
Thr Pro Pro Ala Ala Pro Ala Pro Ala Pro Ala Pro Ala Pro
290                 295                 300
Pro Ala Ala Ala Arg Thr Leu Thr Gly Leu Phe Ala Glu Gln Val Ala
305                 310                 315                 320
Ala Arg Pro Thr Ala Val Ala Val Ser Asp Asp Arg Gly Arg His Thr
                325                 330                 335
Tyr Arg Glu Leu Asp Glu Trp Ser Gly Arg Leu Ala Arg Gly Leu Arg
            340                 345                 350
Lys Ala Gly Val Arg Asp Gly Asp Ala Val Gly Val Cys Leu Asp Arg
        355                 360                 365
Ser Ala Glu Leu Val Ala Val Leu Leu Ala Val Leu Lys Ala Gly Ala
370                 375                 380
Ala Tyr Val Pro Leu Asp Ala Ala Tyr Pro Ala Asp Arg Ile Ala Tyr
385                 390                 395                 400
Thr Val Gly Asp Ala Gly Leu Ala Val Val Thr Thr Ser Ala Asp
                405                 410                 415
Phe Pro Asp Val Asp Gly Val Arg Leu Leu Ala Pro Glu Ser Leu Ala
            420                 425                 430
Glu Ala Gly Asp Asp Pro Gly Ile Pro Leu Ala Thr Pro Ala Gly Pro
        435                 440                 445
Glu Arg Pro Ala Tyr Val Ile Tyr Thr Ser Gly Ser Thr Gly Arg Pro
450                 455                 460
Lys Gly Val Val Val Pro His Ala Asn Val Ser Ala Leu Leu Asp Ala
465                 470                 475                 480
Thr Arg Glu Glu Tyr Ala Leu Gly Pro Gly Asp Val Trp Thr Phe Phe
                485                 490                 495
His Ser Ala Ala Phe Asp Phe Ser Val Trp Glu Ile Trp Gly Cys Leu
            500                 505                 510
Leu Thr Gly Gly His Leu Val Val Pro Tyr Trp Val Ser Arg Ser
        515                 520                 525
Pro Glu Gln Phe His Asp Leu Leu Ala Glu Arg Gly Val Thr Val Leu
530                 535                 540
Asn Gln Thr Pro Ser Ser Phe Thr Gln Leu Val Ala Ala Asp Arg Gly
545                 550                 555                 560
Ala Glu Arg Asp Leu Ala Val Arg Leu Val Ile Phe Gly Gly Glu Pro
                565                 570                 575
Leu Asp Ala Arg Thr Val Leu Pro Trp Leu Asp Arg Arg Pro Glu Ala
            580                 585                 590
Arg Cys Arg Leu Val Asn Met Phe Gly Ile Thr Glu Thr Thr Val His
        595                 600                 605
Val Thr Ala Val Asp Val Thr Arg Ala Ala Ala Leu Ala Gly Ser Arg
610                 615                 620
Ser Val Gly Arg Pro Leu Pro Gly Trp Ala Val Arg Val Leu Asp Glu
625                 630                 635                 640
Gln Arg Arg Glu Val Pro Pro Gly Val Pro Gly Glu Ile Tyr Val Gly
                645                 650                 655
Gly Ala Gly Val Ala Ile Gly Tyr Leu Asn Arg Pro Glu Leu Thr Ala
            660                 665                 670
Glu Arg Phe Val Thr Gly Pro Asp Gly Arg Arg Trp Tyr Arg Ser Gly
        675                 680                 685
Asp Arg Gly Arg Leu Leu Pro Asp Gly Thr Leu Glu His Leu Gly Arg
690                 695                 700
```

```
Leu Asp Asp Gln Val Lys Leu Arg Gly Phe Arg Ile Glu Leu Asp Glu
705                 710                 715                 720

Ile Arg Gly Val Leu Thr Glu Cys Ala Gly Val Ala Ala Ala Ala Val
                725                 730                 735

Val Ile Arg Arg Ser Thr Pro Asp Pro Ala Thr Ala Arg Leu Asp
            740                 745                 750

Ala Tyr Val Ala Glu Ala Gly Ala Thr Pro Val Ala Glu His
        755                 760                 765

Ala Ala Arg Met Leu Pro Ala Tyr Met Cys Pro Ala Thr Phe Thr Phe
770                 775                 780

Leu Asp Ala Leu Pro Met Thr Pro Asn Gly Lys Val Asp Lys Ala Ala
785                 790                 795                 800

Leu Pro Glu Pro Ala Arg Pro Ala Ala Asp Ala Ala Thr Pro Ala
                805                 810                 815

Gly Pro Gly Glu Asp Gly Leu Ala Gly Asp Leu Ala Asp Val Trp Gln
                820                 825                 830

Gln Val Phe Gly Cys Pro Val Thr Val Ser Asp Asn Phe Phe Asp Leu
            835                 840                 845

Gly Gly Asn Ser Leu Leu Ala Val Arg Met Ala Ala Leu Met Arg Arg
850                 855                 860

Arg Gly Leu Pro Arg Leu His Pro Arg Thr Leu Tyr Leu His Pro Thr
865                 870                 875                 880

Val Arg Gly Leu Ala Asp Ala Leu Arg Ser Ala
                885                 890

<210> SEQ ID NO 19
<211> LENGTH: 187
<212> TYPE: PRT
<213> ORGANISM: Actinoplanes sp.

<400> SEQUENCE: 19

Met Arg Asn Leu Arg Arg Thr Thr Gly Ile Gly Leu Leu Ala Leu Leu
1               5                   10                  15

Ser Val Ala Ala Cys Ser Ser Thr Pro Ala Ala Ser Glu Pro Pro
            20                  25                  30

Ser Ala Ala Pro Pro Ser Ala Val Thr Ala Thr Gly Pro Ala Ala Glu
        35                  40                  45

Lys Ala Val Lys Ser Gly Thr Gln Thr Tyr His Gln Ala Leu Asp Ala
    50                  55                  60

Phe Val Ala Ala Ser Asn Lys Gly Thr Thr Asp Thr Thr Glu Ile Gly
65                  70                  75                  80

Lys Tyr Ala Ser Gly Arg Ala Leu Met Thr Phe Gln Gly Ile Leu Ala
                85                  90                  95

Ser Tyr Gln Gln Gln Gly Val His Thr Ser Gly Glu Pro Arg Ile Asp
            100                 105                 110

Glu Pro Val Val Thr Gly Leu Thr Pro Ala Asp Pro Thr Gly Val
        115                 120                 125

Gln Leu Arg Gly Cys Ile Asp Ile Ser Ala Trp Pro Leu Thr Lys Ala
130                 135                 140

Asp Gly Thr Pro Ala Asp Lys Val Gly Gly Gln Gln Gly Ser Gly Pro
145                 150                 155                 160

Ser Ala Ile Leu Ala Asn Val Ala Arg Ser Gly Ala Thr Trp Gln Val
                165                 170                 175

Thr Glu Leu Ala Ile Gln Gly Pro Cys Ala Ala
            180                 185
```

<210> SEQ ID NO 20
<211> LENGTH: 415
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It is expected that the biosynthesized protein will have a formylmethionine residue at this position

<400> SEQUENCE: 20

```
Val Thr Val Arg Arg Trp Leu Pro Ala Gly Leu Thr Val Leu Ala Phe
 1               5                  10                  15

Ala Ala Gly Phe Trp Gln Lys Leu Pro Cys Gln Ala Ala Gly Trp Pro
             20                  25                  30

Asp Asp Thr Ala Thr Leu Phe Gly Arg Tyr Cys Tyr Ser Asp Val Pro
         35                  40                  45

Ile Leu Phe Arg Glu Arg Gly Leu Phe Asp Gly Ile Phe Pro Tyr Glu
     50                  55                  60

Ser Gly Pro Gly Ala Gln Pro Leu Glu Tyr Pro Val Leu Thr Gly Tyr
 65                  70                  75                  80

Leu Met Asp Ala Thr Ala Arg Leu Val Arg Ala Ile Leu Pro Gly Ala
                 85                  90                  95

Asp Val Ala Val Ala Ser Arg Ala Tyr Phe Leu Thr Thr Val Leu Val
            100                 105                 110

Leu Leu Ala Leu Ala Val Leu Thr Val Trp Ala Thr Gly Ala Val Leu
        115                 120                 125

Arg Arg Thr Gly Gly Arg Pro Gly Asp Ala Leu Leu Val Ala Ala Ala
    130                 135                 140

Pro Val Leu Ile Leu Ala Gly Thr Val Asn Trp Asp Leu Leu Ala Val
145                 150                 155                 160

Ala Ala Ala Val Leu Ala Ile Leu Ala Trp Glu Arg Asp Arg Pro Leu
                165                 170                 175

Leu Ala Gly Val Leu Ile Gly Leu Gly Thr Ala Ala Lys Leu Phe Pro
            180                 185                 190

Leu Val Leu Leu Gly Pro Val Leu Leu Cys Leu Arg Gln Arg Arg
        195                 200                 205

Met Arg Arg Phe Ala Arg Val Ala Ala Gly Ala Ala Gly Ala Trp Leu
    210                 215                 220

Leu Val Asn Leu Pro Val Val Ala Leu Gln Pro Asp Gly Trp Met Glu
225                 230                 235                 240

Phe Trp Arg Phe Asn Ala Gly Arg Gly Ala Glu Phe Gly Ser Leu Trp
                245                 250                 255

Phe Ala Leu Asp Gly Leu Gly Leu His Met Pro Ala Val Asn Ala Val
            260                 265                 270

Ala Leu Ala Thr Phe Gly Val Leu Leu Ala Gly Ile Ala Val Leu Ala
        275                 280                 285

Leu Arg Ser Arg Arg Pro Pro Asp Leu Ala Gln Leu Ala Cys Leu Ala
    290                 295                 300

Val Gly Ala Phe Leu Leu Thr Asn Lys Val Tyr Ser Pro Gln Tyr Ala
305                 310                 315                 320

Leu Trp Leu Leu Pro Leu Val Val Ile Ala Arg Gly Arg Val Pro Arg
                325                 330                 335

Trp Pro Val Val Arg Asp Trp Ala Val Trp Gln Ala Ala Glu Val Leu
```

-continued

```
               340                 345                 350
Tyr Trp Leu Ala Val Trp Ser Trp Leu Ala Gly Ser Leu Thr Asp Glu
            355                 360                 365

Arg Gln Tyr Ala Trp Ala Thr Val Leu Arg Val Leu Ala Thr Ala Tyr
        370                 375                 380

Val Cys Gly Gln Val Val Trp Asp Val Leu Ala Ala Pro Arg Pro His
385                 390                 395                 400

Arg Pro Ala Pro Pro Ala Val Ala Glu Pro Ala His Pro Gly
                405                 410                 415
```

<210> SEQ ID NO 21
<211> LENGTH: 491
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It
      is expected that the biosynthesized protein will have a
      formylmethionine residue at this position

<400> SEQUENCE: 21

```
Val Ala Ala Gln Pro Glu Glu Phe Asp Val Ile Val Gly Gly Gly
1               5                   10                  15

Pro Gly Gly Ser Thr Ala Ala Leu Thr Ala Lys Gln Gly Ala Lys
            20                  25                  30

Val Leu Leu Leu Glu Arg Glu Lys Phe Pro Arg Tyr Gln Ile Gly Glu
            35                  40                  45

Ser Leu Leu Pro Ser Thr Val His Gly Val Cys Asn Leu Leu Gly Val
    50                  55                  60

Gly Asp Glu Ile Ala Lys Ala Gly Phe Met Arg Lys His Gly Gly Thr
65                  70                  75                  80

Phe Lys Trp Gly Thr Ser Thr Glu Pro Trp Thr Phe Thr Phe Ala Thr
                85                  90                  95

Ser Pro Arg Met Ala Gly Pro Thr Ser His Ala Phe Gln Val Glu Arg
            100                 105                 110

Arg Arg Phe Asp Gln Ile Leu Leu Glu Asn Ala Arg Arg Leu Gly Val
        115                 120                 125

Asp Val Arg Glu Asn His Pro Val Thr Glu Ala Ile Ala Asp Asp Glu
130                 135                 140

Arg Val Arg Gly Val Arg Phe Thr Gln Asp Gly Gln Thr Arg Thr Ala
145                 150                 155                 160

Leu Ala Arg Phe Val Val Asp Ala Ser Gly Asn Arg Ser Thr Leu His
                165                 170                 175

Thr Thr Val Gly Gly Thr Arg Glu Tyr Ser Pro Phe Phe Arg Asn Leu
            180                 185                 190

Ala Leu Phe Gly Tyr Phe Glu Asn Gly Arg Arg Leu Pro Ala Pro Asn
        195                 200                 205

Ser Gly Asn Ile Leu Cys Val Ala Phe Gly Ser Gly Trp Phe Trp Tyr
210                 215                 220

Ile Pro Leu Ser Glu Thr Leu Thr Ser Val Gly Ala Val Arg Arg
225                 230                 235                 240

Glu Met Ala His Lys Val Gln Gly Asp Gln Lys Ala Leu Phe Glu
                245                 250                 255

Leu Ile Ala Glu Cys Pro Met Ile Ala Asp Phe Leu Gly Asp Ala Thr
            260                 265                 270
```

```
Arg Val Thr Glu Gly Asp Tyr Gly Gln Ile Arg Val Arg Lys Asp Tyr
        275                 280                 285

Ser Tyr Ser Ser Thr Ser Tyr Trp Arg Pro Gly Met Cys Leu Val Gly
        290                 295                 300

Asp Ala Ala Cys Phe Ile Asp Pro Val Phe Ser Ser Gly Val His Leu
305                 310                 315                 320

Ala Thr Tyr Ser Gly Leu Leu Ala Ala Arg Ser Ile Asn Ser Val Leu
                325                 330                 335

Ala Gly Thr Val Asp Glu Asp Arg Ala Phe Thr Glu Phe Glu Gln Arg
                340                 345                 350

Tyr Arg Arg Glu Phe Gly Val Phe His Asp Phe Leu Val Ser Phe Tyr
        355                 360                 365

Asp Met His Val Asp Glu Ser Ser Tyr Phe Trp Ala Ala Arg Lys Val
370                 375                 380

Thr Glu Ser Ser Ala Pro Ala Met Glu Ser Phe Thr Glu Leu Val Gly
385                 390                 395                 400

Gly Ile Ala Ser Gly Glu Asp Ala Leu Thr Gly Ser Thr Glu Leu Val
                405                 410                 415

Arg Arg His Ser Arg Gln Thr Ala Glu Leu Gly Gln Ala Val Ala Gly
                420                 425                 430

Leu Glu Glu Gly Gly Thr Gly Phe Leu Arg Gly Ser Ser Val Val Ala
        435                 440                 445

Gln Ala Met Phe Glu Gly Ser Gln Ile Gln Ala Gly Ala Ile Leu Gly
        450                 455                 460

Pro Glu Gly Thr Gln Glu Gln Pro Leu Phe Glu Gly Gly Leu Thr Pro
465                 470                 475                 480

Ser Gly Asn Gly Leu Thr Trp Val Ala Ala Asp
                485                 490

<210> SEQ ID NO 22
<211> LENGTH: 217
<212> TYPE: PRT
<213> ORGANISM: Actinoplanes sp.

<400> SEQUENCE: 22

Met Thr Ile Arg Val Leu Ile Ala Asp Gln Ala Met Ile Arg Ser
1               5                   10                  15

Gly Leu Arg Leu Ile Leu Glu Asp Glu Pro Asp Ile Glu Val Val Ala
                20                  25                  30

Glu Ala Val Asp Gly Val Asp Ala Val Gln Ala Arg Lys Leu Arg
        35                  40                  45

Pro Asp Val Cys Leu Val Asp Ile Arg Met Pro Arg Ile Asp Gly Ile
50                  55                  60

Glu Val Thr Arg Ser Leu Ala Gly Pro Gly Val Val Asn Pro Leu Arg
65                  70                  75                  80

Val Ile Val Val Thr Thr Phe Asp Ser Asp Glu Tyr Val Tyr Gly Ala
                85                  90                  95

Leu Arg Gly Gly Ala Val Gly Phe Ile Leu Lys Asp Ala Gly Pro Thr
                100                 105                 110

Leu Leu Val Glu Ala Val Arg Ala Ala His Lys Gly Asp Ala Leu Val
                115                 120                 125

Ser Pro Ser Val Thr Val Arg Leu Leu Asn His Leu Asn Ala Ser Ala
130                 135                 140

Ala Pro Ala Gly Ser Glu Pro Ile Pro Leu Ser Asp Arg Glu Leu Glu
145                 150                 155                 160
```

```
Val Ala Arg Ala Ile Ala Arg Gly Arg Thr Asn Gln Glu Ile Ala Ala
                165                 170                 175

Asp Leu Phe Ile Ser Leu Ser Thr Val Lys Gly His Ala Ser Thr Ile
            180                 185                 190

Gln Ser Lys Leu Gly Val Arg Asn Arg Val Gly Val Ala Ala Trp Ala
        195                 200                 205

Trp Glu Asn Arg Leu Val Glu Gly Ser
    210                 215

<210> SEQ ID NO 23
<211> LENGTH: 403
<212> TYPE: PRT
<213> ORGANISM: Actinoplanes sp.

<400> SEQUENCE: 23

Met Asn Ile Ala Ala Ala Thr Gly Pro Ala Ala Gly Asp Gly Ala Gly
1               5                   10                  15

Ile Arg Thr Leu Gly Ser Val Arg Thr Ala Asp Arg Thr Thr Thr Met
            20                  25                  30

Val Ala Asp Ala Gly Leu Ala Val Leu Phe Val Ala Ala Val Val Val
        35                  40                  45

Glu Ala Val Ala Val Ala Gln Ser Trp Gly Leu Ala Tyr Trp Leu Ile
    50                  55                  60

Gly Gly Ala Ala Ala Thr Leu Val Cys Leu Leu Ala Leu Ile Arg Arg
65                  70                  75                  80

Arg Gly Pro Val Pro Cys Ala Ala Gly Leu Thr Ile Ala Ala Gly
                85                  90                  95

Ala Val Val Thr Ala Ala Val Leu His Met Pro Ala Glu Pro Gly Pro
            100                 105                 110

Ala Met Ala Leu Ala Leu Ala Val Leu Thr Gly Ser Ala Val Arg Ala
        115                 120                 125

Ala Pro Thr Ile Pro Ala Phe Ala Val Gly Gly Ala Ala Leu Gly Val
    130                 135                 140

Val Ala Leu Ser Gln Val Ala Ala Ala Thr Trp Asp Ala Gly Pro Ala
145                 150                 155                 160

Pro Val Thr Trp Leu Asn Ile Leu Thr Trp Leu Gly Gly Thr Ala Thr
                165                 170                 175

Gly Leu Ser Leu Arg Thr Val Asp Gly Arg Ala Arg Ala Asn Ala Glu
            180                 185                 190

Arg Ile Arg Gln Glu Glu Arg Leu Glu Leu Ala Arg Glu Leu His Asp
        195                 200                 205

Val Val Ala His His Ile Thr Gly Met Ile Leu Gln Thr Gln Ala Ala
    210                 215                 220

Gln Val Leu Ala Arg Arg Asp Ala Gly Arg Val Pro Glu Arg Leu Ala
225                 230                 235                 240

Val Ile Glu Thr Ala Gly Thr Glu Ala Leu Ala Ala Met Arg Arg Val
                245                 250                 255

Val Gly Leu Leu Arg Asp Ala Asp Asp Gly Pro Pro Ser Ala Pro Glu
            260                 265                 270

Pro Glu Glu Leu Ser Thr Leu Val Glu Arg Phe Ser Arg Gln Gly Gly
        275                 280                 285

Pro Val Arg Leu Thr Thr Pro Asp Gly Met Lys Gln Trp Pro Ile Glu
    290                 295                 300

Val Thr Thr Thr Val Tyr Arg Ile Val Arg Glu Ala Leu Thr Asn Val
```

```
                    305                 310                 315                 320
Ala Arg His Ala Pro His Ala Pro Asn Val Thr Val Thr Val Thr Val
                325                 330                 335

Glu Gln Ala Asp Glu Ile Arg Val Glu Val Thr Asn Asp Ala Ala Ala
            340                 345                 350

Ala Pro Pro Arg Leu His His Arg Gly Gly Tyr Gly Leu Val Gly Met
            355                 360                 365

Arg Glu Arg Val Glu Ser Leu Gly Gly Thr Leu Ser Thr Gly Pro Arg
    370                 375                 380

Pro Gly Gly Gly Trp Ser Val Ala Ala Thr Leu Pro Asn Pro Pro Arg
385                 390                 395                 400

Glu Arg Arg

<210> SEQ ID NO 24
<211> LENGTH: 309
<212> TYPE: PRT
<213> ORGANISM: Actinoplanes sp.

<400> SEQUENCE: 24

Met Lys Ala Met Ser His Glu Arg Ser Thr Pro Val Leu Gln Ala Glu
1               5                   10                  15

Gly Leu Thr Lys Arg Tyr Gly Arg Arg Arg Ala Leu Thr Asp Cys Thr
            20                  25                  30

Leu Ser Val Pro Ser Gly Arg Val Ile Ala Leu Val Gly Pro Arg Gly
        35                  40                  45

Ser Gly Lys Ser Thr Leu Leu Gln Leu Cys Cys Gly Met Val Ala Pro
    50                  55                  60

Ser Arg Gly Arg Ile Arg Val Leu Gly Glu Arg Pro Asp Ala Gly Ala
65                  70                  75                  80

Ala His Leu Ala Arg Val Gly Tyr Val Pro Arg Glu Pro Ala Val Tyr
                85                  90                  95

Gly Ser Phe Thr Val Glu Asp His Leu Thr Met Gly Ala Arg Leu Asn
            100                 105                 110

Pro Arg Trp Asp Arg Arg Leu Ala Asp Arg Arg Ile Ala Ser Ala Gly
        115                 120                 125

Ile Pro Arg Thr Arg Arg Ala Asp Arg Leu Ser Ala Gly Gln Arg Ala
    130                 135                 140

Glu Leu Ala Leu Thr Leu Ala Gly Gly Lys Arg Pro Glu Leu Leu Val
145                 150                 155                 160

Leu Asp Glu Pro Gly Ala Val Leu Asp Ala Pro Ala Arg Ala Ser Phe
                165                 170                 175

Leu Arg Gly Val Leu Asp Phe Val Ala Glu Ile Asp Ala Ser Val Leu
            180                 185                 190

Ile Ser Gly His Pro Ser Gly Glu Val Glu Arg Leu Cys Asp His Leu
        195                 200                 205

Ile Val Leu Ser Asp Ser Arg Val Leu Val Ala Gly Asp Val Arg Asp
    210                 215                 220

Leu Leu Ala Arg His His Arg Ile Ile Ala Pro Arg Gly Glu Leu Asp
225                 230                 235                 240

Arg Leu Pro Pro Gly Met Glu Pro Ile Trp Val Glu Asp Phe Gly Ser
                245                 250                 255

Tyr Ser Gly Gly Val Val Arg Ala Glu Val Asp Leu Pro Arg Arg Pro
            260                 265                 270

Trp Thr Val Glu Arg Val Glu Leu Glu Glu Leu Val Leu Ser Tyr Leu
```

-continued

```
              275                 280                 285
Ser Arg Ala Ser Gly Ala Pro Ala Leu Ala Gly Cys Leu Ile Ala Pro
        290                 295                 300

Gly Gln Pro Gly Ser
305
```

<210> SEQ ID NO 25
<211> LENGTH: 553
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It
      is expected that the biosynthesized protein will have a
      formylmethionine residue at this position

<400> SEQUENCE: 25

```
Val Thr Ala Ala Leu Glu Lys Leu Gly Asp Ala Arg Asp Pro
1               5                   10                  15

Gly Asn Pro Val Gly Tyr Ala Val Leu Ala Ala Asp Glu Arg Gln
            20                  25                  30

Glu Met Leu Ala Glu Gly Glu Arg Leu Leu Asp Arg Tyr Gln Leu Asn
        35                  40                  45

Ala Glu Phe Val Pro Val Ala Tyr Gly Gly Arg Leu Ala Arg Ala Asp
    50                  55                  60

Arg Leu Ala Glu Val Leu Arg Ala Val Trp Arg Arg Asp Pro Cys Leu
65                  70                  75                  80

Gly Leu Gly Tyr Gly Phe Ser Ser Leu Ile Ala Ser Val Asn Val Trp
                85                  90                  95

Cys Ala Gly Asn Glu Glu Gln Arg Arg Ala Ala Gly Leu Leu Leu
            100                 105                 110

Ala Asn Lys Arg Ile Ala Ala Phe His Glu Leu Ala His Gly Thr
        115                 120                 125

Asp Phe Ser Ala Ala Glu Cys Ala Ala Arg Pro Ala Gly Gly Gly Trp
    130                 135                 140

Val Leu Ser Gly His Lys Glu Ile Val Thr Asn Leu Arg Arg Ala Glu
145                 150                 155                 160

Ala Met Val Leu Phe Ala Arg Thr Gly Glu Ala Arg Gly Ser Arg Ser
                165                 170                 175

His Ser Gln Phe Leu Leu Val Arg Asp Glu Leu Pro Ala Ala Arg Ala
            180                 185                 190

Val Asp Arg Pro Arg Tyr Pro Gly Ser Gly Met Arg Gly Ile Asp Leu
        195                 200                 205

Gly Gly Leu Val Phe Asp Asp Cys Pro Val Pro Ser Ser Ala Leu Leu
    210                 215                 220

Gly Glu Gln Gly His Gly Ile Glu Val Ala Leu Arg Ala Tyr Gln Val
225                 230                 235                 240

Thr Arg Met Val Ser Pro Ala Leu Leu Val Gly Pro Leu Asp Ser Ala
                245                 250                 255

Val Arg Leu Ala Thr Glu Met Ala Met Glu Arg Arg Leu Tyr Gly Ala
            260                 265                 270

Ala Val Ala Asp Leu Pro Tyr Val Arg Thr Thr Ile Ala Arg Ala Tyr
        275                 280                 285

Ala Ala Leu Leu Thr Val Asp Val Phe Ser Gly Val Gly Leu Arg Ala
    290                 295                 300
```

-continued

```
Leu His Leu Leu Pro Glu Ala Thr Ala Gly Tyr Ala Pro Ala Val Lys
305                 310                 315                 320

Tyr Leu Thr Ala Gln Ile Val Leu Asp Ala Ile Asp Asp Leu Arg Ser
            325                 330                 335

Val Leu Gly Ala Gln Gly Tyr Leu Arg Gln Gly Pro Tyr Ala Met Phe
        340                 345                 350

Gln Lys Leu Val Arg Asp Ala Ala Pro Ala Ser Phe Ala His Val Ser
    355                 360                 365

Arg Ala Ala Cys Leu Val Met Leu Leu Pro His Leu Pro Arg Leu Ala
370                 375                 380

Arg Arg Ser Trp Thr Ala Glu Glu Pro Pro Asp Asn Val Phe Thr
385                 390                 395                 400

Leu Gly Gly Glu Leu Ser Pro Leu Asp Phe Ser Arg Leu Val Ser Gly
                405                 410                 415

Met Arg Gly Asp Pro Leu Ala Gly Val Leu His Asp Ser Trp His Asp
            420                 425                 430

Glu Gly Pro Val Gly Arg Phe Ala Glu Arg Phe His Arg Glu Leu Thr
        435                 440                 445

Gly Leu Arg Asp Ala Cys Arg Glu Leu Gly Pro Ala Asp Ile Thr Ile
    450                 455                 460

Asp Ala Asn Pro Ala Ala Phe Ala Leu Ala Asp Arg Tyr Thr Val Leu
465                 470                 475                 480

Leu Ala Ala Ala Cys Ala Leu Gly Val Trp Arg Ala Gly Arg Leu
                485                 490                 495

His Arg Pro Ala Leu Leu Ala Val Leu Asp Gly Leu Ala Gly Arg Leu
            500                 505                 510

Gly Gly Glu Ala Val Leu Ser Val Ala Glu Arg Glu His Val Glu His
        515                 520                 525

Gln Leu Phe Glu Met Ala Ala Asp Arg Val Arg Thr Ser Arg Leu Leu
    530                 535                 540

Asp Leu Ser Ala Arg Gln Leu Pro Gly
545                 550
```

<210> SEQ ID NO 26
<211> LENGTH: 585
<212> TYPE: PRT
<213> ORGANISM: Actinoplanes sp.

<400> SEQUENCE: 26

```
Met Thr Val Arg Pro Leu Ala Pro Pro Ala Glu Val Arg Leu Asp Asp
1               5                   10                  15

Leu Leu Gly Pro Glu Asp Ala Trp Asp Ala Glu Thr Ala Ala Arg Asp
            20                  25                  30

Ile Ala Glu Glu Phe Pro Ala Arg Leu His Asp Arg Leu Asn Ser Phe
        35                  40                  45

Gly Leu Gln Ser Trp Tyr Val Pro Pro Glu Trp Gly Gly Ala Pro Gly
    50                  55                  60

Asp His Glu Arg Leu Leu His Leu Trp Arg Ala Val Ala Arg Arg Asp
65                  70                  75                  80

Leu Ser Ala Ala Val Ala His Gly Lys Thr Tyr Leu Gly Ser Ala Pro
                85                  90                  95

Val Trp Leu Ala Gly Asp Asp Gly Gln Arg Ala Thr Leu Ala Ala Ala
            100                 105                 110

Val Leu Ala Gly Thr Pro Val Ala Trp Ala Leu Ser Glu Pro Asp His
        115                 120                 125
```

```
Gly Ala Asp Leu Leu His Gly Thr Thr Thr Ala Leu Pro His Asp Ala
    130                 135                 140

Gly Tyr Arg Leu Arg Gly Leu Lys Trp Pro Ile Asn Asn Ala Thr Arg
145                 150                 155                 160

Ala Arg Tyr Leu Thr Val Leu Ala Arg Thr Gly Arg Ala Gly Asp Ala
                165                 170                 175

Arg Gly Gln Ser Leu Phe Leu Val Asp Lys Glu Ala Leu Ala Pro Gly
            180                 185                 190

Thr Trp Leu Pro Arg Pro Lys Val Ala Thr His Gly Val Arg Gly Ile
        195                 200                 205

Asp Ile Ser Gly Ile Ala Phe Glu Asp Ala Gly Leu Pro Gly Thr Ala
    210                 215                 220

Leu Leu Gly Arg Ala Gly Ser Gly Leu Glu Thr Val Leu Arg Ser Leu
225                 230                 235                 240

Gln Leu Thr Arg Thr Met Cys Ala Gly Leu Ser Leu Gly Ala Gly Asp
                245                 250                 255

Arg Ala Leu Arg Leu Thr Ala Arg Phe Val Ala Gln Arg Met Ile Met
            260                 265                 270

Arg Arg Pro Leu Leu Asp Arg Gly His Pro Ala Gly Ile Leu Ala Arg
        275                 280                 285

Cys Ala Ala Leu Leu Ala Ala Ala Glu Ala Thr Ala Val Val Gly Thr
290                 295                 300

Arg Ser Val His Ser Leu Thr Ala Glu Met Ser Val Thr Ser Ala Ile
305                 310                 315                 320

Val Lys Ala Tyr Val Pro Thr Val Val Asp Arg Val Leu Arg Glu Leu
                325                 330                 335

Ala Glu Leu Leu Gly Ser Arg Ser Phe Leu Arg Asp Glu Tyr Glu His
            340                 345                 350

Gly Met Phe Pro Lys Leu Val Arg Asp His His Val Val Ala Val Phe
        355                 360                 365

Asp Gly Ser Thr Pro Val Val Arg Thr Ala Leu Ala His Gln Phe Pro
    370                 375                 380

Arg Leu Ala Ala Gly Phe Ala Ala Gly Ala Val Ser Ala Glu Gly Leu
385                 390                 395                 400

Ala Glu Ala Ser Ala Ala Gly Gln Pro Pro Pro Leu Asp Arg Gly
                405                 410                 415

Ala Leu Thr Leu Leu Ser Arg His Gly Cys Ser Val Val Gln Ala Leu
            420                 425                 430

Pro Ala Leu Ala Val Ser Ala Ala Val Arg Gly Gly Pro Ala Gly Leu
        435                 440                 445

Ala Arg His Ala Ala Ala Leu Ala Gly Glu Ala Arg Arg Ile Cys Gly
    450                 455                 460

Gln Met Thr Glu Leu Gly Pro Ser Ala Arg Pro Ser Met Val Gly His
465                 470                 475                 480

Glu Leu Ala Ala Ala Tyr Glu Trp Cys Tyr Ala Gly Ala Ala Cys Leu
                485                 490                 495

Leu Leu Trp Thr Ser Ala Glu Gly Arg His Thr Ala Asp Pro Leu Trp
            500                 505                 510

Ala Asp Gly Leu Trp Val Leu Ala Ala Leu Arg Ala Val Arg Arg Glu
        515                 520                 525

Leu Ala Arg Val Leu Arg Ala Pro Ala Pro Asp Pro Gly Pro His Asp
530                 535                 540
```

```
Asp Gly Ala Asp Arg Leu Leu Ala Ala Arg Val Ala Ala Ala Arg
545                 550                 555                 560

Thr Gly Glu Pro Val Thr Pro Phe Gly Thr Ala Leu Arg Pro Pro Ala
                565                 570                 575

Gly Thr Val Arg Ala Glu Asp Gly Arg
            580                 585

<210> SEQ ID NO 27
<211> LENGTH: 587
<212> TYPE: PRT
<213> ORGANISM: Actinoplanes sp.

<400> SEQUENCE: 27

Met Val Ile Asp Ala Ala Thr Gln Pro Thr Val Pro Asp Ala Phe Arg
1               5                   10                  15

Ala Gln Ala Ile Ala Arg Pro Gly Glu Pro Ala Leu Val Val Leu Pro
                20                  25                  30

Gly Asp Pro Asp Ala Glu Pro Val Thr Leu Thr Tyr Ala Glu Leu Asp
            35                  40                  45

Arg Arg Ala Ala Ala Arg Ala Ala Trp Leu Ala Ala Arg Phe Pro Ala
50                  55                  60

Gly Glu Arg Ile Leu Ile Ala Leu Pro Thr Gly Ala Glu Phe Val Glu
65                  70                  75                  80

Leu Tyr Leu Ala Cys Leu Tyr Ala Gly Leu Val Ala Val Pro Ala Pro
                85                  90                  95

Pro Pro Gly Gly Ser Ser Gly Ala Ser Glu Arg Thr Val Gly Ile Ala
            100                 105                 110

Ala Asp Cys Ser Pro Ala Leu Ala Val Val Asn Ala Asp Asp Ala Ala
        115                 120                 125

Pro Leu Thr Ala Val Leu Arg Glu Arg Gly Leu Ser Gly Leu Pro Val
130                 135                 140

Gly Ala Leu Pro Pro Leu Ala Ala Glu Ala Ile Arg Pro Pro Arg Gly
145                 150                 155                 160

Pro Arg Pro Asp Ser Leu Ala Val Leu Gln Tyr Ser Ser Gly Ser Thr
                165                 170                 175

Gly Ser Pro Lys Gly Val Met Leu Ser His Arg Ala Val Leu Ala Asn
            180                 185                 190

Leu Arg Ala Phe Asp Arg Ser Ser Gly His Asn Ser Asp Asp Val Phe
        195                 200                 205

Gly Ser Trp Leu Pro Leu His His Asp Met Gly Leu Phe Ala Met Leu
210                 215                 220

Thr Ala Gly Leu Leu Asn Gly Ala Gly Val Val Leu Met Ser Pro Thr
225                 230                 235                 240

Ala Phe Val Arg Arg Pro Ala Asp Trp Leu Arg Met Met Asp Arg Tyr
                245                 250                 255

Arg Val Thr Ile Ser Ala Ala Pro Asn Phe Ala Tyr Asp Leu Cys Val
            260                 265                 270

Arg Ala Val Arg Asp Glu Gln Ile Ala Gly Leu Asp Leu Ser Arg Ile
        275                 280                 285

Arg Thr Leu Tyr Asn Gly Ser Glu Pro Val Asn Pro Ala Thr Val Arg
290                 295                 300

Ala Phe Thr Glu Arg Phe Ala Pro Phe Gly Leu His Thr His Ala Val
305                 310                 315                 320

Asn Pro Cys Tyr Gly Met Ala Glu Phe Thr Ala Tyr Val Ser Thr Lys
                325                 330                 335
```

```
Val Phe Glu Ala Pro Ala Val Phe Leu Pro Ala Asp Pro Arg Ala Leu
            340                 345                 350

Glu Asp Ala Ala Ser Pro Ala Leu Arg Pro Ala Asp Pro Ala Ala Ala
            355                 360                 365

Arg Glu Ile Pro Gly Val Gly Arg Val Pro Asp Phe Glu Val Leu Ile
            370                 375                 380

Val Asp Pro Asp Gly Leu Arg Pro Leu Pro Glu Gly Arg Val Gly Glu
385                 390                 395                 400

Ile Trp Leu Arg Gly Pro Gly Ala Gly Ala Gly Tyr Trp Gly Arg Thr
                405                 410                 415

Glu Leu Asn Pro Gly Ile Phe Asp Ala Arg Pro Ala Gly Asp Gly Gln
            420                 425                 430

Asp Gly Gly Trp Val Arg Thr Gly Asp Leu Gly Ala Leu Thr Gly Gly
            435                 440                 445

Glu Leu Phe Leu Thr Gly Arg Leu Lys Glu Leu Leu Ile Val His Gly
            450                 455                 460

Arg Asn Leu Ala Pro His Asp Leu Glu Arg Glu Ala Arg Ala Ala His
465                 470                 475                 480

Asp Ala Val Asp His Gln Ile Gly Ala Ala Phe Gly Val Pro Ala Pro
                485                 490                 495

Asp Glu Arg Ile Val Leu Val Gln Glu Val His Pro Arg Thr Pro Leu
            500                 505                 510

Asp Glu Leu Pro Arg Val Ala Ser Ala Val Ser Arg Arg Leu Thr Val
            515                 520                 525

Ser Phe Gly Val Pro Val Arg Asn Val Leu Leu Val Arg Arg Gly Thr
            530                 535                 540

Val Arg Arg Thr Thr Ser Gly Lys Ile Arg Arg Thr Ala Val Arg Glu
545                 550                 555                 560

Arg Phe Leu Ala Gly Gly Ile Thr Ala Leu His Ala Glu Leu Glu Pro
                565                 570                 575

Ala Leu Arg Pro Val Gln Ala Gly Ala Gly Arg
            580                 585

<210> SEQ ID NO 28
<211> LENGTH: 75
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. Ti
      is expected that the biosynthesized protein will have a
      formylmethionine residue at this position

<400> SEQUENCE: 28

Val Pro Asn Pro Phe Glu Asp Pro Asp Ala Asn Tyr Leu Val Leu Val
1               5                   10                  15

Asn Asp Glu Gly Gln His Ser Leu Trp Pro Val Phe Ala Asp Val Pro
            20                  25                  30

Asp Gly Trp Thr Thr Val Phe Gly Glu Ala Gly Arg Gln Asp Cys Leu
            35                  40                  45

Asp Tyr Ile Glu Lys Ser Trp Thr Asp Met Arg Pro Lys Ser Leu Ile
            50                  55                  60

Ala Ala Met Glu Lys Gln Lys Gln Pro Gln Ser
65                  70                  75
```

```
<210> SEQ ID NO 29
<211> LENGTH: 94
<212> TYPE: PRT
<213> ORGANISM: Actinoplanes sp.
<220> FEATURE:
<221> NAME/KEY: misc_feature
<222> LOCATION: (1)..(1
<223> OTHER INFORMATION: V is a non-standard initiator codon. It is
      expected that the biosynthesized protein will have a formylmethio-
      nine residue at this position

<400> SEQUENCE: 29

Val Ala Pro Gly Ala Pro Pro Ala Glu His Gly Glu Ala Val Pro Glu
1               5                   10                  15

Ala Asp Ile Pro Val Leu Arg Asn Arg Ile Asp Glu Ile Asp Ala Ala
                20                  25                  30

Ile Met Arg Leu Trp Gln Glu Arg Ala Ser Ile Ser Gln Lys Ile Gly
            35                  40                  45

Ser Ile Arg Leu Ala Ser Gly Gly Thr Arg Val Val Leu Ser Arg Glu
50                  55                  60

Gln Glu Val Ile Gln Arg Phe Arg Ala Ala Leu Gly Glu Asp Gly Thr
65                  70                  75                  80

Thr Ile Ala Leu Met Leu Leu Arg Ala Gly Arg Gly Pro Leu
                85                  90

<210> SEQ ID NO 30
<211> LENGTH: 619
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It
      is expected that the biosynthesized protein will have a
      formylmethionine residue at this position

<400> SEQUENCE: 30

Val Asp Val Pro Arg Val Arg Pro Pro Gly Ala Ala Pro Ala Pro Arg
1               5                   10                  15

Arg Arg Arg Trp Arg Phe Trp Gln Ser Pro Asp Gly Gln Pro Ala Trp
                20                  25                  30

Ala Arg Pro Ala Leu Leu Gly Ile Ala Ala Leu Ala Ala Val Leu Tyr
            35                  40                  45

Thr Ala Asn Leu Ala Arg Ser Gly Tyr Pro Met Tyr Tyr Ala Val Ala
50                  55                  60

Val Lys Ser Met Ser Val Ser Trp Pro Ala Phe Trp Thr Gly Ala Phe
65                  70                  75                  80

Asp Pro Ala Ala Ser Ile Thr Ile Asp Lys Leu Ala Gly Ala Phe Val
                85                  90                  95

Pro Gln Ala Leu Ser Ala Arg Val Phe Gly Phe His Gln Trp Ser Leu
            100                 105                 110

Ala Leu Pro Gln Ala Val Glu Gly Val Ile Ala Val Leu Val Leu Tyr
        115                 120                 125

Arg Ala Val Arg Arg Trp His Gly Pro Gly Ala Gly Leu Ala Ala Ala
    130                 135                 140

Gly Leu Phe Ala Thr Thr Pro Ile Val Ser Ser Met Phe Gly His Ser
145                 150                 155                 160

Met Glu Asp Gly Ala Leu Thr Leu Cys Leu Val Leu Ala Ala Asp Ala
                165                 170                 175

Phe Gly Ala Ala Val Thr Arg Gly Ser Pro Ala Arg Leu Ala Leu Ala
```

```
                180                 185                 190
Gly Ala Trp Ile Gly Leu Gly Phe Gln Ala Lys Met Met Gln Ala Trp
            195                 200                 205
Leu Val Leu Pro Ala Leu Val Val Thr Tyr Leu Ala Gly Ala Pro Val
210                 215                 220
Arg Ala Arg Ala Arg Val Val His Val Ala Ala Val Ala Ala Thr
225                 230                 235                 240
Leu Ala Val Ser Leu Leu Trp Val Leu Ala Leu Thr Leu Leu Pro Gly
                245                 250                 255
Ser His Arg Pro Trp Ala Asp Gly Thr Thr Ser Gly Asn Ala Phe Ala
            260                 265                 270
Met Val Phe Gly Tyr Asn Gly Phe Asp Arg Ala Gly Ile His Val Pro
            275                 280                 285
Gly Ala Leu Thr Thr Gly Phe Thr Asp Gly Gly Ala Ala Gly Gly
            290                 295                 300
Ser Trp Thr Ala Leu Ala Asp Arg Leu Ala Thr Gln Ile Gly Trp
305                 310                 315                 320
Trp Tyr Pro Leu Ala Leu Thr Gly Leu Leu Gly Leu Ala Arg Trp
                325                 330                 335
Arg Thr Ala Arg Ala Gly Leu Leu Phe Trp Gly Leu Trp Leu Leu Thr
            340                 345                 350
Ala Ala Val Val Leu Ser Arg Ile Thr Ile Gln His Asn Ala Tyr Leu
            355                 360                 365
Ala Val Leu Ala Pro Pro Leu Ala Ala Leu Ala Ala Gly Ala Val
            370                 375                 380
Gln Leu Trp Arg Thr His Arg Asp Gly Thr Ala Pro Trp Leu Leu Pro
385                 390                 395                 400
Ala Val Val Val Gln Ala Gly Trp Thr Leu Trp Leu Ala Thr Arg
                405                 410                 415
Tyr Pro Ser Phe Leu Ala Gly Leu Thr Trp Thr Ala Pro Ile Ala Ala
            420                 425                 430
Val Leu Ala Val Val Leu Ala Ala Arg Pro Thr Ala Arg Arg Pro
            435                 440                 445
Ala Val Val Val Val Ala Gly Leu Leu Ala Val Pro Val Ala Trp
450                 455                 460
Gly Ala Ser Val Leu Asn Pro Arg Tyr Ala Gly Thr Ser Phe Glu Ala
465                 470                 475                 480
Gly Ala Gly Pro Ser Gly Pro Val Gly Val Arg Leu Asp Asp Thr
                485                 490                 495
Thr Asp Arg Leu Thr Pro Gly Leu Arg Arg Leu Asp Asp Tyr Leu Ala
            500                 505                 510
Ala His Arg Asp Gly Arg Thr Tyr Leu Ala Ala Thr Ser Ser Trp Arg
            515                 520                 525
Thr Ala Gly Arg Leu Ile Val Pro Thr Gly His Ser Tyr Leu Pro Leu
            530                 535                 540
Gly Gly Phe Ser Gly Ala Ala Pro Phe Pro Ser Leu Ala Gly Val Gln
545                 550                 555                 560
Arg Leu Val Arg Asp Gly Glu Leu Arg Tyr Phe Val Leu Gly Gly Pro
                565                 570                 575
Glu Gly Leu Gly Gly Glu Ala Thr Glu Ala Tyr Arg Ile Thr Gly Trp
            580                 585                 590
Val Leu Glu Thr Cys Ala Thr Val Pro Pro Ala Glu His Gly Ala Asp
            595                 600                 605
```

Pro Asp Leu Thr Val Leu Arg Cys Asp Lys Pro
    610                 615

<210> SEQ ID NO 31
<211> LENGTH: 355
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It
      is expected that the biosynthesized protein will have a
      formylmethionine residue at this position

<400> SEQUENCE: 31

Val Asp Asn Gly Thr Phe Thr Asp Leu Arg Ile Asp His Ile Glu Phe
1               5                   10                  15

Ala Val Ala Asp Val Glu Ser Ala Ser Ala Pro Phe Thr Glu Gly Tyr
            20                  25                  30

Gly Phe Ser Val Tyr Gly Gly Thr Gly Asp Ala His Ala Pro Val Arg
        35                  40                  45

Arg Val Ala Leu Gly Arg Asp Asp Ile Arg Leu Val Leu Thr Ala Ala
    50                  55                  60

Pro Gly Gly Asp His Pro Ala Met Ala Tyr Val Glu Gln His Gly Asp
65                  70                  75                  80

Gly Val Ser Ala Ile Ala Leu Ser Thr Arg Asp Ala His Ala Ala Phe
                85                  90                  95

Thr Glu Ala Val Arg Arg Gly Ala Val Gly Val Ser Ala Pro Val Thr
            100                 105                 110

Gly Asn Gly Val Thr Val Ala Thr Ile Arg Gly Phe Gly Asp Val Leu
        115                 120                 125

His Thr Phe Val Glu Arg Ala Pro Gly Ala Asp Pro Arg Thr Leu Pro
    130                 135                 140

Gly Leu Glu Leu Arg Arg Pro Ser Pro Thr Arg Phe Asp Ser Gly Leu
145                 150                 155                 160

Gln Ala Ile Asp His Ile Ala Val Cys Leu Glu Pro Gly Thr Leu Asp
                165                 170                 175

Pro Thr Val Asp Phe Tyr Arg Asp Val Leu Asp Phe Glu Met Ile Phe
            180                 185                 190

Glu Glu Arg Ile Leu Val Gly Arg Gln Ala Met Asp Ser Lys Val Val
        195                 200                 205

Gln Ser Arg Ser Gly Gly Val Thr Leu Thr Leu Ile Glu Pro Asp Thr
    210                 215                 220

Ser Leu Glu Gln Gly Gln Ile Asp Thr Phe Leu Lys Asn His Gly Gly
225                 230                 235                 240

Pro Gly Val Gln His Leu Ala Phe Ile Thr Asp Asp Val Leu Arg Ser
                245                 250                 255

Val Gly Arg Met Ser Glu His Gly Val Glu Phe Leu His Thr Pro Asp
            260                 265                 270

Ser Tyr Tyr Gly Arg Leu Pro Gly Arg Ile Pro Gln Ala Gly His Pro
        275                 280                 285

Ile Gln Ala Leu Arg Asp Leu Asn Val Leu Val Asp Gln Asp His Asp
    290                 295                 300

Gly Gln Leu Phe Gln Ile Phe Thr Lys Ser Val His Pro Arg Gly Thr
305                 310                 315                 320

Ile Phe Met Glu Val Ile Glu Arg Met Gly Ala Arg Ser Phe Gly Ser

```
                    325                 330                 335
Gly Asn Ile Lys Ala Leu Tyr Glu Ala Val Glu Leu Asp Met Ser Lys
            340                 345                 350

Gln Ser Ala
        355

<210> SEQ ID NO 32
<211> LENGTH: 429
<212> TYPE: PRT
<213> ORGANISM: Actinoplanes sp.

<400> SEQUENCE: 32

Met Glu Ser Pro Ala Thr His Ala Glu Leu Val Ile Gly Thr Val Leu
1               5                   10                  15

Leu Asp Ile Ala Leu Val Leu Ala Ala Gly Ala Leu Leu Gly Arg Trp
            20                  25                  30

Val Arg Arg Leu Arg Gln Pro Ala Val Ile Gly Glu Ile Leu Ala Gly
        35                  40                  45

Ile Ala Leu Gly Pro Ser Leu Leu Gly Leu Leu Pro Gly Asn Pro Thr
50                  55                  60

Ala Trp Leu Phe Pro Ala Glu Ala Arg Pro Tyr Leu Ser Ala Val Ala
65                  70                  75                  80

Gln Ile Gly Leu Ala Leu Phe Thr Phe Leu Ile Gly Trp Glu Phe Asn
                85                  90                  95

Pro Ala Thr Leu Ala Arg His Arg Gly Thr Ala Ala Val Ser Ile
            100                 105                 110

Gly Ser Ile Ala Val Ser Phe Gly Leu Gly Ile Ala Leu Ala Thr Val
        115                 120                 125

Leu His Pro Arg His Asp Thr Thr Gly Gly Gly Lys Val Gly Phe Thr
130                 135                 140

Glu Phe Ala Leu Phe Leu Gly Val Ala Met Ser Ile Thr Ala Phe Pro
145                 150                 155                 160

Val Leu Ala Arg Ile Leu Ala Glu Arg Leu Thr Gly Thr Arg Val
                165                 170                 175

Gly Ser Ile Ala Leu Val Ser Ala Ala Ile Asp Asp Val Val Ala Trp
            180                 185                 190

Cys Leu Leu Ala Leu Val Thr Ala Ile Ala Thr Ala Ser Gly Pro Val
        195                 200                 205

Gln Leu Val Arg Ile Leu Ala Leu Leu Ala Val Phe Leu Val Val Leu
210                 215                 220

Val Thr Val Val Arg Pro Leu Leu Val Leu Ala Arg Arg Pro Ser
225                 230                 235                 240

Ala Ser Tyr Leu Leu Val Ala Val Val Ala Val Leu Leu Ser Ala
                245                 250                 255

Tyr Ala Thr Thr Trp Ile Gly Leu His Ala Ile Phe Gly Ala Phe Cys
            260                 265                 270

Ala Gly Leu Val Met Pro Arg Glu Pro Ala Ala Ala Leu Arg Glu Arg
        275                 280                 285

Val Arg Gln Pro Leu Glu His Val Ser Val Val Leu Leu Pro Val Phe
290                 295                 300

Phe Ile Val Thr Gly Leu Gly Val Asp Ile Gly Ala Leu Thr Ala Ala
305                 310                 315                 320

Asn Ile Leu Glu Leu Ala Ala Ile Ile Val Ile Ala Cys Ala Gly Lys
                325                 330                 335
```

```
Leu Ala Gly Ala Ile Val Pro Ala Val Ser Leu Gly Met Ser Trp Arg
            340                 345                 350

Asp Ala Arg Thr Leu Gly Leu Leu Val Asn Thr Arg Gly Leu Thr Glu
        355                 360                 365

Leu Val Val Leu Asn Val Gly Leu Gln Leu Ala Val Leu Asp Gly Gln
    370                 375                 380

Met Phe Thr Met Met Val Leu Met Ala Leu Val Thr Thr Ala Leu Ala
385                 390                 395                 400

Gly Pro Leu Ile Gly Ser Ala Arg Thr Pro Ala Ala Gly Ala Pro Ala
                405                 410                 415

Gln Ala Leu Pro Ala Glu Pro Arg Thr Arg Arg Ala Ala
            420                 425

<210> SEQ ID NO 33
<211> LENGTH: 189
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It
      is expected that the biosynthesized protein will have a
      formylmethionine residue at this position

<400> SEQUENCE: 33

Val Ser Asp Glu Ala Ala Val Pro Ser Pro Ala Arg Leu Leu Arg Asp
1               5                   10                  15

Phe Val Asn Thr Tyr Glu Pro Gln Val Asp Asp Glu Ser Leu Ser Thr
            20                  25                  30

Pro Asp Ala Leu Arg Ala Trp Leu Ala Gly Glu Ser Leu Leu Ala Pro
        35                  40                  45

Gly Ala Arg Val Arg Pro Ala Asp Leu Ala Arg Ala Val Ala Leu Arg
    50                  55                  60

Glu Gly Leu Arg Gln Val Leu Leu Gly His Ala Gly His Pro Ala Asp
65                  70                  75                  80

Pro Ala Ala Leu Arg Arg Leu Glu Glu Ile Leu Ala Ala Val Pro Val
                85                  90                  95

Arg Leu Ser Leu Ala Gly Gly Ala Pro Arg Leu Leu Pro Ala Gly Gly
            100                 105                 110

Thr Pro Phe Asp Arg Ala Leu Ala Gly Leu Ile Asp Ala Val Arg Gln
        115                 120                 125

Cys Ala Glu Leu Gln Val Trp Thr Arg Leu Lys Val Cys Asp Arg Asp
    130                 135                 140

Thr Cys Arg Trp Ala Tyr Tyr Asp Ala Ser Arg Asn Gln Ala Arg Arg
145                 150                 155                 160

Trp Cys Ser Met Ala Gly Cys Gly Asn Tyr Ile Lys Met Arg Arg Ala
                165                 170                 175

Tyr Ala Ala Arg Arg Val Arg Gly Ser Ala Gly Ser Ala
            180                 185

<210> SEQ ID NO 34
<211> LENGTH: 309
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon. It
      is expected that the biosynthesized protein will have a
      formylmethionine residue at this position
```

<400> SEQUENCE: 34

```
Val Ala Thr Thr Leu Arg Asp Val Ala Arg Leu Ala Arg Val Ser Val
1               5                   10                  15

Lys Thr Val Ser Asn Val Val Asn Asp His Pro His Val Ser Asp Asp
            20                  25                  30

Val Arg Arg Arg Val Glu Thr Ala Ile Arg Gln Leu Gly Tyr Arg Pro
        35                  40                  45

Asn Leu Val Ala Arg Ala Leu Arg Ser Gly Arg Gly Ser Gly Leu Leu
    50                  55                  60

Ala Leu Ala Met Pro Gly Ala Gly Ala Pro Gln Ser Pro Ala Leu Ile
65                  70                  75                  80

Glu Glu Ile Ile Arg Arg Ala Ala Pro Leu Gly Phe Arg Val Leu Ile
                85                  90                  95

Glu Pro Leu Glu Ser Ser Arg Pro Arg Pro Ala Pro Gly Val Asp
            100                 105                 110

Ala Arg Leu Leu Asn Ala Glu Ala Pro Ala Pro Glu Leu Val Asp Ala
        115                 120                 125

Gln Ala Ala Thr Gly Thr Pro Leu Val Leu Leu Thr Gly Thr Pro Asp
    130                 135                 140

Pro Arg Tyr Asp Cys Val Gly Pro Asp Ala Ala Arg Ala Ala Glu Asp
145                 150                 155                 160

Ala Val Asp His Leu Arg Arg Leu Gly Arg Arg Arg Val Ala Thr Ile
                165                 170                 175

Gly Gly Ser Leu Ser Thr Gly Pro Ala Gly Ser Gly Ser Asp Phe Gly
            180                 185                 190

Ser Gly Ser Gly Ser Gly Ser Gly Ser Gly Ser Gly Ser Gly Ser Gly
        195                 200                 205

Ser Gly Ser Gly Ser Gly Ser Gly Ser Gly Phe Gly Ser Gly
210                 215                 220

Ser Gly Phe Gly Ser Gly Ser Ala Glu Gly Tyr Arg Ala Ala Arg Gln
225                 230                 235                 240

Leu Leu Gly His Glu Asp Arg Pro Asp Ala Ile Val Cys Gly Ser Val
            245                 250                 255

Arg Leu Ala Val Gly Val Ile Arg Ala Ala Ala Asp Ala Gly Leu Arg
        260                 265                 270

Val Pro Glu Asp Val Ala Val Ile Gly Ile Gly Asp Gly Glu Glu Gly
        275                 280                 285

Arg Tyr Thr Arg Pro Ala Leu Thr Thr Val Ala Thr Asp Pro Ala Phe
    290                 295                 300

Ile Ala Gly Lys Ala
305
```

GENE ENCODING A NONRIBOSOMAL PEPTIDE SYNTHETASE FOR THE PRODUCTION OF RAMOPLANIN

CROSS-REFERENCE TO RELATED APPLICATIONS

This application claims benefit under 35 USC §119 of provisional application U.S. Ser. No. 60/239,924 filed on Oct. 13, 2000 and of provisional application U.S. Ser. No. 60/283,296 filed Apr. 12, 2001, and claims benefit under 35 USC §120 of U.S. Ser. No. 09/910,813 which are hereby incorporated by reference in their entirety for all purposes.

FIELD OF INVENTION

The present invention relates to the field of antibiotics, and more specifically to genes involved in the biosynthesis of ramoplanin. The invention provides recombinant methods and materials for producing ramoplanins by recombinant DNA technology.

BACKGROUND

Ramoplanin is a naturally-occurring glycosylated lipodepsipeptide antibiotic active against Gram-positive aerobic and anaerobic bacteria. Ramoplanin kills Gram-positive bacteria by inhibiting one of the enzymes needed to construct the bacterial cell wall. Ramoplanin was first described as antibiotic A/16686 produced by fermentation of *Actinoplanes* sp. ATCC 33076, as described in U.S. Pat. No. 4,303,646. It was subsequently found that three closely related components could be isolated from antibiotic A/16686, which components were named antibiotic A/16686 factors A1, A2, and A3 (Ciabatti et al., 1989, J. Antibiot (Tokyo), Vol. 42, No. 2, pp. 254–267). These substances as well as their preparation and uses are described in U.S. Pat. No. 4,427,656. Three additional factors designated A'1, A'2, and A'3 were later shown to be present in the fermentation medium and were shown to differ from the respective parent components of the original complex by lacking one mannose unit from the glycosidic group (Gastaldo et al., 1992, J. Ind. Microbiol. Vol. 11, No. 1, pp. 13–18).

Ramoplanin consists of a mixture of three related polypeptides having a common cyclic depsipeptide core structure on which is carried a dimannosyl glycosidic group. The three forms of ramoplanin are differentiated by the presence of various acylamide moieties derived from 8-, 9-, or 10-carbon fatty acids that decorate the glycosylated depsipeptide core structure.

Depsipeptides are cyclic or branched peptides containing an ester linkage between a carboxylate group of the peptide and a terminal or side-chain hydroxyl group of the peptide. The ramoplanin depsipeptide core structure contains 17 amino acids. The order of amino acids, from N-terminal to C-terminal, is as follows: amino acid 1: asparagine (Asn); amino acid 2: beta-hydroxyasparagine (HAsn); amino acid 3: 4-hydroxyphenylglycine (HPG); amino acid 4: ornithine (Orn); amino acid 5: threonine (Thr); amino acid 6: HPG; amino acid 7: HPG; amino acid 8: Thr; amino acid 9: phenylalanine (Phe); amino acid 10: Orn; amino acid 11: HPG; amino acid 12: Thr; amino acid 13: HPG; amino acid 14: glycine (Gly); amino acid 15: leucine (Leu); amino acid 16: alanine (Ala); amino acid 17: 3-chloro-4-hydroxyphenylglycine (CHPG). The peptide is cyclized by ester bond formation between the carboxylate group of the C-terminal CHPG and the hydroxyl group of HAsn. The N-terminus of Asn in position 1 is acylated by three different fatty acids, resulting in the three different components A1–A3. Two D-mannose sugars are attached to the HPG in position 11 by a hemiacetal bond.

Many low molecular weight peptides produced by bacteria are synthesized nonribosomally on large multifunctional proteins termed peptide synthetases. (Konz & Marahiel, 1999, Chem. Biol., Vol. 6, pp. R39–R48). Peptide synthetases contain repeated units that each recognize specific amino acids and catalyze their stepwise joining into a peptide chain. The identity of the amino acid recognized by a particular unit can be determined by comparison with other units of known specificity. In many peptide synthetases, there is a strict correlation between the order of repeated units in a peptide synthetase and the order in which the respective amino acids appear in the peptide product, making it possible to correlate peptides of known structure with putative genes encoding their synthesis, as demonstrated by the identification of the mycobactin biosynthetic gene cluster from the genome of Mycobacterium tuberculosis (Quadri et al., 1998, Chem. Biol. Vol. 5, pp. 631–645).

The repeating units of a peptide synthetase are composed of smaller units or "domains" that each carry out a specific role in the recognition, activation, modification and joining of amino acid precursors to form the peptide product. One type of domain, the adenylation (A) domain, is responsible for selectively recognizing and activating the amino acid that is to be incorporated by a particular unit of the peptide synthetase. The activated amino acid is joined to the peptide synthetase through another type of domain, the thiolation (T) domain, that is generally located adjacent to the A domain. Amino acids joined to successive units of the peptide synthetase are subsequently linked together by the formation of amide bonds catalyzed by another type of domain, the condensation (C) domain.

Although the structure of ramoplanin has been identified, there remains the need to obtain novel structures with new activities or enhanced properties. There is also a need to improve production of ramoplanin. Accordingly, there is a need for genetic information regarding the biosynthesis of ramoplanin.

SUMMARY OF THE INVENTION

The present invention provides purified and isolated polynucleotide molecules that encode polypeptides of the ramoplanin biosynthetic pathway in microorganisms. In one form of the invention, polynucleotide molecules are selected from the contiguous DNA sequence (SEQ ID NO: 1) representing the full-length locus of the ramoplanin biosynthetic pathway and containing the 33 ORFs encoding the proteins forming the ramoplanin gene cluster. The amino acid sequence of the proteins is provided in SEQ ID NOS: 2 to 34. Structural and functional characterization is provided for the 33 ORFs.

Thus, in one aspect, the invention provides an isolated nucleic acid comprising a nucleic acid sequence selected from the group consisting of (a) nucleic acid encoding any of ramoplanin ORFs 1 to 33 (SEQ ID NOS: 2 to 34); (b) a nucleic acid encoding a polypeptide encoded by any of ramoplanin ORFs 1 to 33 (SEQ ID NOS: 2 to 34); and (c) a nucleic acid encoding a polypeptide that is at least 75%, preferably 80%, more preferably 85%, still more preferably 90% and most preferably 95% or more identical in amino acid sequence to a polypeptide of ramoplanin ORFs 4, 5, 9 to 19, 22 to 26, 29, 30 and 31 (SEQ ID NOS: 5, 6, 10 to 20, 23 to 27, 30, 31 and 32).

Certain embodiments of the invention specifically exclude one or more of ORFs 1 to 33, most notably ORFs 1, 2, 3, 6, 7, 8, 20, 21, 27, 28, 31 and 32 (SEQ ID NOS: 2, 3, 4, 7, 8, 9, 21, 22, 28, 29, 32 and 33) although other ORFs can be excluded without departing from the scope of the invention. Thus, another embodiment of the invention provides an isolated nucleic acid comprising a nucleic acid sequence selected from the group consisting of: (a) a nucleic acid encoding any of ramoplanin ORFs 4, 5, 9 to 19, 22 to 26, 29, 30 and 31 (SEQ ID NOS: 5, 6, 10 to 20, 23 to 27, 30, 31 and 32); (b) a nucleic acid encoding a polypeptide encoded by any of ramoplanin ORFs 4, 5, 9 to 19, 22 to 26, 29, 30 and 31 (SEQ ID NOS: 5, 6, 10 to 20, 23 to 27, 30, 31 and 32); and (c) a nucleic acid encoding a polypeptide that is at least 75%, preferably 80%, more preferably 85%, still more preferably 90% and most preferably 95% or more identical in amino acid sequence to a polypeptide of ramoplanin ORFs 4, 5, 9 to 19, 22 to 26, 29, 30 and 31 (SEQ ID NOS: 5, 6, 10 to 20, 23 to 27, 30, 31 and 32).

In one embodiment preferred nucleic acids encode at least two, more preferably three, still more preferably four, or most preferably five or more ORFs selected from ORFS 1 to 33 (SEQ ID NOS: 2 to 34) of the ramoplanin locus. In one embodiment, combinations of ORFs selected from ORFs 1 through 33 (SEQ ID NOS 2 to 34) are provided which encode polypeptides that form at least the depsipeptide core structure of ramoplanin. In another embodiment combinations of ORFs selected from ORFs 1 through 33 (SEQ ID NOS: 2 to 34) are provided which encode polypeptides that form at least the fatty-aid side chain of the depsipeptide core structure of ramoplanin. In another embodiment, combinations of ORFs selected from ORFs 1 through 33 (SEQ ID NOS: 2 to 34) are provided which encode polypeptides responsible for the synthesis of 4-hydroxyphenylglycine (HPG) of ramoplanin. In another embodiment, combinations of ORFs selected from ORFs 1 through 33 (SEQ ID NOS: 2 to 34) are provided that encode polypeptides that form at least the beta-hydroxyasparagine residue. In another embodiment, combinations of ORFs selected from ORFs 1 through 33 (SEQ ID NOS: 2 to 34) are provided which are involved in the regulation of ramoplanin biosynthesis. In another embodiment, combinations of ORFs selected from ORFs 1 through 33 (SEQ ID NOS: 2 to 34) are provided which encode polypeptides that are involved in resistance and subcellular localization of the ramoplanin biosynthetic machinery. A single ORF or a combination of ORFs selected from ORFs 1 through 33 (SEQ ID NOS: 2 to 34) are provided to enhance production of ramoplanin by altering the expression level of an ORF selected from ORFs 1 through 33 (SEQ ID NOS: 2 to 34). In another embodiment, the expression level of an ORF selected from ORFs 1 through 33 (SEQ ID NOS: 2 to 34) may be altered to increase the yield of a particular form of ramoplanin.

Those skilled in the art will readily understand that the invention, having provided the polynucleotide sequences encoding polypeptides of the ramoplanin biosynthetic pathway, also provides polynucleotides encoding fragments derived from such peptides. Moreover, the invention is understood to provide naturally occurring variants or derivatives of such polypeptides and fragments derived therefrom, such variants or derivatives resulting from the addition, deletion, or substitution of non-essential amino acids or conservative substitutions of essential amino acids as described herein. Those skilled in the art would also readily understand that the invention, having provided the polynucleotide sequences of the entire genetic locus from *Actinoplanes*, further provides naturally-occurring variants or homologs of the genes of the ramoplanin biosynthetic locus from other microorganisms, in particular, those of the family Actinomycetes.

It is also understood that the invention, having provided the polynucleotide sequences of the entire genetic locus as well as the coding sequences, further provides polynucleotides which regulate the expression of the polypeptides of the biosynthetic pathway. Such regulating polynucleotides include but are not limited to promoter and enhancer sequences, as well as sequences antisense to any of the aforementioned sequences. The antisense molecules are regulators of gene expression in that they are used to suppress expression of the gene from which they are derived. Expression cassettes and vectors comprising a polynucleotide as described herein, as well as cells transformed or transfected with such cassettes and vectors, are also within the scope of the invention.

In one aspect, the invention provides polynucleotides encoding a polypeptide selected from ORFs 9, 11 to 15, 17, 26 and 27 (SEQ ID NOS: 10, 12 to 16, 18, 27 and 28) or naturally occurring variants or derivatives of such polypeptides and fragments derived therefrom, such variants or derivatives resulting from the addition, deletion, or substitution of non-essential amino acids or conservative substitutions of essential amino acids of any one of ORFs 9, 11 to 15, 17, 26 and 27, for use in the synthesis of ramoplanin in vivo or in vitro. Such polynucleotides and polypeptides may also be used to generate derivatives of ramoplanin. In one embodiment, the order in which the modules occur within a single ORF may be changed so that the ramoplanin core structure is altered. In another embodiment, one or more module from one or more ORFs may be deleted or inserted so that the size of the ramoplanin core is altered. The polynucleotides and polypeptides related to ORFs 9, 11 to 15, 17, 26 and 27 may also be used to improve production or to produce variants of other antibiotics of the peptide class. In one embodiment, a module contained in any one or more of ORFs 9, 11 to 15, 17, 26 and 27 may be used to replace an existing module in a peptide synthetase involved in the synthesis of another peptide antibiotic to produce a peptide antibiotic derivative. In another embodiment, a module contained in any one or more of ORFs 9, 11 to 15, 17, 26 and 27 may be inserted into the sequence encoding the peptide synthetase involved in the synthesis of another peptide antibiotic to produce a peptide antibiotic derivative with a longer peptide length. In another embodiment, a module contained in any one or more of ORFs 9, 11 to 15, 17, 26 and 27 may be used in combination with the sequences of the present invention or in combination with other sequences which encode other peptide synthetases, to custom design a peptide antibiotic.

In another aspect, the invention provides polynucleotides encoding ORF17 (SEQ ID NOS: 18), or naturally occurring variants or derivatives of ORF17 and fragments derived therefrom, such variants or derivatives resulting from the addition, deletion, or substitution of non-essential amino acids or conservative substitutions of essential amino acids of ORF17, for use as an adenylation domain in conjunction with other peptide synthetase modules and allowing the incorporation of Thr into a peptide antibiotic precursor.

In another aspect, the invention provides polynucleotides encoding ORF 11, 12 or 26 (SEQ ID NOS: 12, 13 and 27), or naturally occurring variants or derivatives of ORF11, 12 or 26 and fragments derived therefrom, such variants or derivatives resulting from the addition, deletion, or substitution of non-essential amino acids or conservative substitutions of essential amino acids of ORF11, 12 or 26, for incorporating fatty acids into the core structure of a peptide antibiotic precursor. In one embodiment, ORF16, 24 or 25 or their variant or derivative is used in conjunction with ORF11, 12 or 26, for modifying fatty acid structure and/or enhancing fatty acid incorporation into the peptide antibiotic structure. In another embodiment, ORF1, 3, 19 or 29 or their variant or derivative is used in conjunction with ORF11, 12 or 26, for further enhancing fatty acid incorporation into the peptide antibiotic structure.

In another aspect, the invention provides polynucleotides encoding the adenylation and/or condensation domain of a module selected from module 1, 2, 3 and 5 of ORF 13 (SEQ ID NO: 14) and modules 1, 3 and 7 of ORF 14 (SEQ ID NO: 15), or naturally occurring variants or derivatives of such polypeptides and fragments derived therefrom, such variants or derivatives resulting from the addition, deletion, or substitution of non-essential amino acids or conservative substitutions of essential amino acids of an adenylation domain of a module selected from modules 1, 2, 3 and 5 of ORF 13 (SEQ ID NO: 14) and modules 1, 3 and 7 of ORF 14, for incorporating a D-amino acid into the core structure of a peptide antibiotic precursor.

In another aspect, the invention provides polynucleotides encoding any one of ORFs 4, 6, 7, 28 and 30 (SEQ ID NOS: 5, 7, 8, 29 and 31), or naturally occurring variants or derivatives of ORFs 4, 6, 7, 28 or 30 and fragments derived therefrom, such variants or derivatives resulting from the addition, deletion, or substitution of non-essential amino acids or conservative substitutions of essential amino acids of ORF 4, 6, 7, 28 or 30, for synthesis of hydroxyphenylglycine (HPG). In one embodiment, any one of ORFs 4, 6, 7, 28 and 30 or their variant or derivative is used to enhance production of an HPG-containing peptide antibiotic, including but not limited to nocardicin A, vancomycin, aridicin, chloroeremomycin, teicoplanin and related glycopeptide antibiotics, as well as the calcium-dependent antibiotic (CDA) of *Streptomyces coelicolor*.

In another aspect, the invention provides polynucleotides encoding any one of ORFs 2, 3, 8, 19, 23, 29 and 31 (SEQ ID NOS: 3, 4, 9, 20, 24, 30 and 32), or naturally occurring variants or derivatives of ORF 2, 3, 8, 19, 23, 29 or 31 and fragments derived therefrom, such variants or derivatives resulting from the addition, deletion, or substitution of non-essential amino acids or conservative substitutions of essential amino acids of ORF 2, 3, 8, 19, 23, 29 or 31, for enhancing secretion of ramoplanin or its variants and derivatives, or for enhancing uptake of precursors for ramoplanin biosynthesis. In one embodiment, any one of ORFs 2, 8, 23 and 31 may be used to confer resistance to ramoplanin or its variants and derivatives or improve production levels.

In another aspect, the invention provides polynucleotides encoding any one of ORFs 5, 21 and 22 (SEQ ID NOS: 6, 22 and 23), or naturally occurring variants or derivatives of ORF 5, 21 or 22 and fragments derived therefrom, such variants or derivatives resulting from the addition, deletion, or substitution of non-essential amino acids or conservative substitutions of essential amino acids of ORF 5, 21 or 22, for regulating biosynthesis of ramoplanin or its variants and derivatives. In one embodiment, any one of ORFs 5, 21 and 22 may be used to enhance production of ramoplanin or its variants and derivatives. In another embodiment, any one of ORFs 5, 21 and 22 may be used to link expression of ramoplanin or its variants and derivatives to an environmental or cellular signal.

In another aspect, the invention provides polynucleotides encoding ORF20 (SEQ ID NO: 21), or naturally occurring variants or derivatives of ORF20 and fragments derived therefrom, such variants or derivatives resulting from the addition, deletion, or substitution of non-essential amino acids or conservative substitutions of essential amino acids of ORF20, for halogenation of aromatic groups of a peptide antibiotic precursor. In one embodiment, ORF20 or its variants or derivatives are used to chlorinate HPG of a peptide antibiotic precursor.

BRIEF DESCRIPTION OF THE DRAWINGS

Various embodiments of the invention will now be described with reference to the attached Figures:

FIG. 3A is a clustal analysis of adenylation domains of ramoplanin biosynthetic enzymes (amino acids 471–959 of SEQ ID NO:13 (ORF 12), amino acids 518–990 of SEQ ID NO:14 (ORE 13 M1), amino acids 1561–2052 of SEQ ID NO:14 (ORF 13 M2), amino acids 2619–3122 of SEQ ID NO:14 (ORF 13 M3), amino acids 3698–4160 of SEQ ID NO:14 (ORF 13 M4), amino acids 4719–5192 of SEQ ID NO:14 (ORF 13 M5), amino acids 6318–6804 of SEQ ID NO:14 (ORF 13 M7), amino acids 487–993 of SEQ ID NO:15 (ORF 14 M1), amino acids 1568–2041 of SEQ ID NO:15 (ORF 14 M2), amino acids 2603–3095 of SEQ ID NO:15 (ORF 14 M3), amino acids 3672–4135 of SEQ ID NO:15 (ORF 14 M4), amino acids 4699–5199 of SEQ ID NO:15 (ORF 14 M5), amino acids 5777–6280 of SEQ ID NO:15 (ORF 14 M6), amino acids 6840–7343 of SEQ ID NO:15 (ORF 14 M7), amino acids 7926–8380 of SEQ ID NO:15 (ORF 14 M8), and amino acids 309–804 of SEQ ID NO:18 (ORF 17) as defined in table 3). Shown is the alignment of the amino acid sequence (single letter code) of all adenylation domains found in the ramoplanin locus relative to the adenylation domain of gramicidin S synthetase GrsA (SEQ ID NO:35). Adenylation domains of multimodular non-ribosomal peptide synthetases ORF13 and ORF14 are labeled according to their corresponding module M1–M7 and M1–M8, respectively. Note that ORF13 does not contain an adenylation domain in module 6. Highly conserved core motifs A1–A10 of adenylation domains (Konz et al., 1999, Chem. Biol. Vol. 6, pp. R39–48) are highlighted by boxes. Key residues used to predict the substrate specificity of each adenylation domain are highlighted in black (see FIG. 3B).

FIG. 3B shows the predicted specificities of adenylation domains. The model of Challis et al. (Chem. Biol. 2000, Vol. 7, pp. 211–224) was used to extract key residues predicted to dictate the amino acid specificity of each adenylation domain (highlighted in black in FIG. 3A). The corresponding eight residues that align with GrsA amino acids 235, 236, 239, 278, 299, 301, 322, and 330 are grouped with signatures of adenylation domains of known specificities (data kindly provided by Jacques Ravel). The accession number, protein name, and module number as well as the known amino acid specificity is shown for the latter. Abbreviations: Cda, CDA peptide synthetase of *Streptomyces coelicolor*, Cep, chloroeremomycin peptide synthetase of *Amycolatopsis orientalis*; Acm, actinomycin synthetase of *Streptomyces chrysomallus*; Fen, fengycin peptide synthetase of *Bacillus subtilis*; Bac, bacitracin peptide synthetase of *Bacillus licheniformis*; Fxb, exochelin peptide synthetase of *Mycobacterium smegmatis*; Tyc, tyrocidine peptide synthetase of *Brevibacillus brevis*; GrsA, gramicidin peptide synthetase of *Bacillus brevis*; DhbF, siderophore 2,3-dihydroxybenzoate synthetase of *Bacillus subtilis*; Nos, nostopeptolide peptide synthetase of *Nostoc* sp.; Css, cyclosporine peptide synthetase of *Tolypocladium inflatum*; HPG, 4-hydroxy-phenylglycine; 5hOrn, 5-hydroxyornithine; Pch, pyochelin of *Pseudomonas aeruginosa*.

FIG. 3C shows the similarity between ORF26 (SEQ ID NO:27) and acyl-CoA ligases. Shown is the clustal analysis of ORF 26 versus several acyl-Coenzyme A ligases from diverse species: Mb, *Mycobacterium bovis* (SEQ ID NO:36); Mt, *Mycobacterium tuberculosis* (SEQ ID NO:37); Sv, *Streptomyces verticillus* (SEQ ID NO:38); Mx, *Myxococcus xanthus* (SEQ ID NO:39); Bs, *Bacillus subtilis* (SEQ ID NO:40). Highlighted by boxes are the highly conserved core motifs AL1–AL8 of acyl-CoA ligases.

FIG. 5 illustrates two clustal alignments. FIG. 5A shows the local amino acid sequence homology between ORF 10 (amino acids 263 to 318 of SEQ ID NO: 11) and a key motif found in pfam 00753 (SEQ ID NO:41) involved in coordinating two zinc molecules in the beta-lactamase superfamily. (For information regarding the Pfam Families Datebase, see Bateman et al. Nucleic Acids Research, 2000, Vol. 28, No. 1, 263–266). 1SML (SEQ ID NO:42) represents one member of this superfamily for which a crystal structure showing the intimate interaction between the zinc molecule and the highlighted residues is available (Ullah et al., J. Mol Biol., Nov. 20, 1998; 284(1):125–36). FIG. 5B shows the local amino acid sequence homology between ORF 10 (amino acids 405 to 452 of SEQ ID NO: 11) and a key motif found in pfam 00067 (SEQ ID NO:43) involved in coordinating an iron molecule in cytochrome P450 monooxygenases.

DETAILED DESCRIPTION OF THE INVENTION

Ramoplanins are naturally produced by the microorganism *Actinoplanes* sp. ATCC 33076. The genetic locus encoding the biosynthetic pathway for ramoplanin production was isolated and cloned by the procedure described in U.S. Ser. No. 09/910,813, from genomic DNA isolated from a ramoplanin producing strain of *Actinoplanes* sp. ATCC 33076 (obtained from the American Type Culture Collection, Manassas, Va., USA). This newly discovered locus encodes 33 individual proteins involved in the biosynthesis of ramoplanin by this organism. The 33 proteins are encoded by ORFs contained within the contiguous sequence of 88421 base pairs of DNA (SEQ ID NO: 1).

Three deposits, namely *E. coli* DH10B (008CH) strain, *E. coli* DH10B (008CK) strain and *E. coli* DH10 B (008CO) strain each harbouring a cosmid clone of a partial biosynthetic locus for ramoplanin have been deposited with the International Depositary Authority of Canada, Bureau of Microbiology, Health Canada, 1015 Arlington Street, Winnipeg, Manitoba, Canada, R3E 3R2 on Sep. 19, 2001. Clone 008CH, which spans from base pair 5006 to base pair 42974 of SEQ ID NO: 1, was assigned accession number IDAC 190901-3. Clone 008CK, which spans from base pair 34296 to base pair 70934 of SEQ ID NO: 1, was assigned accession number IDAC 190901-1. Clone 008CO, which spans from base pair 52163 to base pair 88333 of SEQ ID NO: 1, was assigned accession number IDAC 190901-2. The cosmids deposited as *E. coli* strains harbouring them are referred to herein as "the deposited cosmids".

Figure 1:
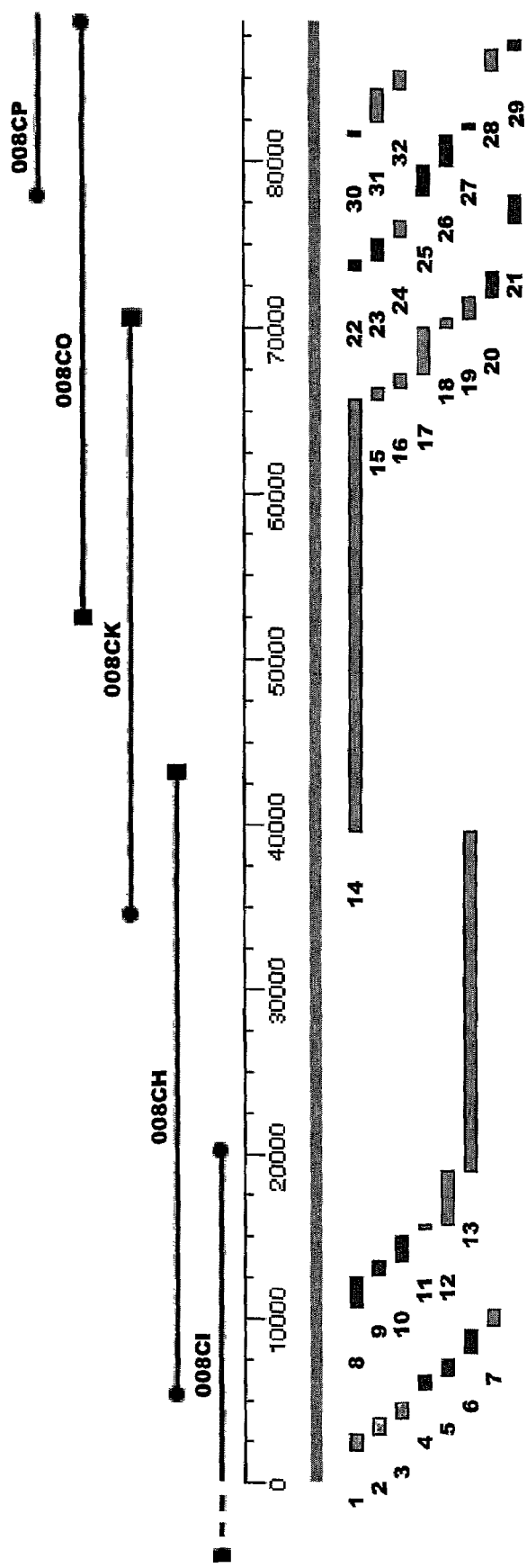
FIG. 1 is a graphical depiction of the ramoplanin biosynthetic locus showing a scale in kb, the relative position and orientation of the 32 ORFs, and the coverage of the deposited cosmids.

As shown in FIG. 1, the deposited cosmids comprise the biosynthetic locus for ramoplanin. The sequence of the polynucleotides comprised in the deposited cosmids, as well as the amino acid sequence of any polypeptide encoded thereby are controlling in the event of any conflict with any description of sequences herein.

The deposit of the cosmids has been made under the terms of the Budapest Treaty on the International Recognition of the Deposit of Micro-organisms for Purposes of Patent Procedure. The deposited cosmids will be irrevocably and without restriction or condition released to the public upon the issuance of a patent. The deposited cosmids are provided merely as convenience to those skilled in the art and are not an admission that a deposit is required for enablement, such as that required under 35 U.S.C. §112. A license may be required to make, use or sell the deposited cosmids, and compounds derived therefrom, and no such license is hereby granted.

Various reagents of the inventions can be isolated from the deposited strains. DNA sequence analysis was performed on various subclones of the inventions and facilitated the identification of the location of various ramoplanin ORFs, including the ORFs encoding the 32 individual proteins of the ramoplanin biosynthetic locus.

The ramoplanin biosynthetic locus spans approximately 88,500 base pairs and contains 32 ORFs. The contiguous nucleotide sequence of SEQ ID NO: 1 (88421 base pairs) contains the 33 deduced proteins listed in SEQ ID NOS: 2 to 34. ORF 1 (SEQ ID NO: 2) represents 333 amino acids deduced from residues 2077 to 3078 (sense strand) of SEQ ID NO: 1. ORF 2 (SEQ ID NO: 3) represents 304 amino acids deduced from residues 3118 to 4032 (sense strand) of SEQ ID NO: 1. ORF 3 (SEQ ID NO: 4) represents 336 amino acids deduced from residues 4038 to 5048 (sense strand) of SEQ ID NO: 1. ORF 4 (SEQ ID NO: 5) represents 283 amino acids deduced from residues 6665 to 5814 (antisense strand) of SEQ ID NO: 1. ORF 5 (SEQ ID NO: 6) represents 336 amino acids deduced from residues 7703 to 6693 (antisense strand) of SEQ ID NO: 1. ORF 6 (SEQ ID NO: 7) represents 444 amino acids deduced from residues 9464 to 8130 (antisense strand) of SEQ ID NO: 1. ORF 7 (SEQ ID NO: 8) represents 356 amino acids deduced from residues 9691 to 10761 (sense strand) of SEQ ID NO: 1. ORF 8 (SEQ ID NO: 9) represents 640 amino acids deduced from residues 12751 to 10829 (antisense strand) of SEQ ID NO: 1. ORF 9 (SEQ ID NO: 10) represents 271 amino acids deduced from residues 13617 to 12802 (antisense strand) of SEQ ID NO: 1. ORF 10 (SEQ ID NO: 11) represents 529 amino acids deduced from residues 15203 to 13614 (antisense strand) of SEQ ID NO: 1. ORF 11 (SEQ ID NO: 12) represents 90 amino acids deduced from residues 15591 to 15863 (sense strand) of SEQ ID NO: 1. ORF 12 (SEQ ID NO: 13) represents 1051 amino acids deduced from residues 15880 to 19035 (sense strand) of SEQ ID NO: 1. ORF 13 (SEQ ID NO: 14) represents 6893 amino acids deduced from residues 19032 to 39713 (sense strand) of SEQ ID NO: 1. ORF 14 (SEQ ID NO: 15) represents 8695 amino acids deduced from residues 39713 to 65800 (sense strand) of SEQ ID NO: 1. ORF 15 (SEQ ID NO: 16) represents 234 amino acids deduced from residues 65826 to 66530 (sense strand) of SEQ ID NO: 1. ORF 16 (SEQ ID NO: 17) represents 274 amino acids deduced from residues 66546 and 67370 (sense strand) of SEQ ID NO: 1. ORF 17 (SEQ ID NO: 18) represents 891 amino acids deduced from residues 67384 to 70059 (sense strand) of SEQ ID NO: 1. ORF 18 (SEQ ID NO: 19) represents 187 amino acids deduced from residues 70099 to 70662 (sense strand) of SEQ ID NO: 1. ORF 19 (SEQ ID NO: 20) represents 415 amino acids deduced from residues 70659 to 71906 (sense strand) of SEQ ID NO: 1. ORF 20 (SEQ ID NO: 21) represents 491 amino acids deduced from residues 73439 to 71964 (antisense strand) of SEQ ID NO: 1. ORF 21 (SEQ ID NO: 22) represents 217 amino acids deduced from residues 74216 to 73563 (antisense strand) of SEQ ID NO: 1. ORF 22 (SEQ ID NO: 23) represents 403 amino acids deduced from residues 75424 to 74213 (antisense strand) of SEQ ID NO: 1. ORF 23 (SEQ ID NO: 24) represents 309 amino acids deduced from residues 75535 to 76464 (sense strand) of SEQ ID NO: 1. ORF 24 (SEQ ID NO: 25) represents 553 amino acids deduced from residues 78110 to 76449 (antisense strand) of SEQ ID NO: 1. ORF 25 (SEQ ID NO: 26) represents 585 amino acids deduced from residues 79864 to 78107 (antisense strand) of SEQ ID NO: 1. ORF 26 (SEQ ID NO: 27) represents 587 amino acids deduced from residues 81624 to 79861 (antisense strand) of SEQ ID NO: 1. ORF 27 (SEQ ID NO: 28) represents 75 amino acids deduced from residues 81909 to 81682 (antisense strand) of SEQ ID NO: 1. ORF 28 (SEQ ID NO: 29) represents 94 amino acids deduced from residues 82346 to 82062 (antisense strand) of SEQ ID NO: 1. ORF 29 (SEQ ID NO: 30) represents 619 amino acids deduced from residues 82587 to 84446 (sense strand) of SEQ ID NO: 1. ORF 30 (SEQ ID NO: 31) represents 355 amino acids deduced from residues 84481 to 85548 (sense strand) of SEQ ID NO: 1. ORF 31 (SEQ ID NO: 32) represents 429 amino acids deduced from residues 85556 to 86845 (sense strand) of SEQ ID NO: 1. ORF 32 (SEQ ID NO: 33) represents 189 amino acids deduced from residues 87372 to 86803 (antisense strand) of SEQ ID NO: 1. ORF 33 (SEQ ID NO: 34) is incomplete and represents 309 amino acids (N-terminus only) deduced from residues 87494 to 88420 (sense strand) of SEQ ID NO:1.

Some ORFs, namely ORFs 4, 7, 8, 9, 12, 16, 17, 19, 20, 27, 28, 29, 30, 32, and 33 (SEQ ID NOS: 5, 8, 9, 10, 13, 17, 18, 20, 21, 25, 28, 29, 30, 31, 33 and 34) are initiated with the non-standard initiation codon GTG (Valine) rather than the standard initiation codon ATG (Methionine). All ORFs are listed with Methionine or Valine amino acids at the amino-terminal position to indicate the specificity of the first codon in the ORF. It is expected, however, that in all cases the biosynthesized protein will contain a methionine residue, and more specifically a formylmethionine residue, at the amino terminal position in keeping with widely accepted principle that protein synthesis in bacteria initiates with methionine (formylmethionine) even when the encoding gene specifies a non-standard initiation codon (see e.g. Stryer, Biochemistry $3^{rd}$ edition, 1998, W. H. Freeman and Co., New York, pp. 752–754).

Section 1: Definitions

The term domain refers to a portion of a molecule, e.g. proteins or nucleic acids, that is structurally and/or functionally distinct from another portion of the molecule.

The term derivative or analog of a molecule refers to a portion derived from or a modified version of the molecule.

The term isolated nucleic acid molecule referred to in the present invention can be a deoxyribonucleic acid molecule (DNA), such as genomic DNA and complementary DNA (cDNA), which can be single (coding or noncoding strand) or double stranded, as well as synthetic DNA, such as synthesized, single stranded polynucleotide. The isolated nucleic acid molecule of the present invention can also be a ribonucleic acid molecule (RNA). In particular embodiments, the nucleic acid can include entire sequence of the gene cluster, the sequence of any one of the ORFs, a sequence encoding an ORF and an associated promoter, or smaller sequences useful for expressing peptides, polypeptides or full length proteins encoded in the fragment of the *Actinoplanes* sp. genome disclosed herein. In particular embodiments the nucleic acid can have natural, non-natural or modified nucleotides or internucleotide linkages or mixtures of these.

The term polynucleotide refers to full length or partial length sequences of ORFs disclosed herein. Polynucelotides of this invention can be either RNA or DNA (cDNA, genomic DNA or synthetic DNA), or modifications, variants, homologs or fragments thereof. If single stranded, the polynucleotides can be a coding or "sense" or positive strand or a complementary or "antisense" or negative strand. Antisense strands can be useful as modulators of the protein or proteins by interacting with RNA encoding the protein(s). Antisense strands are preferably less than full length strands having sequences unique or highly specific for RNA encoding the protein(s). Any one of the polynucleotide sequences of the invention as shown in the sequence listing is (a) a coding sequence, (b) a ribonucleotide sequence derived from transcription of (a), (c) a coding sequence which uses the redundancy or degeneracy of the genetic code to encode the same polypeptides, or (d) a regulatory sequence.

The term polypeptide or protein refers to any chain of amino acids, regardless of length or post-translational modification (e.g. proteolytic processing or phosphorylation). Both terms are used interchangeably in the present application. Those skilled in the art would readily understand that the polypeptides of the invention may be purified from a natural source, i.e., an *Actinoplanes* sp., or produced by recombinant means.

The terms ORF, ramoplanin open reading frame, and ramoplanin ORF refer to an open reading frame in the ramoplanin biosynthetic gene cluster as isolated from *Actinoplanes* sp. The term also embraces the same ORFs as present in other ramoplanin-synthesizing organisms (e.g. other strains and/or species of *Actinoplanes, Streptomyces, Actinomycetes*, and the like). The term encompasses allelic variants and single nucleotide polymorphisms (SNPs). In certain instances the term ramoplanin ORF is used synonymously with the polypeptide encoded by the ramoplanin ORF and may include conservative substitutions in that polypeptide. The particular usage will be clear from context.

The term "homologous amino acid sequence" is any polypeptide which is encoded, in whole or in part, by a nucleic acid sequence which hybridizes at 25–35° C. below critical melting temperature (Tm), to any portion of the coding region nucleic acid sequences of the sequence listing. A homologous amino acid sequence is one that differs from an amino acid sequence shown in the sequence listing by one or more conservative amino acid substitutions. Such a sequence also encompasses allelic variants (defined below) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any amino acid sequence shown in the sequence listing.

Homologous amino acid sequences include sequences that are identical or substantially identical to the amino acid sequences of the sequence listing. By "amino acid sequence substantially identical" it is meant a sequence that is at least 90%, preferably 95%, more preferably 97%, and most preferably 99% identical to an amino acid sequence of reference and that preferably differs from the sequence of reference by a majority of conservative amino acid substitutions. Consistent with this aspect of the invention, polypeptides having a sequence homologous to any one of the amino acid sequences of the sequence listing include naturally-occurring allelic variants, as well as mutants or any other non-naturally occurring variants that retain the inherent characteristics of any polypeptide of the sequence listing.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain optimal alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, more preferably 75% and most preferably 85% identical to any one of the coding sequences of the sequence listing.

The term "conservative substitution" is used in reference to proteins or peptides to reflect amino acid substitutions that do not substantially alter the activity (specificity or binding affinity) of the molecule. Typically conservative amino acid substitutions involve substitutions of one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic Acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "isolated", "purified", or "biologically pure" refer to material which is substantially or essentially free from components which normally accompany it as found in its native state. With respect to nucleic acids and/or polypeptides, the term can refer to nucleic acids or polypeptides that are no longer flanked by the sequences typically flanking them in nature. Such isolated nucleic acids and/or polynucelotides may be part of a vector or composition and still be defined as isolated in that such a vector or composition is not part of the natural environment of such polynucleotide.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g. synthetic sequences having codons different than the native gene). Similarly, a host cell transformed with a construct which is not normally present in the host cell would be considered heterologous for purposes of this invention.

The term allelic variant refers to an alternate form of a polypeptide that is characterized as having a substitution, deletion, or addition of one or more amino acids that does not alter the biological function of the polypeptide.

The term "biological function" refers to the function of the polypeptide in the cells in which it naturally occurs. A polypeptide can have more than one biological function.

Section 2: Isolation, Preparation and Expression of Ramoplanin Nucleic Acids

Nucleic acids derived from the ramoplanin gene cluster can be isolated, optionally modified and inserted into a host cell to create and/or modify a metabolic (biosynthetic) pathway and thereby enable that host cell to synthesize and/or modify various metabolites. Alternatively, the ramoplanin gene cluster nucleic acids can be expressed in the host cell and the encoded ramoplanin polypeptide(s) recovered for use as chemical reagents, e.g. in the ex vivo synthesis and/or chemical modification of various metabolites. Either application typically entails insertion of one or more nucleic acids encoding one or more isolated and/or modified ramoplanin ORFs in a suitable host cell. The nucleic acid(s) are typically in an expression vector, a construct containing control elements suitable to direct expression of the ramoplanin polypeptides. The expressed ramoplanin polypeptides in the host cell then act as components of a metabolic/biosynthetic pathway (in which case the synthetic product of the pathway is typically recovered) or the ramoplanin polypeptides themselves are recovered. Using the sequence information provided herein, cloning and expression of ramoplanin nucleic acids can be accomplished using routine and well known methods.

A. Ramoplanin Nucleic Acids

The nucleic acids comprising the ramoplanin gene cluster are identified in Table 2 and are listed in the sequence listing provided herein. In particular, Table 2 identifies genes and functions of ORFs in the ramoplanin biosynthetic gene cluster. Using the sequence information provided therein, primers suitable for amplification/isolation of one or more ORFs can be determined according to standard methods well known to those of skill in the art (e.g. using methods described in Innis (1990) *PCR Protocols: A Guide to Methods and Applications* Academic Press Inc. San Diego, Calif., etc; using computer applications such as Vector NTI Suite™, InforMax, Gaithersberg, Md., USA).

Primers suitable for amplification/isolation of any one or more of the ORFs are designed according to the nucleotide sequence information provided in the sequence listing. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. Typically such amplifications will utilize the DNA or RNA of an organism containing the requisite genes (e.g. *Actinoplanes* sp.) as a template. A standard PCR reaction contains typically 0.5 to 5 Units of Taq DNA polymerase per 100 µL, 20 to 200 µM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for denaturation of G+C-rich targets. Adding DMSO to a final concentration of 5–10% is beneficial for PCR amplification of high G+C templates such as those from Actinoplanes sp. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: Tm=81.5+0.5×(% G+C)+1.6 log (positive ion concentration)−0.6×(% formamide). Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4–16 hours at 42° C., in 6×SSC containing 50% formamide, or (ii) within 4–16 hours at 65° C. in an aqueous 6×SSC solution (1 M NaCl, 0.1 M sodium citrate (pH 7.0)).

In one embodiment, this invention provides nucleic acids for the recombinant expression of a ramoplanin (e.g. a ramoplanin or an analogue thereof). Such nucleic acids include isolated gene cluster(s) comprising ORFs encoding polypeptides sufficient to direct the synthesis of the ramoplanin. In other embodiments of this invention, the ORFs may be unchanged, but the control elements (e.g. promoters, ribosome binding sites, terminators, enhancers etc) may be modified. In still other embodiments, the nucleic acids may encode selected components (e.g. one or more ORFs or modified ORFs) and/or may optionally contain other heterologous biosynthetic elements including, but not limited to non-ribosomal polypeptide synthetases (NRPS) modules or enzymatic domains.

Such variations may be introduced by design, for example to modify a known molecule in a specific way, e.g. by replacing a single substitutent of the ramoplanin with another, thereby creating a derivative ramoplanin molecule of predicted structure. Alternatively, variations can be made randomly, for example by making a library of molecular variants of a known ramoplanin by systematically or haphazardly replacing one or more ORFs in the biosynthetic pathway.

Useful homologs and fragments thereof that do not occur naturally are designed using known methods for identifying regions of a polypeptide that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using the BLAST homology searching algorithm of Altschul et al., Nucleic Acids Res. 25:3389–3402 (1997).

Alternatively, identification of homologous polypeptides or polypeptide derivatives encoded by polynucleotides of the invention which have activity in the ramoplanin biosynthetic pathway may be achieved by screening for cross-reactivity with an antibody raised against the polypeptide of reference having an amino acid sequence of SEQ ID NOS 2 to 34. The procedure is as follows: an antibody is raised against a purified reference polypeptide, a fusion polypeptide (for example, an expression product of MBP, GST, or His-tag systems), or a synthetic peptide derived from the reference polypeptide. Where an antibody is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the antibody diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After 1 hour incubation at 37° C., the plate is washed with PBS/Tween buffer. The antibody is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antibody dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Using the information provided herein other approaches to cloning the desired sequences will be apparent to those of skill in the art, for example, the ramoplanin genes and/or optionally NRPS modules or enzymatic domains of interest can be obtained from an organism that expresses such, using recombinant methods, such as by screening cDNA or genomic libraries, derived from cells expressing the gene, or by deriving the gene from a vector known to include the same. The gene can then be isolated and combined with other desired biosynthetic elements using standard techniques. If the gene in question is already present in a suitable expression vector, it can be combined in situ with, e.g. other domains or subunits, as desired. The gene of interest can be produced synthetically, rather than cloned. The nucleotide sequence can be designed with the appropriate codons for the particular amino acid sequence desired. In general, one will select preferred codons for the intended host in which the sequence will be expressed. The complete sequence can be assembled from overlapping oligonucleotides prepared by standard methods and assembled into a complete coding sequence (see e.g., Edge (1981) *Nature* 292:756; Nambair et al. (1984) *Science* 233:1299; Jay et al. (1984) *J. Biol. Chem.* 259:6311). In addition, it is noted that custom gene synthesis is commercially available (see e.g. Operon Technologies, Alameda, Calif.).

Examples of such techniques and instructions sufficient to direct persons of skill through many cloning exercises are found in Berger and Kimmel (1989) *Guide to Molecular Cloning Technique, Methods in Enzymology* 152 Academic Press, Inc., San Diego, Calif. (Berger); Sambrook et al. (1989) *Molecular Cloning—A Laboratory Manual* ($2^{nd}$ ed.) Vol. 1–3, Cold Spring Harbor Laboratory, Cold Spring Harbor Press, N.Y.; Ausubel (1994) *Current Protocols in Molecular Biology,* Current Protocols, a joint venture between Greene Publishing Associates, Inc. and John Wiley & Sons, Inc. U.S. Pat. No. 5,017,478; and European Patent No 0 246 864.

B. Expression of Ramoplanin ORFs

Preferably, a recombinant expression system is selected from prokaryotic hosts. Bacterial cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form. Any transducible cloning vector can be used as a cloning vector for the nucleic acid constructs of this invention. However, where large clusters are to be expressed, it is preferable that phagemids, cosmids, P1s, YACs, BACs, PACs, HACc or similar cloning vectors be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

In preferred embodiments of this invention, vectors are used to introduce ramoplanin biosynthesis genes or gene clusters into host (e.g. *Streptomyces*) cells. With the guidelines described below, however, a selection of vectors, expression control sequences and hosts may be made without undue experimentation and without departing from the scope of this invention. Numerous vectors for use in particular host cells are well known to those of skill in the art. For example Malpartida and Hopwood, (1984) *Nature*, 309:462–464; Kao et al., (1994), *Science*, 265: 509–512; and Hopwood et al., (1987) *Methods Enzymol.*, 153:116–166 all describe vectors for use in various *Streptomyces* hosts. In selecting a vector, the appropriate host must be chosen such that it is compatible with the vector which is to exist and possibly replicate in it. Considerations are made with respect to the vector copy number, the ability to control the copy number and expression of other proteins such as antibiotic resistance. In one preferred embodiment, Streptomyces vectors are used that include sequences that allow their introduction and maintenance in *E. coli*. Such *Streptomyces/E. coli* shuttle vectors have been described (see, for example, Vara et al., (1989) *J. Bacteriol*, 171:5872–5881; Guilfoile & Hutchinson (1991) *Proc. Natl. Acad. Sci. USA*, 88; 8553–8557.)

The wildtype and/or modified ORFs of this invention can be inserted into one or more expression vectors, using methods known to those of skill in the art. Expression vectors (e.g., plasmids) are widely known and are readily available to those skilled in the art. For bacterial vectors, the polynucleotide of the invention is inserted into the bacterial genome or remains in a free state as part of a plasmid. Methods for transforming host cells with expression vectors are well-known in the art. Expression vectors will include control sequences operably linked to the desired ORF. In selecting an expression control sequence, a number of variables are considered. Among the important variables are the relative strength of the sequence (e.g. the ability to drive expression under various conditions), the ability to control the sequence's function and compatibility between the polynucleotide to be expressed and the control sequence (e.g. secondary structures are considered in order to avoid hairpin structures which may prevent efficient transcription).

Suitable expression systems for use with the present invention include systems that function in eucaryotic and/or prokaryotic host cells. However, as explained above, prokaryotic systems are preferred, and in particular, systems compatible with *Streptomyces* sp. are of particular interest.

The choice of the expression cassette depends on the host system selected as well as the features desired for the expressed polypeptide or natural product. Typically, an expression cassette includes a promoter that is functional in the selected host system and can be constitutive or inducible; a ribosome binding site; a start codon (ATG) if necessary; optionally a region encoding a leader peptide; a DNA molecule of the invention; a stop codon; and optionally a 3' terminal region (translation and/or transcription terminator). Where applicable, i.e. secreted or membrane proteins, the leader peptide encoding region is adjacent to the polynucleotide of the invention and placed in proper reading frame.

The leader peptide-encoding region, if present, is homologous or heterologous to the DNA molecule encoding the mature polypeptide and is compatible with the secretion apparatus of the host used for expression. The ORF constituted by the DNA molecule of the invention, solely or together with the leader peptide, is placed under the control of the promoter so that transcription and translation occur in the host system. Promoters and leader peptide encoding regions are widely known and available to those skilled in the art. Particularly useful promoters include control sequences derived from ramoplanin and/or NRPS gene clusters. Other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the beta-lactamase (bla) promoter system, bacteriophase lambda PL, and T5. In addition, synthetic promoters (U.S. Pat. No. 4,551,433), which do not occur in nature also function in bacterial host cells. In *Streptomyces*, numerous promoters have been described including constitutive promoters, such as ErmE and TcmG (Shen and Hutchinson, (1994) *J. Biol. Chem.* 269: 30726–30733), as well as controllable promoters such as actI and actIII (Pleper et al., (1995) *Nature*, vol. 378: 263–266; Pieper et al., (1995) *J. Am. Chem. Soc.*, 117: 11373–11374; and Wiesmann et al., (1995) *Chem. & Biol.* 2: 583–589).

Other regulatory sequences may also be desirable which allow for regulation of expression of the ORFs relative to the growth of the host cell. Regulatory sequences are known to those skill in the art, and examples include those which cause the expression of a gene to be turned on or off in response to a chemical or physical stimulus, including the presence of a regulatory compound. Other type of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

Various ramoplanin ORFs, and/or NRPS clusters or subunits of interest can be cloned into one or more recombinant vectors as individual cassettes, with separate control elements, or under the control of, e.g., a single promoter. The ORFs can include flanking restriction sites to allow for the easy deletion and insertion of other open reading frames so that hybrid synthetic pathways can be generated. The design of such unique restriction sites is known to those of skill in the art and can be accomplished using the techniques described above, such a site-directed mutagenesis and PCR.

Methods of cloning and expressing large nucleic acids such as gene clusters, including NRPS-encoding gene clusters, in cells including *Streptomyces* are well known to those skilled in the art (see, e.g., Stutzman-Engwall and Hutchinson (1989) *Proc. Ntl. Acad. Sci. USA*, 86: 3135–3139: Motamedi and Hutchinson (1987) *Proc. Natl. Acad. Sci. USA*, 84: 4445–4449; Grimm et al. (1994) *Gene*, 151: 1–10; Kao et al. (1994) *Science*, 265: 509–512; and Hopwood et al. (1987) *Meth. Enzymol.*, 153: 116–166). In some examples, nucleic acid sequences of well over 100 kb have been introduced into cells, including prokaryotic cells, using vector-based methods (see for example, Osoegawa et al., (1998) *Genomics,* 52: 1–8; Huang et al., (1996) *Nucl. Acids, Res.,* 24: 4202–4209).

C. Host Cells

The vectors described above can be used to express various protein components of the ramoplanin and/or ramoplanin shunt metabolites, and/or other modified metabolites for subsequent isolation and/or to provide a biological synthesis of one or more desired biomolecules (e.g. ramoplanin and/or a ramoplanin analogue, etc). Where one or more proteins of the ramoplanin biosynthetic gene cluster are expressed (e.g. overexpressed) for subsequent isolation and/or characterization, the proteins are expressed in any prokaryotic or eukaryotic cell suitable for protein expression. In selecting the host, unicellular hosts are selected which are compatible with the selected vector, tolerant of any possible toxic effects of the expressed product, able to secrete the expressed product efficiently if such is desired, able to express the product in the desired conformation, easily scaled up, and having regard to ease of purification of the final product, which may be the expressed polypeptide or the natural product, e.g. an antibiotic, which is a product of the biosynthetic pathway of which the expressed polypeptide is a part. In one preferred embodiment, the proteins are expressed in *E. coli.*

Host cells for the recombinant production of the ramoplanin, ramoplanin metabolites, shunt metabolites, etc. can be derived from any organism with the capability of harboring a recombinant ramoplanin gene cluster and/or subset thereof. Thus, the host cells of the present invention can be derived from either prokaryotic or eucaryotic organisms. Preferred host cells are those of species or strains (e.g. bacterial strains) that naturally express ramoplanin. Suitable host cells include, but are not limited to *Actinomycetes, Actinoplanetes,* and *Streptomycetes, Actinomadura, Micromonospra,* and the like. Particularly preferred host cells include, but are not limited to *Streptomyces globisporus, Streptomyces lividans, Streptomyces coelicolor, Microsmonospora echinospora* spp. *calichenisis, Actionamadura verrucosopora, Micromonospora chersina,* and *Streptomyces carzinostaticus.*

D. Recovery of the Expression Product

Recovery of the expression product (e.g., ramoplanin, ramoplanin analog, ramoplanin biosynthetic pathway polypeptide, etc.) is accomplished according to standard methods well known to those skilled in the art. Thus for example where ramoplanin biosynthetic gene cluster proteins are to be expressed and isolated, the proteins can be expressed with a convenient tag to facilitate isolation (e.g. a $His_6$) tag. Other standard protein purification techniques are suitable and well known to those of skill in the art (see, e.g. (Quadri et al. 1998) *Biochemistry* 37: 1585–1595; Nakano et al. (1992) *Mol. Gen. Genet.* 232: 313–321, etc).

A polypeptide or polypeptide derivative of the invention may be purified by affinity chromatography using as a ligand either an antibody or a compound related to ramoplanin or other lipodepsipeptide which binds to the polypeptide. The antibody is either polyclonal or monoclonal. Purified IgGs are prepared from an antiserum using standard methods (see, e.g., Coligan et al., Current Protocols in Immunology (1994) John Wiley & Sons, Inc., New York, N.Y.). Conventional chromatography supports are described in, e.g., Antibodies: A Laboratory Manual, D. Lane, E. Harlow, Eds. (1988).

Consistent with this aspect of the invention, polypeptide derivatives are provided that are partial sequences of the amino acid sequences of SEQ ID NOS: 2 to 34, partial sequences of polypeptide sequences homologous to the amino acid sequences of SEQ ID NOS: 2 to 34, polypeptides derived from full-length polypeptides by internal deletion, and fusion proteins.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to improve production of ramoplanin or generate novel analogues of the antibiotic or natural products of the lipodepsipeptide class as described herein.

A fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

Polynucleotides of 30 to 600 nucleotides encoding partial sequences of sequences homologous to nucleotide sequences of SEQ ID NOS: 2 to 34 are retrieved by PCR amplification using the parameters outlined above and using primers matching the sequences upstream and downstream of the 5' and 3' ends of the fragment to be amplified. The template polynucleotide for such amplification is either the full length polynucleotide homologous to a polynucleotide sequence of SEQ ID NOS: 2 to 34, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20–30 bases are to be obtained, the formula for calculating the Tm is as follows: $Tm=4\times(G+C)+2\times(A+T)$. For example, an 18 nucleotide fragment of 50% G+C would have an approximate Tm of 54° C. Short peptides that are fragments of the polypeptide sequences of SEQ IS NOS: 2 to 34 or their homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Where components (e.g. ramoplanin ORFs) are used to synthesize and/or modify various biomolecules (e.g.

ramoplanins, ramoplanin analogues, shunt metabolites, or even compounds unrelated to ramoplanin, i.e. biocatalysts) the desired product and/or shunt metabolites(s) are isolated according to standard methods well known to those of skill in the art (see,. e.g., Carreras and Khosla (1998) *Biochemistry* 37: 2084–2088, Deutscher (1990) *Methods in Ensymology* Volume 182: *Guide to Protein Purification*, M. Deutscher, ed.

E. Probes

The sequence information provided in the present application enables the design of specific nucleotide probes and primers that are used for identifying and isolating putative lipdepsipeptide-producing microorganisms. Accordingly, an aspect of the invention provides a nucleotide probe or primer having a sequence found in or derived by degeneracy of the genetic code from a sequence shown in the sequence listing.

The term "probe" as used in the present application refers to DNA (preferably single stranded) or RNA molecules (or modifications or combinations thereof) that hybridize under the stringent conditions, as defined above, to nucleic acid molecules of SEQ ID NOS: 1 to 34, or to sequences homologous to those of SEQ ID NOS: 1 to 34, or to their complementary or anti-sense sequences. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of a sequence disclosed in SEQ ID NOS: 1 to 34 or that are complementary to such sequences. Probes may contain modified bases such as inosine, methyl-5-deoxycytidine, deoxyuridine, dimethylamino-5-deoxyuridine, or diamino-2, 6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used for identifying and isolating putative lipdepsipeptide-producing microorganisms, as capture or detection probes. Such capture probes are conventionally immobilized on a solid support, directly or indirectly, by covalent means or by passive adsorption. A detection probe is labeled by a detection marker selected from: radioactive isotopes, enzymes such as peroxidase, alkaline phosphatase, enzymes able to hydrolyze a chromogenic or fluorogenic or luminescent substrate, compounds that are chromogenic or fluorogenic or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art. Primers can also be used as probes.

As described herein, the invention also encompasses (i) a reagent comprising a probe of the invention for detecting and/or isolating putative lipdepsipeptide-producing microorganisms; (ii) a method for detecting and/or isolating putative lipdepsipeptide-producing microorganisms, in which DNA or RNA is extracted from the microorganism and denatured, and exposed to a probe of the invention, for example, a capture probe or detection probe or both, under stringent hybridization conditions, such that hybridization is detected; and (iii) a method for detecting and/or isolating putative lipdepsipeptide-producing microorganisms, in which (a) a sample is recovered or derived from the microorganism, (b) DNA is extracted therefrom, (c) the extracted DNA is primed with at least one, and preferably two, primers of the invention and amplified by polymerase chain reaction, and (d) the amplified DNA fragment is produced.

EXAMPLES

The following examples are offered to illustrate, but not to limit the claimed invention.

Example 1

Identification of the Ramoplanin Biosynthetic Locus in *Actinoplanes* sp. ATCC 33076.

*Actinoplanes* sp. ATCC 33076 was previously shown to naturally produce ramoplanins, a group of biologically active lipodepsipeptides (U.S. Pat. No. 4,303,646). The genetic locus involved in the production of this compound was not previously identified. *Actinoplanes* sp. ATCC 33076 was obtained from the American Tissue Culture Collection (ATCC) Manassas, Va., and cultured according to standard microbiological techniques (Kieser et al. *Practical Streptomyces Genetics*, John Innes Centre, Norwich Research Part, Colney, Norwich NR4 7UH, England, 2000). Confluent mycelia from oatmeal agar plates were used for the extraction of genomic DNA as previously described (Kieser et al., supra) and the size range of the DNA obtained was assessed on agarose gels by electrical field inversion techniques as described by the manufacturer (FIGE, BioRad). The DNA serves for the preparation of a small size fragment genomic sampling library, i.e. the small-insert library, as well as a large size fragment cluster identification library, i.e. the large-insert library. Both libraries contained DNA fragments generated randomly from genomic DNA and, therefore, they represent the entire genome of *Actinoplanes* sp.

For the generation of the small-insert library, genomic DNA was randomly sheared by sonication. DNA fragments having a size range between 1.5 and 3 kb were fractionated on a agarose gel and isolated using standard molecular biology techniques (Sambrook et al., Molecular Cloning, $2^{nd}$ Ed. Cold Spring Harbor Laboratory Press, 1989). The ends of the obtained DNA fragments were repaired using T4 DNA polymerase (Roche) as described by the supplier. This enzyme creates DNA fragments with blunt ends that can be subsequently cloned into an appropriate vector. The repaired DNA fragments were subcloned into a derivative of pBluescript SK+ vector (Stratagene) which does not allow transcription of cloned DNA fragments. This vector was selected as it contains a convenient polylinker region surrounded by sequences corresponding to universal sequencing primers such as T3, T7, SK, and KS (Stratagene). The unique EcoRV restriction site found in the polylinker region was used as it allows insertion of blunt-end DNA fragments. Ligation of the inserts, use of the ligation products to transform *E. coli*

DH10 B host, selection for recombinant clones, and isolation of plasmids carrying the *Actinoplanes* sp. genomic DNA fragments were performed using well-known methods (Sambrook et al., supra). The insert size of 1.5 to 3 kb was confirmed by electrophoresis on agarose gels. Using this procedure a library of small size random genomic DNA fragments is generated that is representative of the entire genome of the studied microorganism. The number of individual clones that can be generated is infinite but only a small number is further analyzed to sample the microorganism's genome.

To generate the large-insert library, high molecular weight genomic DNA was partially digested with a frequent cutting restriction enzyme, Sau3A (G|ATC). This enzyme generates random fragments of DNA ranging from the initial undigested size of the DNA to short fragments of which the length is dependent upon the frequency of the enzyme DNA recognition site in the genome and the extent of the DNA digestion. Conditions generating DNA fragments having an average length of ~40 kb were chosen (Sambrook et al., supra). The Sau3A restricted DNA was ligated into the BamHI site of the SuperCos-1 cosmid cloning vector (Stratagene) and packaged into phage particles (Gigapack III XL, Stratagene) as specified by the supplier. *E. coli* strain DH10 B was used as host and 864 recombinant clones carrying cosmids were selected and propagated to generate the large-insert library. Considering an average size of 8 Mb for an actinomycetes genome and an average size of 35 kb of genomic insert per cosmid in the large insert library, a library of 864 clones represents a 3.78-fold coverage of the microorganism's entire genome. Subsequently, the *Actinoplanes* sp. large-insert library was transferred onto membrane filters (Schleicher & Schnell) as specified by the manufacturer.

The small insert library was analyzed by sequence determination of the cloned genomic DNA inserts. The universal primers KS or T7, referred to as forward (F) primer, were used to initiate polymerization of labeled DNA. Extension of at least 700 bp from the priming site can be routinely achieved using the TF, BDT v2.0 sequencing kit as specified by the supplier (Applied Biosystems). Sequence analysis of the generated fragments (Genomic Sequence Tags, GSTS) was performed using a 3700 ABI capillary electrophoresis DNA sequencer (Applied Biosystems). The average length of the DNA sequence reads was ~700 bp. Further analysis of the obtained GSTs was performed by sequence homology comparison to various protein sequence databases. The DNA sequences of the obtained GSTs were translated into amino acid sequences and compared to the National Center for Biotechnology Information (NCBI) nonredundant protein database and the proprietary Ecopia natural product biosynthetic gene Decipher™ database using previously described algorithms (Altschul et al., supra). Sequence similarity with known proteins of defined function in the database enables one to make predictions on the function of the partial protein that is encoded by the translated GST.

A total of 882 *Actinoplanes* sp. GSTs were analyzed by sequence comparison. Sequence alignments displaying an E value of at least e-5 were considered as significantly homologous and retained for further evaluation. The E value relates the expected number of chance alignments with an alignment score at least equal to the observed alignment score. An E value of 0.00 indicates a perfect homolog. The E values are calculated as described in Altschul et al. J. Mol. Biol., October 5; 215(3) 403–10. The E value assists in the determination of whether two sequences display sufficient similarity to justify an inference of homology.

GSTs showing similarity to a gene of interest can be at this point selected and used to identify larger segments of genomic DNA including the gene of interest. Ramoplanins produced by *Actinoplanes* sp. belong to the family of nonribosomal polypeptide antibiotics. Nonribosomal polypeptides are synthesized by nonribosomal peptide synthetase (NRPS) enzymes that perform a series of condensations and modifications of amino acids. Many members of this enzymatic class are found in protein databases rendering possible the identification of an unknown NRPS by sequence similarity. Analysis of the *Actinoplanes* sp. GSTs revealed the presence of three GSTs having similarity to known NRPS proteins in the NCBI nonredundant protein database (Table 1). The obtained E values confirm that these GSTs encode partial NRPS sequences. The three NRPS GSTs were selected for the generation of oligonucleotide probes which were then used to identify gene clusters harboring the specific NRPS genes in the large insert library.

TABLE 1

| | Length (bp) | Proposed function | Homology | Probability | Proposed function of protein match |
|---|---|---|---|---|---|
| GST1 | 632 | NRPS | PIR T36248 | $3.00^{E}\text{-}20$ | CDA peptide synthetase I in *Streptomyces coelicolor* |
| GST2 | 592 | NRPS | PIR T36248 | $5.00^{E}\text{-}28$ | CDA peptide synthetase I in *Streptomyces coelicolor* |
| GST3 | 502 | NRPS | PIR T36180 | $7.00^{E}\text{-}31$ | CDA peptide synthetase I in *Streptomyces coelicolor* |

Oligonucleotide probes were designed from the nucleotide sequence of the selected GSTs, radioactively labeled, and hybridized to the large-insert library using standard molecular biology techniques (Sambrook et al., supra, Schleicher & Schnell). Positive clones were identified, cosmid DNA was extracted (Sambrook et al., supra) and entirely sequenced using a shotgun sequencing approach (Fleischmann et al., *Science*, 269:496–512). Identification of the original GSTs, used to generate the oligonucleotide probes, within the DNA sequence of the obtained cosmids confirmed that these cosmids indeed carried the gene cluster of interest.

Generated sequences were assembled using the Phred-Phrap algorithm (University of Washington, Seattle, USA) recreating the entire DNA sequence of the cosmid insert. Reiterations of hybridizations of the large-insert library with probes derived from the ends of the original cosmid allow indefinite extension of sequence information on both sides of the original cosmid sequence until the complete sought-after gene cluster is obtained. Application of this method on *Actinoplanes* sp. and use of the above-described NRPS GST probes yielded 6 cosmids. Complete sequence of these cosmids and analysis of the proteins encoded by them undoubtedly demonstrated that the gene cluster obtained was indeed responsible for the production of ramoplanin. Subsequent inspection of the ramoplanin biosynthetic cluster sequence, approximately 88.5 kilo base pairs, revealed the presence of three additional GSTs from the small-insert library, bringing the total number of ramoplanin locus GSTs to six.

Example 2

Genes and Proteins Involved in the Biosynthesis of Ramoplanin:

The biological function of the 32 ramoplanin biosynthetic proteins was assessed by computer comparison of each protein with proteins found in the GenBank database of protein sequences (National Center for Biotechnology Information, National Library of Medicine, Bethesda, Md. USA) using the BLASTP algorithm (Altschul et al., 1997, Nucleic Acids Res. Vol. 25, pp. 3389–3402). Significant amino acid sequence homologies found for each protein in the ramoplanin locus are shown in Table 2.

TABLE 2

Proposed functions of the proteins of the ramoplanin biosynthetic pathway based on sequence comparison

| ORF | SEQ ID NO | #aa | proposed function | GenBank accession | probability | % identity | % similarity | proposed function of GenBank match |
|---|---|---|---|---|---|---|---|---|
| 1 | 2 | 333 | unknown; membrane protein | CAB48902 | 5.00E-22 | 27 | 41 | possible membrane protein, unknown function, in *Streptomyces coelicolor* |
| 2 | 3 | 304 | ABC transporter | CAB48901 | 3.00E-55 | 42 | 59 | probale ABC transporter ATP-binding protein from *Streptomyces coelicolor* |
| | | | | AAF81232 | 7.00E-32 | 31 | 47 | ABC transporter ATP-binding protein found in nonactin biosynthetic locus of *Streptomyces griseus* |
| | | | | AAF12291 | 4.00E-29 | 34 | 51 | ABC transporter, ATP-binding protein from *Deinococcus radiodurans* |
| 3 | 4 | 336 | unknown; membrane protein | CAB48902 | 2.00E-15 | 35 | 50 | possible membrane protein, unknown function, in *Streptomyces coelicolor* |
| 4 | 5 | 283 | oxidoreductase similar to prephenate dehydrogenases | CAA11792 | 2.00E-69 | 53 | 63 | similar to prephenate dehydrogenase; chloroeremomycin biosynthesis in *Amycolatopsis orientalis* |
| | | | | CAB38592 | 2.00E-67 | 50 | 62 | probable oxidoreductase similar to prephenate dehydrogenase; calcium-dependent antibiotic biosynthesis in *Streptomyces coelicolor* |
| | | | | AAF67499 | 3.00E-66 | 47 | 64 | putative oxidoreductase protein similar to prephenate dehydrogenase; novobiocin biosyntehsis in *Streptomyces spheroides* |
| 5 | 6 | 336 | transcriptional regulator similar to StrR | CAA07385 | 1.00E-74 | 46 | 58 | StrR DNA-binding protein/regulator of 5'-hydroxystreptomycin biosynthesis in *Streptomyces glaucescens*; positive transcriptional regulator of strU, strVW genes |
| | | | | CAB45047 | 2.00E-74 | 47 | 62 | probable transcriptional regulator in chloroeremomycin biosyntehetic locus of *Amycolatopsis orientalis*; similar to other regulators of antibiotic biosynthesis |
| | | | | CAA68515 | 4.00E-70 | 47 | 60 | putative regulatory protein StrR in streptomycin biosynthetic locus in *Streptomyces griseus* |
| | | | | AAB66654 | 6.00E-68 | 44 | 59 | SpcR putative transcriptional regulator of spectinomycin biosynthesis in *Streptomyces flavopersicus* |
| | | | | AAF67500 | 9.00E-58 | 42 | 61 | NovG putative regulatory protein in novobiocin biosynthetic locus of *Streptomyces spheroides* |
| 6 | 7 | 444 | Amino-transferase | CAB38598 | 1.00E-123 | 56 | 67 | possible aminotransferase found in the calcium-dependent antibiotic biosynthetic locus of *Streptomyces coelicolor* |
| | | | | CAA11790 | 1.00E-101 | 47 | 62 | protein similar to aminotransferase found in the chloroeremomycin biosynthetic locus of *Amycolatopsis orientalis* |
| 7 | 8 | 356 | oxidoreductase similar to glycolate oxidases | CAB38520 | 1.00E-115 | 60 | 70 | putative glycolate oxidase found in calcium-dependent antibiotic biosynthetic locus of *Streptomyces coelicolor* |
| | | | | AAA34030 | 6.00E-77 | 47 | 62 | spinach glycolate oxidase from *Spinacia oleracea* |
| | | | | CAB78838 | 2.00E-75 | 45 | 60 | glycolate oxidase-like protein from *Arabidopsis thaliana* |
| | | | | CAA11762 | 4.00E-75 | 47 | 61 | protein similar to glycolate oxidase in chloroeremomycin biosynthetic locus of *Amycolatopsis orientalis* |
| 8 | 9 | 640 | ABC transporter involved in resistance/transport | CAA11793 | 0 | 55 | 71 | protein similar to mdr/ABC transporter found in chloroeremomycin biosynthetic locus of *Amycolatopsis orientalis* |
| | | | | AAF67494 | 1.00E-114 | 38 | 57 | NovA ABC transporter in novobiocin biosynthetic locus of *Streptomyces spheroides* |
| | | | | CAB38879 | 1.00E-78 | 34 | 50 | probable ABC transporter found in the calcium-dependent antibiotic biosynthetic locus of *Streptomyces coelicolor* |
| 9 | 10 | 271 | esterase/hydrolase | CAB38877 | 6.00E-66 | 48 | 63 | probable hydrolase found in the calcium-dependent antibiotic biosynthetic locus of *Streptomyces coelicolor* |
| | | | | CAA11784 | 9.00E-58 | 44 | 56 | protein similar to haloperoxidase found in chloroeremomycin biosynthetic locus of *Amycolatopsis orientalis* |
| | | | | CAA71338 | 2.00E-45 | 41 | 54 | putative thioesterase found in streptothricin biosynthetic locus of *Streptomyces sp.* strain F20 |
| 10 | 11 | 529 | unknown | AAB3O311 | 2.00E-29 | 41 | 56 | unknown protein found in putative chloramphenicol biosynthetic locus of *Streptomyces venezuelae* |

TABLE 2-continued

Proposed functions of the proteins of the ramoplanin biosynthetic pathway based on sequence comparison

| ORF | SEQ ID NO | #aa | proposed function | GenBank accession | probability | % identity | % similarity | proposed function of GenBank match |
|---|---|---|---|---|---|---|---|---|
| 11 | 12 | 90 | acyl carrier protein | AAA22001 | 6.00E-08 | 33 | 54 | polyketide synthase in Anabaena PCC7120 |
|  |  |  |  | CAA98988 | 8.00E-08 | 37 | 57 | polyketide synthase found in the phenolpthiocerol biosynthetic locus of Mycobacterium tuberculosis |
|  |  |  |  | AAF62883 | 7.00E-07 | 39 | 55 | type I polyketide synthase found in the epothilone biosynthetic locus of Sorangium cellulosum |
| 12 | 13 | 1051 | nonribosomal peptide synthetase | CAB15186 | 0 | 38 | 55 | nonribosomal peptide synthetase involved in siderophore 2,3-dihydroxybenzoate biosynthesis in Bacillus subtilis |
|  |  |  |  | AAD56240 | 0 | 38 | 55 | DhbF peptide synthetase involved in siderophore production in Bacillus subtilis |
|  |  |  |  | AAC38442 | 1.00E-179 | 40 | 52 | actinomycin synthetase II peptide synthetase found in the actinomycin biosynthetic locus of Streptomyces chrysomallus |
| 13 | 14 | 6893 | nonribosomal peptide synthetase | AAC80285 | 0 | 36 | 52 | SyrE peptide synthetase found in the syringomycin biosynthetic locus of Pseudomonas syringae |
|  |  |  |  | AAC45930 | 0 | 31 | 48 | TycC tyrocidine synthetase 3 found in the tyrocidine biosynthetic locus of Brevibacillus brevis |
| 14 | 15 | 8695 | nonribosomal peptide synthetase | AAC80285 | 0 | 36 | 51 | SyrE peptide synthetase found in the syringomycin biosynthetic locus of Pseudomonas syringae |
|  |  |  |  | AAC45930 | 0 | 32 | 49 | TycC tyrocidine synthetase 3 found in the tyrocidine biosynthetic locus of Brevibacillus brevis |
| 15 | 16 | 234 | thioesterase | AAC69333 | 2.00E-30 | 36 | 50 | PikAV thioesterase II found in the methymycin/pikromycin biosynthetic locus of Streptomycees venezuelae |
|  |  |  |  | AAC01736 | 6.00E-30 | 34 | 49 | thioesterase found in the rifamycin biosynthetic locus of Amycolatopsis mediterranei |
|  |  |  |  | CAA57967 | 2.00E-29 | 39 | 48 | protein with similarity to thioesterases found in the pyochelin biosynthetic locus of Pseudomonas aeruginosa |
|  |  |  |  | AAA79279 | 1.00E-28 | 34 | 48 | thioesterase found in the bialaphos biosynthetic locus of Streptomyces hygroscopicus |
| 16 | 17 | 274 | short chain secondary alcohol dehydrogenase/ | CAB54559 | 7.00E-49 | 39 | 58 | Rhodococcus erythropolis LimC carveol dehydrogenase, a nicotinoprotein belonging to the short chain alcohol dehydrogenase/reductase superfamily |
|  |  |  | 3-ketoacyl-acyl carrier protein reductase | CAA15546 | 3.00E-46 | 39 | 54 | hypothetical problem from Mycobacterium tuberculosis, similar to dehydrogenases |
|  |  |  |  | AAF64503 | 9.00E-43 | 39 | 53 | cholesterol oxidase from Nocardioides simplex |
|  |  |  |  | CAA68181 | 2.00E-38 | 38 | 54 | UcpA protein, belongs to alcohol dehydrogenase/rybitol dehydrogenase family |
|  |  |  |  | AAC44307 | 4.00E-36 | 34 | 53 | FabG 3-ketoacyl-acyl carrier protein reductase from Bacillus subtilis |
|  |  |  |  | CAA77599 | 1.00E-33 | 36 | 49 | beta ketoacyl reductase in unknown polyketide biosynthetic locus of Streptomyces cinnamonensis |
| 17 | 18 | 891 | threonine-specific adenylate ligase | CAA67248 | 1.00E-143 | 49 | 58 | Pristinamycin I synthase 2 nonribosomal peptide synthetase in the pristinamycin biosynthetic locus of Streptomyces pristinaespiralis |
|  |  |  |  | AAC38442 | 1.00E-141 | 49 | 57 | actinomycin synthetase II nonribosomal peptide synthetase in the actinomycin biosynthetic locus of Streptomyces chrysomallus |
|  |  |  |  | CAB38518 | 1.00E-138 | 48 | 58 | CDA pepetide synthetase I found in the calcium-dependent antibiotic biosynthetic locus of Streptomyces coelicolor |
| 18 | 19 | 187 | unknown | none |  |  |  |  |
| 19 | 20 | 415 | transmembrane protein | CAB42730 | 2.00E-82 | 43 | 57 | probable transmembrane protein from Streptomyces coelicolor |
|  |  |  |  | CAB02537 | 5.00E-59 | 39 | 50 | probable membrane protein from Mycobacterium tuberculosis |
|  |  |  |  | AAF25828 | 2.00E-56 | 35 | 48 | putative transmembrane protein Mycobacterium smegmatis |
| 20 | 21 | 491 | halogenase/hydroxylase | CAA11780 | 1.00E-180 | 63 | 76 | protein similar to non-heme oxygenase/halogenase found in chloroeremomycin biosyntehtic locus of Amycolatopsis orientalis |
|  |  |  |  | CAA76550 | 1.00E-178 | 63 | 75 | BhaA protein similar to halogenase, found in the balhimycin biosynthetic locus of Amycolatopsis mediterranei |
|  |  |  |  | AAB49297 | 1.00E-176 | 62 | 74 | hypothetical hydroxylase a found in the vancomycin biosynthetic locus of Amycolatopsis orientalis |
|  |  |  |  | AAD24884 | 6.00E-37 | 30 | 46 | PltA putative halogenase found in the pyoluteorin biosynthetic locus of Pseudomonas fluorescens |
| 21 | 22 | 217 | two-component response regulator | CAB59507 | 9.00E-58 | 52 | 71 | Streptomyces coelicolor protein highly similar to various putative two-component response regulators |
|  |  |  |  | CAA22374 | 8.00E-52 | 52 | 66 | probable luxR family response regulator from Streptomyces coelicolor |

TABLE 2-continued

Proposed functions of the proteins of the ramoplanin biosynthetic pathway based on sequence comparison

| ORF | SEQ ID NO | #aa | proposed function | GenBank accession | probability | % identity | % similarity | proposed function of GenBank match |
|---|---|---|---|---|---|---|---|---|
| | | | | CAB50960 | 3.00E-51 | 49 | 66 | probable two-component system response regulator from *Streptomyces coelicolor* |
| | | | | CAB42025 | 3.00E-48 | 49 | 64 | probable two-component system regulator from *Streptomyces coelicolor* |
| | | | | CAB38597 | 3.00E-38 | 44 | 58 | AbsA2, two component response regulator from *Streptomyces coelicolor*, acts as part of a two component signal transduction system |
| 22 | 23 | 403 | two-component sensory protein kinase | CAB42041 | 1.00E-38 | 37 | 48 | Probable two-component system sensor kinase from *Streptomyces coelicolor* |
| | | | | CAB51250 | 1.00E-34 | 32 | 44 | probable two-component system sensor kinase from *Streptomyces coelicolor* |
| | | | | CAB89761 | 1.00E-34 | 34 | 42 | probable two-component system sensor kinase from *Streptomyces coelicolor* |
| | | | | CAB38596 | 3.00E-27 | 31 | 43 | AbsA1, two component sensor kinase from *Streptomyces coelicolor*, acts as part of a two component signal transduction system |
| 23 | 24 | 309 | ABC transporter involved in resistance/transport | CAB48901 | 2.00E-45 | 41 | 55 | probable ABC transporter ATP-binding protein from *Streptomyces coelicolor* |
| | | | | CAB49966 | 4.00E-28 | 33 | 55 | ATP-binding transport protein from *Pyrococcus abyssi* |
| | | | | AAF12291 | 9.00E-28 | 38 | 56 | ABC transporter, ATP-binding protein from *Deinococcus radiodurans* |
| 24 | 25 | 553 | acyl-CoA dehydrogenase | AAD45605 | 2.00E-18 | 25 | 44 | isovaleryl-CoA dehydrogenase from *Arabidopsis thaliana* |
| | | | | CAB55554 | 7.00E-18 | 24 | 43 | isovaleryl-CoA dehydrogenase from *Pisum sativum* |
| | | | | CAB46799 | 4.00E-16 | 29 | 44 | probable acyl-CoA dehydrogenase from *Streptomyces coelicolor* |
| | | | | CAA16488 | 9.00E-14 | 29 | 39 | RedW acyl-coa dehydrogenase in the undecylprodigiosin biosynthetic locus of *Streptomyces coelicolor* |
| | | | | AAF08800 | 3.00E-13 | 23 | 44 | YngJ protein found in the mycosubtilin biosynthetic locus of *Bacillus subtilis* |
| 25 | 26 | 585 | acyl-CoA dehydrogenase | CAB61531 | 2.00E-27 | 26 | 43 | FadE fatty acid acyl-CoA dehydrogenase found in *Streptomyces lividans* |
| | | | | CAB07077 | 6.00E-22 | 24 | 39 | *Mycobacterium tuberculosis* protein highly similar to acyl-CoA dehydrogenase |
| | | | | CAA17679 | 2.00E-21 | 26 | 43 | probable Acyl-CoA dehydrogenase found in *Mycobacterium tuberculosis* |
| 26 | 27 | 587 | acyl-CoA ligase | AAG02359 | 1.00E-115 | 45 | 56 | BlmVI peptide synthetase in bleomycin biosynthetic locus of *Stretomyces verticillus* |
| | | | | AAC44128 | 1.00E-94 | 38 | 53 | Mx1 peptide synthetase B in saframycin biosynthetic locus of *Myxococcus xanthus* |
| | | | | CAA16183 | 1.00E-85 | 37 | 49 | polyketide synthase found in the undecylprodigiosin biosynthetic locus of *Streptomyces coelicolor* |
| | | | | CAB05426 | 3.00E-84 | 35 | 51 | Fad29 probable acyl-CoA synthetase found in *Mycobacterium tuberculosis* |
| | | | | CAA17589 | 2.00E-82 | 36 | 51 | Fad24 probable acyl-CoA synthetase found in *Mycobacterium tuberculosis* |
| | | | | CAB01395 | 1.00E-81 | 35 | 50 | Fad25 probable acyl-CoA synthetase found in *Mycobacterium tuberculosis* |
| | | | | AAB52538 | 2.00E-78 | 34 | 50 | acyl-CoA synthetase from *Mycobacterium bovis* |
| | | | | CAB36629 | 4.00E-78 | 35 | 52 | putative acyl-CoA synthase from *Mycobacterium leprae* |
| 27 | 28 | 75 | unknown | CAB38589 | 1.00E-24 | 70 | 80 | small conserved hypothetical protein found in the calcium-dependent antibiotic biosynthetic locus of *Streptomyces coelicolor* |
| | | | | CAB08480 | 3.00E-22 | 67 | 77 | MbtH possibly involved in mycobactin synthesis in *Mycobacterium tuberculosis* |
| | | | | CAA11799 | 3.00E-19 | 74 | 89 | hypothetical protein found in chloroeremomycin biosynthetic locus of *Amycolatopsis orientalis* |
| 28 | 29 | 94 | chorismate mutase-like protein | CAB02002 | 2.00E-15 | 50 | 69 | hypothetical protein in *Mycobacterium tuberculosis* |
| | | | | CAB82023 | 2.00E-11 | 46 | 59 | hypothetical protein in *Streptomyces coelicolor* |
| | | | | CAB72783 | 7.00E-03 | 36 | 59 | chorismate mutase¶rephenate dehydratase from *Campylobacter jejuni* |
| | | | | AAC75649 | 6.00E-02 | 30 | 50 | chorismate mutase-T and prephenate dehydrogenase protein from *E. coli* |
| 29 | 30 | 619 | membrane protein | CAB16086 | 2.00E-56 | 28 | 43 | unknown protein in *Bacillus subtilis* |
| | | | | CAA05568 | 4.00E-34 | 35 | 54 | YkcB unknown protein in *Bacillus subtilis* |
| | | | | CAB76994 | 0.01 | 26 | 35 | putative integral membrane protein in *Streptomyces coelicolor* |
| | | | | AAC18892 | 0.049 | 29 | 37 | transmembrane protein from *Streptomyces aureofaciens* |
| 30 | 31 | 355 | 4-hydroxyphenylpyruvate dioxygenase | CAA11761 | 5.00E-87 | 50 | 63 | protein similar to hydroxyphenyl pyruvate dioxygenase found in the chloroeremomycin biosynthetic locus of *Amycolatopsis orientalis* |

TABLE 2-continued

Proposed functions of the proteins of the ramoplanin biosynthetic pathway based on sequence comparison

| ORF | SEQ ID NO | #aa | proposed function | GenBank accession | probability | % identity | % similarity | proposed function of GenBank match |
|---|---|---|---|---|---|---|---|---|
| | | | | CAB38519 | 1.00E-69 | 44 | 54 | probable 4-hydroxyphenylpyruvate acid dioxygenase found in the calcium-dependent antibiotic biosynthetic locus of *Streptomyces coelicolor* |
| | | | | CAB51008 | 2.00E-49 | 36 | 51 | probable 4-hydroxyphenylpyruvic acid dioxygenase found in *Streptomyces coelicolor* |
| | | | | AAA50231 | 3.00E-49 | 36 | 50 | 4-hydroxyphenylpyruvic acid dioxygenase from *Streptomyces avermitilis* |
| 31 | 32 | 429 | transmembrane transporter | CAB45049 | 4.00E-81 | 46 | 64 | putative integral membrane ion antiporter found in the chloroeremomycin biosynthetic locus of *Amycolatopsis orientalis* |
| | | | | BAA16991 | 3.00E-72 | 39 | 56 | sodium/proton antiporter from *Synechocystis sp.* |
| | | | | CAA23036 | 8.00E-65 | 37 | 57 | putative sodium/protein exchanging protein from *Arabidopsis thaliana* |
| | | | | AAF26906 | 1.00E-41 | 30 | 48 | protein similar to sodium/proton and drug/proton antiporters found in the epothilone biosynthetic locus of *Sorangium cellulosum* |
| 32 | 33 | 189 | unknown | CAB72201 | 1.00E-11 | 31 | 41 | hypothetical protein in *Streptomyces coelicolor* |
| | | | | CAB56690 | 2.00E-08 | 31 | 42 | hypothetical protein in *Streptomyces coelicolor* |
| 33 | 34 | 309 | Unknown, incomplete | none | | | | |

The correlation between the order of repeated units in most peptide synthetases and the order in which the respective amino acids appear in the peptide product makes it possible to correlate peptides of known structure with putative genes encoding their synthesis, as demonstrated by the identification of the mycobactin biosynthetic gene cluster from the genome of *Mycobacterium tuberculosis* (Quadri et al., 1998, Chem. Biol. Vol. 5, pp. 631–645). This principle has been used here to assign a biosynthetic role for each repeating unit of the ramoplanin peptide synthetases described in this invention, as diagrammed in FIGS. 2A, B and C. The approximate boundaries, at the amino acid level, of the domains of the repeating units (modules) of each ORF are tabulated in Table 3, wherein C represents a condensation domain, A represents an adenylation domain, T represents a thiolation domain and Te represents a thioesterase domain.

TABLE 3

Approximate boundaries of domains of each module at the amino acid level

| | | |
|---|---|---|
| Orf 12 | | |
| Module 1: | C | 1–470 |
| | A | 471–959 |
| | T | 961–1030 |
| Orf 13 | | |
| Module 1: | C | 1–517 |
| | A | 518–990 |
| | T | 991–1059 |
| Module 2: | C | 1106–1560 |
| | A | 1561–2052 |
| | T | 2054–2122 |
| Module 3: | C | 2159–2618 |
| | A | 2619–3122 |
| | T | 3123–3191 |
| Module 4: | C | 3237–3697 |
| | A | 3698–4160 |
| | T | 4161–4228 |
| Module 5: | C | 4241–4718 |
| | A | 4719–5192 |
| | T | 5193–5260 |
| Module 6: | C | 5307–5754 |
| | T | 5755–5824 |
| Module 7: | C | 5838–6317 |
| | A | 6318–6804 |
| | T | 6805–6873 |
| Orf 14 | | |
| Module 1: | C | 1–486 |
| | A | 487–993 |
| | T | 994–1062 |
| Module 2: | C | 1109–1567 |
| | A | 1568–2041 |
| | T | 2042–2110 |
| Module 3: | C | 2122–2602 |
| | A | 2603–3095 |
| | T | 3097–3165 |
| Module 4: | C | 3212–3671 |
| | A | 3672–4135 |
| | T | 4136–4202 |
| Module 5: | C | 4217–4698 |
| | A | 4699–5199 |
| | T | 5200–5268 |
| Module 6: | C | 5317–5776 |
| | A | 5777–6280 |
| | T | 6281–6350 |
| Module 7: | C | 6363–6839 |
| | A | 6840–7343 |
| | T | 7344–7411 |
| Module 8: | C | 7458–7925 |
| | A | 7926–8380 |
| | T | 8381–8449 |
| | Te | 8450–8695 |

A. Formation of the Lipodepsipeptide Core Structure:

Nine proteins, encoded by ORFs 9, 11, 12, 13, 14, 15, 17, 26 and 27 (SEQ ID NOS: 10, 12, 13, 14, 15, 16, 18, 27 and 28), are likely to be involved in the formation of the lipodepsipeptide core structure of ramoplanin. ORFs 11, 12, 13, 14 and 17 (SEQ ID NOS: 12, 13, 14, 15 and 18) show significant similarity to peptide synthetases or peptide synthetase domains. Analysis of the adenylation domains found in these ORFs allows the amino acid that is incorporated by each unit to be identified (see FIGS. 3A and B). The following amino acid specificities are consistent with these comparisons: ORF 12: asparagine (Asn); ORF 13, module 1: 4-hydroxyphenylglycine (HPG); ORF 13, module 2: ornithine (Orn); ORF 13, module 3: threonine (Thr); ORF 13, module 4: HPG; ORF 13, module 5: HPG; ORF 13, module 6 contains no adenylation domain; ORF 13, module 7: phenylalanine (Phe); ORF 14, module 1: Orn; ORF 14, module 2: HPG; ORF 14, module 3: Thr; ORF 14, module 4: HPG; ORF 14, module 5: glycine (Gly); ORF 14, module 6: leucine (Leu); ORF 14, module 7: unspecified; ORF 14, module 8: HPG; ORF 17, threonine (Thr). The numbers and predicted amino acid substrate specificities of the peptide synthetase repeating units are in precise agreement with the structure of the ramoplanin peptide core, providing conclusive evidence that the genetic locus described here is responsible for the biosynthesis of ramoplanin.

The amino acid specificity of adenylation domains may be altered by mutagenesis (Stachelhaus et al., 1999, Chem. Biol. Vol. 6, pp. 493–505; Challis et al., Chem. Biol., 2000, Vol. 7, pp. 211–224) or by swapping domains between peptide synthetases (Stachelhaus et al., 1995, Science Vol. 269, pp. 482–485; Schneider et al., 1998, Mol. Gen. Genet. Vol. 257, pp. 308–318; de Ferra et al., 1998, J. Biol. Chem. Vol. 272, pp. 25304–25309) and thereby generate derivatives of a natural peptide product.

Figure 2A:
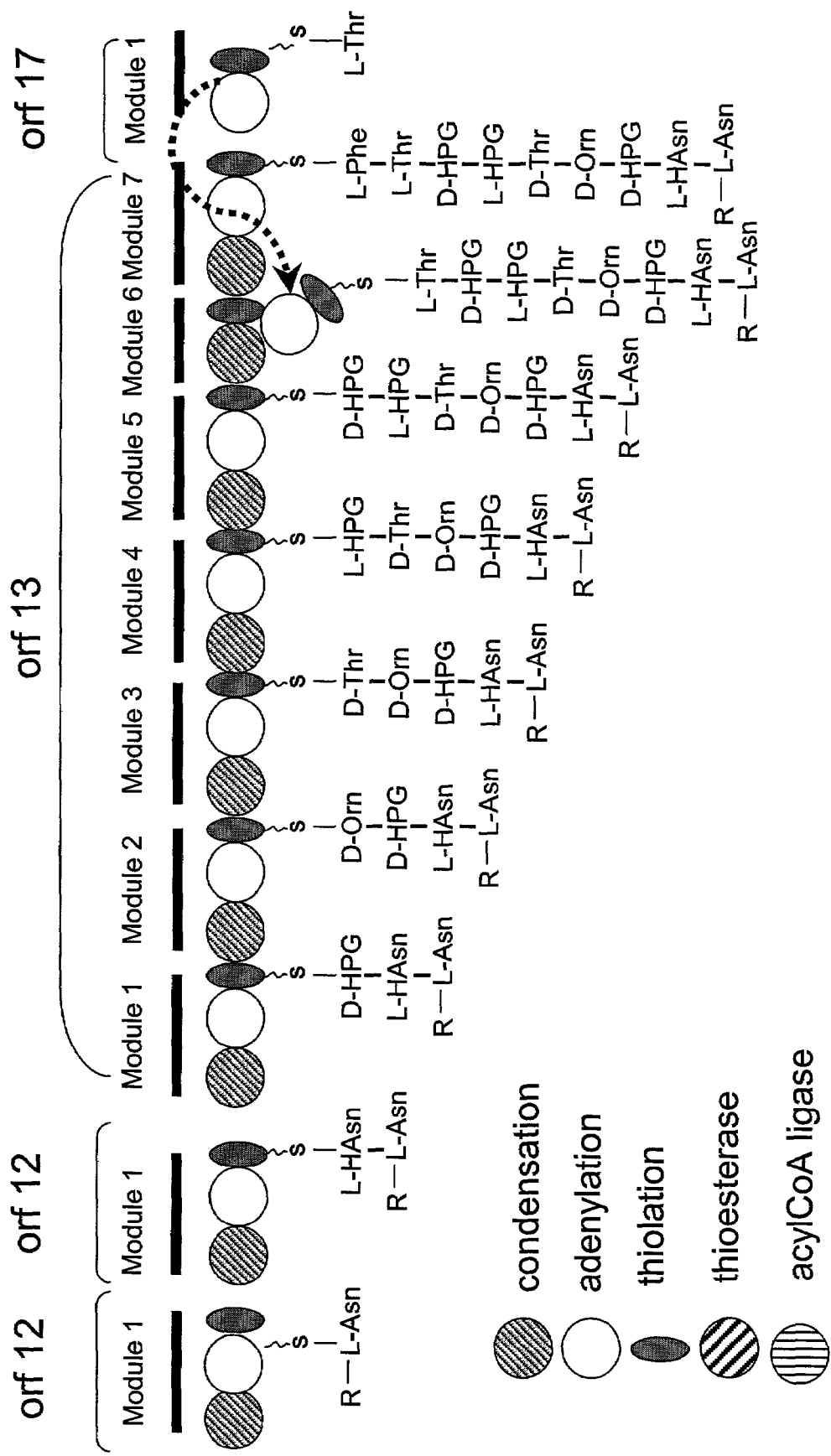
FIG. 2A is a model for the biosynthesis of ramoplanin. The ramoplanin chain is assembled in stepwise fashion through the concerted activities of consecutive modules of the ramoplanin peptide synthetases. Domains in each module are denoted by the circular and oval symbols as indicated. R denotes the fatty acyl group that caps the N-terminus of the first amino acid (Asn) incorporated into the ramoplanin peptide (see FIG. 2B). Note that ORF 12 recognizes Asn and is proposed to incorporate both Asn residues found in the ramoplanin peptide; hydroxylation of the second Asn residue may occur before or after recognition and activation of the amino acid. The thick dotted arrow indicates that the ORF 17 protein interacts with module 6 of the ORF 13 product to catalyze the incorporation of Thr at the appropriate position. The thin dotted line indicates that the side chain hydroxyl group of the beta-hydroxyasparagine residue undergoes nucleophilic attack upon the thioester bond linking the ramoplanin product with module 8 of ORF 14, resulting in the cyclization and release of the peptide product. Abbreviations: HAsn, beta-hydroxyasparagine; other abbreviations are as in the text.
Figure 2A:
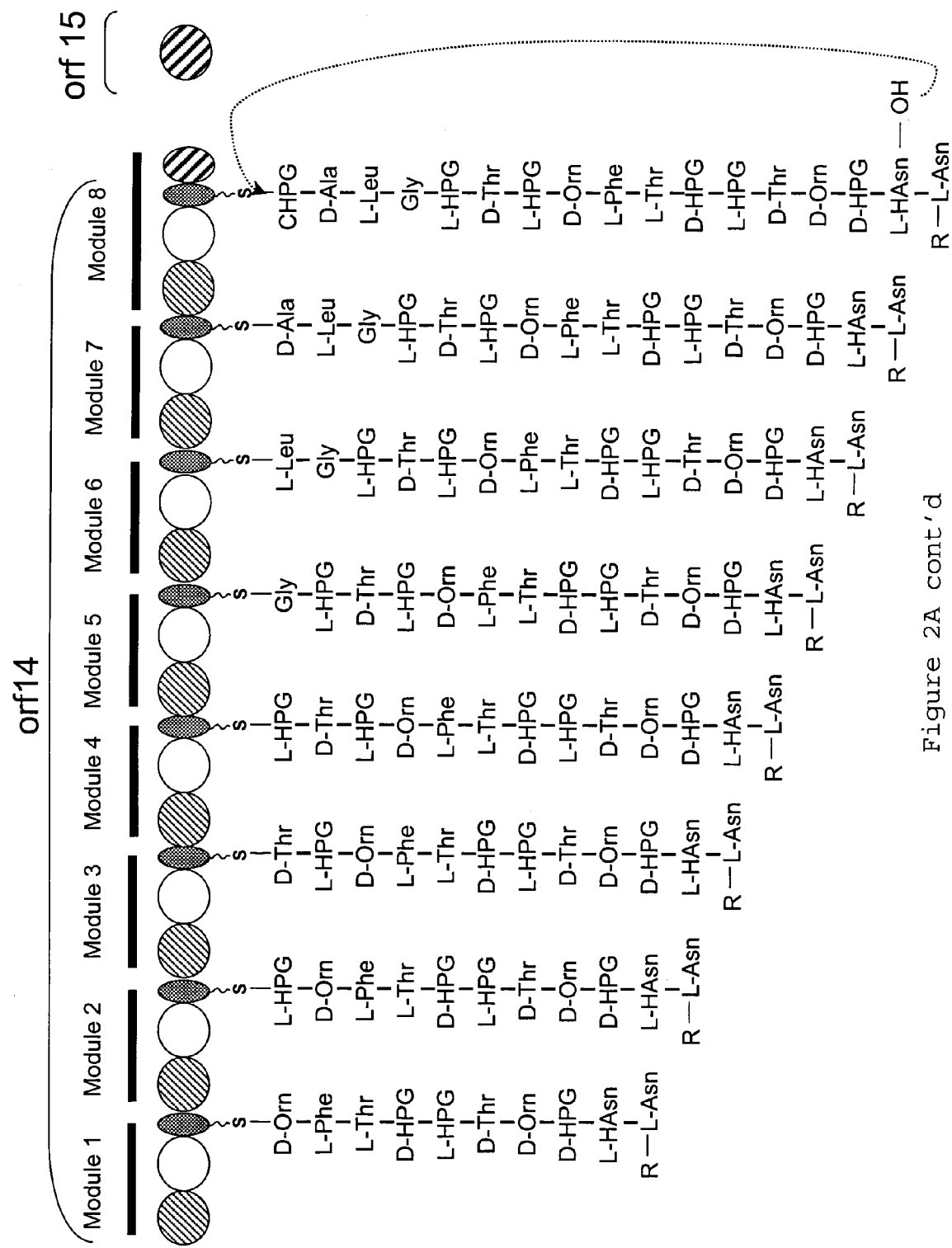

A model for the biosynthesis of the ramoplanin peptide core structure can be built by comparing the specificity and order of the repeating units in the ramoplanin peptide synthetases with the order of the amino acid substituents in ramoplanin (diagrammed in FIGS. 2A and C). ORF 12 (SEQ ID NO: 13) contains the only adenylation domain specifying Asn and therefore may catalyze the incorporation of the first two (Asn) amino acid residues into the peptide chain. Subsequent amino acids are incorporated in the precise order in which the respective units occur in the adjacent ORFs 13 and 14 (SEQ ID NOS: 14 and 15). The only exception to the colinearity of peptide synthetase units and the order of incorporation of amino acids into ramoplanin occurs at module 6 of ORF 13 (SEQ ID NO: 14). This module contains condensation and thiolation domains, but is lacking an adenylation domain. The structure of ramoplanin indicates that a Thr must be incorporated into the peptide chain at this position. ORF 17 (SEQ ID NO: 18) encodes an unusual peptide synthetase unit having an adenylation domain that specifies Thr, but lacks a conventional condensation domain. According to the model diagrammed in FIG. 2A, the ORF 17 (SEQ ID NO: 18) protein interacts with module 6 of ORF 13 (SEQ ID NO: 14) and substitutes for the missing adenylation domain of this module, thus catalyzing the incorporation of Thr into the growing ramoplanin peptide precursor at the appropriate position. Such a trans interaction between peptide synthetase units has a precedent in the biosynthesis of the lipodepsipeptide antibiotic syringomycin. In the syringomycin system, the adenylation domain of the SyrB1 protein, which lacks a condensation domain, is proposed to interact with and complement the activity of a SyrE1 peptide synthetase unit that contains a condensation domain but is lacking an adenylation domain (Guenzi et al., 1998, J. Biol. Chem. Vol. 273, pp. 32857–32863).

Figure 2B:
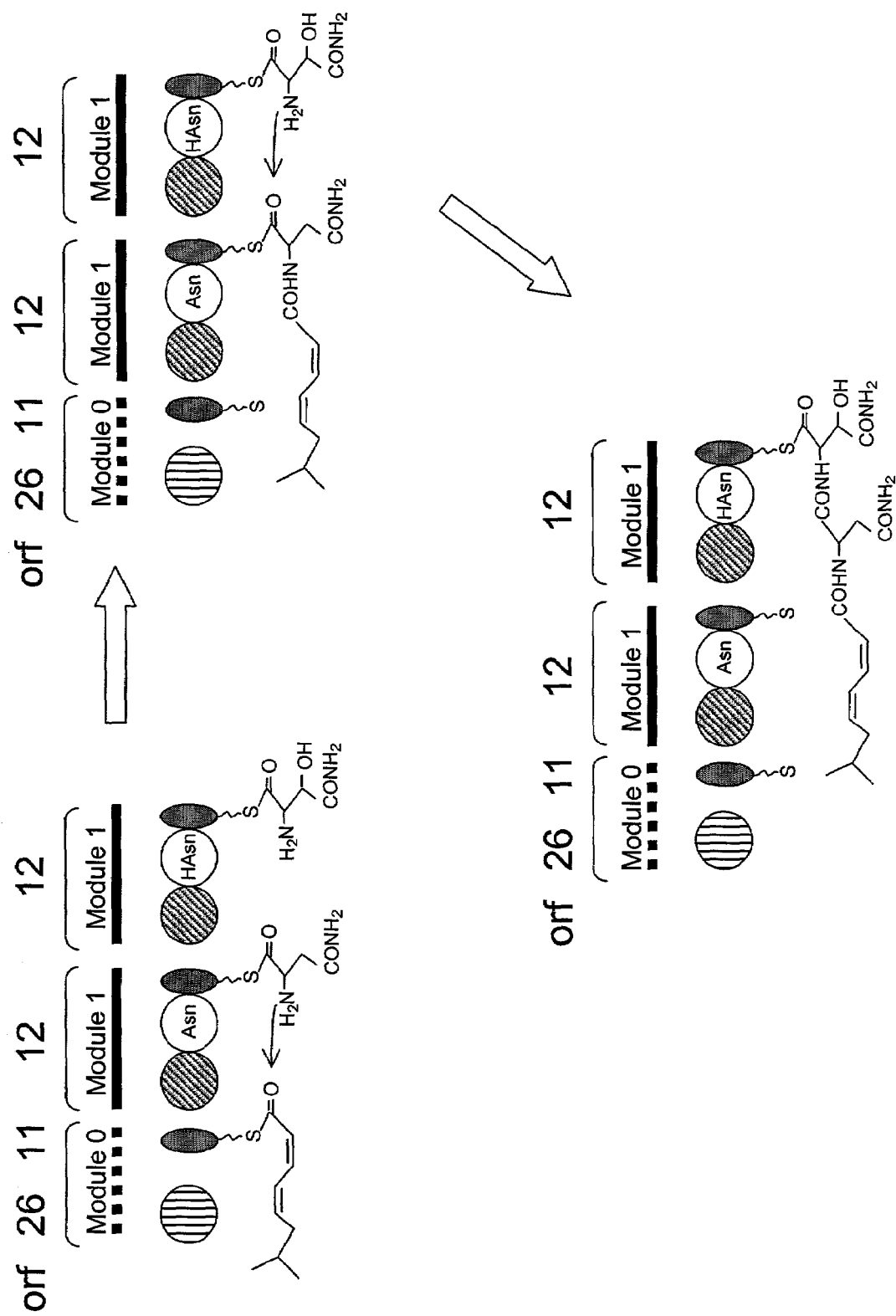
FIG. 2B is a model for the initiation of ramoplanin peptide synthesis using a fatty acid starter group. ORF 11 and ORF 26 are proposed to act coordinately as a starter unit, using a fatty acid group to prime the assembly of the peptide chain. Symbols are as in FIG. 2A.
Figure 2C:
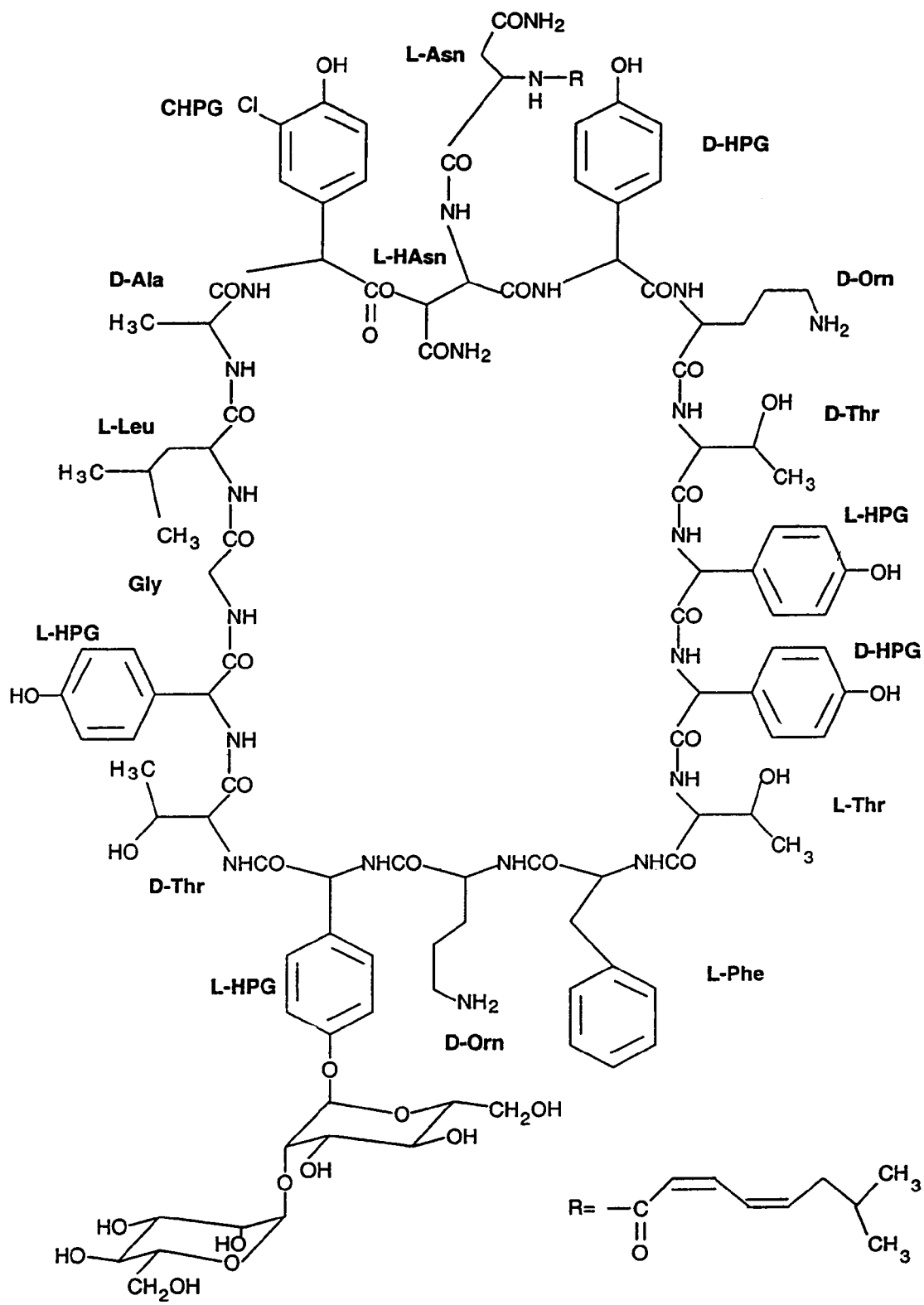
FIG. 2C illustrates the structure of ramoplanin. Shown are the positions of amino acid substituents, as well as an embodiment wherein the acylamide moiety is derived from an eight-carbon fatty acid (R). Alternative fatty acyl chaims may also be incorporated at this position.

The peptide synthetase encoded by ORF 12 (SEQ ID NO: 13) is unusual for a starter unit in having a condensation domain at the N-terminus of the protein. Most peptide synthetase starter units described to date contain adenylation domains at their N-terminus that are responsible for activating the first amino acid (the "starter" amino acid) that is incorporated into the peptide product. In contrast, the ramoplanin starter unit encoded in ORF 12 (SEQ ID NO: 13) has a condensation domain at the N-terminus of the protein, indicating that the initiation of peptide synthesis may occur in an unusual fashion. The N-terminus of the ramoplanin peptide is modified by one of three possible fatty acid groups, suggesting that the construction of the ramoplanin peptide may start with a fatty acid rather than an amino acid. A proposed mechanism of chain initiation using a fatty acid starter group is diagrammed in FIG. 2B. According to this model, the condensation domain at the N-terminus of ORF 12 (SEQ ID NO: 13) catalyzes the linkage of amino acid 1 (Asn) bound to module 1 to a fatty acid bound to the acyl carrier protein encoded by ORF 11 (SEQ ID NO: 12) via amide bond formation, providing an "acyl-N-capped" amino acid intermediate for further chain extension.

ORFs 11 and 26 (SEQ ID NOS: 12 and 27) are proposed to cooperate in the activation and transfer of fatty acid precursors to the ORF 12 (SEQ ID NO: 13) peptide synthetase. ORF 26 (SEQ ID NO: 27) shows similarity to acyl-CoA ligases, proteins of the adenylate-forming superfamily of enzymes that catalyze the activation of fatty acids via an activated adenylate intermediate. ORF 11 (SEQ ID NO: 12) shows similarity to acyl carrier proteins and peptide synthetase thiolation domains that accept activated adenylate intermediates. As diagrammed in FIG. 2B, the activity of these two ORFs may generate activated fatty acid thioesters that serve as the initiating groups for the synthesis of the ramoplanin lipopeptide core structure. ORF 26 (SEQ ID NO: 27) may be replaced or mutated, alone or in combination with the condensation domain of ORF 12 (SEQ ID NO: 13), in order to generate derivatives of ramoplanin having alternative fatty acids.

The final unit in most peptide synthetases contains a special C-terminal thioesterase domain, postulated to be involved in product release. Release of the complete peptide product from the peptide synthetase requires a thioesterase function that is generally found at the C-terminus of the peptide synthetase. ORF 14 (SEQ ID NO: 15) contains a C-terminal thioesterase domain, and may be involved in peptide release and cyclization by catalyzing the formation of the ester bond between the carboxylate goup of the C-terminal HPG and the hydroxyl group of HAsn, resulting in a free cyclic depsipeptide structure. ORF 15 (SEQ ID NO: 16) may also play a role in peptide release and/or cyclization. ORF 15 (SEQ ID NO: 16) shows strong similarity to thioesterases that are frequently found associated with peptide synthetases and are postulated to be involved in the release of peptide products or intermediates and may also be involved in the release and/or cyclization of the ramoplanin peptide. ORF 9 (SEQ ID NO: 10) shows similarity to esterases of the alpha/beta hydrolase fold family and may also be involved in peptide release.

ORF 27 (SEQ ID NO: 28) shows strong similarity to several small conserved proteins encoded by genes that are frequently found to be associated with peptide synthetase genes and are therefore likely to play a role in peptide biosynthesis.

B. Epimerization of L-amino Acids into Corresponding D-amino Acids:

An unexpected feature of the ramoplanin peptide synthetases is the absence of epimerization domains in the repeating units. Epimerization domains catalyze the conversion of L-amino acids into the corresponding D-amino acids. Ramoplanin contains seven D-amino acid units. Most bacterial peptide synthetases that incorporate D-amino acids do so by first recognizing and incorporating the corresponding L-amino acid and subsequently altering the configuration to the D-form through the activity of the epimerization domain. The lack of epimerization domains in the ramoplanin peptide synthetases despite the presence of D-amino acids in the final natural product may be due to specific recognition of D-amino acids by the adenylation domains found in modules 1, 2, 3 and 5 of ORF 13 (SEQ ID NO: 14) and modules 1, 3 and 7 of ORF 14 (SEQ ID NO: 15). The direct recognition and incorporation of D-amino acids by peptide synthetases has been postulated for the eukaryotic cyclosporin and HC toxin peptide synthetases (Weber et al., 1994, Curr. Genet Vol. 26, pp. 120–125; Scott-Craig et al., 1992, J. Biol. Chem. Vol. 267, pp. 26044–26049).

Alternatively, epimerization may be catalyzed by cellular amino acid epimerases/epimerases of primary or secondary metabolism, as has been proposed for the incorporation of D-valine in the gramicidin and tyrocidine systems (Pfeifer et al., 1995, Biochem. Vol. 34, pp. 7450–7459; Stein et al., 1995, Biochem. Vol. 34, pp. 4633–4642).

Yet another explanation is that specialized domains within the NRPSs may have evolved the ability to carry out dual functions. One domain that stands out as a candidate for having such dual functions is the condensation domain. Normally within a typical NRPS module that introduces a D-amino acid into the peptide product, epimerization (E) domains follow the thiolation (T) domain. In terms of linear domain organization on NRPS enzymes condensation (C) domains and epimerization (E) domains can be thought of as occupying equivalent positions. That is, in an NRPS with multiple modules that is devoid of E domains, a C domain from any given module is found directly adjacent to the thiolation (T) domain of the upstream module. In addition, C domains and E domains also share a considerable amount of sequence similarity. Several highly conserved core motifs are shared between C and E domains. One particularly important motif that is common to both C and E domains is the histidine motif HHXXXDG (SEQ ID NO: 44) which has been shown by mutagenesis to form part of the active site (Stachelhaus et al.; *Journal of Biological Chemistry* 1998; 273:22773–22781). Thus, the C domains of modules 2, 3, 4 and 6 of OFR 13 (SEQ ID NO:14) and modules 2, 4 and 8 of ORF 14 (SEQ ID NO: 15) may be capable of amino acid epimerization as well as amide bond formation and be responsible for the 7-D-amino acid residues found in ramoplanin.

C. Formation of Fatty-acid Side Chains:

The ramoplanin depsipeptide core structure may carry one of three different medium-chain fatty acids attached to the N-terminus of Asn in position 1, resulting in the three different ramoplanin components A1–A3. Little is known about the biosynthetic origin of the three unsaturated fatty acid precursors, octa-2,4-dienoic acid (a C8 fatty acid) and its analogs 7-methylocta-2,4-dienoic acid (C9) and 8-methylnona-2,4-dienoic acid (C10). These medium-chain fatty acids may be derived from longer chain fatty acids by beta-oxidative degradation. It has been shown that the yields of component A2, carrying the octa-2,4-dienoic acid moiety, can be increased by adding the amino acid leucine to the fermentation medium of the producing organism, indicating that branched-chain amino acids may also serve as biosynthetic precursors to the fatty acid side chains of ramoplanin (European patent EP259780). Three proteins encoded by the ramoplanin locus, namely ORFs 16, 24, 25 (SEQ ID NOS: 17, 25 and 26), show similarity to enzymes associated with fatty acid metabolism and therefore may be involved in the generation of the fatty acid side chains for attachment to the depsipeptide core structure of ramoplanin. ORFs 24 and 25 (SEQ ID NOS: 25 and 26) are highly similar to each other and to flavin-dependent acyl-CoA dehydrogenases, enzymes involved in the degradation of fatty acids and in the degradation of leucine to fatty acid intermediates. These ORFs may channel branched-chain amino acid and fatty acid intermediates into the ramoplanin biosynthetic pathway. In addition, the dehydrogenase activity of ORFs 24 and 25 (SEQ ID NOS: 25 and 26) may be responsible for generating the two double bonds found in the unsaturated fatty acid groups of ramoplanin. ORF 16 (SEQ ID NO: 17) may also be involved in generating the fatty acid group of ramoplanin as it shows strong similarity to 3-oxoacyl-acyl carrier protein reductases, NAD-dependent enzymes of primary metabolism that are also involved in fatty acid degradation.

Figure 4:
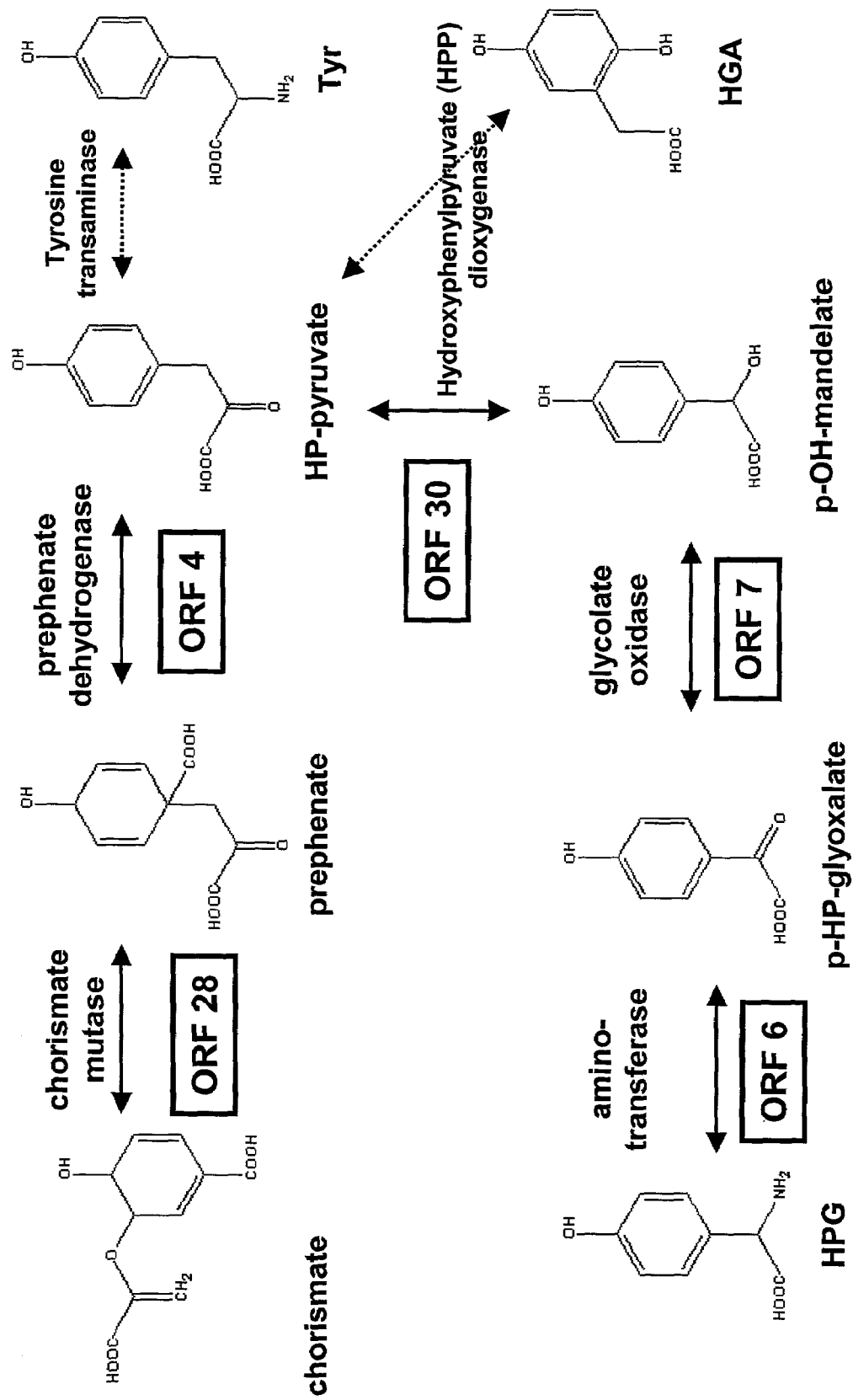
FIG. 4 illustrates the proposed biosynthetic pathway of the unusual amino acid 4-hydroxyphenylglycine (HPG). Chorismate (1), prephenate (2) and 4-hydroxyphenylpyruvate (3) are intermediates in the biosynthesis of the amino acid tyrosine (4). ORF 28 shows similarity to chorismate mutases of primary metabolism and therefore may catalyze the conversion of (1) to (2). ORF 4 shows amino acid similarity to prephenate dehydrogenases of primary metabolism and therefore may catalyze the conversion of (2) to (3). ORF 30 shows amino acid similarity to 4-hydroxyphenylpyruvate dioxygenases, which convert (3) to homogentisate (5), an important intermediate in the metabolism of tyrosine. ORF30 may therefore catalyze a similar oxidative decarboxylation reaction to generate 4-hydroxymandelate (6). ORF 7 shows amino acid similarity to glycolate oxidases, which catalyze the conversion of glycolate to glyoxalate. ORF 7 may therefore convert the glycolate structure found in (6) to the corresponding glyoxalate structure to produce 4-hydroxyphenylglyoxalate (7). ORF 6 shows amino acid similarity to many aminotransferases, and may catalyze the conversion of (7) to HPG (8). Biochemical studies with radiolabeled amino acids have established that the HPG residues of the antibiotic vancomycin are derived from tyrosine, and structures 6, 7, and 8 were proposed as possible intermediates in HPG biosynthesis (Nicas et al., in Biotechnology of Antibiotics, Marcel Dekker, Inc., 1997, pp. 363–392 and references therein).

D. Amino-acid 4-hydroxyphenylglycine (HPG) Synthesis:

Five proteins encoded by the ramoplanin locus, namely ORF 4, ORF 6, ORF 7, ORF 28 and ORF 30 (SEQ ID NOS: 5, 7, 8, 29 and 31), are likely to be involved in synthesizing the unusual amino acid 4-hydroxyphenylglycine (HPG) which serves as a substrate for incorporation into the lipodepsipeptide core structure of ramoplanin. The natural occurrence of HPG in secondary metabolites is relatively infrequent, the best-known examples being nocardicin A; vancomycin, aridicin, chloroeremomycin, teicoplanin and related glycopeptide antibiotics; the calcium-dependent antibiotic (CDA) of *Streptomyces coelicolor*; and ramoplanin. Biochemical studies have indicated that the HPG residues of the antibiotics vancomycin, aridicin, and nocardicin are derived from the common amino acid tyrosine and a pathway for the synthesis of HPG from tyrosine has been proposed (Nicas et al., in Biotechnology of Antibiotics, Marcel Dekker, Inc., 1997, pp. 363–392 and references therein; Chung et al., 1986, J. Antibiotics Vol. 1986, pp. 642–651; Hosoda et al., 1977, Agric. Biol. Chem. Vol. 41, pp. 1007–1012; Hammond et al., 1982, J. Chem. Soc. (Chem. Comm.), Vol. 1982, pp. 344–346). However, analysis of the ORFs encoded by the ramoplanin biosynthetic locus provides evidence for an alternative pathway, as illustrated in FIG. 4. The combined activities of ORF 4, ORF 6, ORF 7, ORF 28 and ORF 30 (SEQ ID NOS: 5, 7, 29, and 31) would allow conversion of intermediates of tyrosine metabolism into the unusual amino acid HPG. Proteins showing similarity to ORFs 4, 6, 7 and 30 (SEQ ID NOS: 5, 7, 8 and 31) can be found in the biosynthetic loci encoding CDA and chloroeremomycin, two natural products that also contain HPG substituents, although the roles of these proteins in the biosynthesis of the respective natural products were not proposed (GenBank accession numbers AL035640, AL035707, and AL035654; van Wageningen et al. 1997, Chem. Biol. Vol. 5, pp. 155–162).

E. Resistance and/or Localization Proteins:

Eight proteins encoded by the ramoplanin locus (ORF 1, ORF 2, ORF 3, ORF 8, ORF 19, ORF 23, ORF 29 and ORF 31) are likely to be membrane-associated proteins that are involved in resistance and/or the subcellular localization of the ramoplanin biosynthetic machinery. ORFs 2, 8, and 23 (SEQ ID NOS: 3, 9 and 24) show similarity to the superfamily of ATP binding cassette transport proteins involved in target-specific secretion and are likely to be involved in the transport of ramoplanin or biosynthetic precursors across the cytoplasmic membrane, providing a possible mechanism for resistance to the toxic effects of the antibiotic or increased production of ramoplanin. ORF 31 (SEQ ID NO: 32) shows similarity to various sodium/proton and drug/proton antiporters and may also provide a means to transport ramoplanin across the cytoplasmic membrane. ORFs 1, 3, 19 and 29 (SEQ ID NOS: 2, 4 and 20) show similarity to various transmembrane proteins of unknown function and may be involved in localizing the ramoplanin biosynthetic machinery to the cytoplasmic membrane in order to provide access to lipid and fatty acid precursors.

F. Proteins Involved in Regulation of Ramoplanin Biosynthesis:

Three proteins encoded by the ramoplanin locus, namely ORF 5, ORF 21, ORF 22 (SEQ ID NOS: 6, 22 and 23), are likely to be involved in the regulation of ramoplanin biosynthesis. ORF 5 (SEQ ID NO: 6) shows similarity to a number of transcriptional regulators of antibiotic biosynthesis. This protein is likely to regulate the transcription of one or more genes in the ramoplanin genetic locus. ORFs 21 and 22 (SEQ ID NOS: 22 and 23) show homology to 2-component signal transduction systems, such as the Abs A1/A2 system involved in the global regulation of antibiotic synthesis of *Streptomyces coelicolor*. These ORFs may act coordinately to regulate the expression of ramoplanin biosynthetic genes and the production of ramoplanin in response to environmental or cellular signals.

G. Chlorination of Terminal HPG Residue:

ORF 20 (SEQ ID NO: 21) shows similarity to halogenases involved in the chlorination of secondary metabolites, including the PrnC halogenase of *Pseudomonas fluorescens* responsible for the chlorination of an aromatic precursor of pyrrolnitrin biosynthesis and a halogenase proposed to be responsible for the chlorination of a tyrosine residue in chloroeremomycin. This protein most likely catalyzes the chlorination of the terminal HPG residue incorporated into the ramoplanin peptide core, generating the 3-chloro-HPG form.

H. Beta-hydroxyasparagine Residue Formation:

As disclosed in U.S. Ser. No. 60/283,296, ORF 10 (SEQ ID NO: 11) is a member of a new family of metal cofactor hydroxylase enzymes. This discovery is very surprising because one would have expected that cytochrome P450 enzymes would be implicated in the beta-hydroxylation reaction requied to generate beta-hydroxyasparagine.

The possibility that a novel mechanism for beta-hydroxylation of amino acid residues may be operative in the biosynthesis of ramoplanin was first suggested by the fact that none of the ORFs encoded by the ramoplanin biosynthetic locus displayed significant amino acid sequence homology to the known cytochrome P450 monooxygenases by BLASTP analysis. ORF 10, ORF 18 and ORF 32 (SEQ ID NOS: 11, 19 and 33) could not initially be assigned a putative role in the biosynthesis of ramoplanin and were considered as candidate asparagine beta-hydroxylases. ORF 10 (SEQ ID NO: 11) shows homology to a protein of unknown function in the bleomycin biosynthetic locus of *Streptomyces verticillus* and to a partial protein of unknown function found in putative chloramphenicol biosynthetic locus of *Streptomyces venezuelae*. Significantly, bleomycin and chloramphenicol also contain a beta-hydroxylated amino acid residue. ORF 18 (SEQ ID NO: 19) shows no similarity to proteins in the GenBank database, while ORF 32 (SEQ ID NO: 33) shows similarity to hypothetical bacterial proteins of unknown function in *Streptomyces coelicolor*. Since enzymes that catalyze hydroxylation reactions commonly use metal cofactors, ORFs 10, 18 and 32 (SEQ ID NOS: 11, 19 and 33) were further analyzed for the presence of amino acid motifs that are associated with the binding of metal cofactors.

FIG. 5 illustrates clustal alignments showing sequence homology between ORF 10 (SEQ ID NO: 11) and various metal ligand motifs. In each of the clustal alignments: (i) a line above the alignment is used to mark strongly conserved positions; (ii) an asterisk "*" indicates positions which have a single, fully conserved residues; (iii) a colon ":" indicates that one of the following strong groups is fully conserved: S, T or A; N, E, Q or K; N, H, Q or K; N, D, E or Q; Q, H, R or K; M, I, L or V; M, I, L or F; H or Y; and F, Y or W; and (iv) a period "." indicates that one of the following weaker groups is fully conserved: C, S or A; A, T or V; S, A or G; S, T, N or K; S, T, P or A; S, G, N or D; S, N, D, E, Q or K; N, D, E, Q, H or K; N, E, Q, H, R or K; F, V, L, I or M: and H, F or Y.

ORF 10 (SEQ ID NO: 11) contains two amino acid sequence motifs that are frequently found in enzymes that use metal cofactors. The N-terminal region of ORF 10 (SEQ ID NO: 11) contains a cluster of histidine residues (the His-motif) that shows significant local sequence homology to a conserved histidine motif found in several zinc-binding beta-lactamases. FIG. 5A shows the local amino acid sequence homology between ORF 10 (SEQ ID NO: 11) and a key motif involved in coordinating two zinc molecules in the beta-lactamase superfamily. The alignment depicts amino acids 263 to 318 of ORF 10 (SEQ ID NO: 11), amino acids 42 to 99 of a member of the beta-lactamase superfamily, the L1 metallo-beta-lactamase (1SML) from *Stenotrophomonas maltophilia* for which the crystal structure has been determined (Ullah et al., 1998, *J Mol. Biol.,* 125–136), and amino acids 12 to 67 of the consensus sequence for pfam00753, i.e. the beta-lactamase superfamily motif (Bateman et al., 2000, *Nucleic Acids Research*, Vol. 28, No. 1, 263–266). Highlighted in black are residues demonstrated in the L1 metallo-beta-lactamase to co-ordinate zinc and their counterparts in the other two sequences. X-ray crystal structure analysis demonstrates that the histidine residues in this conserved motif are responsible for binding the zinc metal cofactor (Ullah et al., 1998, *J. Mol. Biol.,* 125–136). The precise alignment and conserved spacing of the amino acid residues in the His-motif of ORF 10 (SEQ ID NO: 11) as compared to the zinc-binding beta-lactamases indicates that ORF 10 (SEQ ID NO: 11) is likely to bind a metal cofactor.

FIG. 5B shows the local amino acid sequence homology between ORF 10 (SEQ ID NO: 11) and a key motif involved in coordinating an iron molecule in cytochrome P450 monooxygenases. The alignment depicts amino acids 405 to 452 of ORF 10 (SEQ ID NO: 11) and amino acids 370 to 421 of the consensus sequence for pfam00067, i.e. the cytochrome P450 motif (Bateman et al., 2000, *Nuecleic Acids Research*. Vol. 28, No. 1, 263–266). The region of ORF 10 (SEQ ID NO: 11) in highlight is in relatively good agreement with the Prosite motif PSO0086 required for binding iron (Hofmann et al., 1999, *Nuecleic Acids Research*, Vol. 27, No. 1, 215–219). Notably, the least variable positions of this motif are present in ORF 10 (SEQ ID NO: 11), i.e. residues Phe-423, Gly-425, Cys-428, and Gly-430). The C-terminal region of ORF 10 (SEQ ID NO: 11) contains a cluster of amino acid residues that shows significant local sequence homology to a motif frequently found in cytochrome P450 monooxygenases (the Cys-motif). This motif includes a cysteine residue that is highly conserved in the cytochrome P450 monooxygenases and that has been shown by X-ray crystal structure analysis to be involved in binding the iron metal cofactor required for catalysis. The Cys-motif of ORF 10 (SEQ ID NO: 11) is likely to contribute to the binding of a metal cofactor. The presence of two amino acid sequence motifs that are found in well-characterized metal-binding enzymes indicates that ORF 10 (SEQ ID NO: 11) is likely to be a metal-binding enzyme. Thus, the ORF 10 (SEQ ID NO: 11) is likely to be responsible for the formation of beta-hydroxyasparagine during the synthesis of ramoplanin.

Example 3

Expression Analysis

A—Acyl Starter Unit Chain Initiation

To investigate the involvement of an acyl starter unit chain in chain initiation of the ramoplanin NRPS system, ORF 11, ORF 12, and ORF 26 (SEQ ID NOS: 12 to 14) were individually PCR-amplified using oligonucleotide primer pairs that introduced convenient restriction enzyme sites at either end of each ORF as well as ten consecutive histidine tags at the N-terminus. These recombinant N-terminal HIS10-tagged ORFs were subcloned into an E. coli expression vector and the resulting plasmids were introduced into E. coli which were then grown under conditions that lead to high level expression of the recombinant ORFs. Cells were pelleted and disrupted, and the recombinant ORF 11, ORF 12, and ORF 26 (SEQ ID NOS: 12, 13 and 27) proteins were purified by nickel affinity chromatography. The ORF 11 and ORF 26 (SEQ ID NOS: 12 and 27) proteins are readily obtained as soluble protein preparations whereas the solubility of ORF 26 (SEQ ID NO: 27) is more reduced presumably due to its large size.

Based on sequence homology, ORF 11 (SEQ ID NO: 12) is predicted to be an acyl or amino acyl carrier protein. Purified recombinant ORF 11 (SEQ ID NO: 12) protein can be primed to its holo form in vitro using purified Sfp from Bacillus subtilis and coenzyme A, as indicated by an increase in mass by MALDI-MS that corresponds to the addition of the 4'-phosphopantetheine moiety of coenzyme A. The fact that recombinant ORF 11 is amenable to this posttranslational modification that converts it from an inactive apo into the active holo form confirms that it is indeed an acyl or amino acyl carrier protein.

The availability of solube recombinant ORF 26 together with solube, holo ORF 11 (described above) provides a means to confirm ORF 26's role in the transfer of the short chain fatty acids onto holo ORF 11. Such an experiment using as substrate the $^{14}$C-radiolabeled long chain fatty acid palmetic acid was inconclusive. These findings are consistent with the hypothesis that ORF 26 is specific for shorter chain fatty acids such as the three 8- to 10-carbon unsaturated fatty acids found in ramoplanins rather than long chain saturated fatty acids such as 16-carbon palmitic acid. Substrate specificity is further examined by synthesis of the fatty acyl groups that are naturally found linked to the amino terminus of the ramoplanin peptide.

B—beta-hydroxyasparagine

To confirm characterization of ORF 10 (SEQ. ID NO: 11) as a beta-hydroxylase and to confirm the role of ORF 10 (SEQ. ID NO: 11) in hydroxylation of asparagine at the beta position, a recombinant N-terminal His10-tagged ORF 10 E. coli expression system was designed as described above for ORFs 11, 12 and 26 (SEQ ID NOS: 12, 13 and 27). Purified recombinant ORF 10 (SEQ ID NO: 11) protein was obtained in a soluble form by nickel affinity chromatography. The fact that the purified recombinant protein does not display the characteristic absorption spectrum of heme-containing enzyme indicates that ORF 10 (SEQ ID NO: 11) is not a P450 enzyme. The ORF 10 (SEQ ID NO: 11) metal-binding motifs mentioned above therefore co-ordinate a non-heme iron or a metal other than iron.

Figure 6:
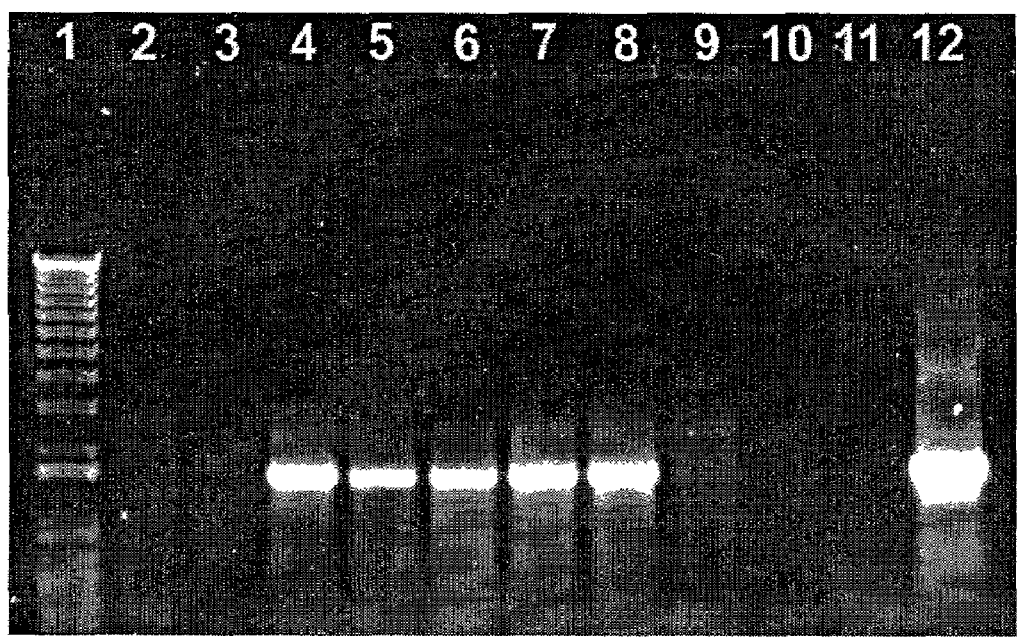
FIG. 6 illustrates a RT-PCR analysis of recombinant *S. lividans* clones expressing ramoplanin ORF 10 (SEQ ID NO: 11).

As an alternative source of native ORF 10 (SEQ ID NO: 11), a Streptomyces expression system was employed. ORF 10 (SEQ ID NO: 11) was amplified by high fidelity PCR using two specific oligonucleotides, namely primer sequences (5' to 3') N-oligo: CACACAGAATTCAC-CAGCGCCACTCGCGCTT (SEQ ID NO:45), and C-oligo: CACACATCGATGGGCAACGCCGATCAGCCG (SEQ ID NO:46). This primer pair introduces convenient restriction enzyme sites at either end of the ORF 10 gene but does not introduce any exogenous amino acids. The amplified genes were then subcloned using ClaI and EcoRI restriction enzymes into a Streptomyces/E.coli expression shuttle vector, pECO1202. Following confirmation of the cloned sequences, Streptomyces lividans TK24 was transformed with this construct. Five independent transformants were selected for further analysis. Cultures were grown for 48 hours in a gyrating 30° C. incubator using 25 ml erlenmeyer flasks containing 5 ml of Tryptic Soy Broth (TSB, Difco). Total RNA was extracted from the cell pellets using the RNeasy kit (Qiagen). The integrity and concentration of the RNA was monitored by agarose gel electrophoresis. Subsequently, reverse transcription was performed using 1 ug total RNA primed with an antisense primer sequence located in the vector just downstream of the stop codon. Following reverse transcription of each sample and appropriate controls, 20 cycles of PCR were performed using the original ORF-specific oligonucleotides, N-oligo and C-oligo. According to the RT-PCR analysis, the five recombinant S. lividans clones express relatively high levels of ORF 10-specific mRNA and the size of the RT-PCR product is as expected. FIG. 6 shows the RT-PCR analysis of recombinant S. lividans clones expressing ramoplanin ORF 10, wherein is lane 1 is 1 kb DNA ladder; lane 2 is untransformed S. lividans; lane 3 is S. lividans transformed with empty expression vector; lanes 4–8 are five different S. lividans recombinant clones expressing ramoplanin orf 10; lane 9 is an S. lividans recombinant clone expressing an unrelated gene; lane 10 is negative control performed without RNA; lane 11 is negative control performed without RT; lane 12 is positive control for PCR using plasmid DNA.

To confirm that these recombinant strains actually produce the expected ORF 10 protein lysates were analyzed by SDS-PAGE. Briefly, cell pellets from the above cultures were resuspended in cold extraction buffer (0.1M Tris-HCl, pH 7.6, 10 mM MgCl$_2$, 1 mM PMSF) and sonicated four times for 20 sec on ice with 1 min intervals. Soluble proteins were recovered by centrifugation for 10 min at 20,000×g and the total protein concentration was determined using the Bradford reagent (Biorad). Equal amounts of total soluble protein were subjected to 10% SDS-PAGE analysis. Proteins were visualized by staining with coomassie brilliant blue.

Figure 7:
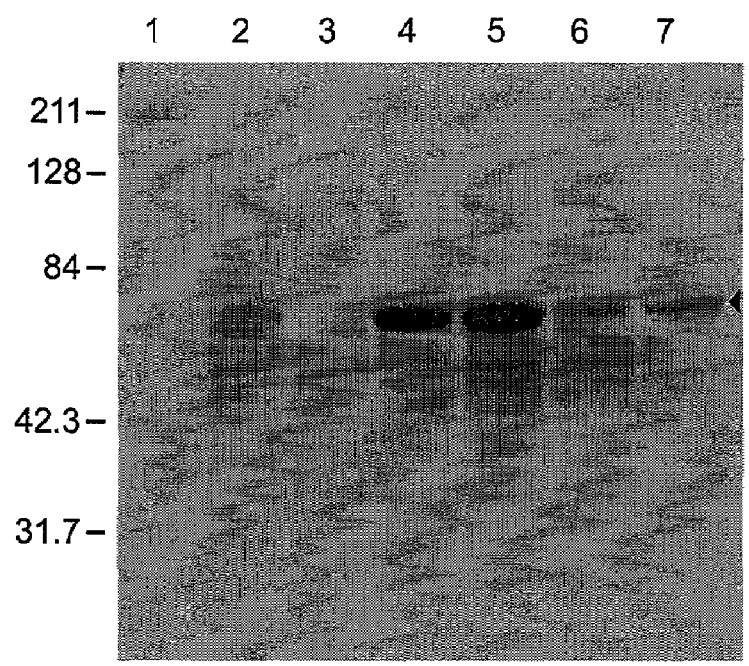
FIG. 7 illustrates a SDS-PAGE analysis of recombinant *S. lividans* clones expressing ramoplanin ORF 10 (SEQ ID NO: 11).

As shown in FIG. 7, the four recombinant strains tested contain a significant amount of protein with an apparent mobility of approximately 60 kilodaltons, consistent with the-predicted molecular mass of 58916.80 kilodaltons for the ORF 10 protein. FIG. 7 is the SDS-PAGE analysis of recombinant S. lividans clones expressing ramoplanin ORF 10 (SEQ ID NO.:11). The soluble fraction of protein lysates was subjected to 10% SDS-PAGE and stained with coomassie blue. Lane 1 is molecular weight standards with sizes in kilodaltons indicated to the left; lane 2 is untransformed S. lividans; lane 3 is S. lividans transformed with empty expression vector; lanes 4 to 7 are four different S. lividans recombinant clones expressing ramoplanin ORF 10 (SEQ.

ID NO.:11). The approximately 60 kDa ORF 10 gene product is clearly visible in lanes 4 to 7, as indicated by the arrowhead to the right.

It is to be understood that the embodiments described herein are for illustrative purposes only and that various modifications or changes in light thereof will be suggested to persons skilled in the art and are to be included within the spirit and purview of this application and scope of the appended claims. All publications, patents and patent applications and sequences from GenBank and other databases referred to herein are incorporated by reference in their entirety for all purposes.

The invention claimed is:

1. An isolated nucleic acid comprising a polynucleotide which encodes a domain of a ramoplanin nonribosomal peptide synthetase, wherein said ramoplanin nonribosomal peptide synthetase comprises the amino acid sequence of SEQ ID NO: 15 and wherein said domain is a condensation domain, an adenylation domain, a thiolation domain, or a thioesterase domain.

2. The isolated nucleic acid of claim 1, wherein said domain is a condensation domain.

3. The isolated nucleic acid of claim 2, wherein said nucleic acid comprises a coding sequence identical to or complementary to a nucleic acid selected from the group consisting of: nucleotides 39713–41171 of SEQ ID NO: 1; nucleotides 43037–44413 of SEQ ID NO:1; nucleotides 46076–47518 of SEQ ID NO:1; nucleotides 49346–50725 of SEQ ID NO:1; nucleotides 52361–53806 of SEQ ID NO:1; nucleotides 55661–57040 of SEQ ID NO:1; nucleotides 58799–60229 of SEQ ID NO:1 and nucleotides 62084–63487 of SEQ ID NO:1.

4. The isolated nucleic acid of claim 1, wherein said polynucleotide encodes a condensation domain comprising an amino acid sequence selected from the group consisting of: amino acids 1–486 of SEQ ID NO: 15; amino acids 1109–1567 of SEQ ID NO: 15; amino acids 2122–2602 of SEQ ID NO: 15; amino acids 3212–3671 of SEQ ID NO: 15; amino acids 4217–4698 of SEQ ID NO: 15; amino acids 5317–5776 of SEQ ID NO: 15; amino acids 6363–6839 of SEQ ID NO: 15 and amino acids 7458–7925 of SEQ ID NO: 15.

5. The isolated nucleic acid of claim 1, wherein said polynucleotide encodes an adenylation domain comprising an amino acid sequence selected from the group consisting of: amino acids 487–993 of SEQ ID NO: 15; amino acids 1568–2041 of SEQ ID NO: 15; amino acids 2603–3095 of SEQ ID NO: 15; amino acids 3672–4135 of SEQ ID NO: 15; amino acids 4699–5199 of SEQ ID NO: 15; amino acids 5777–6280 of SEQ ID NO: 15; amino acids 6840–7343 of SEQ ID NO: 15 and amino acids 7926–8380 of SEQ ID NO: 15.

6. The isolated nucleic acid of claim 1, wherein said polynucleotide encodes a thiolation domain comprising an amino acid sequence selected from the group consisting of: amino acids 994–1062 of SEQ ID NO: 15; amino acids 2042–2110 of SEQ ID NO: 15; amino acids 3097–3165 SEQ ID NO: 15; amino acids 4136–4202 of SEQ ID NO: 15; amino acids 5200–5268 of SEQ ID NO: 15; amino acids 6281–6350 of SEQ ID NO: 15; amino acids 7344–7411 of SEQ ID NO: 15 and amino acids 8381–8449 of SEQ ID NO: 15.

7. The isolated nucleic acid of claim 1, wherein said polynucleotide encodes a thioesterase domain comprising the amino acid sequence of amino acids 8450–8695 of SEQ ID NO. 15.

8. The isolated nucleic acid of claim 1, wherein said nucleic acid comprises a coding sequence identical to or complementary to nucleotides 39713–65800 of SEQ ID NO: 1 or a sequence that encodes an amino acid sequence of SEQ ID NO: 15.

9. The isolated nucleic acid of claim 1, wherein said nucleic acid is identical to or complementary to SEQ ID NO: 1.

10. The isolated nucleic acid of claim 1, wherein said domain is an adenylation domain.

11. The isolated nucleic acid of claim 10, wherein said nucleic acid comprises a coding sequence identical to or complementary to a nucleic acid selected from the group consisting of: nucleotides 41172–42691 of SEQ ID NO: 1; nucleotides 44414–45835 of SEQ ID NO:1; nucleotides 47519–48997 of SEQ ID NO:1; nucleotides 50726–52117 of SEQ ID NO:1; nucleotides 53807–55309 of SEQ ID NO:1; nucleotides 57041–58552 of SEQ ID NO:1; nucleotides 60230–61741 of SEQ ID NO:1 and nucleotides 63488–64852 of SEQ ID NO:1.

12. The isolated nucleic acid of claim 1, wherein said domain is a thiolation domain.

13. The isolated nucleic acid of claim 12, wherein said nucleic acid comprises a coding sequence identical to or complementary to a nucleic acid selected from the group consisting of: nucleotides 42692–42898 of SEQ ID NO: 1; nucleotides 45836–46042 of SEQ ID NO:1; nucleotides 49001–49207 of SEQ ID NO:1; nucleotides 52118–52318 of SEQ ID NO:1; nucleotides 55310–55516 of SEQ ID NO:1; nucleotides 58553–58762 of SEQ ID NO:1; nucleotides 61742–61945 of SEQ ID NO:1 and nucleotides 64853–65059 of SEQ ID NO:1.

14. The isolated nucleic acid of claim 1, wherein said domain is a thioesterase domain.

15. The isolated nucleic acid of claim 14, wherein said nucleic acid comprises a coding sequence identical to or complementary to nucleotides 65060–65797 of SEQ ID NO:1.

16. The isolated nucleic acid of claim 1, comprised in any one of cosmid 008CK (IDAC 190901-1), cosmid 008CO (IDAC 190901-2) or cosmid 008CH (IDAC 190901-3).

17. An expression vector comprising a nucleic acid of claim 1.

18. A host cell transformed with an expression vector of claim 17.

19. A method of preparing a nonribosomal peptide, comprising transforming a host cell with an expression vector of claim 17, culturing said host cell under conditions such that a nonribosomal peptide synthetase is produced and catalyzes the synthesis of said nonribosomal peptide.

20. An isolated nucleic acid comprising a polynucleotide which encodes a module of a nonribosomal peptide synthetase comprising a domain of the ramoplanin nonribosomal peptide synthetase of SEQ ID NO: 15 wherein said domain is a condensation domain, an adenylation domain, a thiolation domain, or a thioesterase domain.

21. The isolated nucleic acid of claim 20, wherein said polynucleotide encodes a module of a nonribosomal peptide synthetase comprising a condensation domain and a thiolation domain of the ramoplanin nonribosomal peptide synthetase of SEQ ID NO:15.

22. The isolated nucleic acid of claim 20, wherein said polynucleotide encodes a module of a nonribosomal peptide synthetase comprising a condensation domain, an adenylation domain and a thiolation domain of the ramoplanin nonribosomal peptide synthetase of SEQ ID NO:15.

23. An expression vector comprising a nucleic acid of claim 20.

24. A host cell transformed with an expression vector of claim 23.

25. A method of preparing a nonribosomal peptide, comprising transforming a host cell with an expression vector of claim 24, culturing said host cell under conditions such that a nonribosomal peptide synthtease is produced and catalyzes the synthesis of said nonribosomal peptide.

* * * * *